United States Patent
Cartledge et al.

(10) Patent No.: US 9,913,716 B2
(45) Date of Patent: Mar. 13, 2018

(54) ACTIVELY CONTROLLABLE STENT, STENT GRAFT, HEART VALVE AND METHOD OF CONTROLLING SAME

(71) Applicant: Edwards Lifesciences CardiAQ LLC, Irvine, CA (US)

(72) Inventors: Richard Cartledge, Boca Raton, FL (US); Kevin W. Smith, Coral Gables, FL (US); Thomas O. Bales, Jr., Coral Gables, FL (US); Max Pierre Mendez, Miami, FL (US); Korey Kline, Miami, FL (US); Matthew A. Palmer, Miami, FL (US); Michael Walter Kirk, Miami, FL (US); Carlos Rivera, Cooper City, FL (US); Derek Dee Deville, Coral Gables, FL (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 15/414,239

(22) Filed: Jan. 24, 2017

(65) Prior Publication Data
US 2017/0128198 A1     May 11, 2017

Related U.S. Application Data

(63) Continuation of application No. 13/656,717, filed on Oct. 21, 2012, now Pat. No. 9,566,178.

(Continued)

(51) Int. Cl.
*A61F 2/24* (2006.01)
*A61F 2/966* (2013.01)
(Continued)

(52) U.S. Cl.
CPC ............ *A61F 2/243* (2013.01); *A61F 2/2418* (2013.01); *A61F 2/2436* (2013.01);
(Continued)

(58) Field of Classification Search
CPC .......... A61F 2/24; A61F 2/2412; A61F 2/243; A61F 2/2418; A61F 2/844; A61F 2/966;
(Continued)

(56) References Cited

U.S. PATENT DOCUMENTS

| 6,875,231 B2 * | 4/2005 | Anduiza | A61F 2/2418 |
| | | | 623/1.15 |
| 6,893,459 B1 * | 5/2005 | Macoviak | A61F 2/2403 |
| | | | 623/2.11 |

(Continued)

*Primary Examiner* — Alvin Stewart
(74) *Attorney, Agent, or Firm* — Klarquist Sparkman, LLP; AnneMarie Kaiser

(57) ABSTRACT

A delivery apparatus can include a handle portion and at least one rotatable drive shaft. The handle portion can have an actuation mechanism with a motor. The rotatable drive shaft can have a proximal end portion and a distal end portion. The proximal end portion of the rotatable drive shaft can be coupled to the motor, and the distal end portion of the rotatable drive shaft can be configured to be releasably coupled to a prosthetic heart valve. The actuation mechanism can be configured to control and monitor expansion of the prosthetic heart valve and to control and monitor torque of the motor.

24 Claims, 109 Drawing Sheets

Related U.S. Application Data

(60) Provisional application No. 61/682,558, filed on Aug. 13, 2012, provisional application No. 61/601,961, filed on Feb. 22, 2012, provisional application No. 61/591,753, filed on Jan. 27, 2012, provisional application No. 61/585,937, filed on Jan. 12, 2012, provisional application No. 61/550,004, filed on Oct. 21, 2011.

(51) Int. Cl.
*A61F 2/07* (2013.01)
*A61F 2/958* (2013.01)
*A61F 2/06* (2013.01)
*A61F 2/848* (2013.01)
*A61F 2/95* (2013.01)

(52) U.S. Cl.
CPC ............ *A61F 2/2439* (2013.01); *A61F 2/966* (2013.01); *A61F 2/07* (2013.01); *A61F 2/958* (2013.01); *A61F 2002/061* (2013.01); *A61F 2002/075* (2013.01); *A61F 2002/077* (2013.01); *A61F 2002/8483* (2013.01); *A61F 2002/8486* (2013.01); *A61F 2002/9505* (2013.01); *A61F 2002/9517* (2013.01); *A61F 2002/9534* (2013.01); *A61F 2220/0016* (2013.01); *A61F 2220/0025* (2013.01); *A61F 2220/0033* (2013.01); *A61F 2220/0041* (2013.01); *A61F 2220/0091* (2013.01); *A61F 2230/0054* (2013.01); *A61F 2250/001* (2013.01); *A61F 2250/0006* (2013.01); *A61F 2250/006* (2013.01); *A61F 2250/0007* (2013.01)

(58) Field of Classification Search
CPC ................ A61F 2/95; A61F 2002/011; A61F 2002/9505; A61F 2002/9511; A61F 2002/9517; A61F 11/00; A61B 17/00; A61B 17/08; A61B 17/58; A61B 17/60; A61B 17/70; A61M 29/00; A61M 29/02; A61M 2029/025
See application file for complete search history.

(56) References Cited

U.S. PATENT DOCUMENTS

| | | | |
|---|---|---|---|
| 6,951,571 B1* | 10/2005 | Srivastava | A61F 2/2418 623/1.24 |
| 7,041,132 B2* | 5/2006 | Quijano | A61F 2/2412 623/2.11 |
| 7,235,093 B2* | 6/2007 | Gregorich | A61F 2/91 623/1.11 |
| 7,258,696 B2* | 8/2007 | Rabkin | A61F 2/95 606/191 |
| 7,326,236 B2* | 2/2008 | Andreas | A61F 2/95 623/1.11 |
| 7,887,583 B2* | 2/2011 | Macoviak | A61F 2/2403 623/2.38 |
| 8,226,707 B2* | 7/2012 | White | A61F 2/2412 623/1.12 |
| 8,647,378 B2* | 2/2014 | Mews | A61F 2/91 623/1.11 |
| 8,685,080 B2* | 4/2014 | White | A61F 2/2412 623/1.26 |
| 8,852,261 B2* | 10/2014 | White | A61F 2/2412 623/1.15 |
| 9,039,756 B2* | 5/2015 | White | A61F 2/2412 623/1.24 |
| 9,259,314 B2* | 2/2016 | White | A61F 2/2412 |
| 9,566,178 B2* | 2/2017 | Cartledge | A61F 2/966 |
| 2004/0049266 A1* | 3/2004 | Anduiza | A61F 2/2418 623/2.11 |
| 2008/0027483 A1* | 1/2008 | Cartledge | A61B 5/061 606/201 |
| 2009/0099638 A1* | 4/2009 | Grewe | A61F 2/966 623/1.11 |
| 2010/0049313 A1* | 2/2010 | Alon | A61F 2/2418 623/2.11 |
| 2011/0066224 A1* | 3/2011 | White | A61F 2/2412 623/1.15 |
| 2011/0219603 A1* | 9/2011 | White | A61F 2/2412 29/428 |
| 2011/0224781 A1* | 9/2011 | White | A61F 2/2412 623/1.24 |
| 2011/0230956 A1* | 9/2011 | White | A61F 2/2412 623/1.16 |
| 2011/0245918 A1* | 10/2011 | White | A61F 2/2412 623/2.11 |
| 2011/0288629 A1* | 11/2011 | White | A61F 2/2412 623/1.15 |
| 2012/0089217 A1* | 4/2012 | Mews | A61F 2/91 623/1.15 |
| 2012/0323316 A1* | 12/2012 | Chau | A61F 2/2418 623/2.18 |
| 2013/0046373 A1* | 2/2013 | Cartledge | A61F 2/966 623/1.11 |
| 2013/0158656 A1* | 6/2013 | Sutton | A61F 2/2436 623/2.11 |
| 2013/0166017 A1* | 6/2013 | Cartledge | A61F 2/93 623/1.15 |
| 2013/0310923 A1* | 11/2013 | Kheradvar | A61F 2/2439 623/2.11 |
| 2014/0018911 A1* | 1/2014 | Zhou | A61F 2/2436 623/2.11 |
| 2015/0201918 A1* | 7/2015 | Kumar | A61B 17/1622 606/104 |
| 2015/0257779 A1* | 9/2015 | Sinelnikov | A61B 8/12 600/439 |
| 2017/0160152 A1* | 6/2017 | Hamel | G01L 3/108 |

* cited by examiner

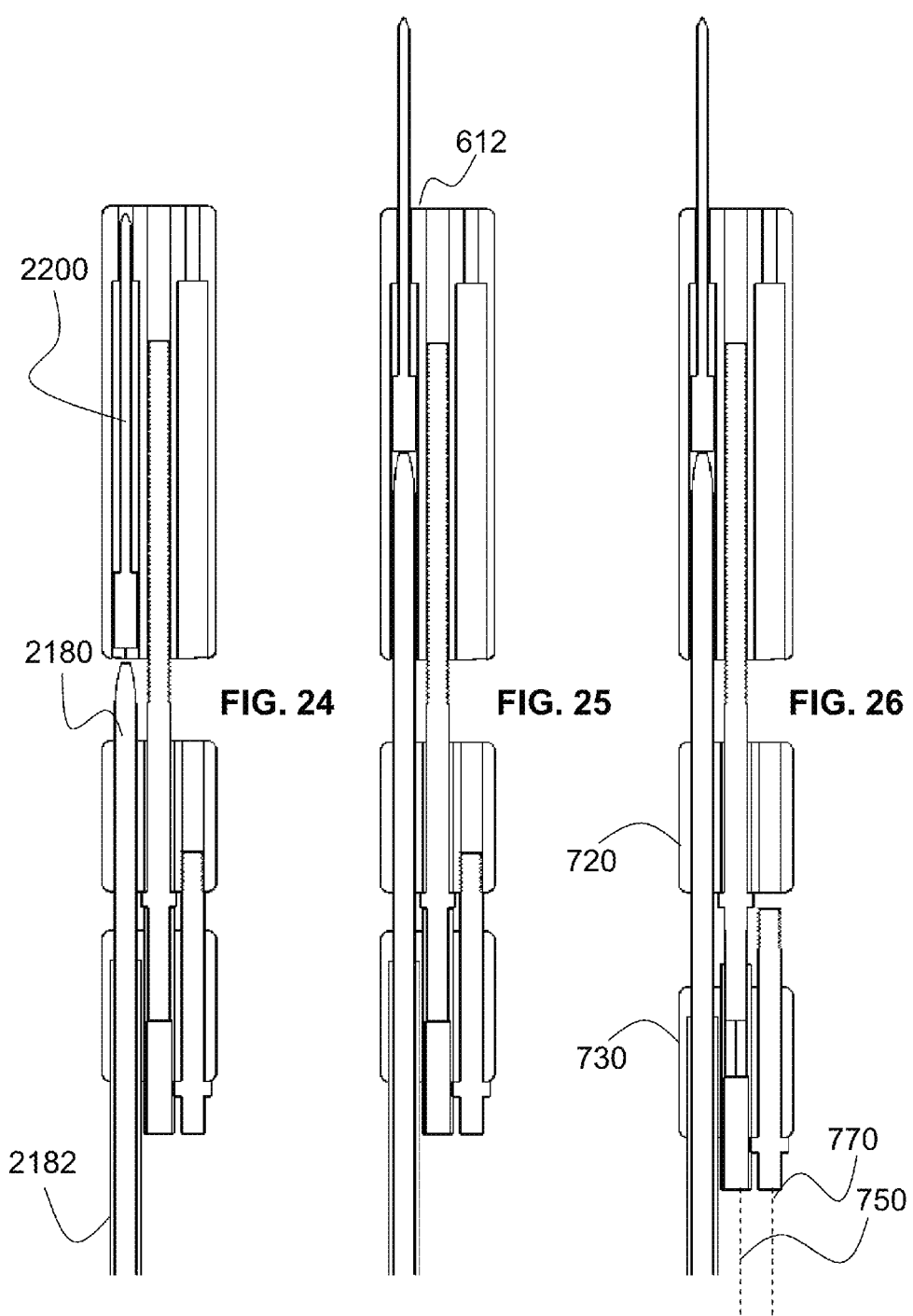

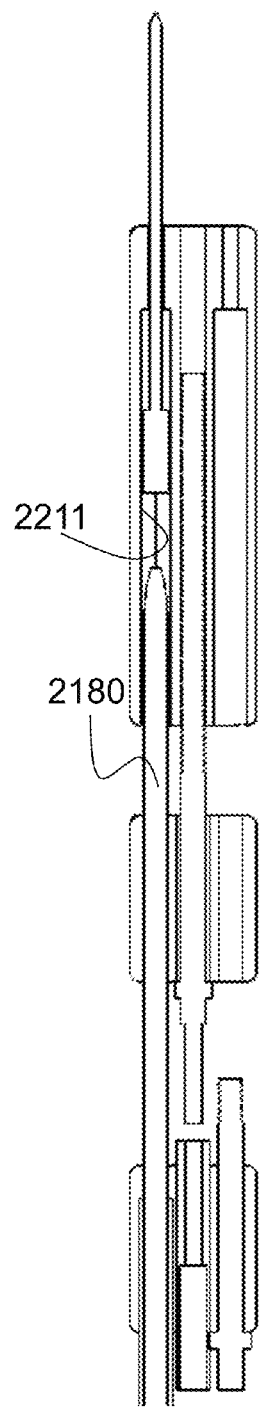

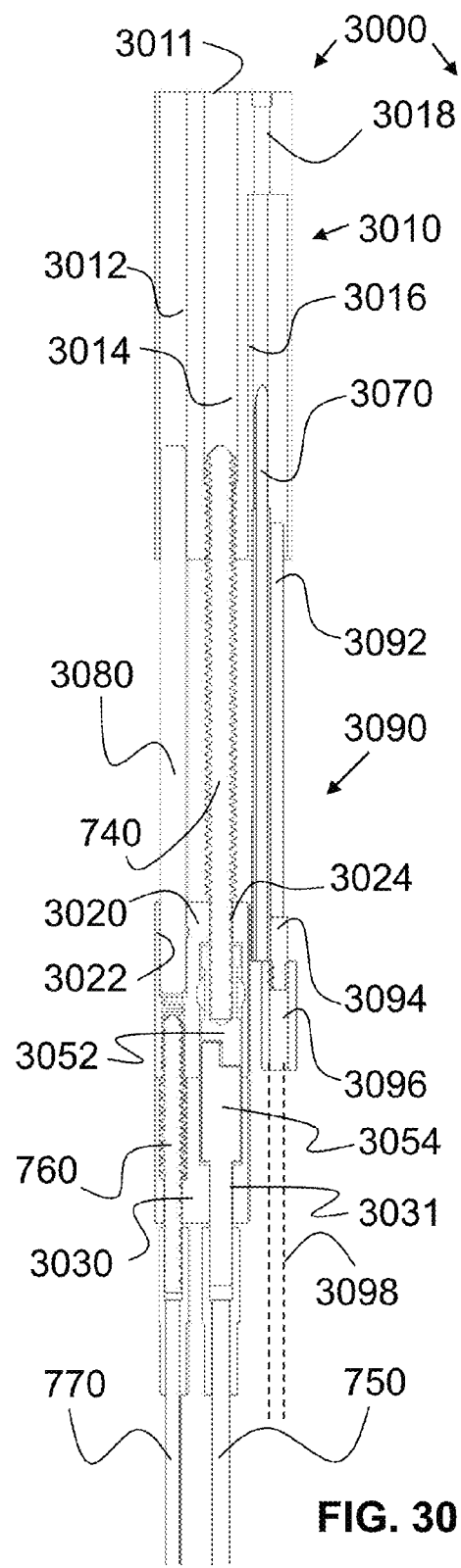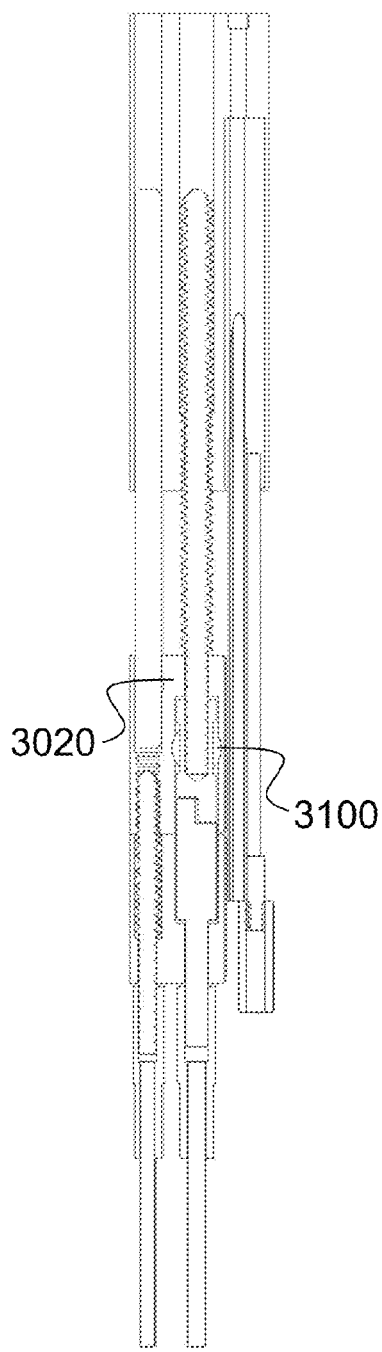
FIG. 30
FIG. 31

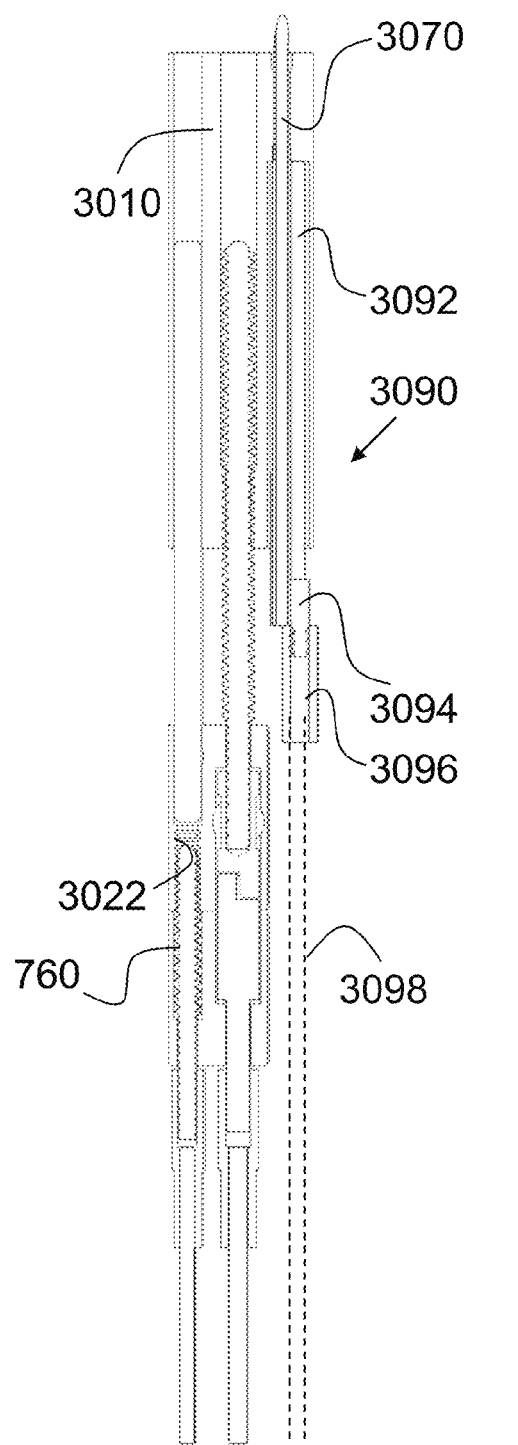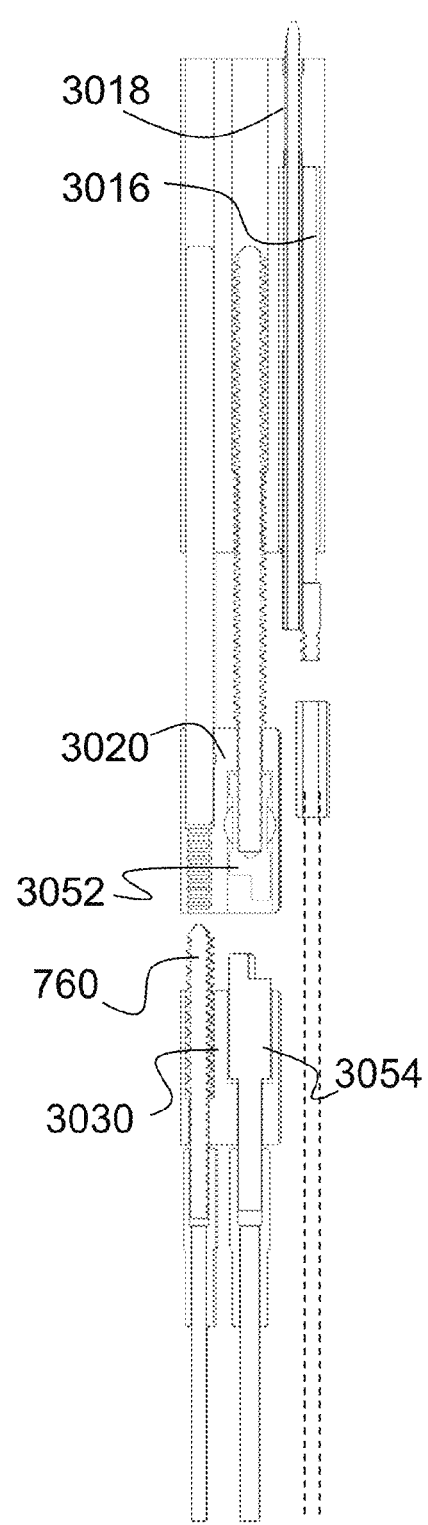
FIG. 32  FIG. 33

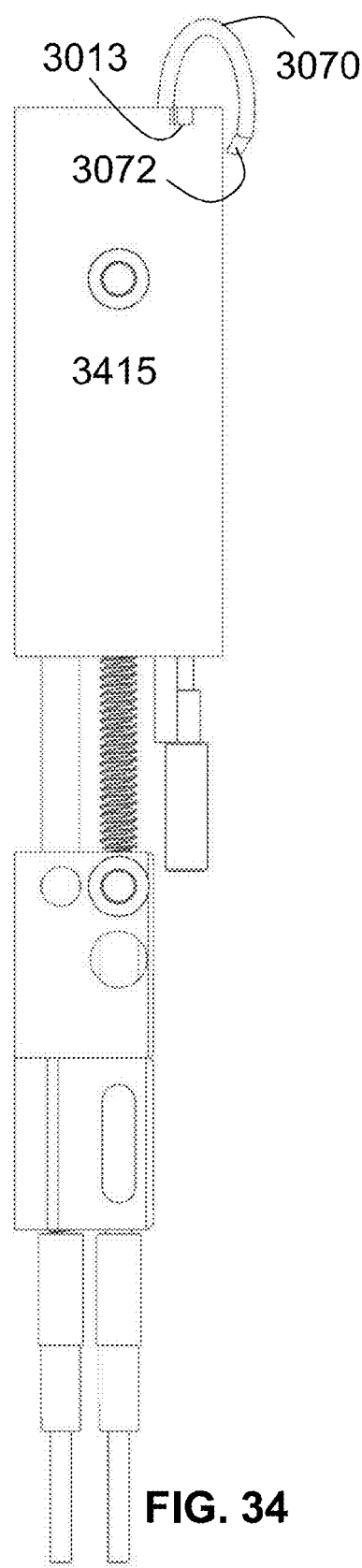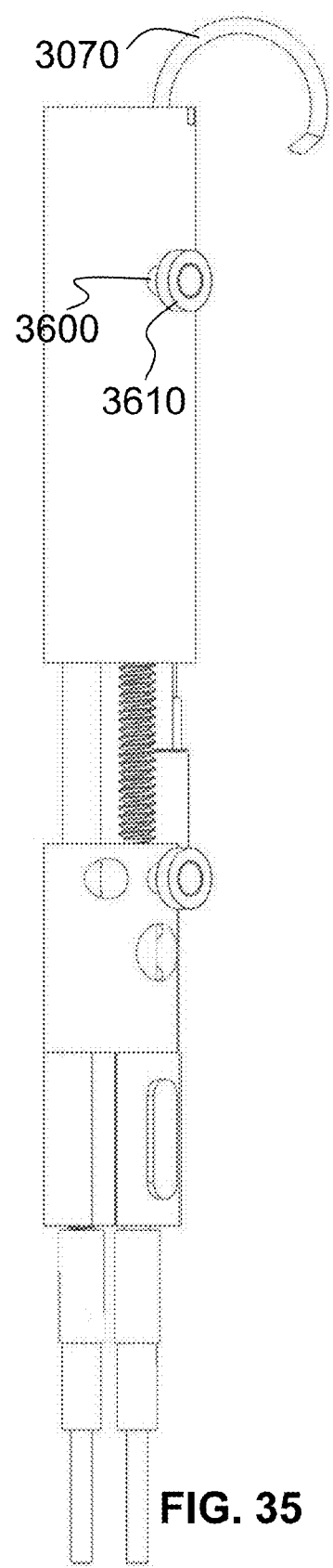

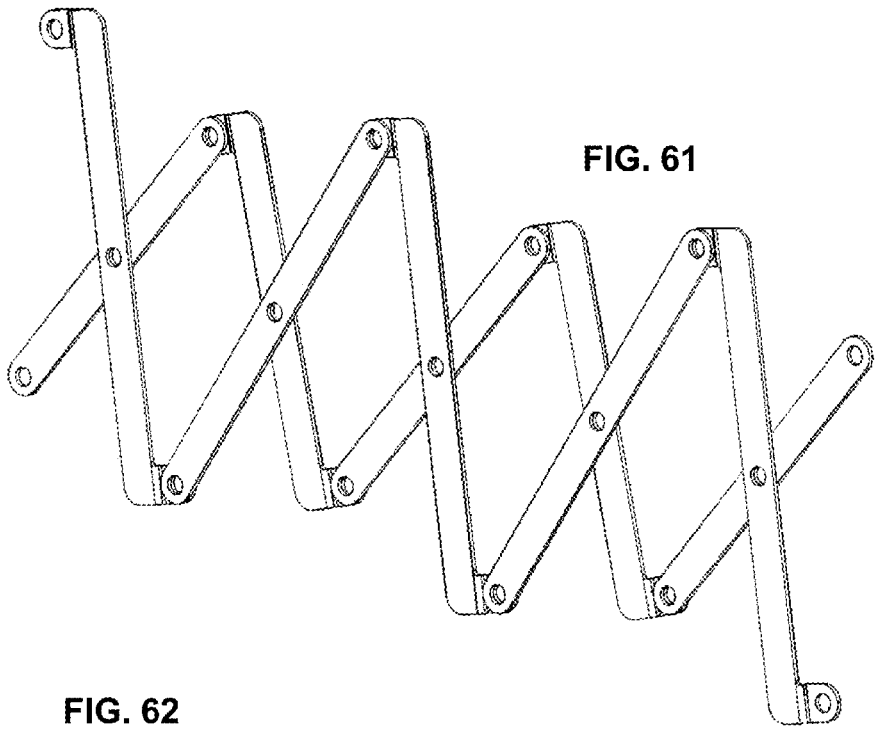
FIG. 61
FIG. 62
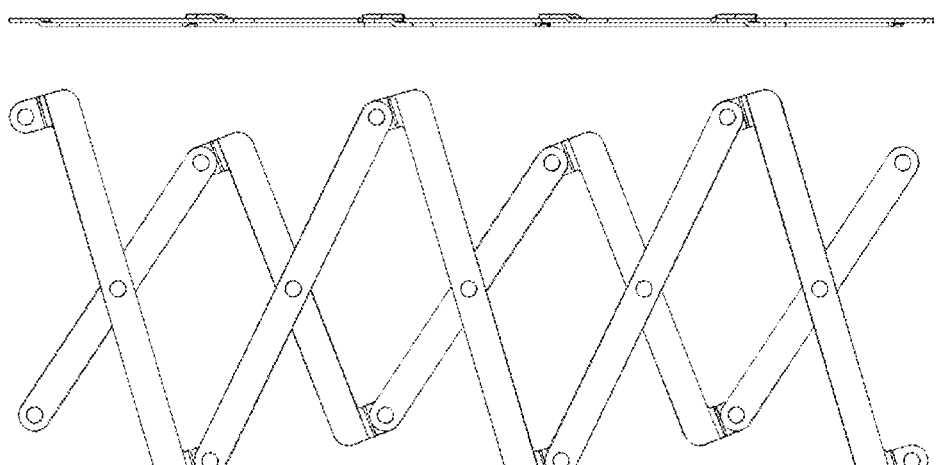
FIG. 63

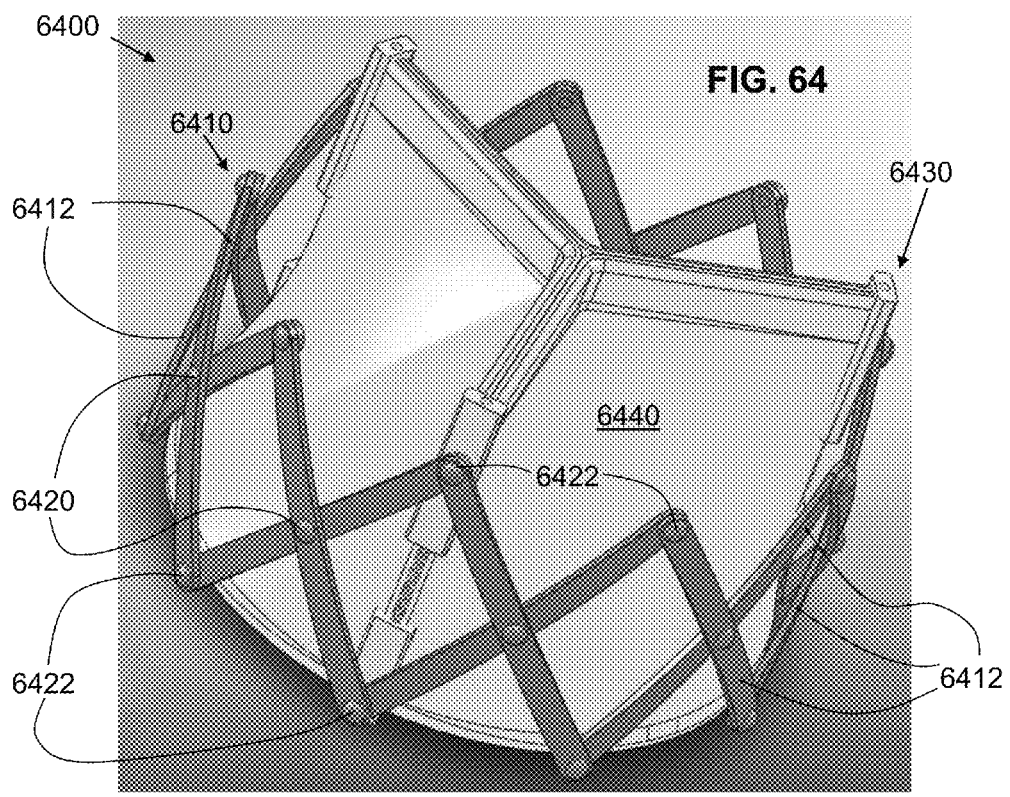
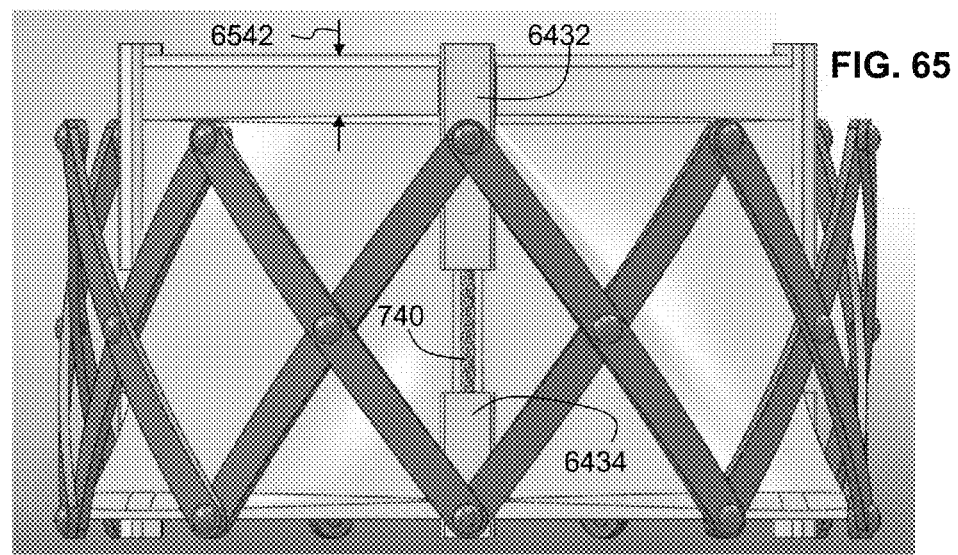

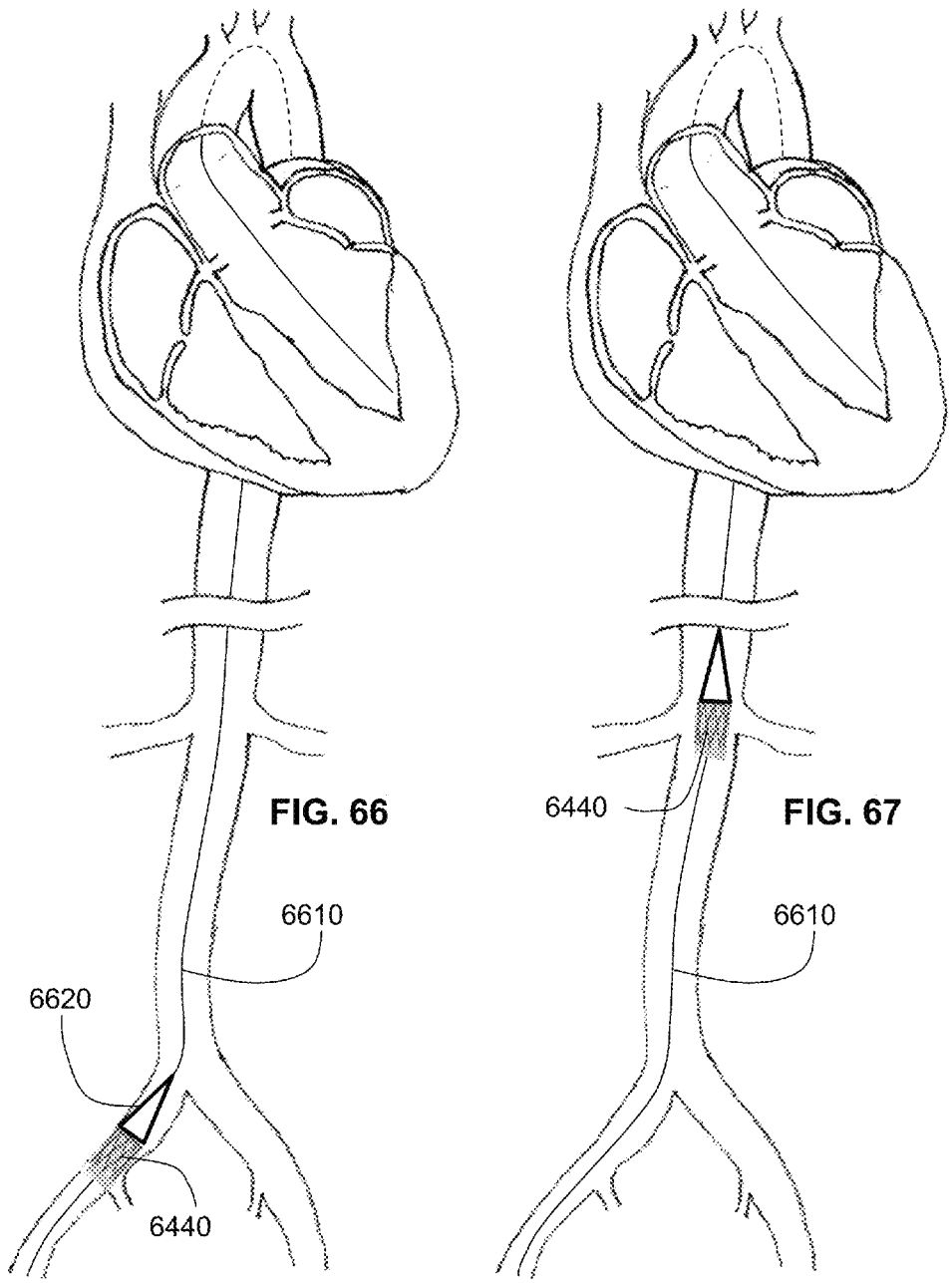

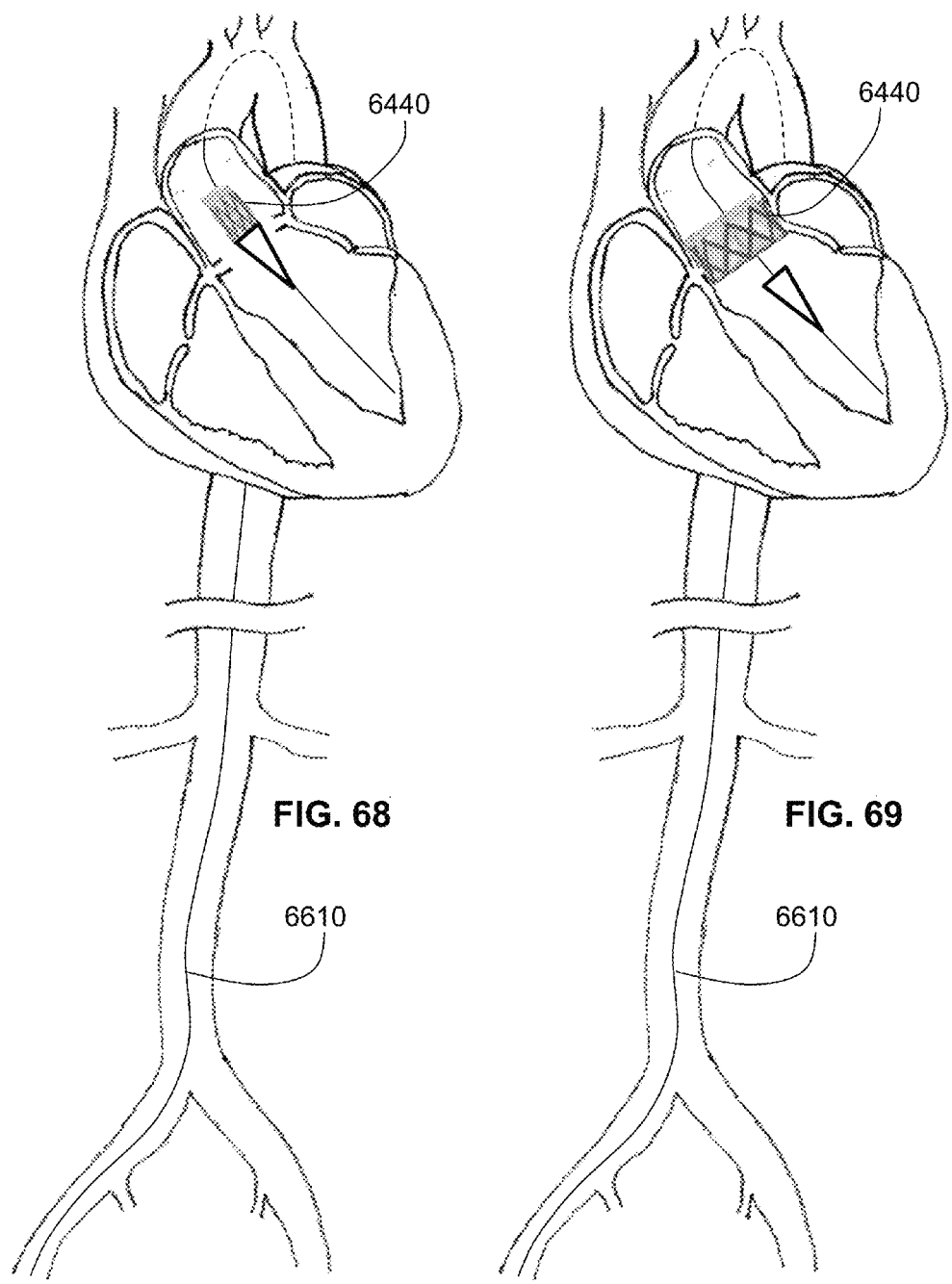

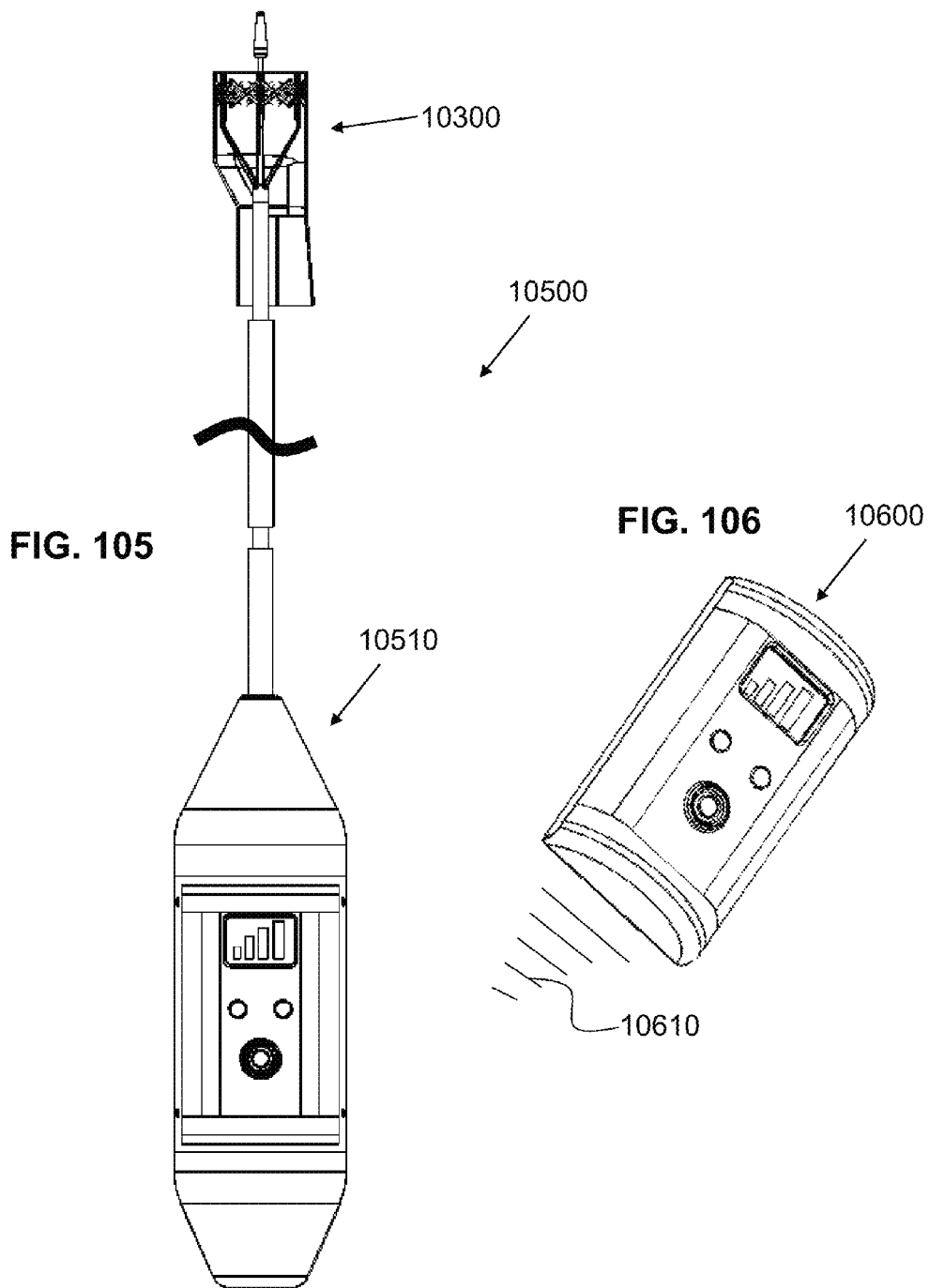

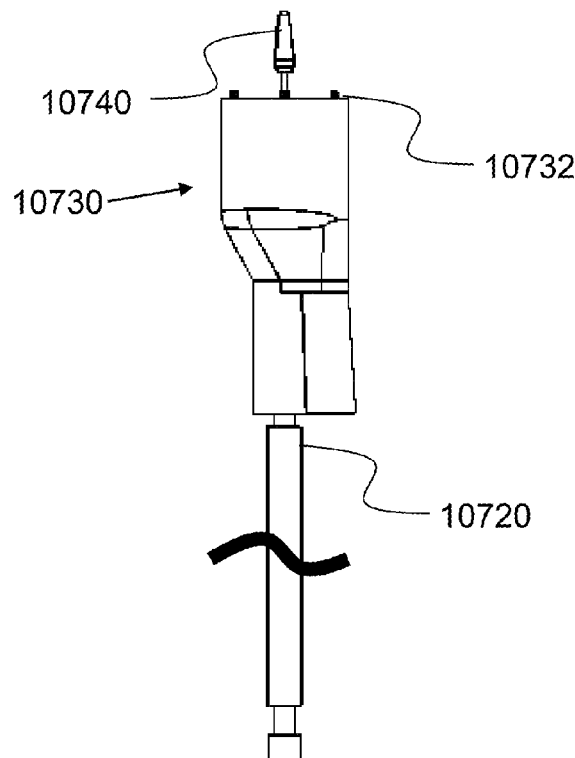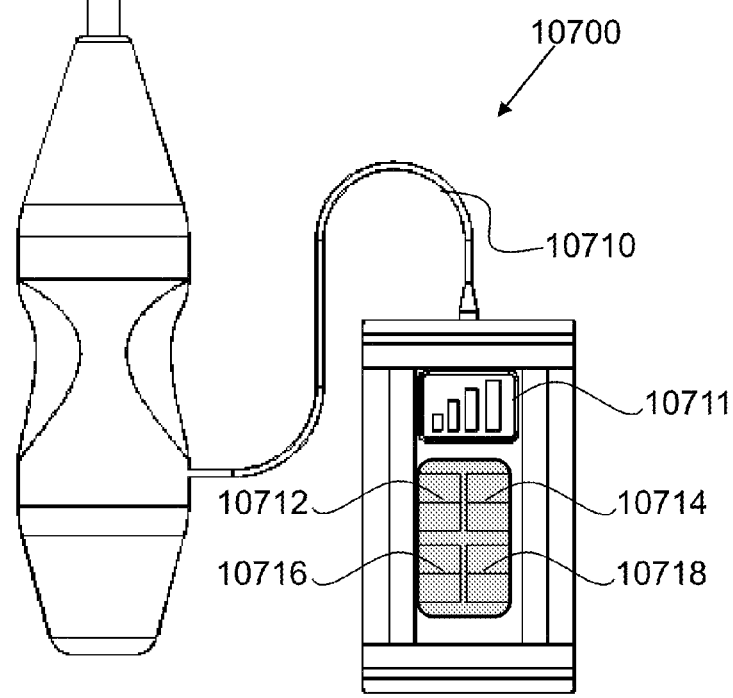
FIG. 107

ACTIVELY CONTROLLABLE STENT, STENT GRAFT, HEART VALVE AND METHOD OF CONTROLLING SAME

CROSS-REFERENCE TO RELATED APPLICATIONS

This application is a continuation of U.S. patent application Ser. No. 13/656,717, filed Oct. 21, 2012, which claims the benefit of U.S. Provisional Patent Application Nos. 61/682,558, filed Aug. 13, 2012, 61/601,961, filed Feb. 22, 2012, 61/591,753, filed Jan. 27, 2012, 61/585,937, filed Jan. 12, 2012, and 61/550,004, filed Oct. 21, 2011, all of which are incorporated by reference herein in their entireties.

This application is also related to U.S. Pat. Nos. 8,252,036 and 9,408,607, U.S. patent application Ser. No. 13/339,236, and U.S. Provisional Patent Application Nos. 60/834,401, 60/834,627, 61/222,646, 61/428,114, all of which are incorporated by reference herein in their entireties.

FIELD OF THE INVENTION

The present invention lies in the field of stents, stent grafts, heart valves (including aortic, pulmonary, mitral and tricuspid), and methods and systems for controlling and implanting stents, stent grafts and heart valves.

BACKGROUND OF THE INVENTION

Medical and surgical implants are placed often in anatomic spaces where it is desirable for the implant to conform to the unique anatomy of the targeted anatomic space and secure a seal therein, preferably without disturbing or distorting the unique anatomy of that targeted anatomic space.

While the lumens of most hollow anatomic spaces are ideally circular, in fact, the cross-sectional configurations of most anatomic spaces are, at best, ovoid, and may be highly irregular. Such lumenal irregularity may be due to anatomic variations and/or to pathologic conditions that may change the shape and topography of the lumen and its associated anatomic wall. Examples of anatomic spaces where such implants may be deployed include, but are not limited to, blood vessels, the heart, other vascular structures, vascular defects (such as thoracic and abdominal aortic aneurysms), the trachea, the oropharynx, the esophagus, the stomach, the duodenum, the ileum, the jejunum, the colon, the rectum, ureters, urethras, fallopian tubes, biliary ducts, pancreatic ducts, or other anatomic structures containing a lumen used for the transport of gases, blood, or other liquids or liquid suspensions within a mammalian body.

For a patient to be a candidate for existing endograft methods and technologies, to permit an adequate seal, a proximal neck of, ideally, at least 12 mm of normal aorta must exist downstream of the left subclavian artery for thoracic aortic aneurysms or between the origin of the most inferior renal artery and the origin of the aneurysm in the case of abdominal aneurysms. Similarly, ideally, at least 12 mm of normal vessel must exist distal to the distal extent of the aneurysm for an adequate seal to be achieved. The treatment of Aortic Stenosis through Transcather Aortic Valve Replacement (TAVR) is becoming more common. The limitations of current TAVR techniques do not allow for repositioning of the implant once it has been deployed in place. Further, the final expanded diameter of the current devices is fixed making presizing a critical and difficult step.

Migration of existing endografts has also been a significant clinical problem, potentially causing leakage and profusion of aneurysms and/or compromising necessary vascular supplies to arteries such as the coronary, carotid, subclavian, renal, or internal iliac vessels. This problem only has been addressed partially by some existing endograft designs, in which barbs or hooks have been incorporated to help retain the endograft at its intended site. However, most existing endograft designs are solely dependent on radial force applied by varying length of stent material to secure a seal against the recipient vessel walls.

Because of the limitations imposed by existing vascular endograft devices and endovascular techniques, a significant number of abdominal and thoracic aneurysms repaired in the U.S. are still managed though open vascular surgery, instead of the lower morbidity of the endovascular approach.

Pre-sizing is required currently in all prior art endografts. Such pre-sizing based on CAT-scan measurements is a significant problem. This leads, many times, to mis-sized grafts. In such situations, more graft segments are required to be placed, can require emergency open surgery, and can lead to an unstable seal and/or migration. Currently there exists no endograft that can be fully repositioned after deployment.

Thus, a need exists to overcome the problems with the prior art systems, designs, and processes as discussed above.

SUMMARY OF THE INVENTION

The invention provides surgical implant devices and methods for their manufacture and use that overcome the hereinafore-mentioned disadvantages of the heretofore-known devices and methods of this general type and that provide such features with improvements that increase the ability of such an implant to be precisely positioned and sealed, with better in situ accommodation to the local anatomy of the targeted anatomic site. The invention provide an adjustment tool that can remotely actuate an adjustment member(s) that causes a configuration change of a portion(s) of an implant, which configuration change includes but is not limited to diameter, perimeter, shape, and/or geometry or a combination of these, to create a seal and provide retention of an implant to a specific area of a target vessel or structure even when the cross-sectional configuration of the anatomic space is non-circular, ovoid, or irregular.

The invention provides an actively controllable stent, stent graft, stent graft assembly, heart valve, and heart valve assembly, and methods and systems for controlling and implanting such devices that overcome the hereinafore-mentioned disadvantages of the heretofore-known devices and methods of this general type and that provide such features with control both in opening and closing and in any combination thereof even during a surgical procedure or after completion of a surgical procedure.

One exemplary aspect of the present invention is directed towards novel designs for endovascular implant grafts, and methods for their use for the treatment of aneurysms (e.g., aortic) and other structural vascular defects. An endograft system for placement in an anatomic structure or blood vessel is disclosed in which an endograft implant comprises, for example, a non-elastic tubular implant body with at least an accommodating proximal end. Accommodating, as used herein, is the ability to vary a configuration in one or more ways, which can include elasticity, expansion, contraction, and changes in geometry. Both or either of the proximal and distal ends in an implant according to the present invention further comprise one or more circumferential expandable sealable collars and one or more expandable sealing devices, capable of being expanded upon deployment to achieve the desired seal between the collar and the vessel's inner wall. Exemplary embodiments of such devices can be found in U.S. Pat. Nos. 8,252,036 and 9,408,607, which have been incorporated by reference herein in their entireties. Further embodiments of endovascular implants and delivery systems and methods according to the present invention may be provided with retractable retention tines or other retention devices allowing an implant to be repositioned before final deployment. In other embodiments, the implant can be repositioned after final deployment. An endograft system according to the present invention further comprises a delivery catheter with an operable tubular sheath capable of housing a folded or compressed endograft implant prior to deployment and capable of retracting or otherwise opening in at least its proximal end to allow implant deployment. The sheath is sized and configured to allow its placement via a peripheral arteriotomy site, and is of appropriate length to allow its advancement into, for example, the aortic valve annulus, ascending aorta, aortic arch, and thoracic or abdominal aorta, as required for a specific application. Sheath movement is provided in a novel manner by manual actuation and/or automatic actuation.

While some post-implantation remodeling of the aortic neck proximal to an endovascular graft (endograft) has been reported, existing endograft technology does not allow for the management of this condition without placement of an additional endograft sleeve to cover the remodeled segment. Exemplary prostheses of the present invention as described herein allow for better accommodation by the implant of the local anatomy, using an actively controlled expansion device for the sealing interface between the prosthesis collar and the recipient vessel's inner wall. Furthermore, exemplary prostheses of the present invention as disclosed herein are provided with a controllably releasable disconnect mechanism that allows remote removal of an adjustment tool and locking of the retained sealable mechanism after satisfactory positioning and sealing of the endograft. In some exemplary embodiments according to the present invention, the controllably releasable disconnect mechanism may be provided in a manner that allows post-implantation re-docking of an adjustment member to permit post-implantation repositioning and/or resealing of a prostheses subsequent to its initial deployment.

Certain aspects of the present invention are directed towards novel designs for sealable endovascular implant grafts and endovascular implants, and methods for their use for the treatment of aortic aneurysms and other structural vascular defects and/or for heart valve replacements. Various embodiments as contemplated within the present invention may include any combination of exemplary elements as disclosed herein or in the co-pending patent applications referenced above.

In an exemplary embodiment according to the present invention, a sealable vascular endograft system for placement in a vascular defect is provided, comprising an elongated main implant delivery catheter with an external end and an internal end for placement in a blood vessel with internal walls. In such an exemplary embodiment, the main implant delivery catheter further comprises a main implant delivery catheter sheath that may be openable or removable at the internal end and a main implant delivery catheter lumen containing within a compressed or folded endovascular implant. Further, an endovascular implant comprises a non-elastic tubular implant body with an accommodating proximal end terminating in a proximal sealable circumferential collar that may be expanded by the operator to achieve a fluid-tight seal between the proximal sealable circumferential collar and the internal walls of the blood vessel proximal to the vascular defect. Moreover, an endovascular implant may further comprise a non-elastic tubular implant body with an accommodating distal end terminating in a distal sealable circumferential collar controlled by a distal variable sealing device, which may be expanded by the operator to achieve a fluid-tight seal between the distal sealable circumferential collar and the internal walls of the blood vessel distal to the vascular defect.

In a further exemplary embodiment according to the present invention, an implant interface is provided for a sealable attachment of an implant to a wall within the lumen of a blood vessel or other anatomic conduit.

In a yet further exemplary embodiment according to the present invention, an implant gasket interface is provided for a sealable attachment of an implant to a wall within the lumen of a blood vessel or other anatomic conduit, wherein the sealable attachment provides for auto-adjustment of the seal while maintaining wall attachment to accommodate post-implantation wall remodeling.

Still other exemplary embodiments of endografts and endograft delivery systems according to the present invention serve as universal endograft cuffs, being first placed to offer their advantageous anatomic accommodation capabilities, and then serving as a recipient vessel for other endografts, including conventional endografts.

Furthermore, exemplary embodiments of endografts and endograft delivery systems according to the present invention may be provided with a mechanism to permit transfer of torque or other energy from a remote operator to an adjustment member comprising a sealable, adjustable circumferential assembly controlled by an adjustment tool, which may be detachable therefrom and may further cause the assembly to lock upon detachment of the tool. In some exemplary embodiments of the present invention, the variable sealing device may be provided with a re-docking element that may be recaptured by subsequent operator interaction, allowing redocking and repositioning and/or resealing of the endograft at a time after its initial deployment.

Moreover, the various exemplary embodiments of the present invention as disclosed herein may constitute complete endograft systems, or they may be used as components of a universal endograft system as disclosed in co-pending patent applications that may allow the benefits of the present invention to be combined with the ability to receive other endografts.

Additionally, the present invention encompasses sealable devices that may be used in other medical devices such as adjustable vascular cannulas or other medical or surgical devices or implants, such as heart valves.

With the foregoing and other objects in view, there is provided, in accordance with the invention, a surgical implant including an implant body and a selectively adjustable assembly attached to the implant body, having adjustable elements, and operable to cause a configuration change in a portion of the implant body and, thereby, permit implantation of the implant body within an anatomic orifice to effect a seal therein under normal physiological conditions.

Although the invention is illustrated and described herein as embodied in an actively controllable stent, stent graft, stent graft assembly, heart valve, and heart valve assembly, and methods and systems for controlling and implanting such devices, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 24 is a fragmentary, cross-sectional view of the jack assembly of FIG. 23 with a needle pusher in a partially actuated state before extension of the needle;

FIG. 25 is a fragmentary, cross-sectional view of the jack assembly of FIG. 24 with the needle pusher in another partially actuated state with the needle pusher in another partially actuated state with an extension of the needle;

FIG. 26 is a fragmentary, cross-sectional view of the jack assembly of FIG. 25 with the drive sub-assembly in a partially disconnected state without retraction of the needle pusher;

FIG. 27 is a fragmentary, cross-sectional view of the jack assembly of FIG. 26 with the drive sub-assembly in a further partially disconnected state with partial retraction of the needle pusher;

FIG. 28 is a fragmentary, cross-sectional view of the jack assembly of FIG. 27 with the drive sub-assembly in a still a further partially disconnected state with further retraction of the needle pusher;

FIG. 29 is a fragmentary, cross-sectional view of the jack assembly of FIG. 23 with the drive sub-assembly and the needle pusher in a disconnected state;

FIG. 30 is a fragmentary, cross-sectional view of another alternative exemplary embodiment of a jack assembly according to the invention in a stent-contracted state with a drive sub-assembly in a connected state and with a needle sub-assembly in a retracted state;

FIG. 31 is a fragmentary, cross-sectional view of the jack assembly of FIG. 30 in a partially stent-expanded state;

FIG. 32 is a fragmentary, cross-sectional view of the jack assembly of FIG. 31 with the needle sub-assembly in an actuated state with extension of the needle;

FIG. 33 is a fragmentary, cross-sectional view of the jack assembly of FIG. 32 with the drive sub-assembly in a disconnected state and the needle sub-assembly in a disconnected state;

FIG. 34 is a fragmentary, perspective view of the jack assembly of FIG. 33 with the extended needle rotated slightly to the right of the figure.

FIG. 35 is a fragmentary, perspective view of the jack assembly of FIG. 34 rotated to the right by approximately 45 degrees;

FIG. 61 is a side perspective view of the stent system portion of FIG. 58 in a partially expanded state;

FIG. 62 is a top plan view of the stent system portion of FIG. 61;

FIG. 63 is a side elevational view of the stent system portion of FIG. 61;

FIG. 64 is a perspective view of a downstream side of an exemplary embodiment of a replacement valve assembly according to the invention in an expanded state;

FIG. 65 is a side elevational view of the valve assembly of FIG. 64;

FIG. 66 is a fragmentary, perspective view of a delivery system according to the invention for the aortic valve assembly of FIG. 64 with the aortic valve assembly in the process of being implanted and in the right iliac artery;

FIG. 67 is a fragmentary, perspective view of the delivery system and aortic valve assembly of FIG. 66 with the aortic valve assembly in the process of being implanted and in the abdominal aorta;

FIG. 68 is a fragmentary, perspective view of the delivery system and aortic valve assembly of FIG. 66 with the aortic valve assembly in the process of being implanted and being adjacent the aortic valve implantation site;

FIG. 69 is a fragmentary, perspective view of the delivery system and aortic valve assembly of FIG. 66 with the aortic valve assembly implanted in the heart;

FIG. 105 is a fragmentary, front elevational and partially cross-sectional view of a self-contained, self-powered, actively controllable stent graft delivery and integral control system according to the invention with the prosthesis in an expanded state with the graft material in cross-section showing a rear half thereof;

FIG. 106 is a perspective view of the control portion of the system of FIG. 105 as a wireless sub-system;

FIG. 107 is a fragmentary, front elevational view of another exemplary embodiment of a self-contained, self-powered, actively controllable stent graft delivery and separate tethered control system according to the invention with different controls and with the prosthesis in an expanded state;

Figure 120:
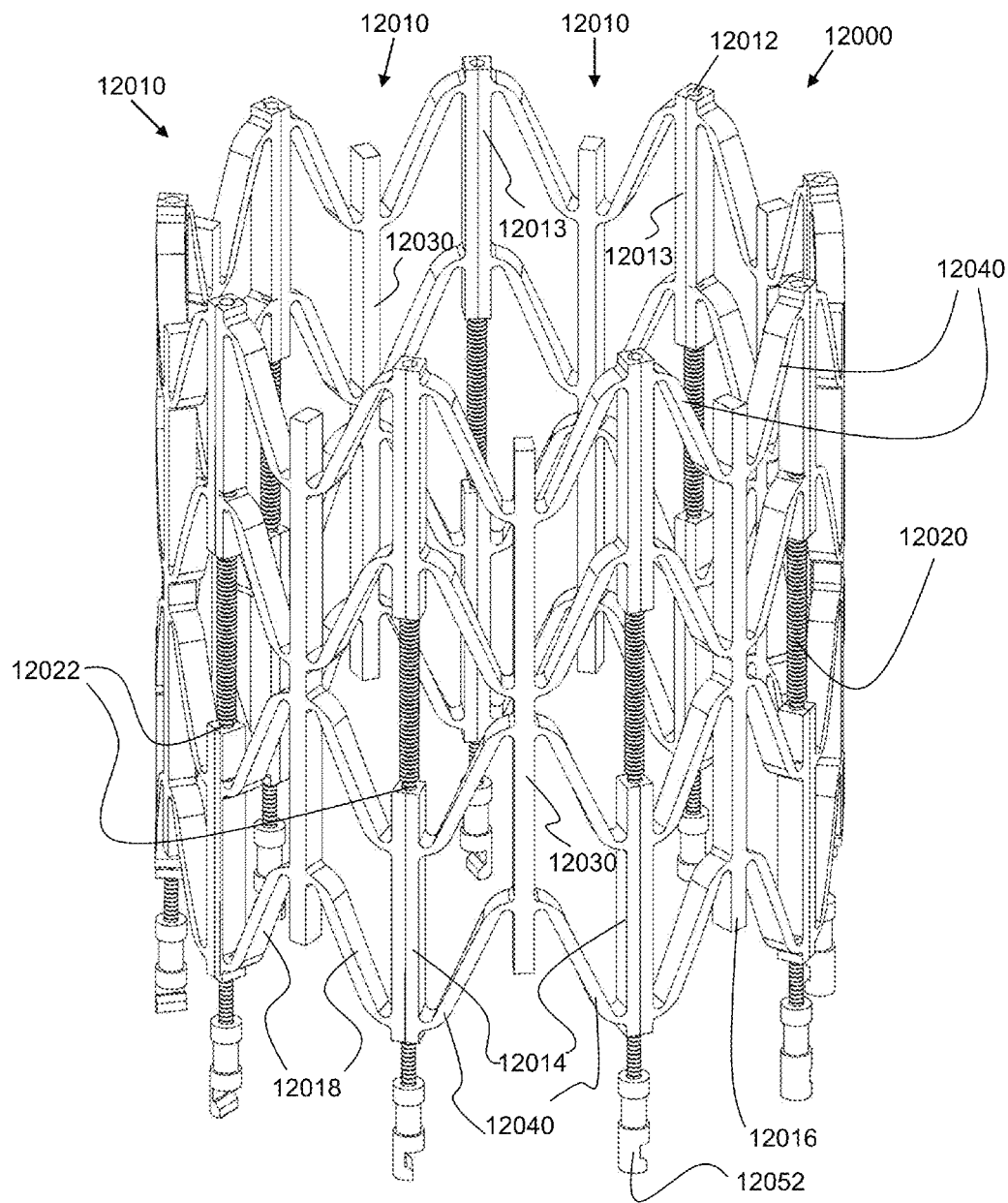
Figure 121:
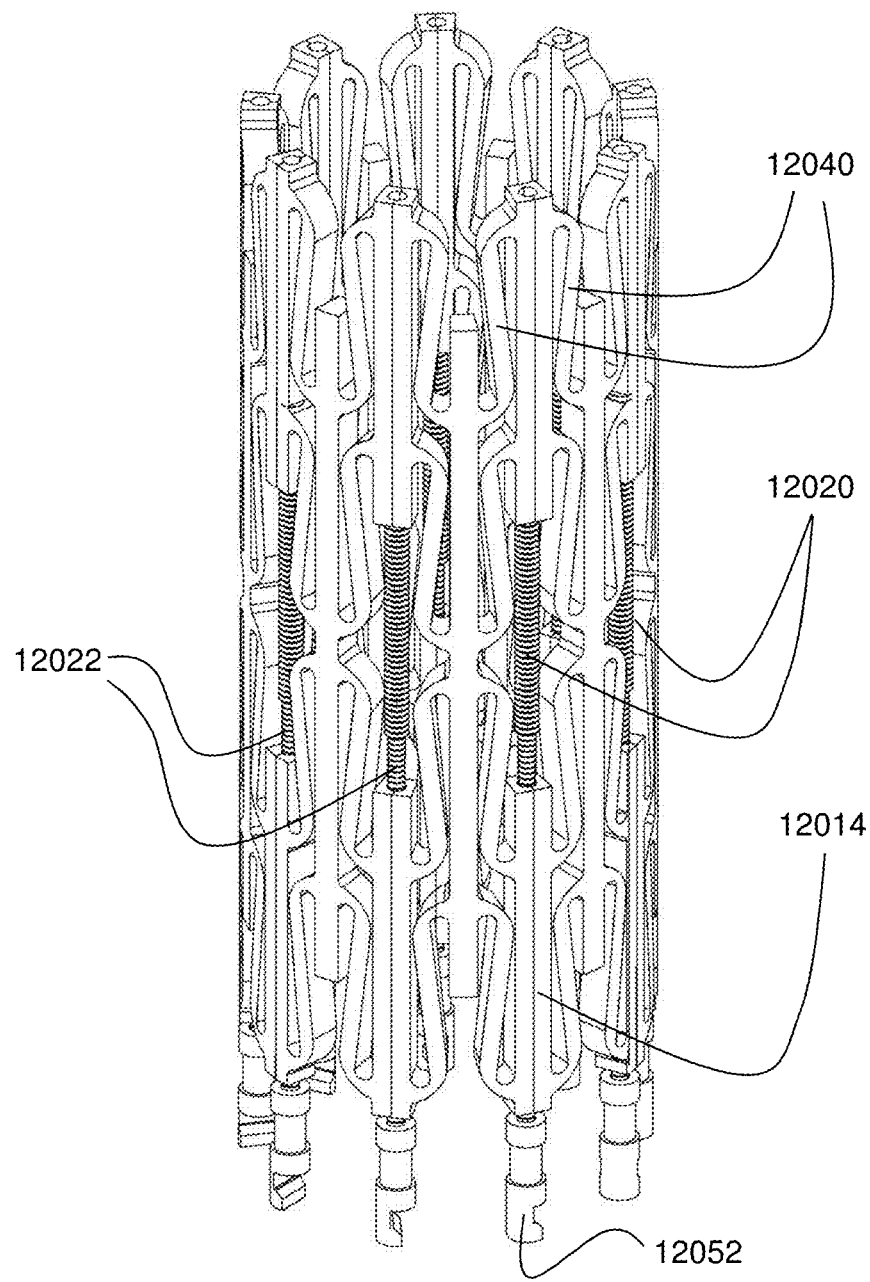
Figure 122:
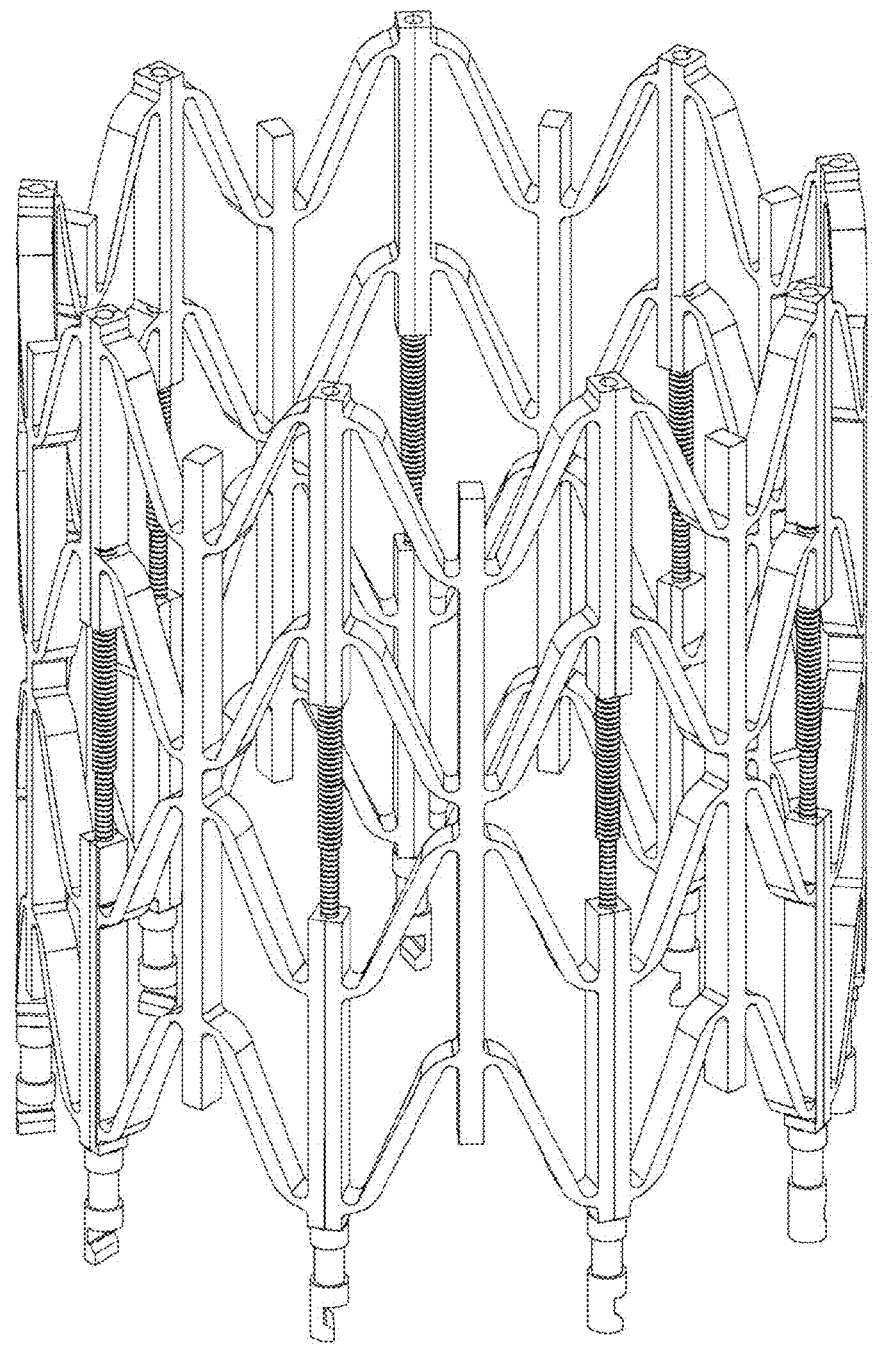
Figure 123:
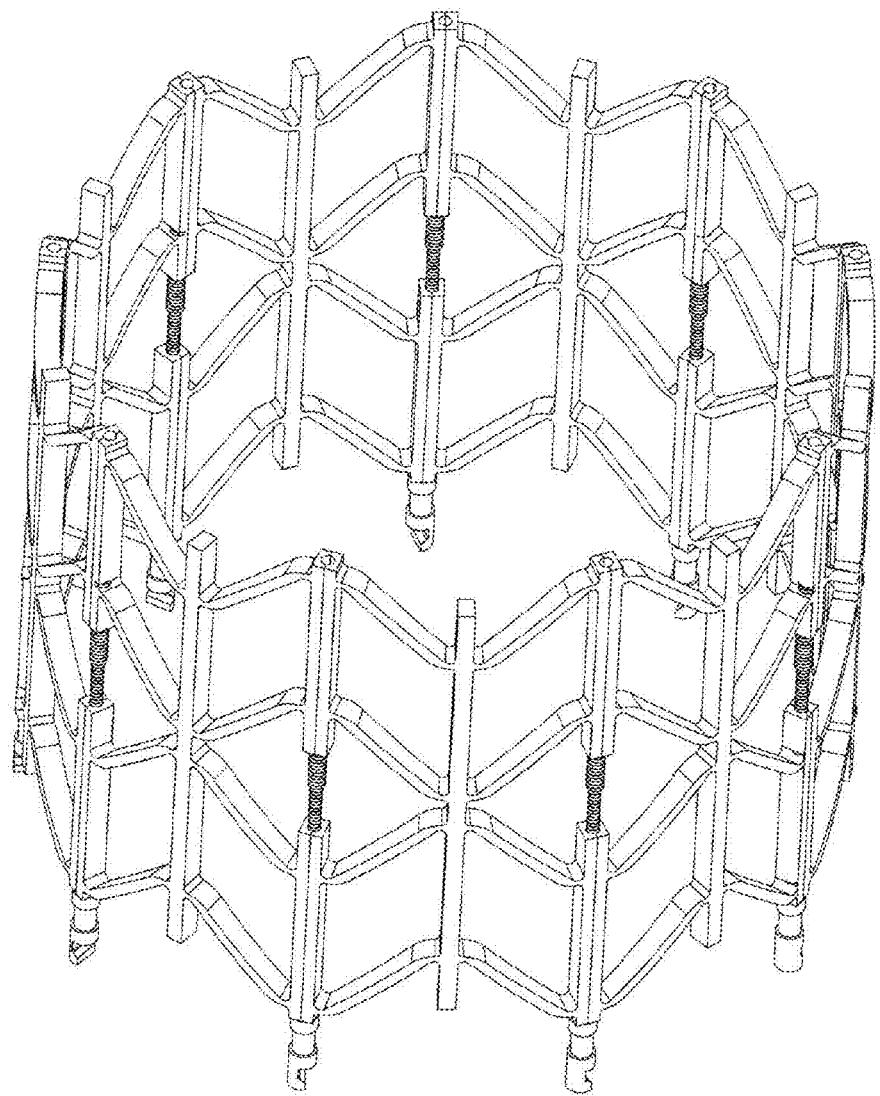
Figure 124:
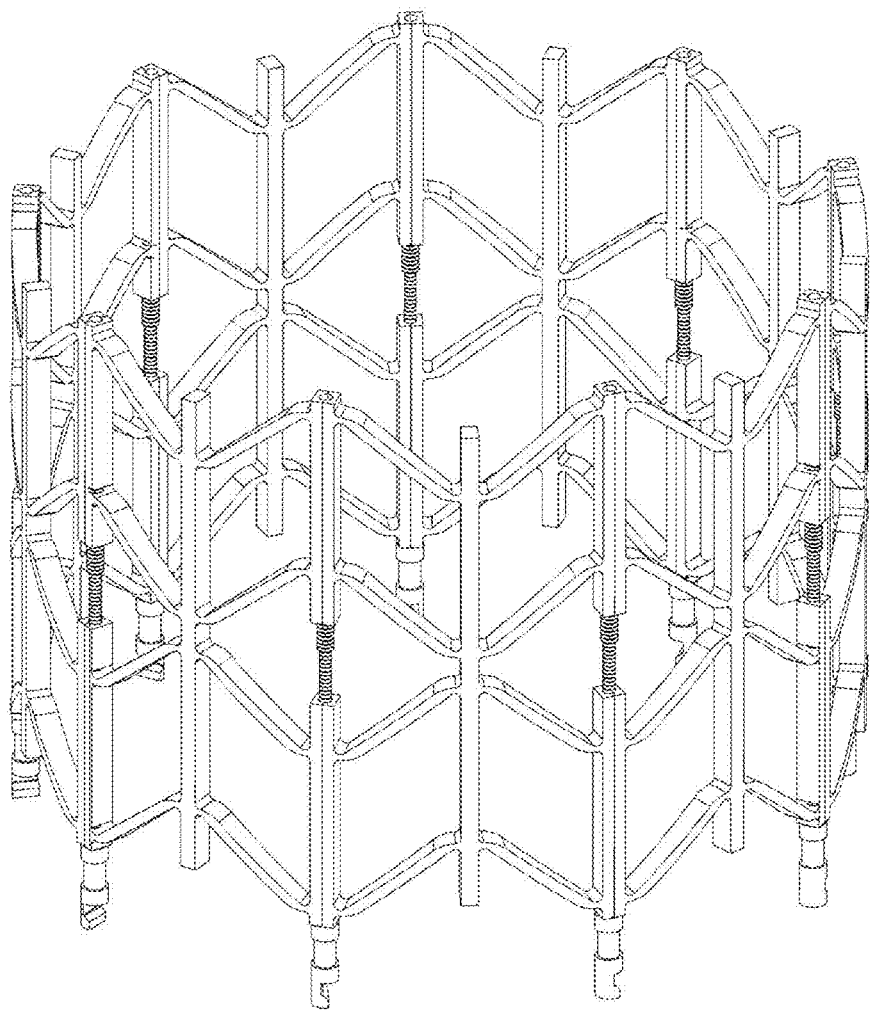
Figure 125:
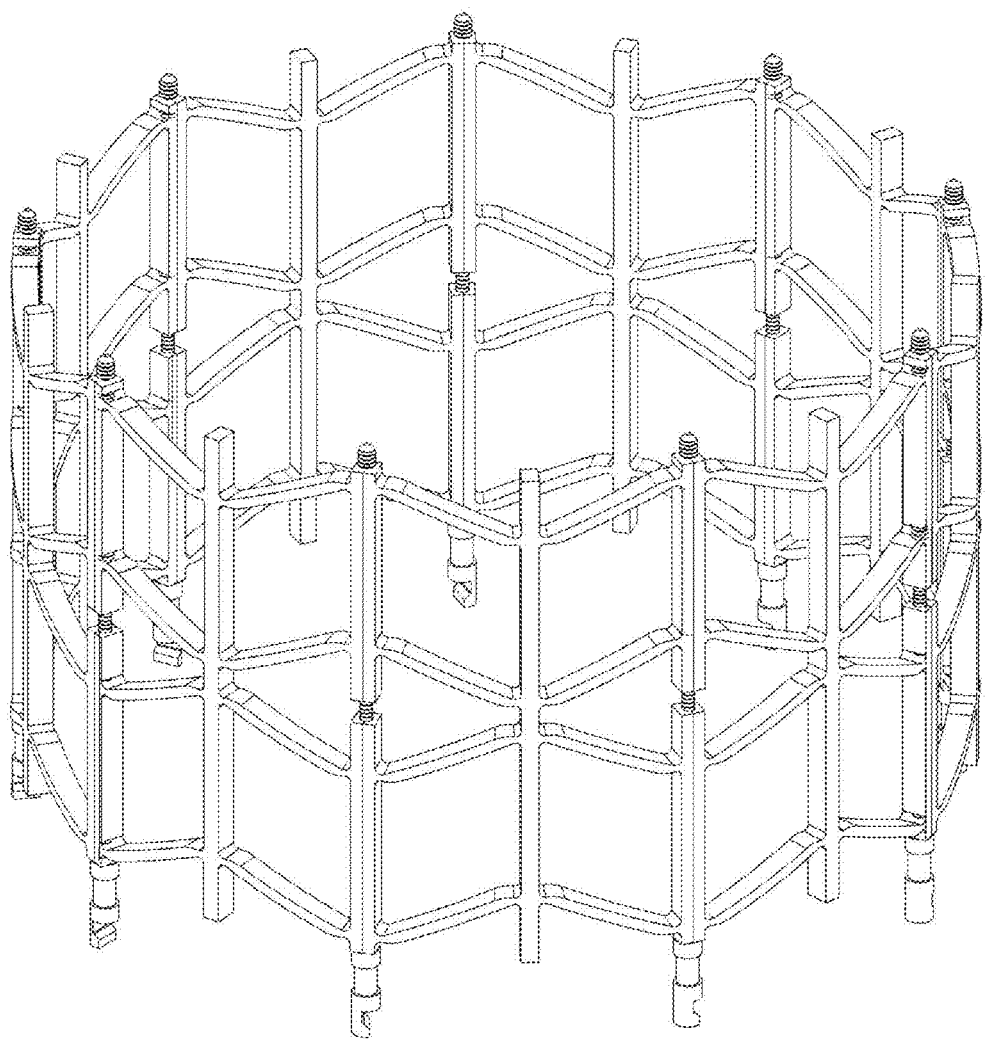
Figure 126:
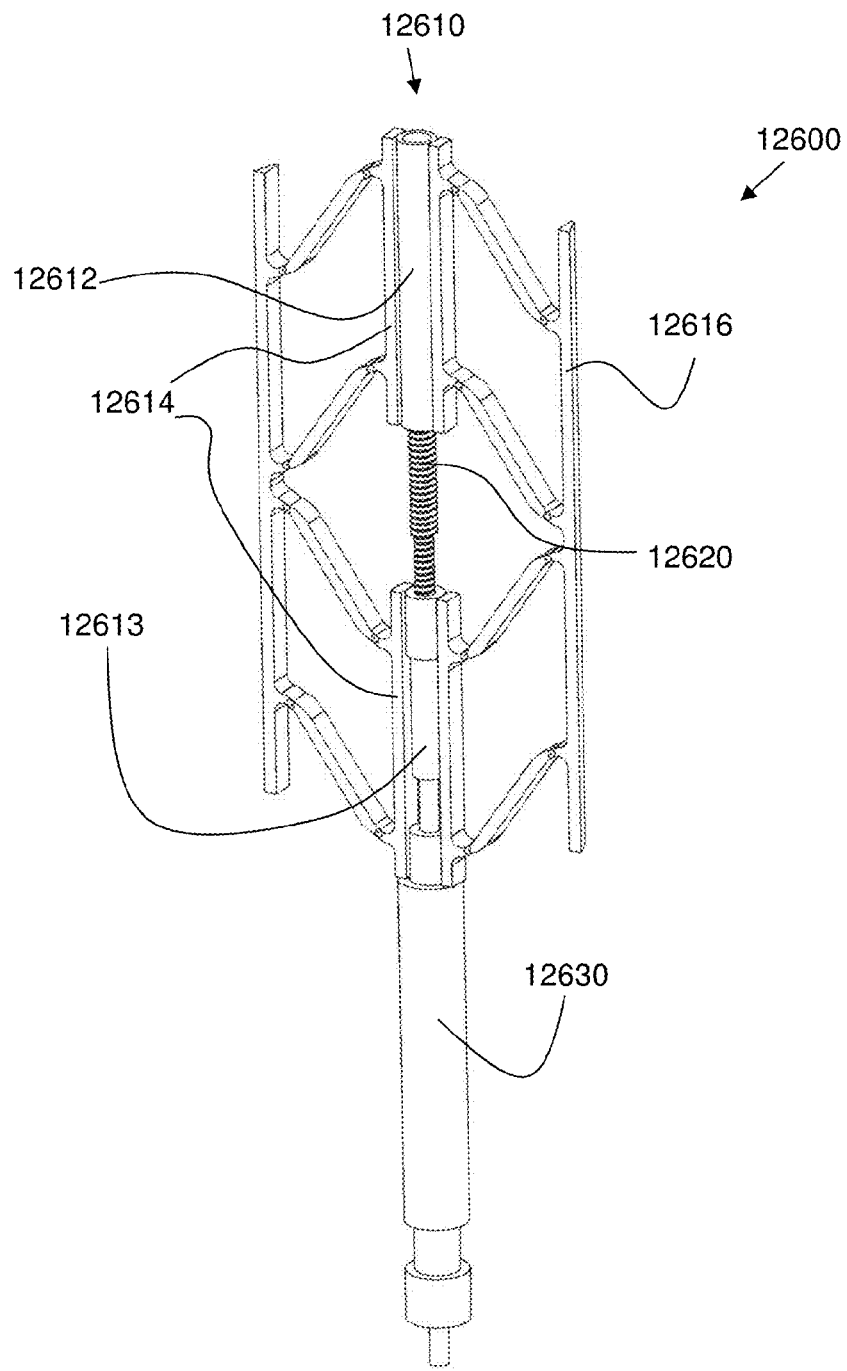
Figure 127:
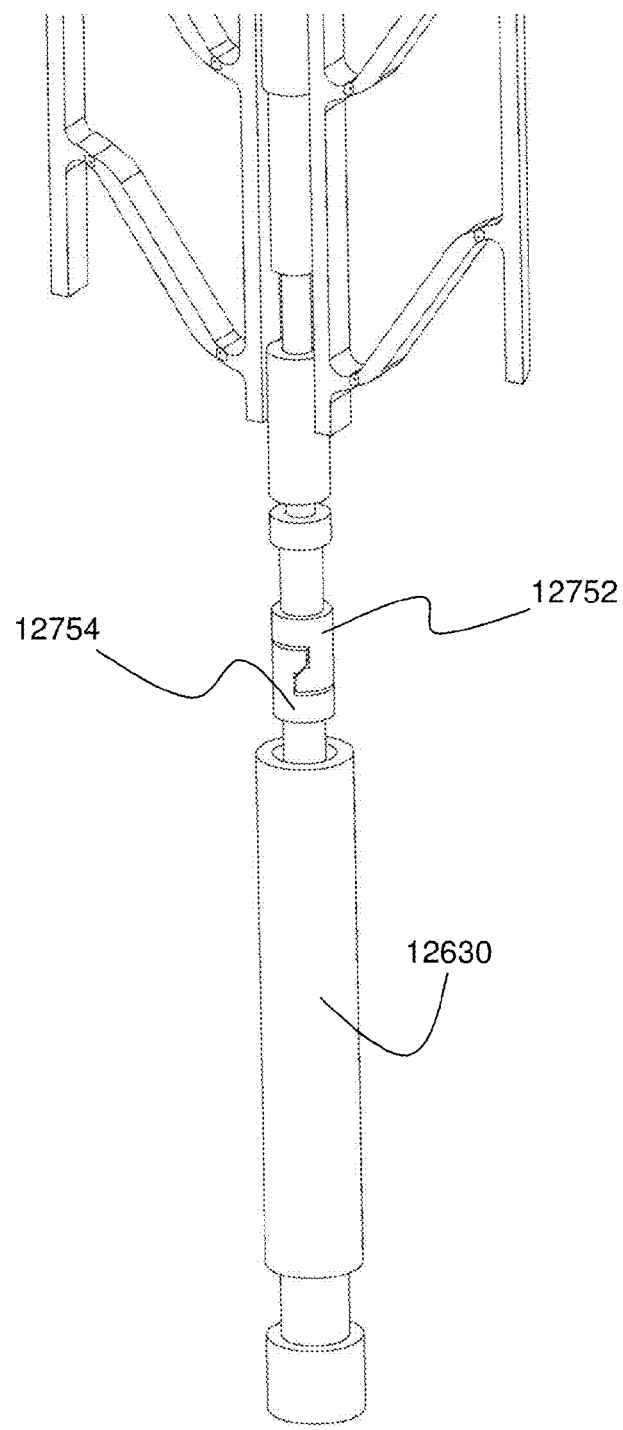
Figure 128:
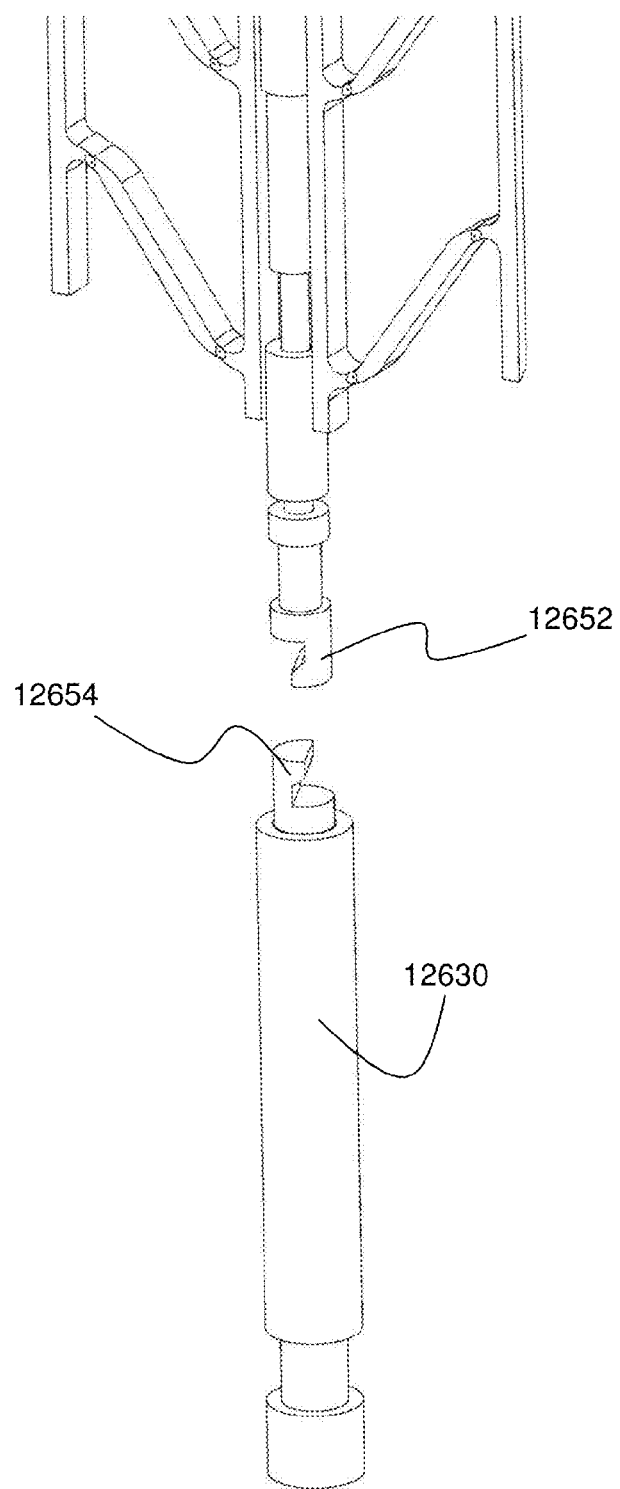
Figure 129:
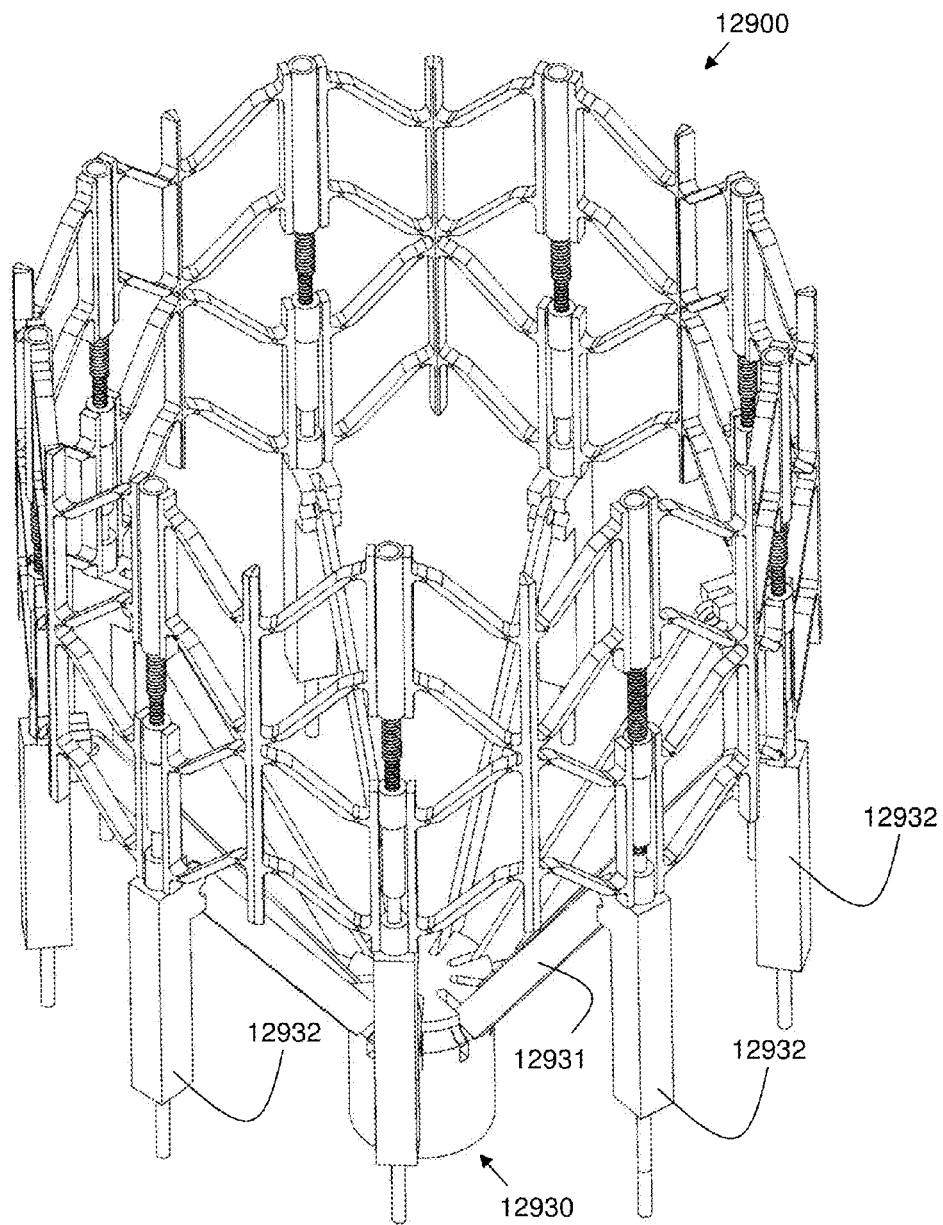
Figure 130:
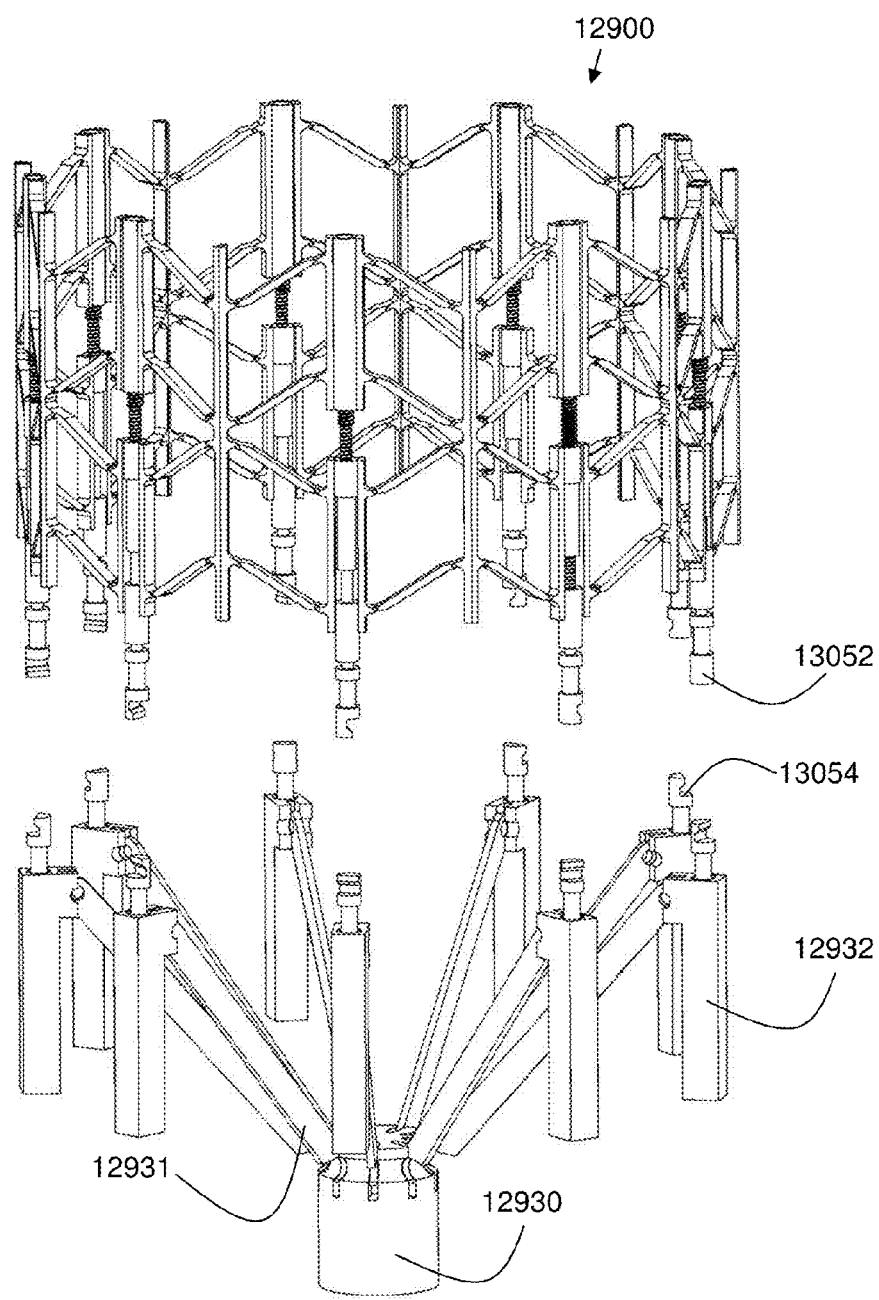
Figure 131:
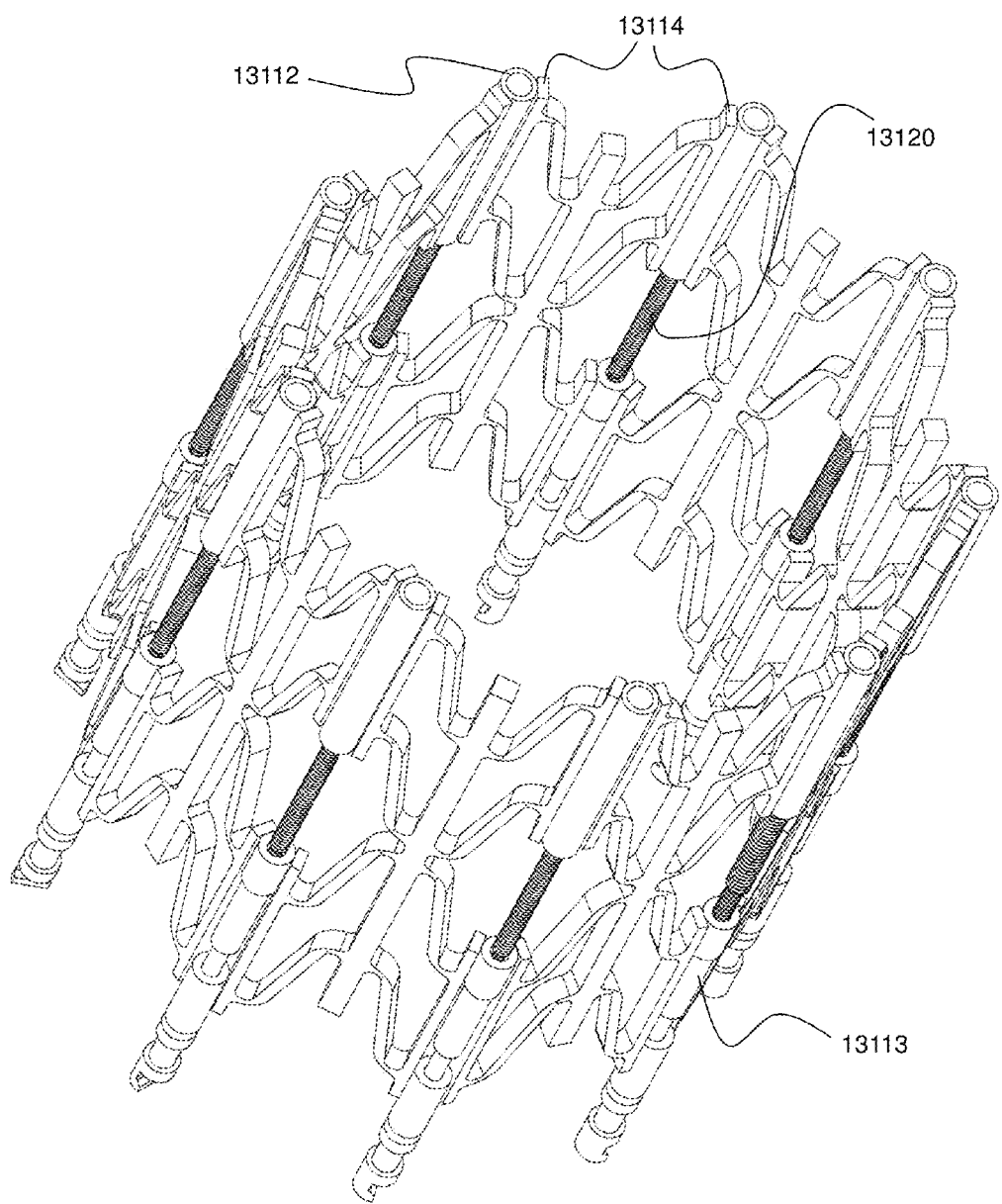
Figure 132:
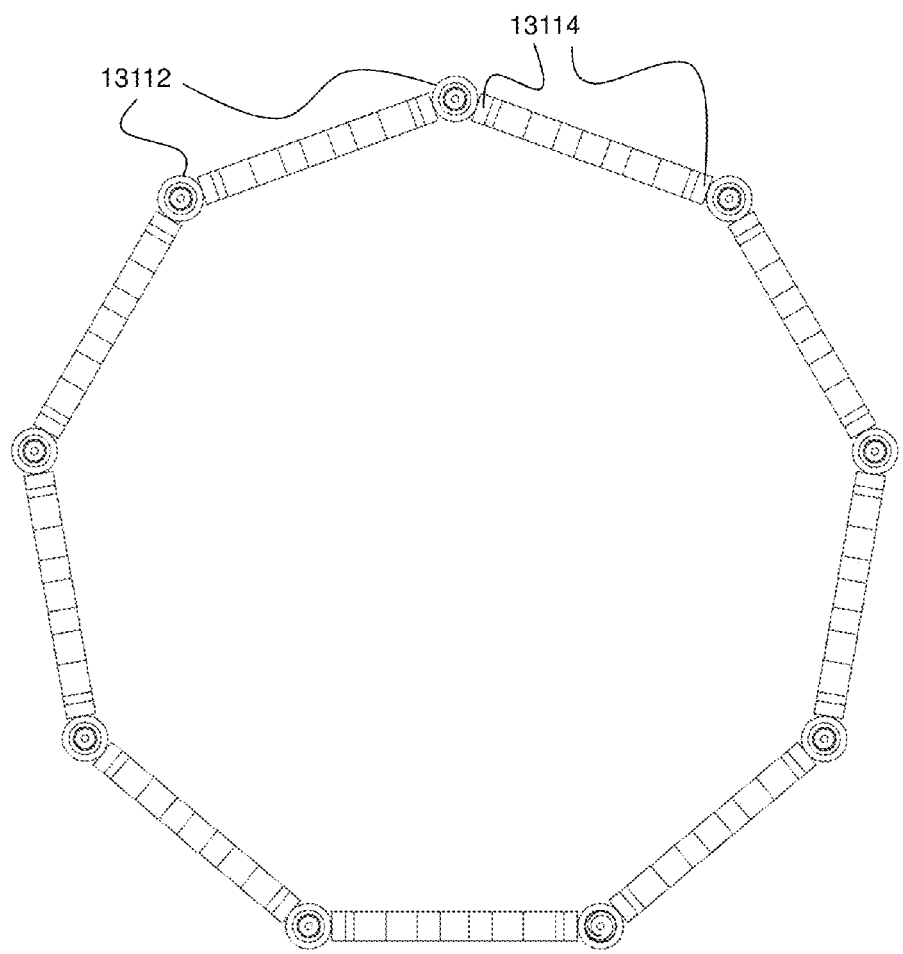
Figure 133:
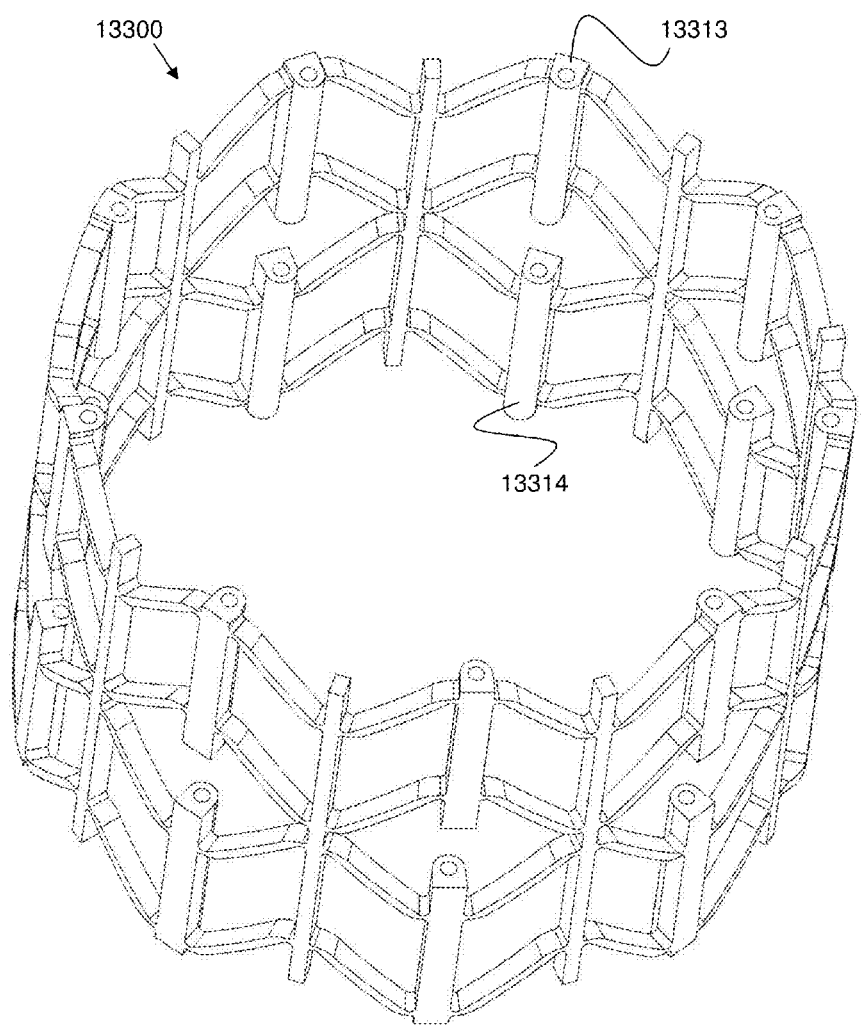
Figure 134:
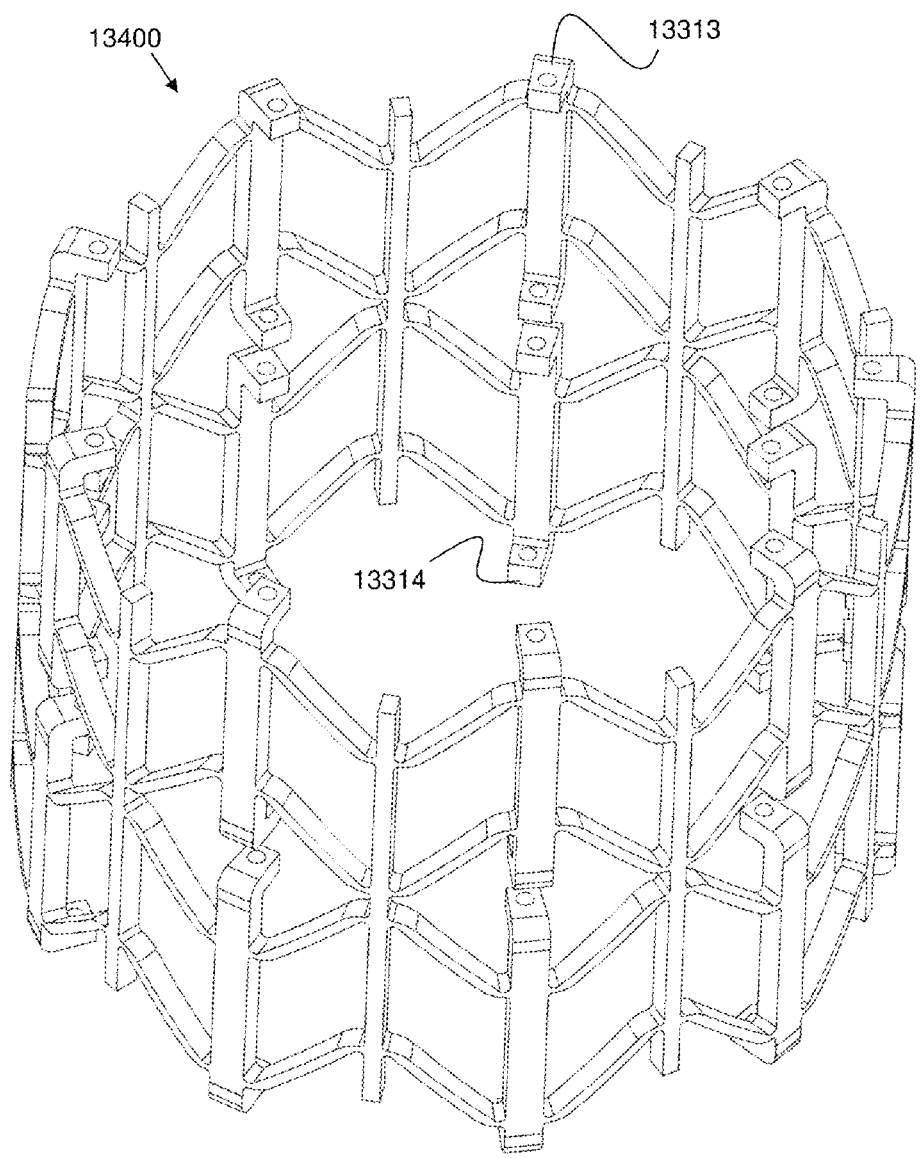
Figure 135:
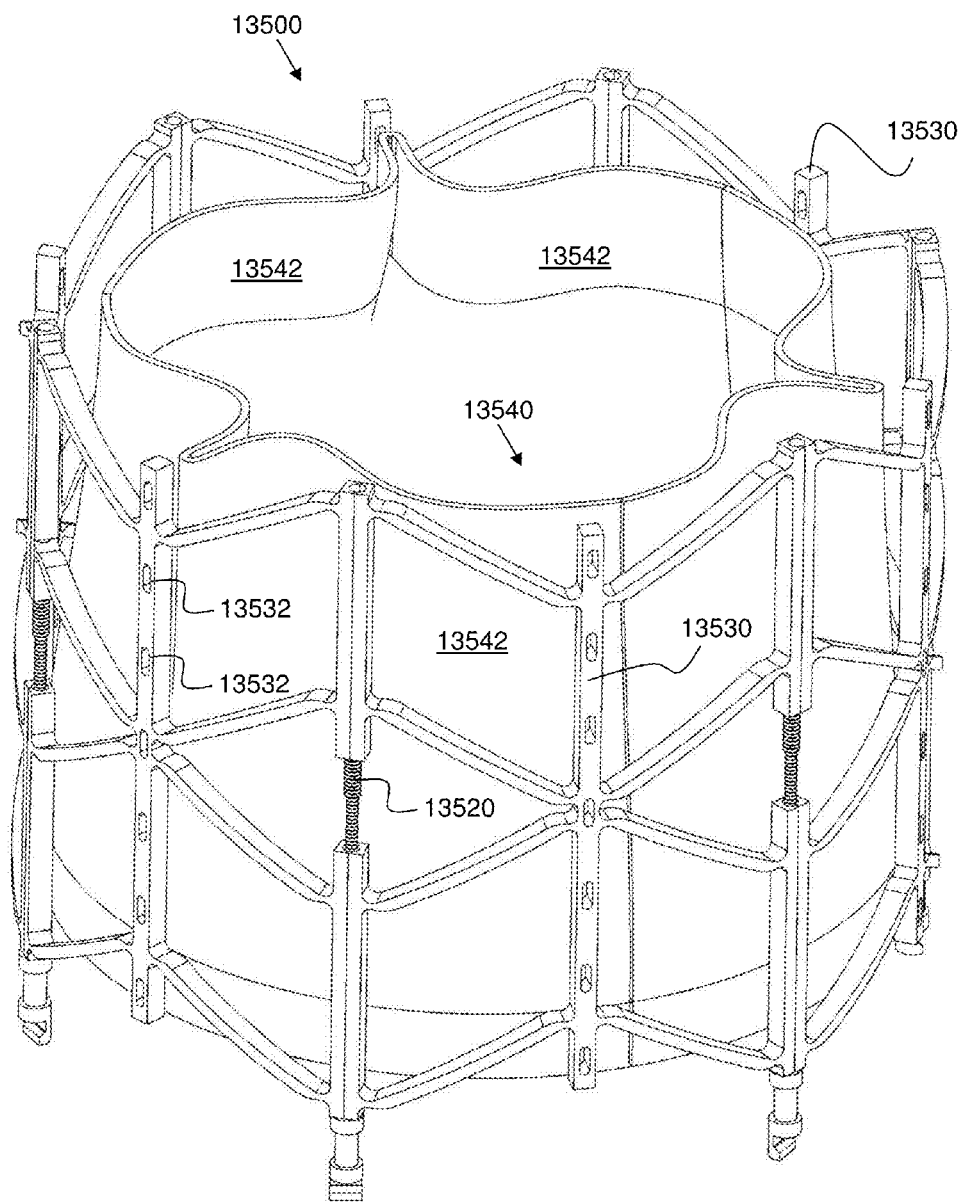
Figure 136:
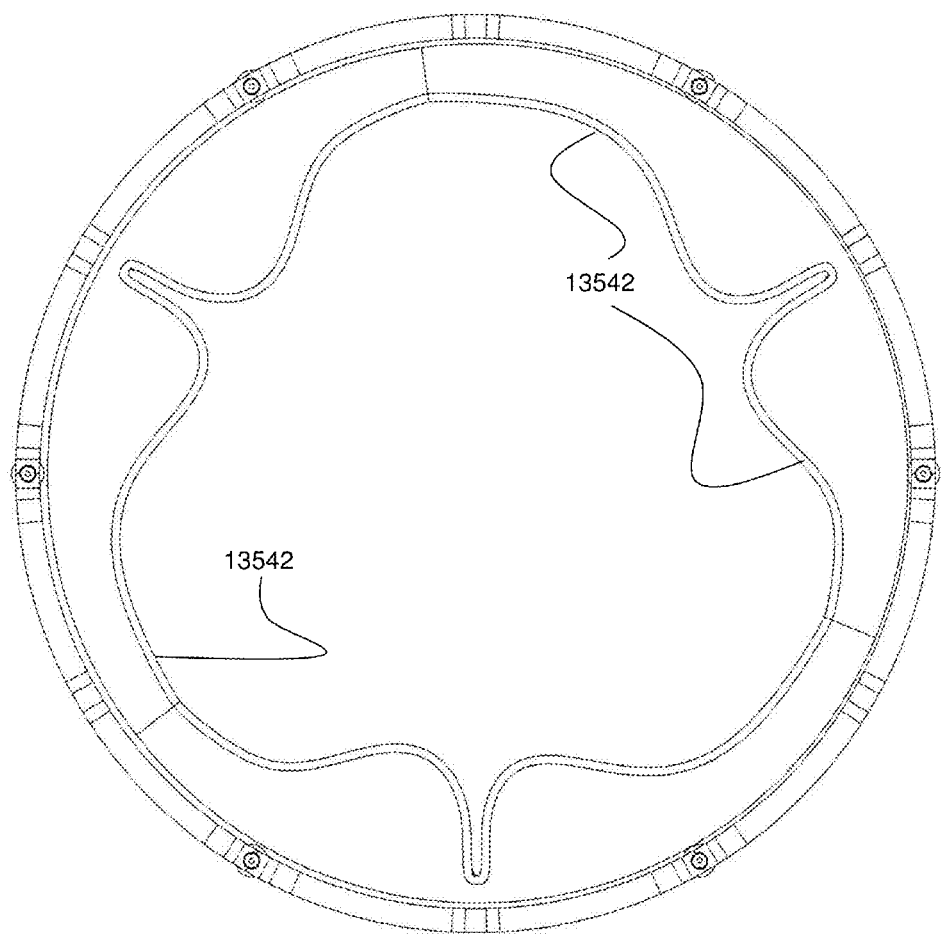
Figure 137:
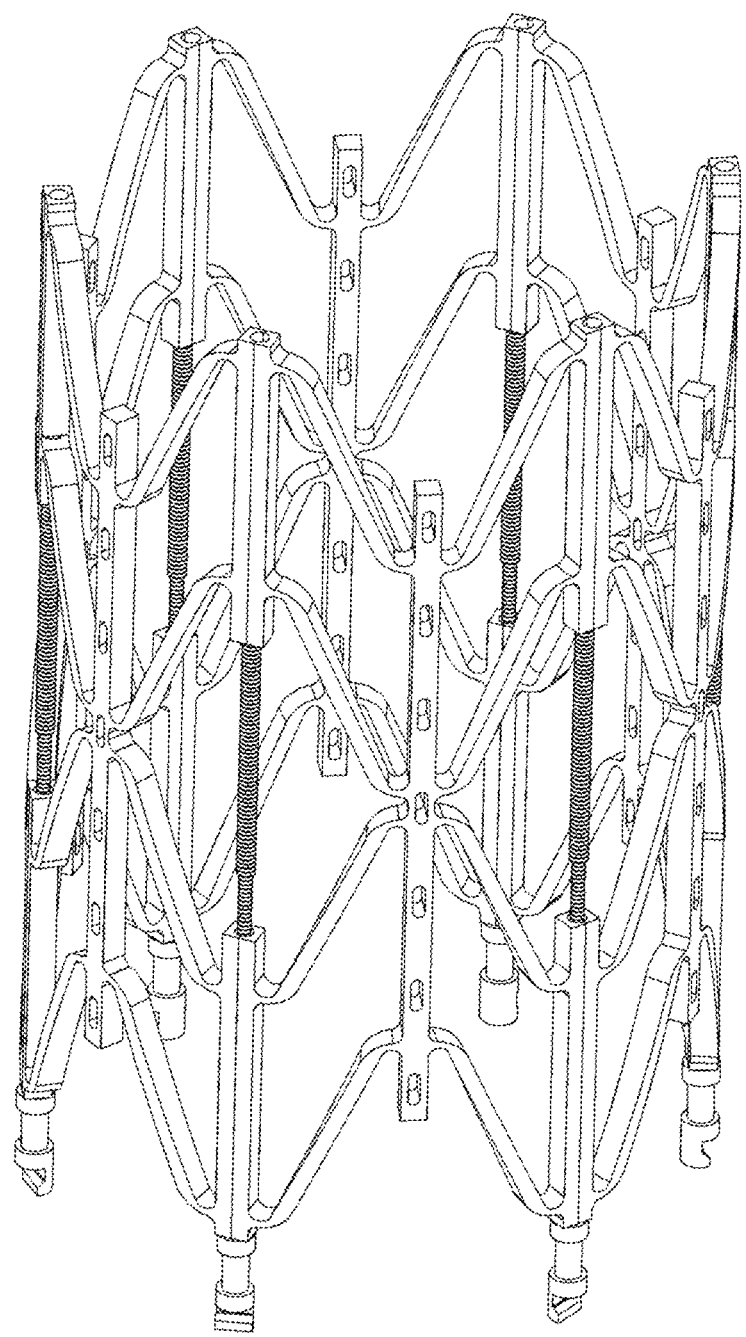
Figure 138:
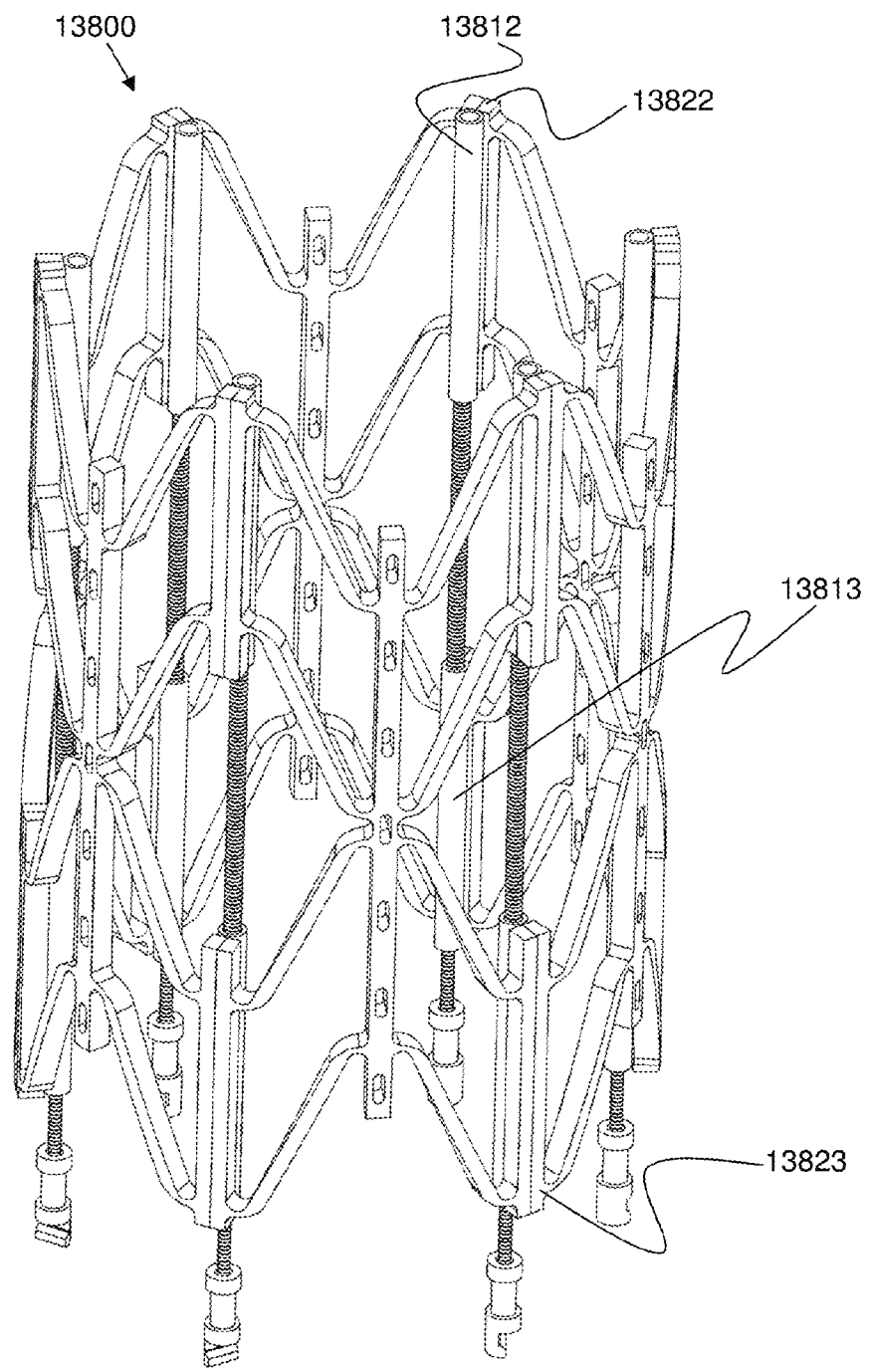
Figure 139:
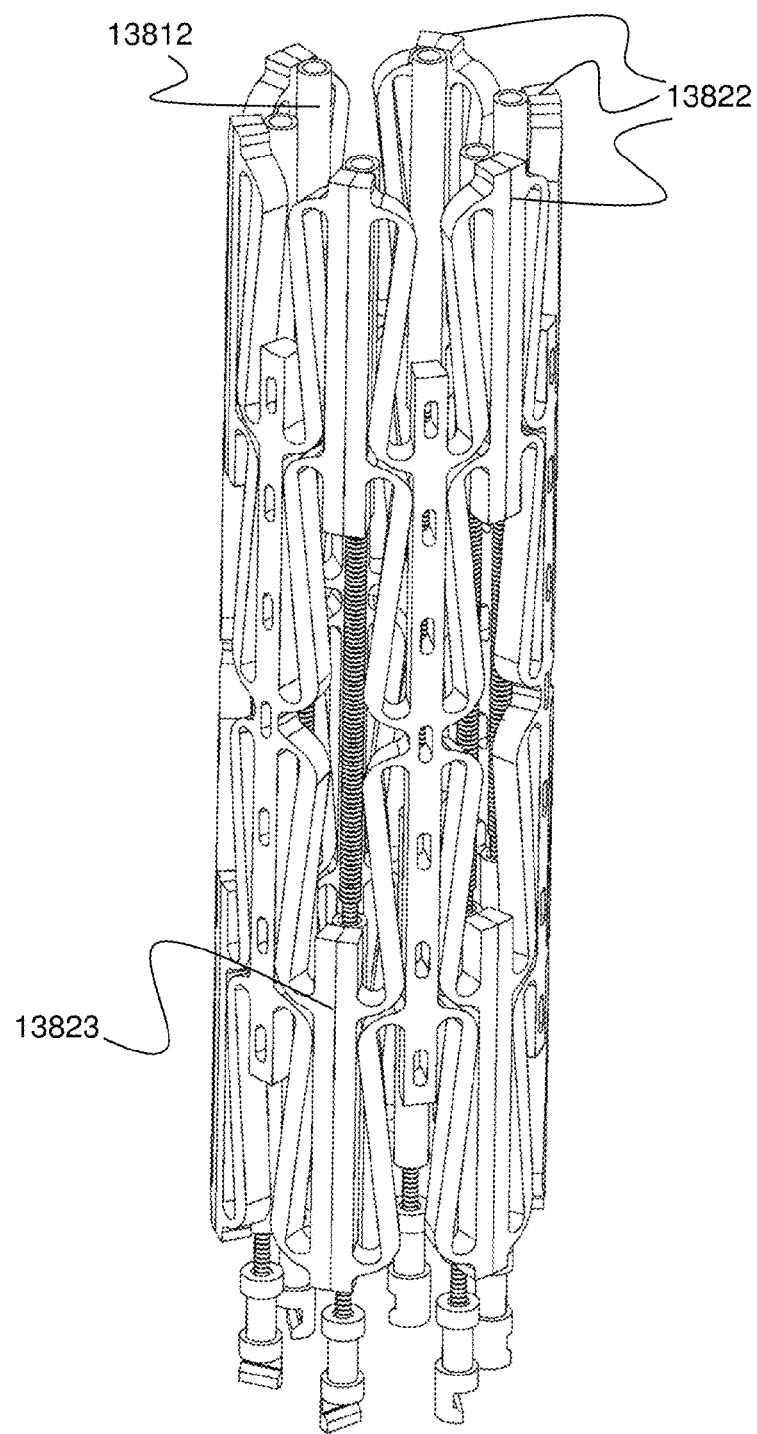
Figure 140:
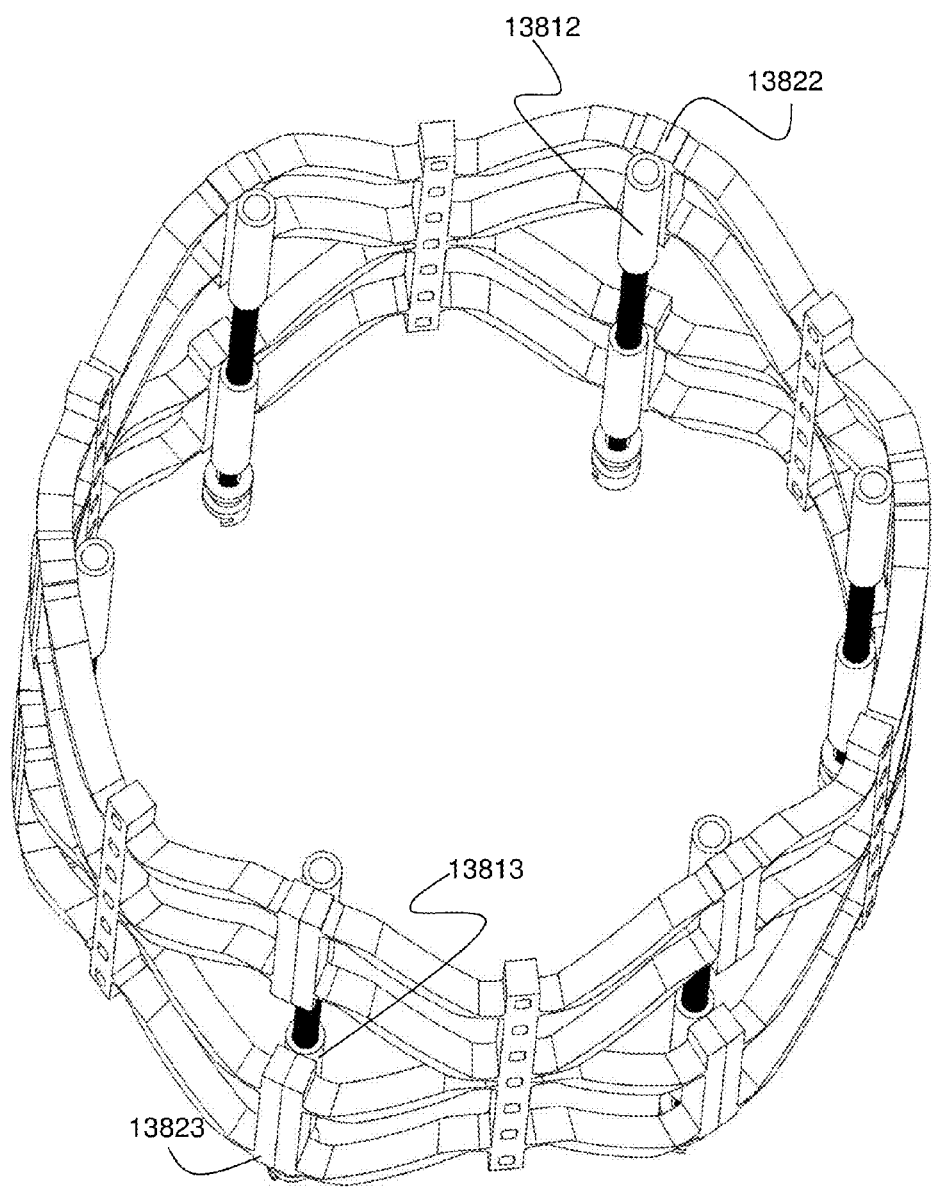
Figure 141:
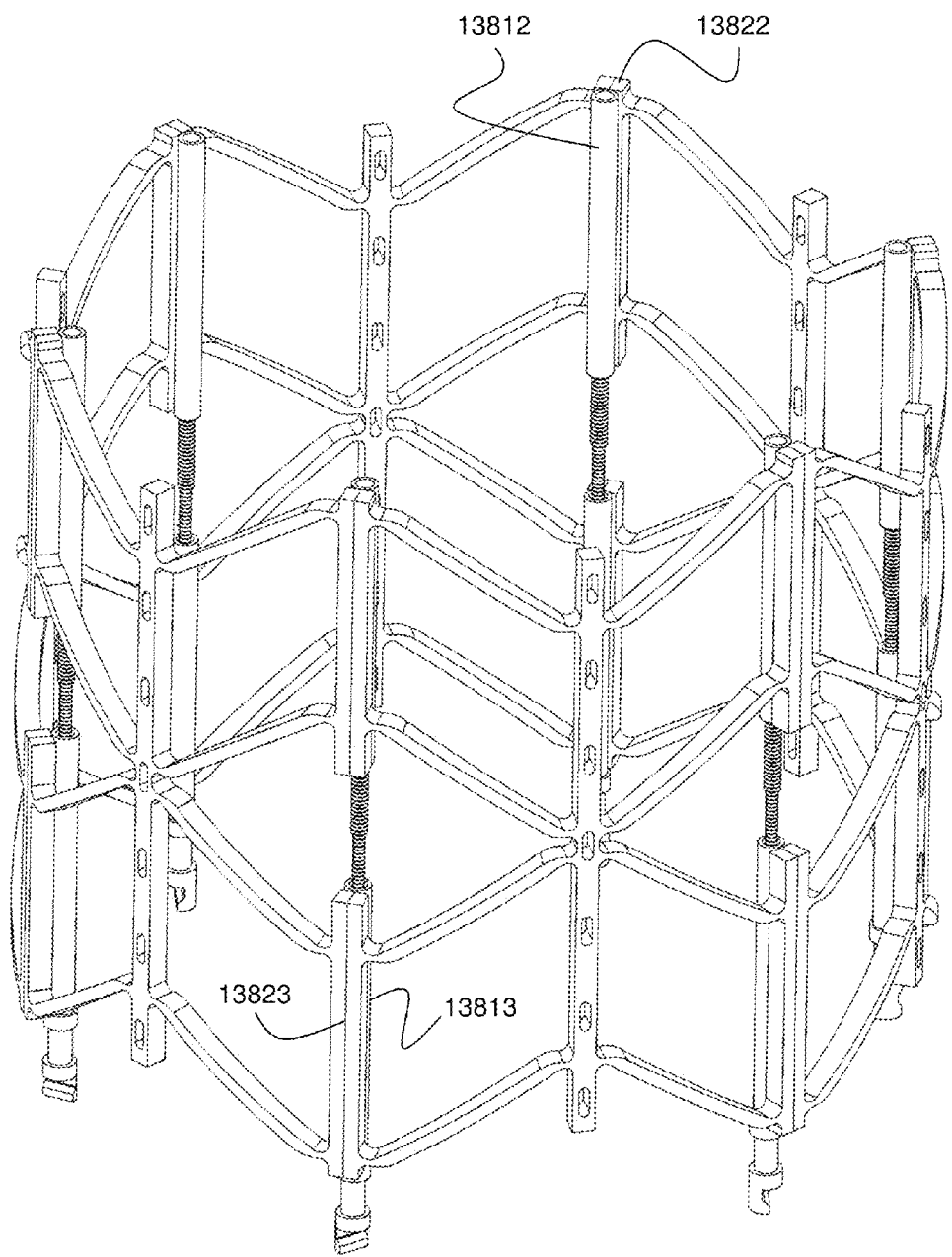
Figure 142:
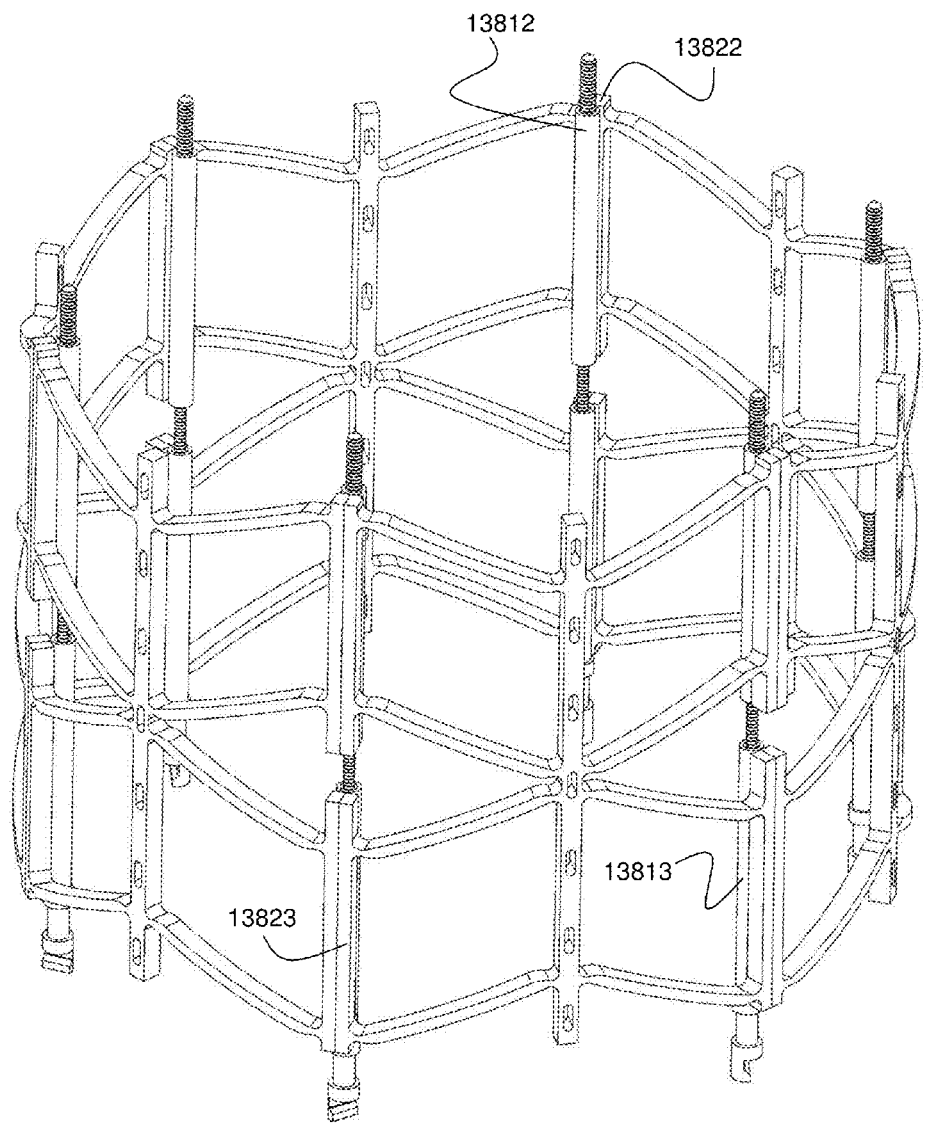

FIG. 120 is a perspective view of an exemplary embodiment of a self-expanding/forcibly-expanding lattice of an implantable stent assembly having nine lattice segments in a native, self-expanded position with jack screw assemblies disposed between adjacent pairs of repeating portions of the lattice, with jack screws through a wall of the lattice, and with each jack screw backed out in a thread-non-engaged state to allow crimp of lattice for loading into a stent delivery system;

FIG. 121 is a perspective view of the lattice of FIG. 120 in a contracted/crimped state for loading into the stent delivery system with each jack screw in a thread-non-engaged state;

FIG. 122 is a perspective view of the lattice of FIG. 121 after being allowed to return to the native position of the lattice in a deployment site with each jack screw in a thread-engaged state for further outward expansion or inward contraction of the lattice;

FIG. 123 is a perspective view of the lattice of FIG. 122 partially expanded from the state shown in FIG. 122 with each jack screw in a thread-engaged state for further outward expansion or inward contraction of the lattice;

FIG. 124 is a tilted perspective view of the lattice of FIG. 123 partially expanded from the state shown in FIG. 123 with each jack screw in a thread-engaged state for further outward expansion or inward contraction of the lattice;

FIG. 125 is a perspective view of the lattice of FIG. 124 further expanded near a maximum expansion of the lattice with each jack screw in a thread-engaged state;

FIG. 126 is a fragmentary, enlarged perspective and longitudinal cross-sectional view of a portion of two adjacent halves of repeating portions of an alternative exemplary embodiment of a self-expanding/forcibly-expanding lattice of an implantable stent assembly with a separate jack screw assembly connecting the two adjacent halves and with a lattice-disconnect tube of a stent delivery system in an engaged state covering a pair of drive screw coupler parts therein and with the jack screw in a thread-engaged state for further outward expansion or inward contraction of the lattice;

FIG. 127 is a fragmentary, further enlarged portion of the two adjacent halves of the repeating portions and intermediate jack screw assembly of FIG. 125 with the disconnect tube in a disengaged state with respect to the pair of drive screw coupler parts;

FIG. 128 is a fragmentary enlarged portion of the two adjacent halves of the repeating portions and intermediate jack screw assembly of FIG. 125 with the disconnect tube in a disengaged state and with the pair of drive screw coupler parts disconnected from one another;

FIG. 129 is a perspective view of another exemplary embodiment of a self-expanding/forcibly-expanding lattice of an implantable stent assembly having nine separate lattice segments with an exemplary embodiment of a proximal disconnect block of a stent delivery system as an alternative to the disconnect tube of FIGS. 126 to 128 with the proximal disconnect block in an engaged state covering a pair of drive screw coupler parts therein and with each jack screw in a thread-engaged state for further outward expansion or inward contraction of the lattice;

FIG. 130 is a perspective view of the lattice of FIG. 129 with the proximal disconnect blocks of the delivery system disconnected from the lattice with the proximal disconnect block in a disengaged state with respect to the pair of drive screw coupler parts and illustrating how all of the pairs of drive screw coupler parts can be coupled for simultaneous release;

FIG. 131 is a perspective view of another exemplary embodiment of a self-expanding/forcibly-expanding lattice of an implantable stent assembly having nine separate lattice segments connected to intermediate tubes for jack screws with each jack screw in a thread-engaged state for further outward expansion or inward contraction of the lattice;

FIG. 132 is a top plan view of the lattice of FIG. 131;

FIG. 133 is a perspective view of another exemplary embodiment of a self-expanding/forcibly-expanding lattice of an implantable stent assembly having nine lattice segments with locally thicker sections of lattice to accommodate and connect to non-illustrated jack screw assemblies;

FIG. 134 is a perspective view of another exemplary embodiment of a self-expanding/forcibly-expanding lattice of an implantable stent assembly having nine lattice segments with bent-over tabs for connecting to non-illustrated jack screw assemblies;

FIG. 135 is a perspective view of another exemplary embodiment of a self-expanding/forcibly-expanding lattice of an implantable valve assembly having six lattice segments in an expanded position with jack screw assemblies disposed between adjacent pairs of repeating portions of the lattice and having three valve leaflets and jack screws through a wall of the lattice in a thread-non-engaged state of the jack screw;

FIG. 136 is a plan view of the valve assembly of FIG. 135;

FIG. 137 is a plan view of the valve assembly of FIG. 135 in a partially compressed state of the lattice without the valve leaflets and with each jack screw in a thread-non-engaged state;

FIG. 138 is a perspective view of another exemplary embodiment of a self-expanding/forcibly-expanding lattice of an implantable valve assembly having six lattice segments in a native, self-expanded position with jack screw assemblies attached at an interior surface between adjacent pairs of segments of the lattice without the valve leaflets and with each of the jack screws in a thread-engaged state for further outward expansion or inward contraction of the lattice;

FIG. 139 is a perspective view of the lattice of FIG. 138 in a contracted/crimped state for loading into the stent delivery system with each jack screw in a thread-non-engaged state;

FIG. 140 is a tilted perspective view of the lattice of FIG. 138;

FIG. 141 is a perspective view of the lattice of FIG. 138 partially expanded from the state shown in FIG. 138 with each jack screw in an engaged state for further outward expansion or inward contraction of the lattice; and FIG. 142 is a perspective view of the lattice of FIG. 138 further expanded near a maximum expansion of the lattice with each jack screw in an engaged state for further outward expansion or inward contraction of the lattice;

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

The terms "program," "programmed", "programming," "software," "software application," and the like as used herein, are defined as a sequence of instructions designed for execution on a computer system. A "program," "software," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the present invention. Referring now to the figures of the drawings in detail and first, particularly to FIGS. 1 to 19, there is shown a first exemplary embodiment of an actively controllable stent deployment system 100 according to the invention. Even though this exemplary embodiment is illustrated as a stent deployment system without the presence of a stent graft, this embodiment is not to be considered as limited thereto. Any stent graft embodiment according the invention as disclosed herein can be used in this embodiment. The stent graft is not shown in these figures for clarity. Further, as used herein, the terms "stent" and "stent graft" are used herein interchangeably. Therefore, any embodiment where a stent is described without referring to a graft should be considered as referring to a graft additionally or in the alternative, and any embodiment where both a stent and a graft are described and shown should be considered as also referring to an embodiment where the graft is not included.

In contrast to prior art self-expanding stents, the actively controllable stent deployment system 100 includes a stent lattice 110 formed by interconnected lattice struts 112, 114. In this exemplary embodiment, pairs of inner and outer struts 114, 112 are respectively connected to adjacent pairs of inner and outer struts 114, 112. More particularly, each pair of inner and outer struts 114, 112 are connected pivotally at a center point of each strut 114, 112. The ends of each inner strut 114 of a pair is connected pivotally to ends of adjacent outer struts 112 and the ends of each outer strut 112 of a pair is connected pivotally to ends of adjacent inner struts 114. In such a configuration where a number of strut pairs 114, 112 are connected to form a circle, as shown in each of FIGS. 1 to 19, a force that tends to expand the lattice 110 radially outward will pivot the struts 114, 112 at each pivot point and equally and smoothly expand the entire lattice 110 from a closed state (see, e.g., FIG. 3) to any number of open states (see FIGS. 4 to 13). Similarly, when the stent lattice 110 is at an open state, a force that tends to contract the stent lattice 110 radially inward will pivot the struts 114, 112 at each pivot point and equally and smoothly contract the entire stent lattice 110 towards the closed state. This exemplary configuration, therefore, defines a repeating set of one intermediate and two outer pivot points about the circumference of the stent lattice 110. The single intermediate pivot point 210 is, in the exemplary embodiment shown in FIGS. 1 to 19, located at the centerpoint of each strut 112, 114. On either side of the single intermediate pivot point 210 is a vertically opposing pair of outer pivot points 220.

Figure 7:
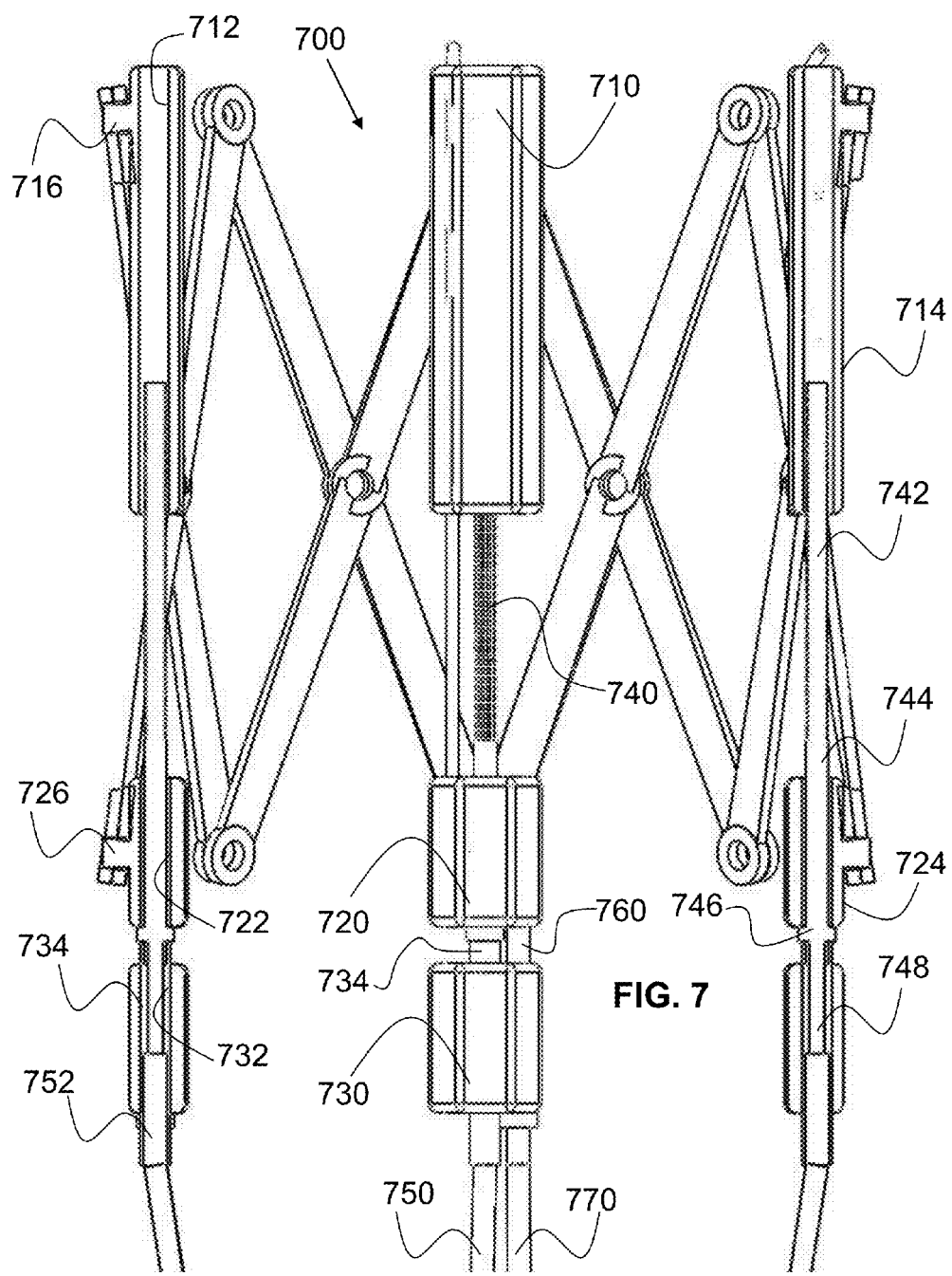
FIG. 7 is a fragmentary, longitudinally cross-sectional view of a rear half of the stent deployment system of FIG. 6.
Figure 8:
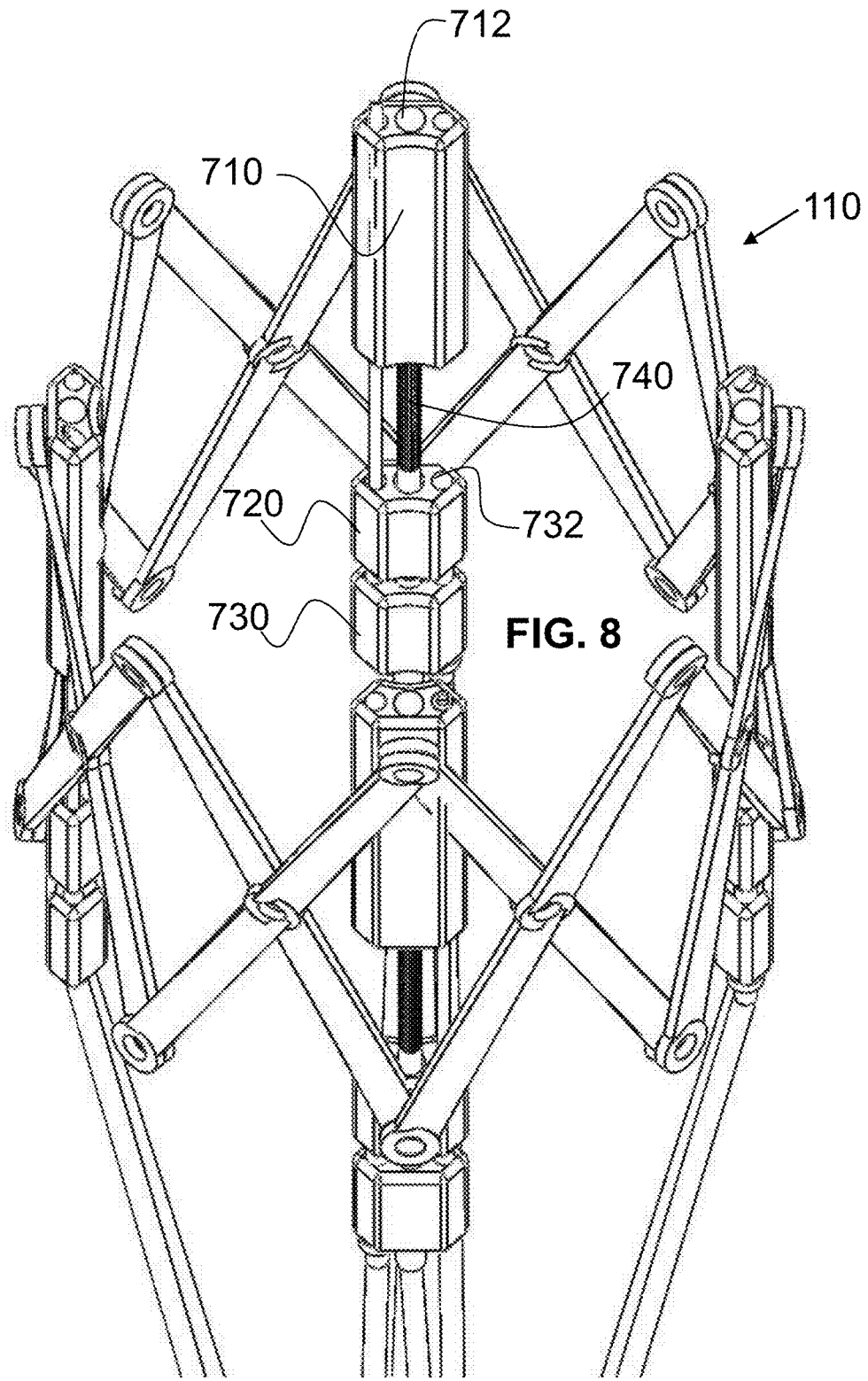
FIG. 8 is a fragmentary, perspective view of the stent deployment system of FIG. 6.
Figure 9:
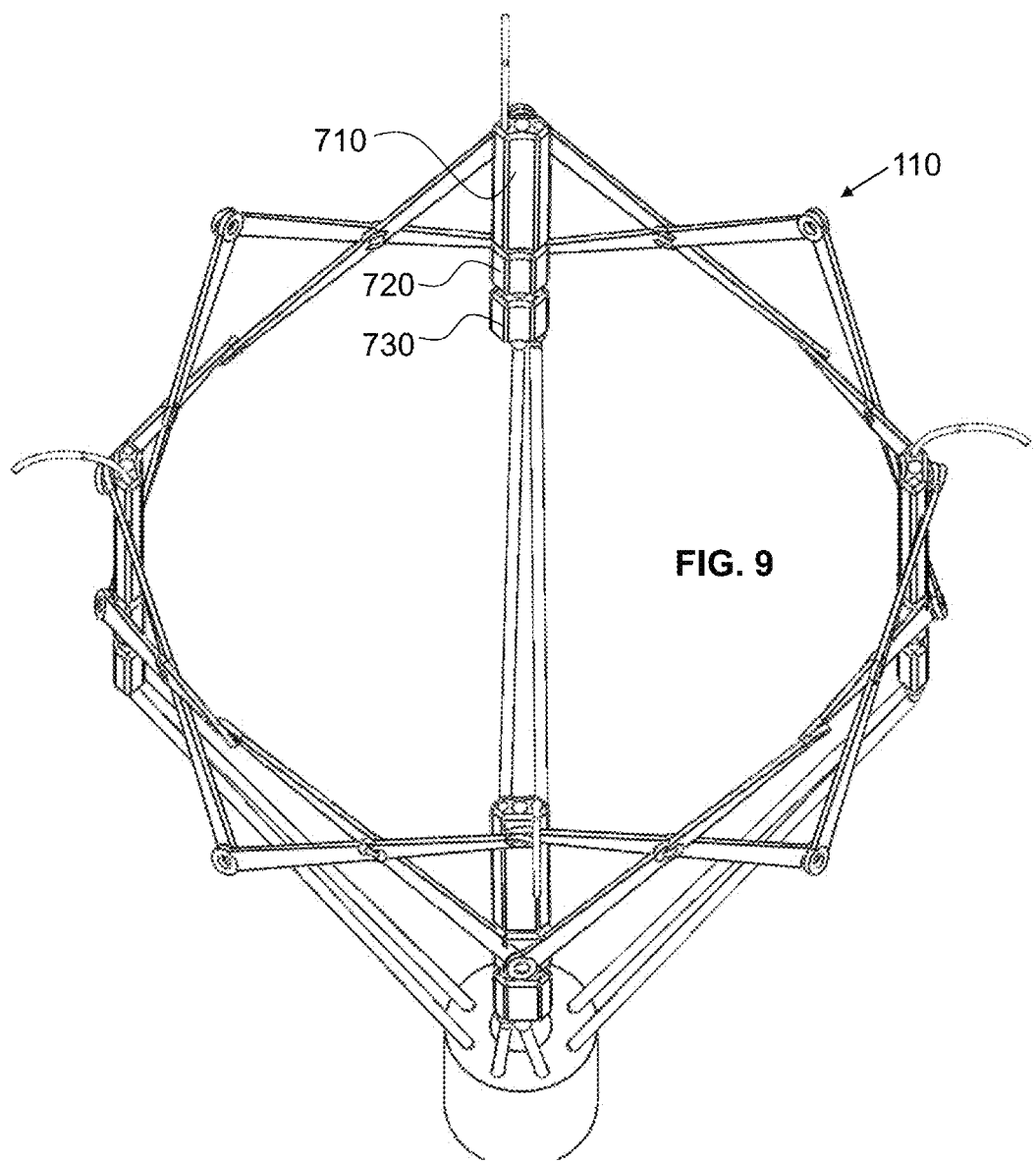
FIG. 9 is a fragmentary, perspective view of the stent deployment system of FIG. 1 from above the distal end with the system in an expanded state and with the assembly-fixed needles in an extended state.

To provide such expansion and contraction forces, the actively controllable stent deployment system 100 includes at least one jack assembly 700 that is present in each of FIGS. 1 to 19 but is described, first, with regard to FIG. 7. Each jack assembly 700 has a distal drive block 710, a proximal drive block 720, and a disconnector drive block 730. A drive screw 740 connects the distal drive block 710 to the proximal drive block 720. The drive screw 740 has a distal threaded drive portion 742 having corresponding threads to a threaded drive bore 712 of the distal drive block 710. The drive screw 740 has an intermediate unthreaded portion 744 that rotates freely within a smooth drive bore 722 of the proximal drive block 720. In the embodiment shown, the inner diameter of the smooth drive bore 722 is slightly larger than the outer diameter of the unthreaded portion 744 so that the unthreaded portion 744 can freely rotate within the smooth drive bore 722 with substantially no friction. The drive screw 740 also has an intermediate collar 746 just proximal of the proximal drive block 720. The outer diameter of the intermediate collar 746 is greater than the inner diameter of the smooth drive bore 722. Lastly, the drive screw 740 has a proximal key portion 748 extending from the intermediate collar 746 in a proximal direction. The jack assembly 700 is configured to retain the drive screw 740 within the distal drive block 710 and the proximal drive block 720 in every orientation of the stent lattice 110, from the closed state, shown in FIG. 3, to a fully open state, shown in FIG. 11, where the distal drive block 710 and the proximal drive block 720 touch one another.

Each jack assembly 700 is attached fixedly to the stent lattice 110 at a circumferential location thereon corresponding to the vertically opposing pair of outer pivot points 220. In one exemplary embodiment of the jack assembly 700 shown in FIGS. 1 to 19, the outer surface 714 of the distal drive block 710 and the outer surface 724 of the proximal drive block 720 each have a protruding boss 716, 726 having an outer shape that is able to fixedly connect to a respective one of the outer pivot points 220 of the stent lattice 110 but also rotationally freely connect thereto so that each of the inner and outer struts 114, 112 connected to the boss 716, 726 pivots about the boss 716, 726, respectively. In this exemplary embodiment, each boss 716, 726 is a smooth cylinder and each outer pivot point 220 is a cylindrical bore having a diameter corresponding to the outer smooth surface of the cylinder but large enough to pivot thereon without substantial friction. The materials of the boss 716, 726 and the outer pivot points 220 of the inner and outer struts 114, 112 can be selected to have substantially frictionless pivoting.

Accordingly, as the drive screw 740 rotates between the open and closed states, the unthreaded portion 744 of the drive screw 740 remains longitudinally stable within the proximal drive block 720. In contrast, the distal threaded drive portion 742 progressively enters the threaded drive bore 712 from the proximal end to the distal end thereof as the stent lattice 110 expands outwardly. As shown in the progressions of FIG. 2 to FIG. 4 and FIGS. 5 to 7 to 8 to 9, as the drive screw 740 rotates within the proximal drive block 720, the distal drive block 710 moves closer and closer to the proximal drive block 720, thereby causing a radial expansion of the stent lattice 110.

To implant the stent lattice 110 in a tubular anatomic structure (such as a vessel or a valve seat), the stent lattice 110 needs to be disconnected from the delivery system. Delivery of the stent lattice 110 to the anatomic structure will be described in further detail below. When the stent lattice 110 enters the implantation site, it will be most likely be in the closed state shown in FIG. 3, although for various reasons, the stent lattice 110 can be expanded partially, if desired, before reaching the implantation site. For purposes of explaining the disconnect, the extent of expansion is not relevant. When at the implantation site, the stent lattice 110 will be expanded by rotating the drive screw 740 in a corresponding expansion direction (the direction of threads of the drive screw 740 and the drive bore 712 will determine if the drive screw 740 needs to be rotated clockwise or counter-clockwise). The stent lattice 110 is expanded to a desired expansion diameter, for example as shown in the progression of FIGS. 4 to 9 or FIGS. 10 to 11, so that it accommodates to the natural geometry of the implantation site, even if the geometry is non-circular or irregular. When the implantation diameter is reached, e.g., in FIGS. 9 and 11, the jack assemblies 700 need to be disconnected from the remainder of the stent deployment system 100.

To accomplish disconnect of the jack assemblies 700, the disconnector drive block 730 is provided with two lumens. A first lumen, the drive lumen 732, accommodates a drive wire 750 that is able to rotationally engage the proximal key portion 748. In the exemplary embodiment shown, which is most clearly illustrated in FIG. 19, the proximal key portion 748 has a square cross-sectional shape. A drive wire bushing 734 rotationally freely but longitudinally fixedly resides in the drive lumen 732. The drive wire bushing 734 is connected to the drive wire 750 either as an integral part thereof or through a connection sleeve 752. Regardless of the connection design, any rotation of the drive wire 750 in either direction will cause a corresponding rotation of the drive wire bushing 734. A key hole 738 at the distal end of the disconnector drive block 730 and having an internal shape corresponding to a cross-section of the proximal key portion 748 allows a rotationally fixed but longitudinally free connection to occur with the proximal key portion 748. In the exemplary embodiment shown in FIG. 19, the key hole 738 also has a square cross-sectional shape.

Figure 14:
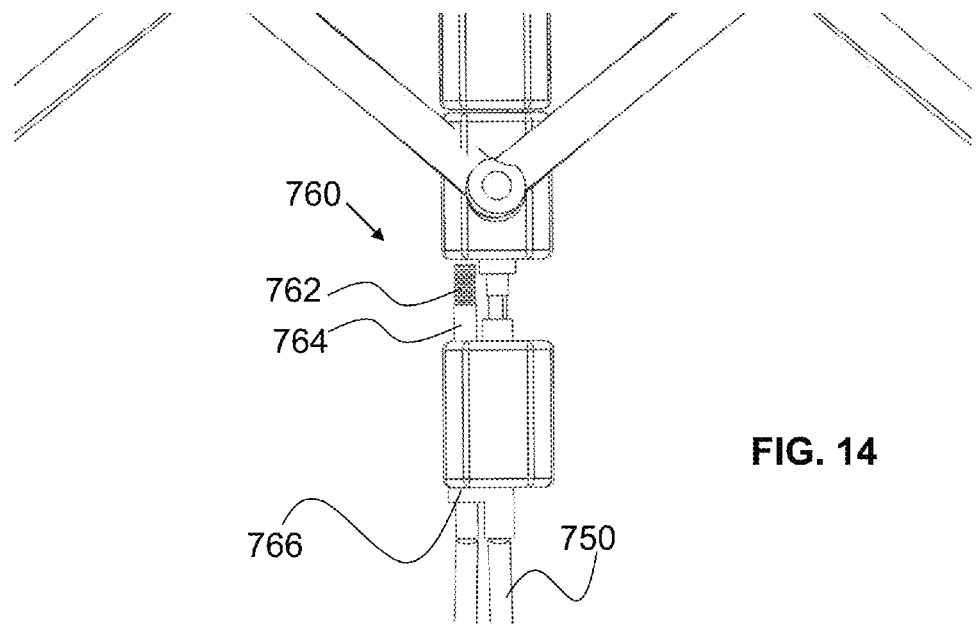
FIG. 14 is a fragmentary, longitudinally cross-sectional view of an enlarged portion of the stent deployment system of FIG. 12 in the partially disengaged state.
Figure 15:
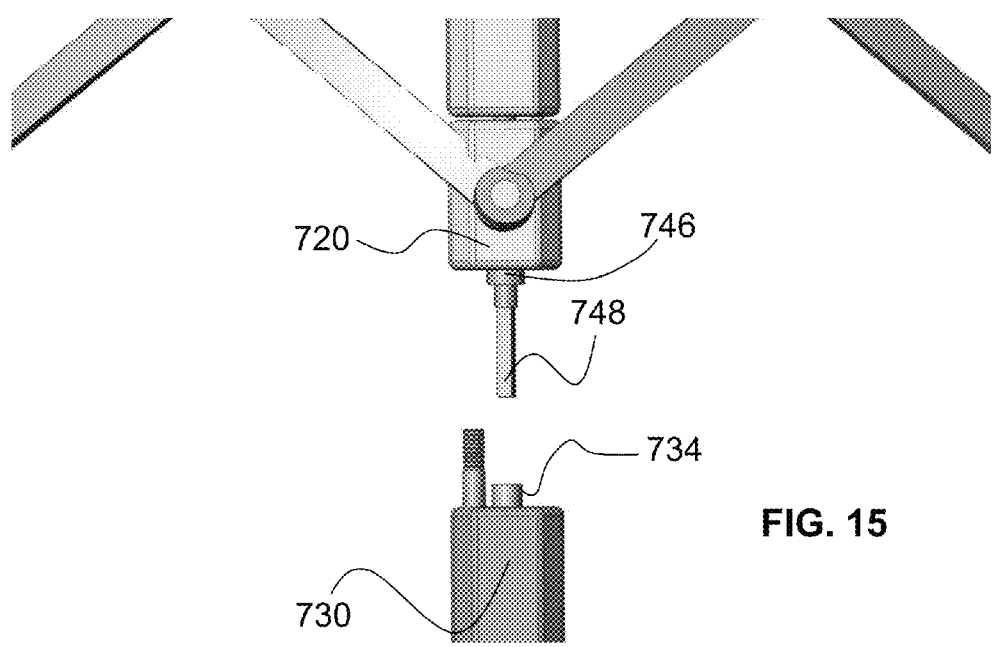
FIG. 15 is a fragmentary, longitudinally cross-sectional view of an enlarged portion of the stent deployment system of FIG. 13 in a disengaged state.
Figure 16:
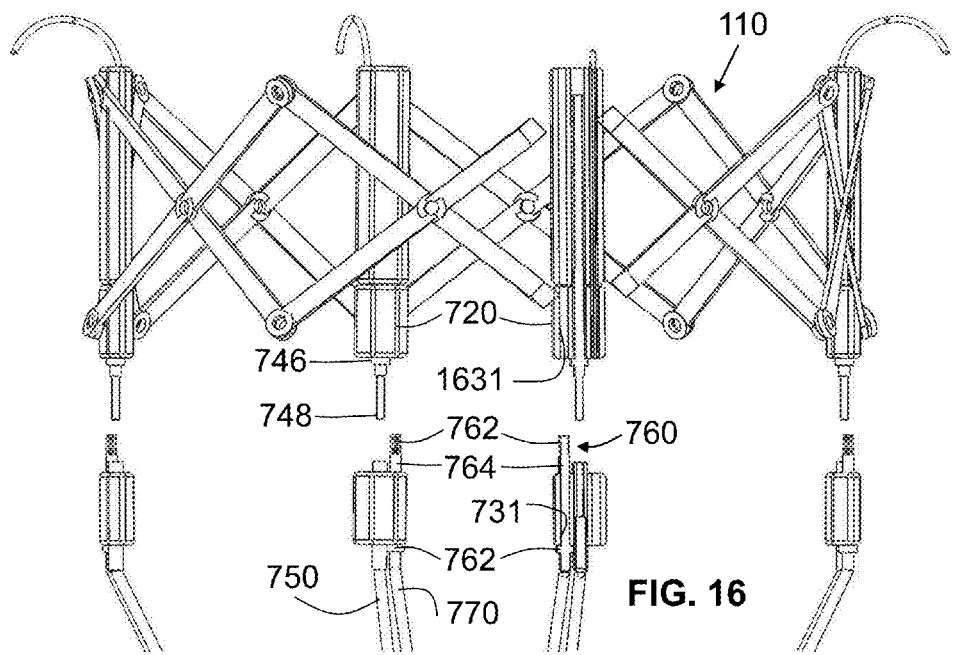
FIG. 16 is a fragmentary, partially cross-sectional, side elevational view of the stent deployment system of FIG. 9 rotated about a longitudinal axis, with the deployment control assembly in the disengaged state, and showing a cross-section of a portion of the deployment control assembly.

The disconnector drive block 730 also has a second lumen, a disconnect lumen 731, which is best shown in FIGS. 14 and 16. Residing in the disconnect lumen 731 in a rotationally free but longitudinally fixed manner is a retainer screw 760. The retainer screw 760 has a distal threaded portion 762, an intermediate shaft 764, and a proximal connector 766. The distal threaded portion 762 has an exterior thread corresponding to an internal thread of a connect lumen 1631, which is located in the proximal drive block 720 and is coaxial with the disconnect lumen 731. The intermediate shaft 764 has a smooth exterior surface and a cross-sectional shape that is slightly smaller than the cross-sectional shape of the disconnect lumen 731 so that it can be rotated freely within the disconnect lumen 731 substantially without friction. The proximal connector 766 has a flange with an outer diameter greater than the inner diameter of the disconnect lumen 731. The proximal connector 766 is connected at a proximal end thereof to a disconnect wire 770, which connection can either be an integral part thereof or through a secondary connection, such as a weld or connection sleeve.

With such a configuration of the proximal drive block 720 and the disconnector drive block 730 of a jack assembly 700, rotation in a securing direction will longitudinally secure the proximal drive block 720 to the disconnector drive block 730 so that the stent lattice 110 remains connected to the drive wire 750 and the disconnect wire 770. In the connected state, the stent lattice 110 may be extended outward and retracted inward as many times until implantation alignment according to the surgeon's desire. Likewise, rotation in a disconnecting direction will longitudinally release the proximal drive block 720 from the disconnector drive block 730 so that the stent lattice 110 disconnects entirely from the drive wire 750 and the disconnect wire 770.

Figure 10:
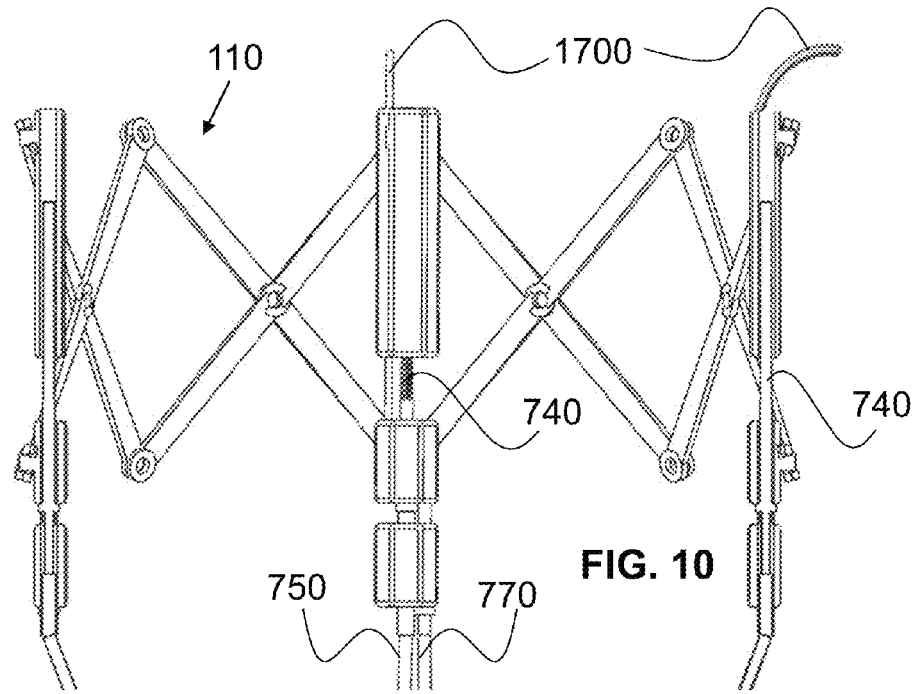
FIG. 10 is a fragmentary, longitudinal cross-sectional view of the stent deployment system of FIG. 11 showing the rear half in a partially expanded state of the stent lattice.
Figure 11:
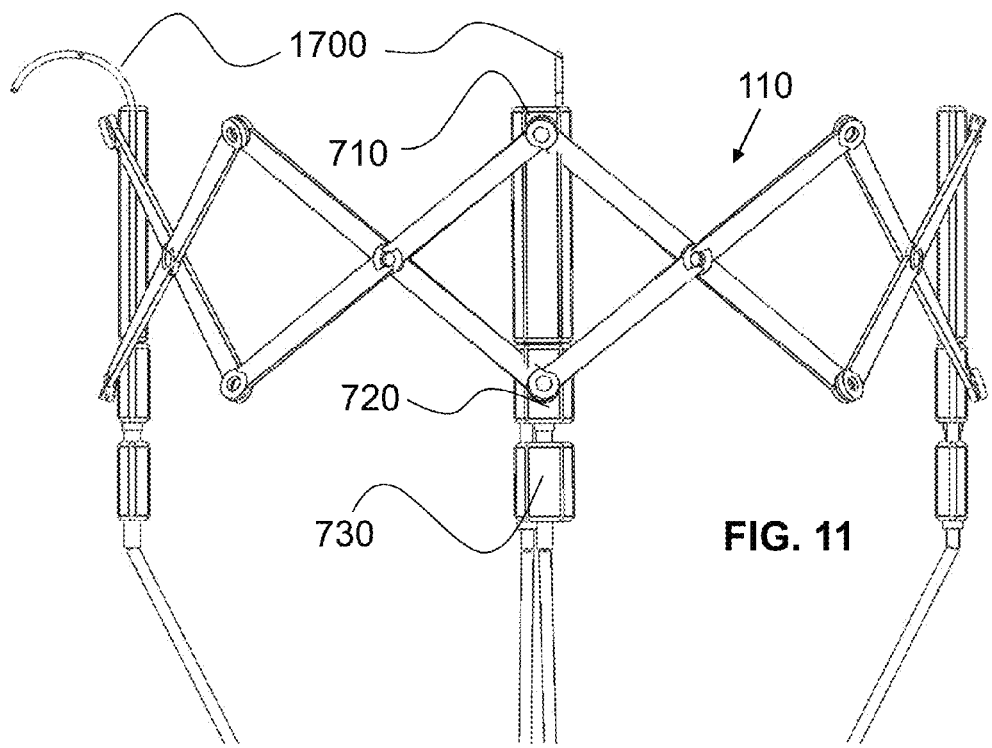
FIG. 11 is a fragmentary, longitudinal cross-sectional view of the stent deployment system of FIG. 10 showing the front half in a further expanded state.
Figure 12:
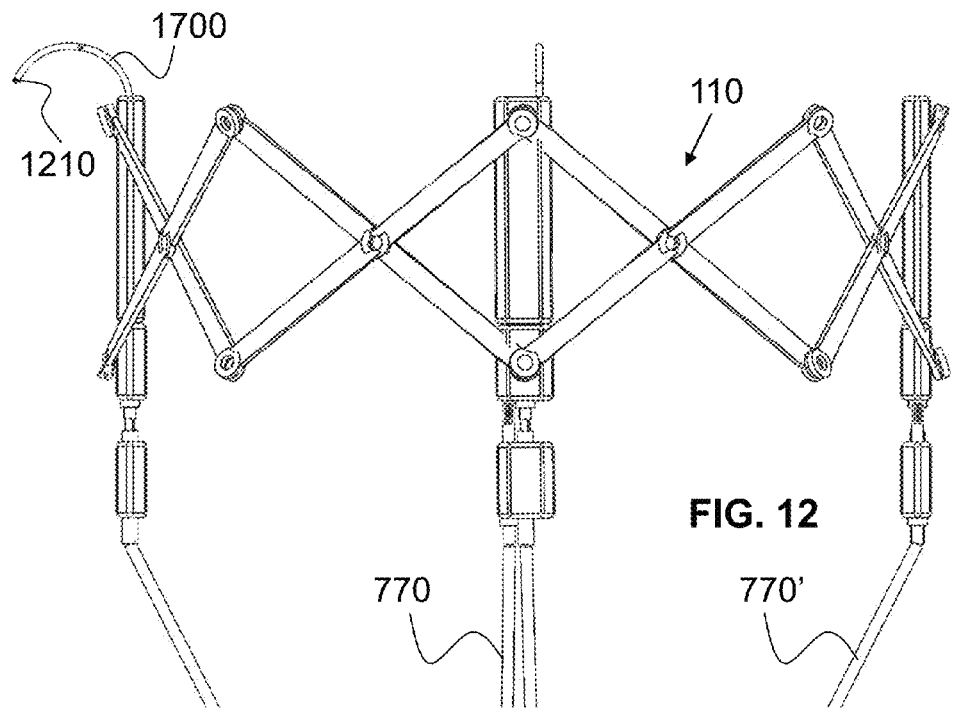
FIG. 12 is a fragmentary, longitudinal cross-sectional view of the stent deployment system of FIG. 11 with a deployment control assembly in a partially disengaged state.
Figure 13:
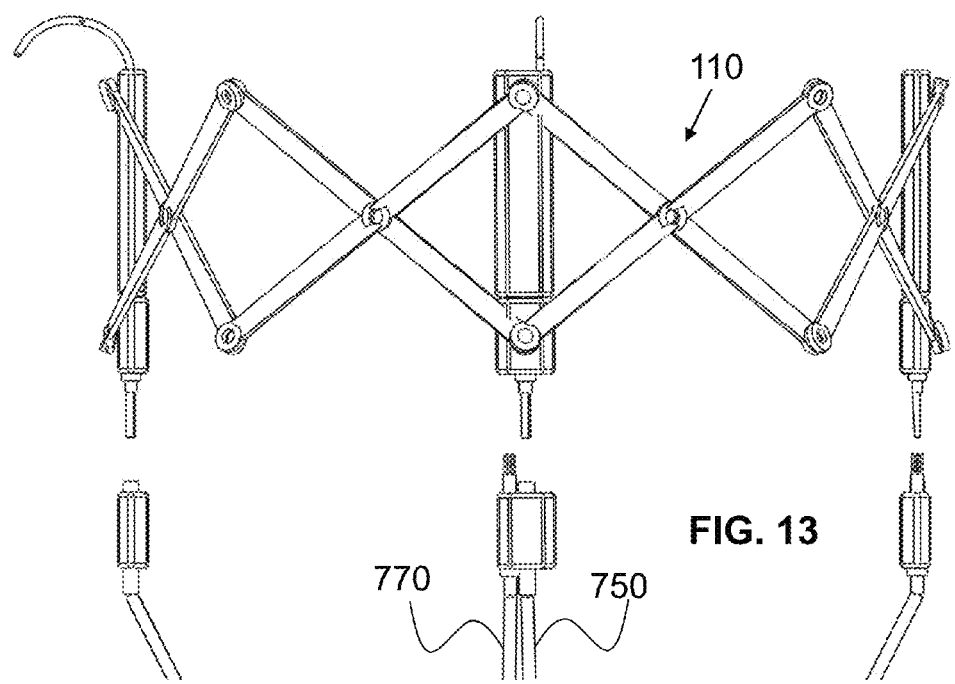
FIG. 13 is a fragmentary, longitudinally cross-sectional view of the stent deployment system of FIG. 12 with the deployment control assembly in a disengaged state.

This process is illustrated with regard to FIGS. 10 to 19. In the exemplary illustration of FIG. 10, the stent lattice 110 is not fully expanded. Because the distal threaded portion 762 of the retainer screw 760 is threaded within the connect lumen 1631 of the proximal drive block 720, the disconnector drive block 730 remains longitudinally fixed to the proximal drive block 720—ideally, a configuration that exists from the time that the stent deployment system 100 first enters the patient and at least up until implantation of the stent lattice 110 occurs. Expansion of the stent lattice 110 is finished in the configuration of FIG. 11 and, for purposes of this example, it is assumed that the stent lattice 110 is correctly implanted at the implantation site. Therefore, disconnection of the delivery system can occur. It is noted that this implantation position just happens to be at a circumferential extreme of the stent lattice 110 because the distal drive block 710 and the proximal drive block 720 are touching. In actual use, however, it is envisioned that such touching does not occur when expanded for implantation and, in such a state, there is a separation distance between the distal drive block 710 and the proximal drive block 720 to give the stent lattice 110 room to expand into the implantation site if needed. Disconnection of the stent lattice 110 begins by rotating the disconnect wire 770 in a direction that unscrews the threaded portion 762 of the retainer screw 760 from the connect lumen 1631. As the stent lattice 110 is implanted with expansive force at the implantation site, the disconnector drive block 730 moves proximally as unthreading occurs. Complete unthreading of the retainer screw 760 is shown in FIGS. 12 and 14. In a configuration with more than one jack assembly 700 (the configuration of FIGS. 1 to 19 has 4, for example), each disconnect wire 770, 770' will rotate synchronously to have each disconnector drive block 730 disconnect from its respective proximal drive block 720 substantially simultaneously, as shown in FIG. 12. Such synchronous movement will be described in greater detail below. With the stent lattice 110 implanted, as shown in FIGS. 13, 15, 18, and 19, the delivery system for the stent lattice 110 can be withdrawn proximally away from the implantation site and be retracted out from the patient.

It is noted that the exemplary embodiment of FIGS. 1 to 19 shows the actively controllable stent deployment system 100 as having four jack assemblies 700 equally spaced around the circumference of the lattice 110. This configuration is merely exemplary and any number of jack assemblies 700 can be used to expand and contract the lattice 110, including a minimum of one jack assembly 700 in total and a maximum of one jack assembly 700 for each intersection between each inner and outer strut pair 112, 114. Herein, three and four jack assemblies 700 are depicted and used to show particularly well performing configurations. By using an even number, counter-rotating screws can be used to null the torque.

Figure 20:
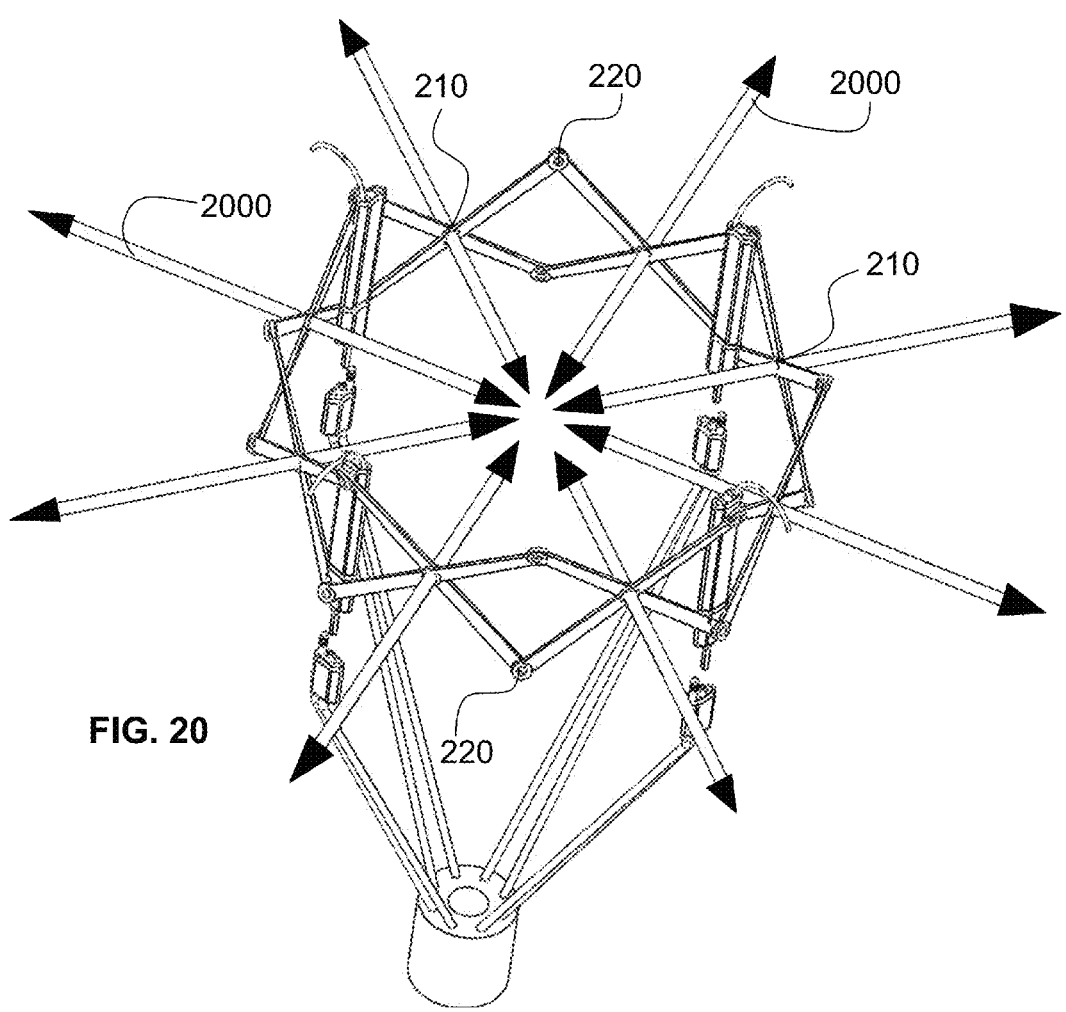
FIG. 20 is a fragmentary, perspective view of the stent deployment system of FIG. 18 with a diagrammatic illustration of paths of travel of strut crossing points as the stent is moved between its expanded and contracted states.
Figure 21:
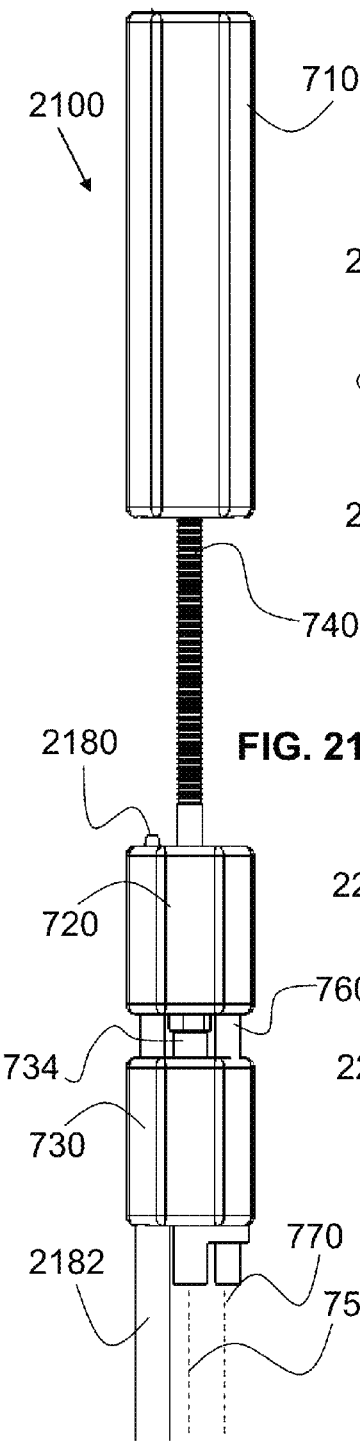
FIG. 21 is a fragmentary, side elevational view from an outer side of an alternative exemplary embodiment of a jack assembly according to the invention in a stent-contracted state with a drive sub-assembly in a connected state and with a needle sub-assembly in a retracted state.
Figure 22:
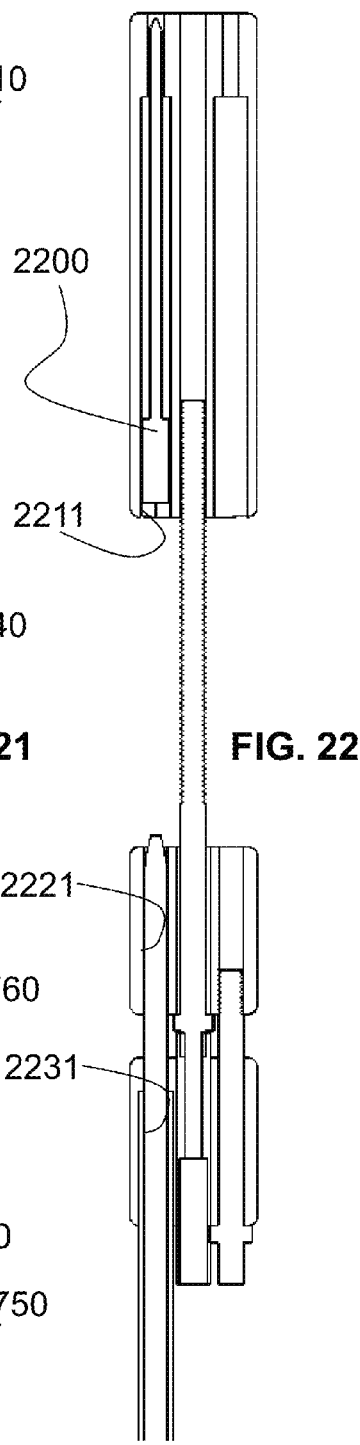
FIG. 22 is a fragmentary, cross-sectional view of the jack assembly of FIG. 21.
Figure 23:
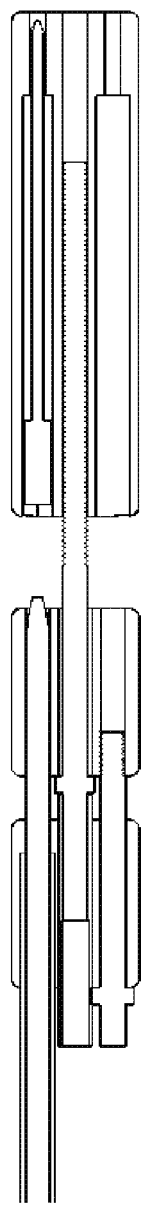
FIG. 23 is a fragmentary, cross-sectional view of the jack assembly of FIG. 21 in a partially stent-expanded state.

FIG. 20 is provided to further explain how the stent lattice 110 moves when it is expanded and contracted. As set forth above, the actively controllable stent deployment system 100 is based upon the construction of the stent lattice 110 and the attachment of the proximal and distal drive blocks 720, 710 of at least one jack assembly 700 to at least one set of the vertically opposing upper and lower pivot points 220 of the stent lattice 110. With the exemplary connections 716, 726 and pivot points 210, 220 shown in FIGS. 1 to 19, a longitudinal vertical movement of one of the proximal or distal drive blocks 720, 710 with respect to the other will expand or contract the stent lattice 110 as described herein. FIG. 20 illustrates with solid cylinders 2000 a radial path of travel that each intermediate pivot point 210 will traverse as the stent lattice 110 is moved between its expanded (e.g., FIG. 9) and contracted (e.g., FIG. 2) states. Because the travel path is linear, the stent lattice 110 expands and contracts smoothly and equally throughout its circumference.

It is noted that the struts 112, 114 shown in FIGS. 1 to 19 appear to not be linear in certain figures. Examples of such non-linearity are the struts in FIGS. 10 and 11. Therein, each strut 112, 114 appears to be torqued about the center pivot point such that one end is rotated counter-clockwise and the other is rotated clockwise. This non-linearity can create the hourglass figure that will help fix the graft into an implantation annulus and to create a satisfactory seal at the top edge of the implant. The non-linear illustrations are merely limitations of the computer design software used to create the various figures of the drawings. Such non-linear depictions should not be construed as requiring the various exemplary embodiments to have the rotation be a part of the inventive struts or strut configuration. Whether or not the various struts 112, 114 will bend, and in what way they will bend, is dependent upon the characteristics of the material that is used to form the struts 112, 114 and upon how the pivot joints of the lattice 110 are created or formed. The exemplary materials forming the struts 112, 114 and the pivots and methods for creating the pivots are described in further detail below. For example, they can be stamped, machined, coined or similar from the family of stainless steels and cobalt chromes.

Figure 17:
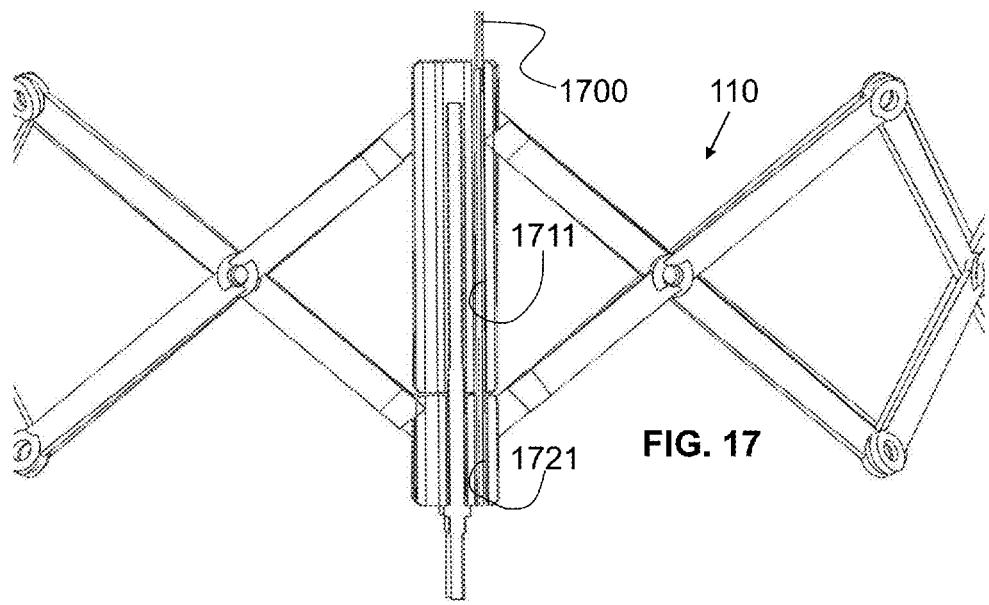
FIG. 17 is a fragmentary, longitudinally cross-sectional view of the stent deployment system of FIG. 16 showing a cross-section of a drive portion of a stent assembly with a fixed needle.
Figure 18:
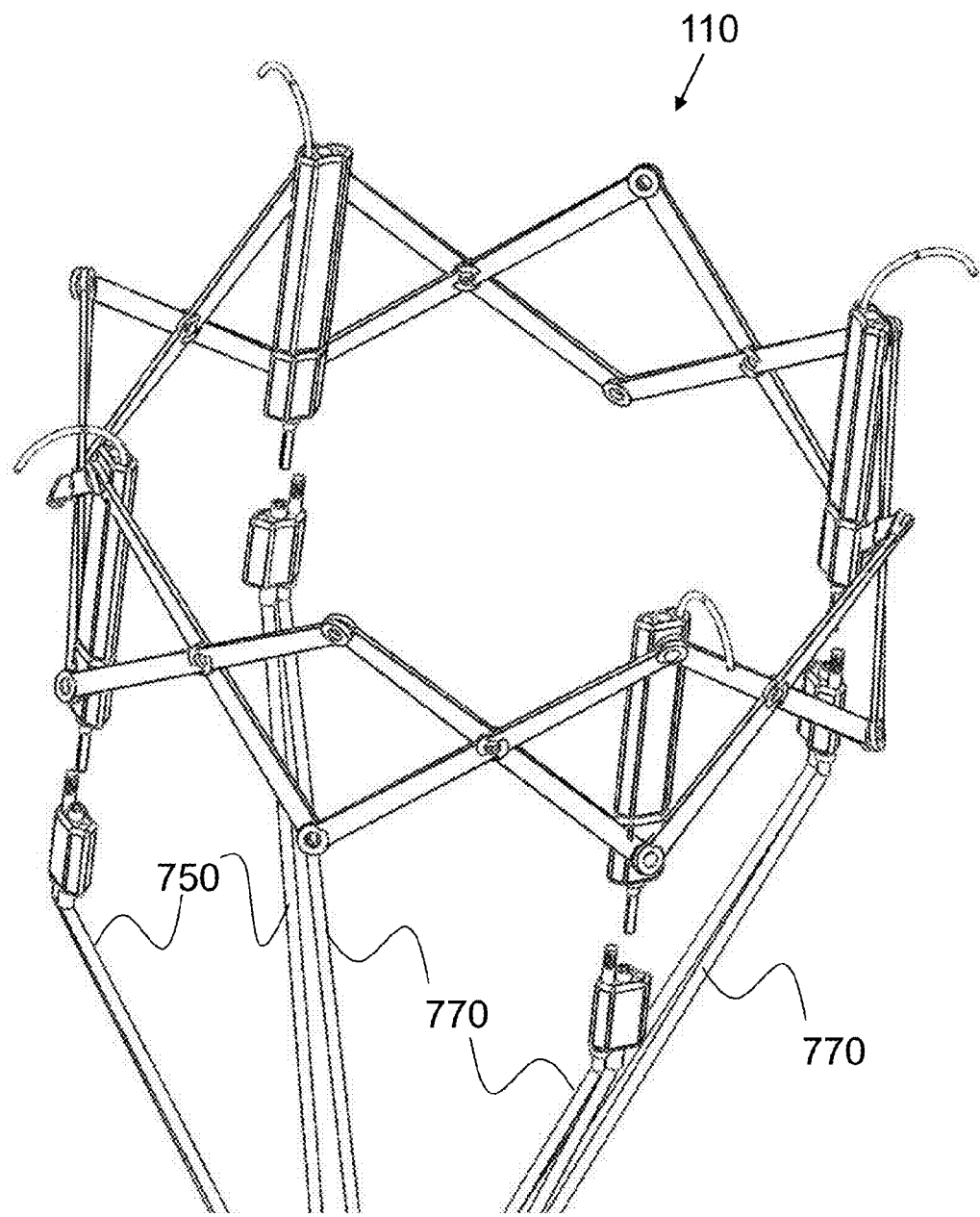
FIG. 18 is a fragmentary, perspective view of the stent deployment system of FIG. 16.
Figure 19:
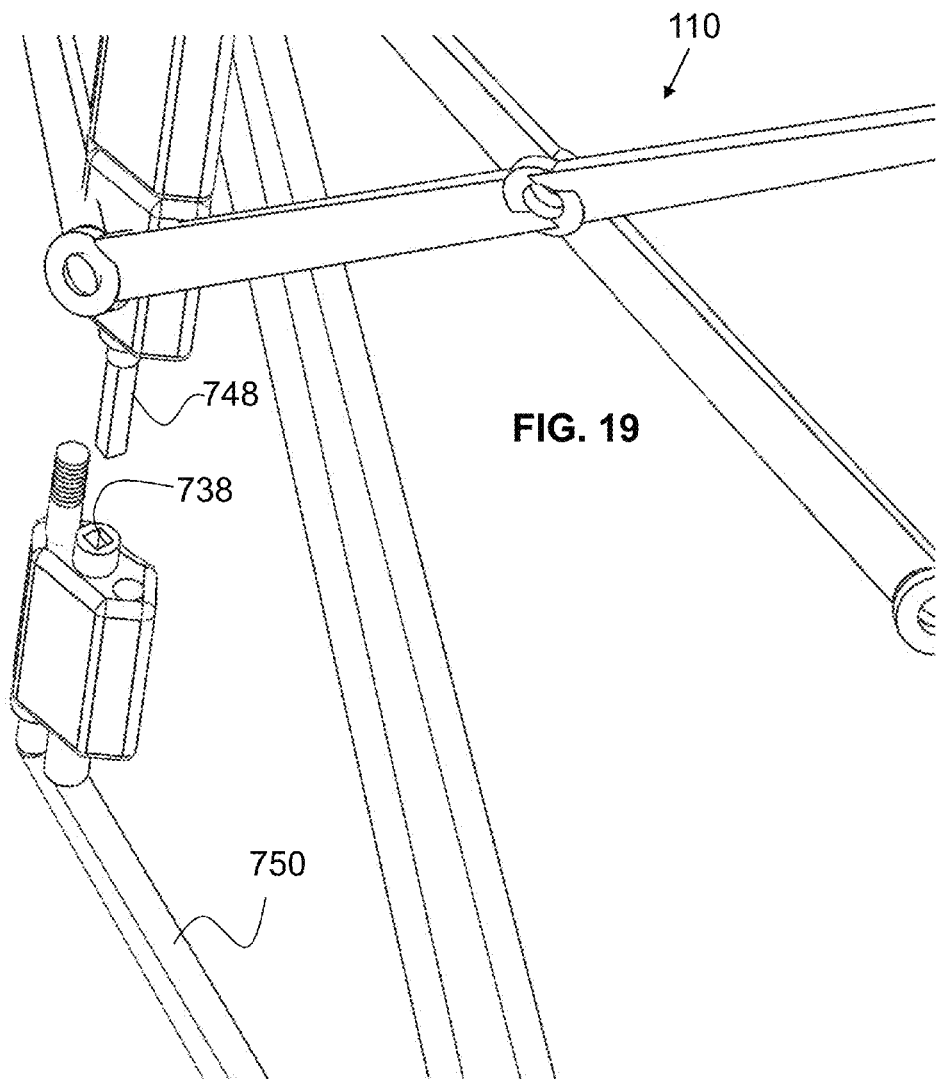
FIG. 19 is a fragmentary, perspective view of an enlarged portion of the stent deployment system of FIG. 18.

With the invention, force is applied actively for the controlled expansion of the stent lattice 110. It may be desirable to supplement the outwardly radial implantation force imposed on the wall at which the stent lattice 110 is implanted. Prior art stent grafts have included barbs and other similar devices for supplementing the outward forces at the implantation site. Such devices provide a mechanical structure(s) that impinge(s) on and/or protrude(s) into the wall of the implantation site and, thereby, prevent migration of the implanted device. The systems and methods of the invention include novel ways for supplementing the actively applied outward expansion force. One exemplary embodiment includes actively controllable needles, which is described, first, with reference to FIG. 17. In this exemplary embodiment, the distal drive block 710 and the proximal drive block 720 contain a third lumen, a distal needle lumen 1711 and a proximal needle lumen 1721. Contained within both of the distal and proximal needle lumens 1711, 1721 is a needle 1700. In an exemplary embodiment, the needle 1700 is made of a shape memory material, such as Nitinol, for example. The needle 1700 is preset into a shape that is, for example, shown in the upper left of FIG. 12. A portion that remains in the distal and proximal needle lumens 1711, 1721 after implantation of the stent lattice 110 can be preset into a straight shape that is shown in FIG. 17. A tissue-engaging distal portion of the needle 1700, however, is formed at least with a curve that, when extended out of the distal drive block 710, protrudes radially outward from the center longitudinal axis of the stent lattice 110. In such a configuration, as the needle 1700 extends outward, it drives away from the outer circumferential surface 714 (see FIG. 5) of the distal drive block 710 (i.e., towards the viewer out from the plane shown in FIG. 5). The needle 1700 also has a longitudinal extent that places the distal tip 1210 within the distal needle lumen 1711 when the stent lattice 110 is in the closed state, e.g., shown in FIG. 2.

Figure 5:
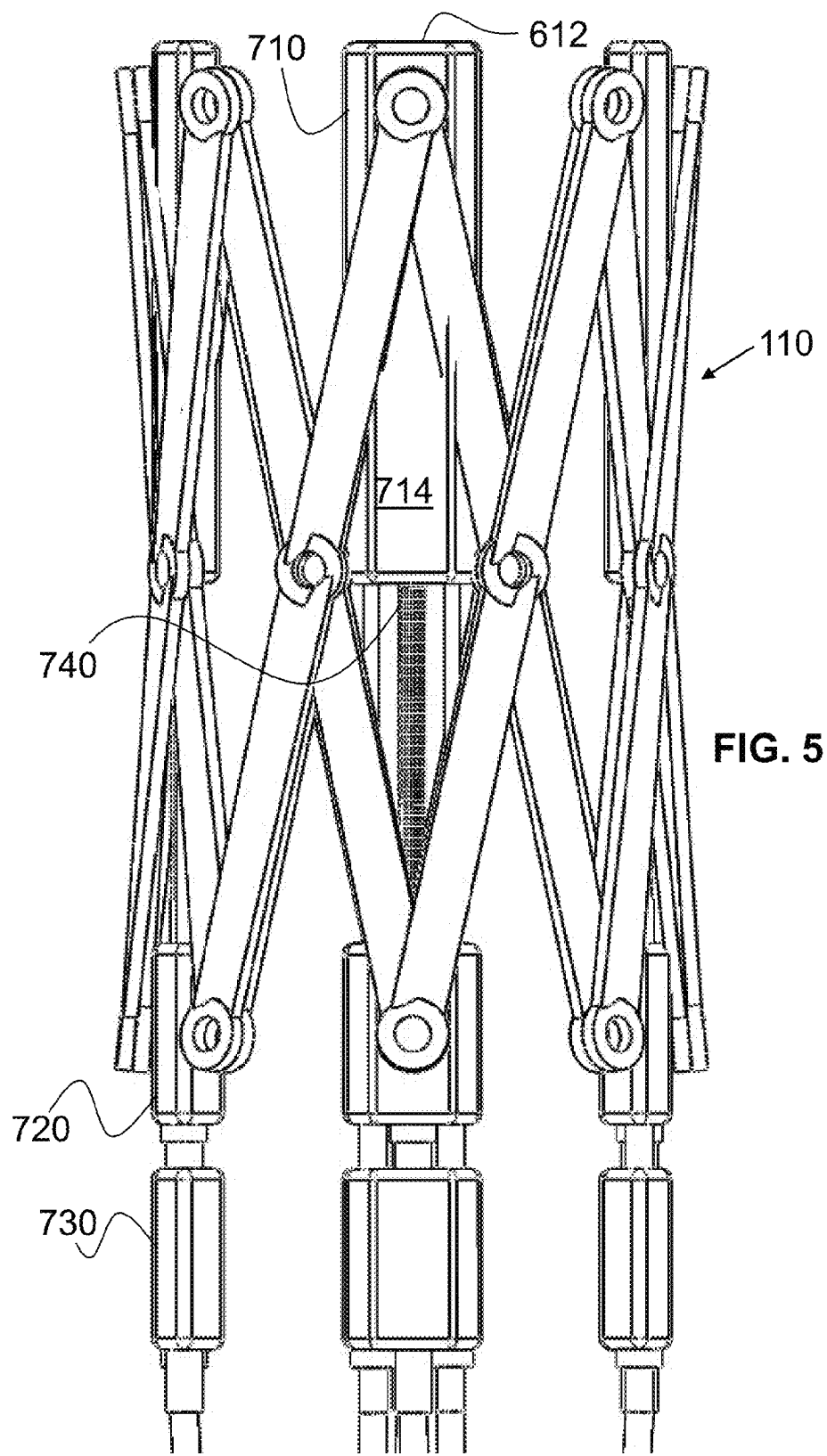
FIG. 5 is a fragmentary, side elevational view of the stent deployment system of FIG. 2 in a partially deployed state.

Deployment of the needles 1700 in each jack assembly 700 (or the number of needles can be any number less than the number of jack assemblies 700) is illustrated, for example, starting with FIG. 5. In this example, the needles 1700 in each of the four jack assemblies 700 has a length that is shorter than the longitudinal end-to-end distance of the proximal and distal drive blocks 720, 710 because the needles 1700 have not yet protruded from the distal upper surface 612 of each distal drive block 710 even though the stent lattice 110 is partially expanded. When the stent lattice 110 has expanded slightly further, however, as shown in FIG. 7, the needles 1700 begin protruding from the distal upper surface 612. As the needles 1700 are prebent as set forth above, the needles 1700 immediately begin bending into the natural pre-set curved shape. See also FIGS. 7 and 8. FIG. 10 illustrates two needles 1700 even further extended out from the distal needle lumen 1711 (only two are shown because this is a cross-section showing only the rear half of the stent lattice 110). FIG. 11 illustrates two needles 1700 in a fully extended position (as the distal and proximal drive blocks 710, 720 touch one another in the most-expanded state of the stent lattice 110). FIGS. 9, 13, 16, 17, 18, and 21 also show the needles 1700 in an extended or fully extended state.

Figure 1:
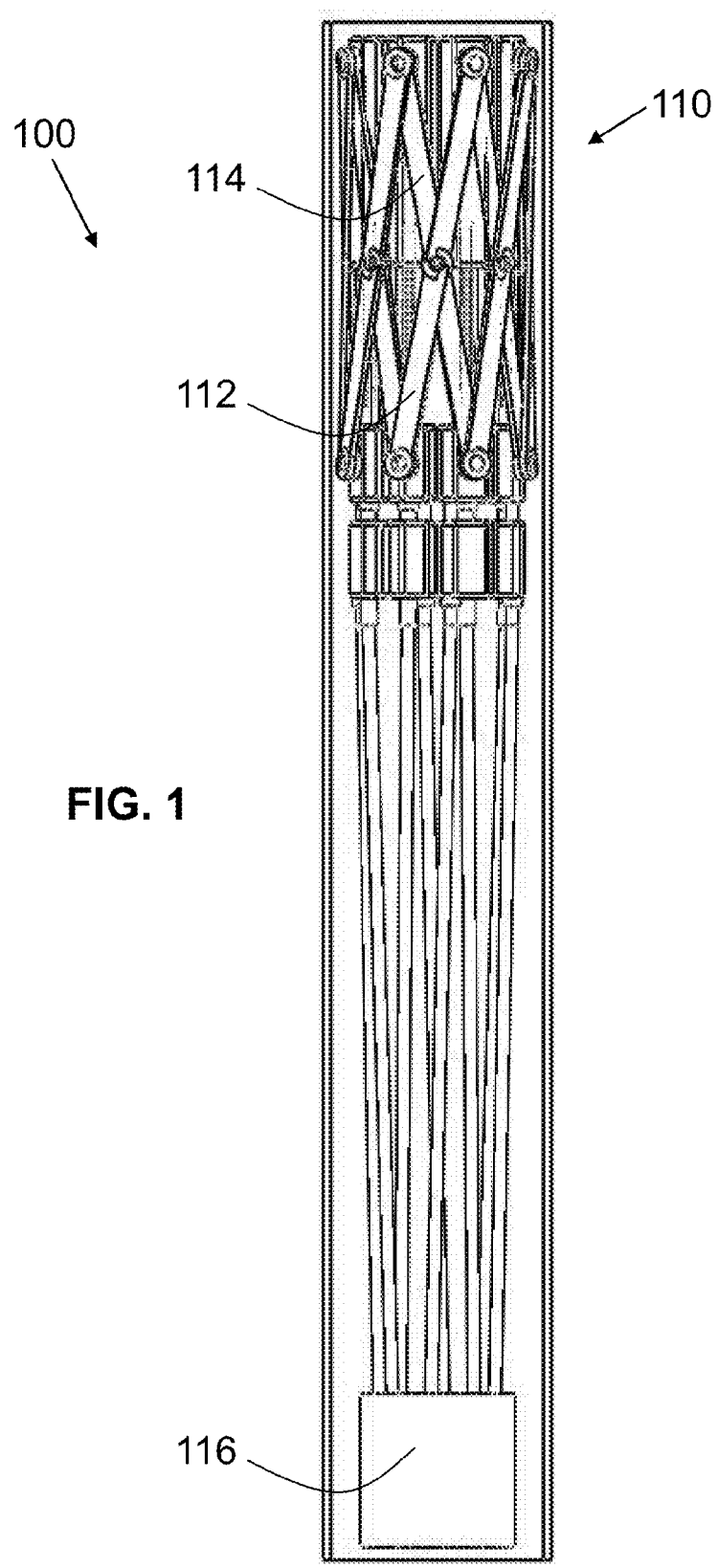
FIG. 1 is a fragmentary, partially longitudinally cross-sectional, side elevational view of an exemplary embodiment of an actively controllable stent/stent graft deployment system of the present invention in a non-deployed state with a front half of the outer catheter removed.
Figure 2:
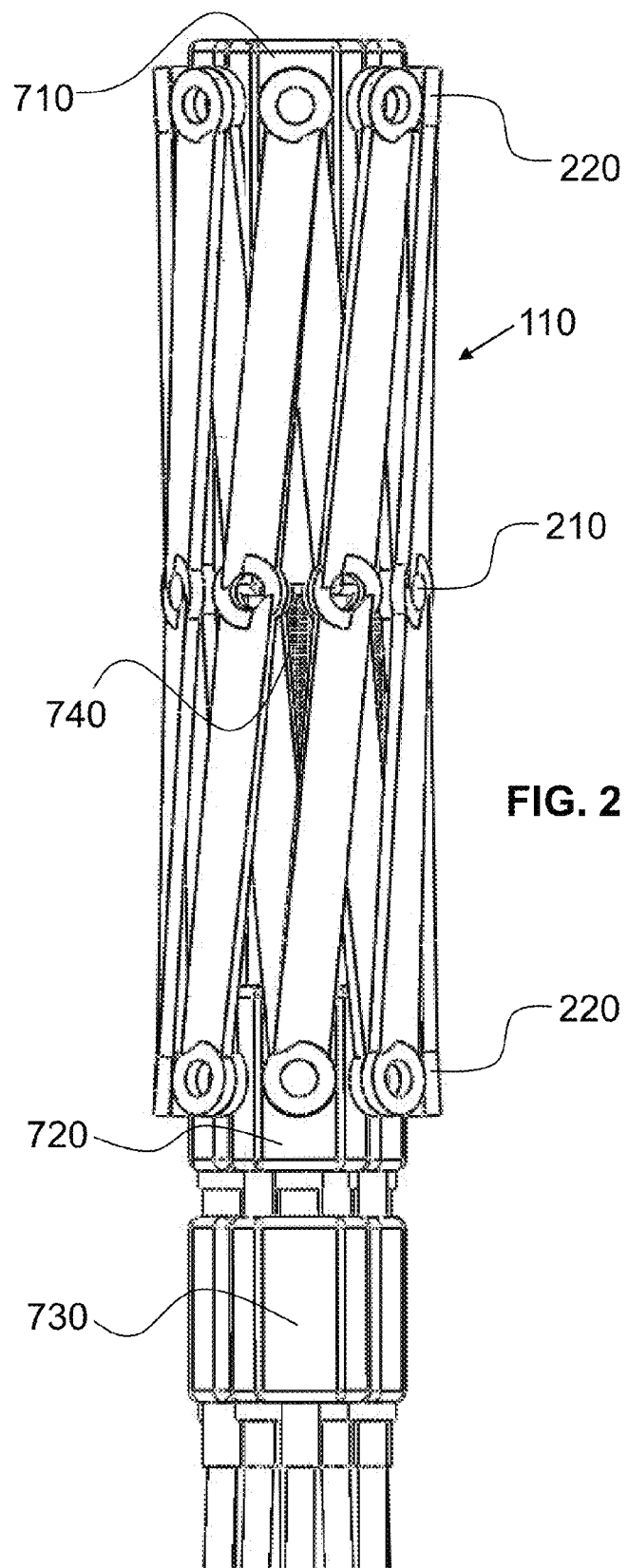
FIG. 2 is a fragmentary, side elevational view of an enlarged distal portion of the stent deployment system of FIG. 1.
Figure 3:
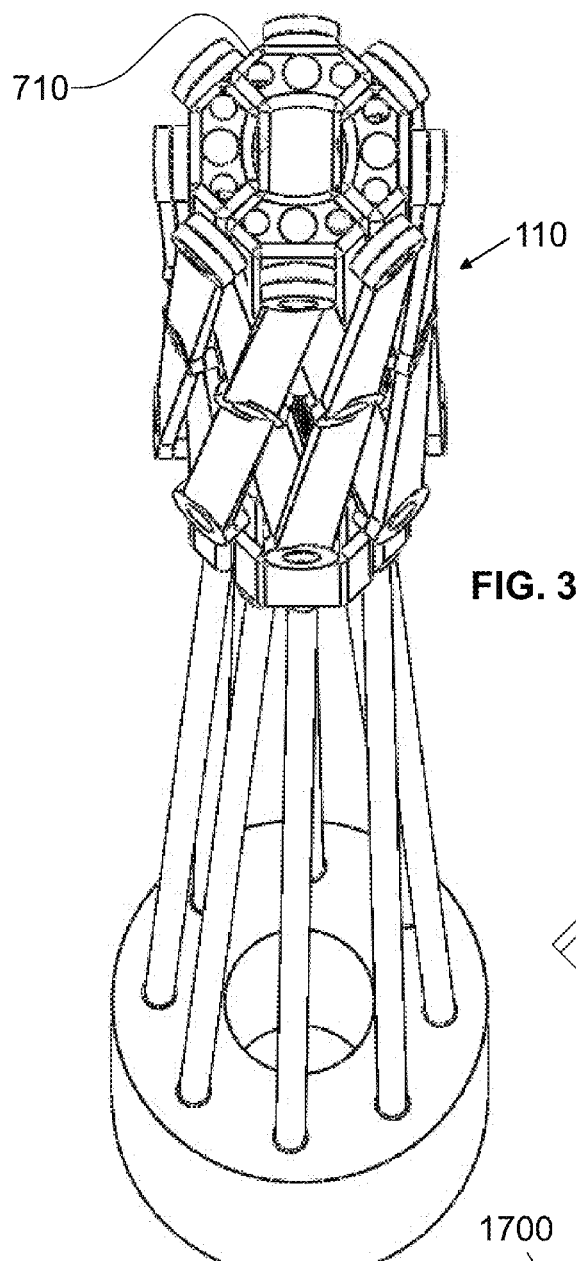
FIG. 3 is a fragmentary, perspective view of the stent deployment system of FIG. 1 from above the distal end.
Figure 6:
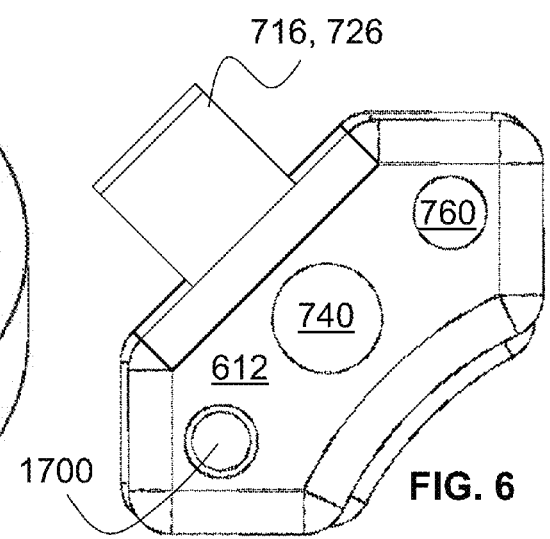
FIG. 6 is a is a top plan view of a drive portion of the stent deployment system of FIG. 2.
Figure 4:
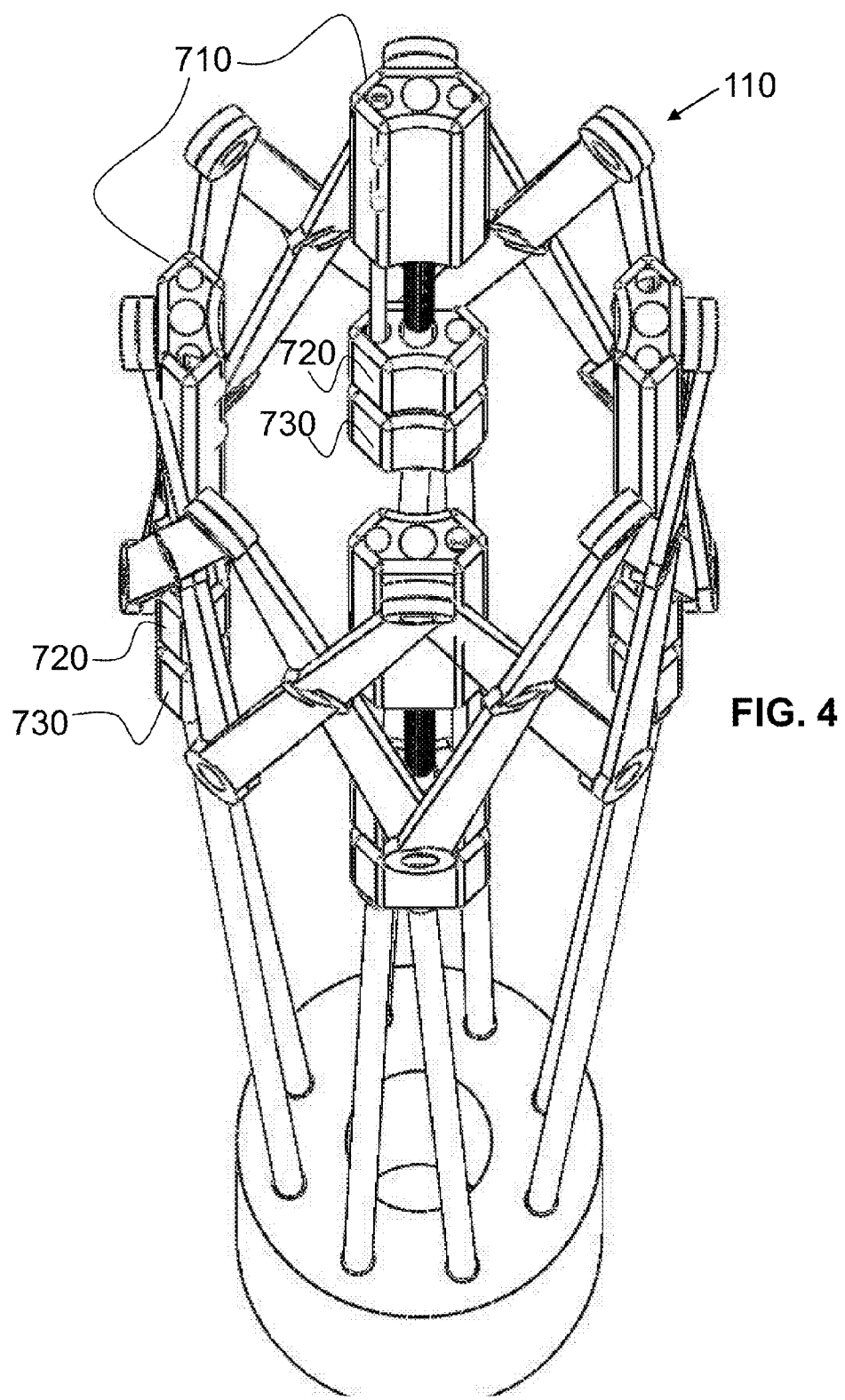
FIG. 4 is a fragmentary, perspective view of the stent deployment system of FIG. 1 from above the distal end with the system in a partially deployed state.

How the needles 1700 each extend from the distal drive block 710 can be explained in a first exemplary embodiment with reference to FIG. 17. A proximal portion of the needle 1700 is connected fixedly inside the proximal needle lumen 1721. This can be done by any measure, for example, by laser welding. In contrast, the intermediate and distal portions of the needle 1700 is allowed to entirely freely slide within the distal needle lumen 1711. With the length set as described above, when the distal and proximal drive blocks 710, 720 are separated completely, as shown in FIG. 3, the needle 1700 resides in both distal and proximal needle lumens 1711, 1721. As one of the distal and proximal drive blocks 710, 720 begins to move towards the other (as set forth above, the exemplary embodiment described with regard to these figures has the distal drive block 710 move towards the proximal drive block 720), the proximal portion of the needle 1700 remains in the proximal needle lumen 1721 but the distal portion of the needle 1700 begins to exit the distal upper surface 612, which occurs because the intermediate and distal portions of the needle 1700 are slidably disposed in the distal needle lumen 1711. This embodiment where the proximal portion of the needle 1700 is fixed in the proximal needle lumen 1721 is referred to herein as dependent control of the needles 1700. In other words, extension of the needles 1700 out from the distal needle lumen 1711 occurs dependent upon the relative motion of the distal and proximal drive blocks 710, 720.

Alternatively, the supplemental retention of the stent lattice 110 at the implantation site can occur with independent control of the needles. FIGS. 21 to 29 illustrate such an exemplary embodiment of a system and method according to the invention. Where similar parts exist in this embodiment to the dependently controlled needles 1700, like reference numerals are used. The jack assembly 2100 is comprised of a distal drive block 710, a proximal drive block 720, a disconnector drive block 730, a drive screw 740, a drive wire 750 (shown diagrammatically with a dashed line), a retainer screw 760, and a disconnect wire 770. Different from the jack assembly 700 of FIGS. 1 to 19, the jack assembly 2100 also includes a needle 2200 and a needle pusher 2210 and both the proximal drive block 720 and the disconnector drive block 730 each define a co-axial third lumen therein to accommodate the needle pusher 2210. More specifically, the distal drive block 710 includes a first pusher lumen 2211, the proximal drive block 720 includes a second pusher lumen 2221 and the disconnector drive block 730 includes a third pusher lumen 2231. As described above, the retainer screw 760 keeps the proximal drive block 720 and the disconnector drive block 730 longitudinally grounded to one another up until and after implantation of the stent lattice 110 and separation of the delivery system occurs. Rotation of the drive screw 740 causes the distal drive block 710 to move towards the proximal drive block 720, thereby expanding the stent lattice 110 to the desired implantation diameter. This movement is shown in the transition between FIG. 22 and FIG. 23. Now that the stent lattice 110 is determined to be properly implanted within the implantation site, it is time to deploy the needles 2200. Deployment starts by advancing the needle pusher 2180 as shown in FIG. 24. The needle pusher 2810 can, itself, be the control wire for advancing and retracting the needle 2200. Alternatively, and/or additionally, a needle control wire 2182 can be attached to or shroud the needle pusher 2180 to provide adequate support for the needle pusher 2180 to function. Continued distal movement of the needle pusher 2180 causes the needle 2200 to extend out from the distal upper surface 612 and, due to the preset curvature of the memory-shaped needle 2200, the needle tip curves outward and into the tissue of the implantation site. This curvature is not illustrated in FIG. 25 because the curvature projects out of the plane of FIG. 25.

Now that the stent lattice 110 is implanted and the needles 2200 are extended, disconnection of the stent lattice 110 occurs. First, as shown in FIG. 26, the retainer screw 760 is rotated to disconnect the proximal drive block 720 from the disconnector drive block 730 and a proximally directed force is imparted onto one or both of the drive wire 750 and the disconnect wire 770. This force moves the disconnector drive block 730 distally to remove the proximal key portion 748 of the drive screw 740 out from the keyhole 738, as shown in the progression from FIGS. 26 to 27. Simultaneously, distal movement of the disconnector drive block 730 starts the withdrawal of the needle pusher 2180 from the first pusher lumen 2211 (if not retracted earlier). Continued distal movement of the disconnector drive block 730 entirely removes the needle pusher 2180 from the first pusher lumen 2211, as shown in FIG. 28. Finally, withdrawal of the stent lattice delivery system entirely from the implantation site removes the needle pusher 2180 out from the second pusher lumen 2221 leaving only the implanted stent lattice 110, the jack assembly(ies) 2100, and the needle(s) 2200 at the implantation site.

FIGS. 30 to 37 illustrate another exemplary embodiment of an independent needle deployment system and method according to the invention. Where similar parts exist in this embodiment to the embodiments described above, like reference numerals are used. The jack assembly 3000 is comprised of a distal drive block 3010, a proximal drive block 3020, a disconnector drive block 3030, a drive screw 3040, a drive wire 750, a retainer screw 760, and a disconnect wire 770. The jack assembly 3000 also includes a needle 3070 and a needle movement sub-assembly 3090. The needle movement sub-assembly 3090 is comprises of a needle support 3092, a needle base 3094, a needle disconnect nut 3096, and a needle disconnect wire 3098.

The distal drive block 3010 defines three longitudinal lumens. The first is a support rod lumen 3012 and is defined to slidably retain a support rod 3080 therein. As rotational torque is imparted when any screw associated with the jack assembly 3000 rotates, the support rod 3080 is employed to minimize and/or prevent such torque from rotating the distal and proximal drive blocks 3010, 3020 and disconnector drive block 3030 with respect to one another and, thereby, impose undesirable forces on the stent lattice 110. The longitudinal length of the support rod 3080 is selected to not protrude out from the distal upper surface 3011 of the distal drive block 3010 in any expansion or retracted state of the stent lattice 110. The second vertically longitudinal lumen is the drive screw lumen 3014. As in previous embodiments, the drive screw lumen 3014 is configured with internal threads corresponding to external threads of the drive screw 740 and the longitudinal vertical length of the drive screw lumen 3014 is selected to have the drive screw 740 not protrude out from the distal upper surface 3011 of the distal drive block 3010 in any expansion or retracted state of the stent lattice 110. Finally, the distal drive block 3010 defines a needle assembly lumen that is comprises of a relatively wider proximal needle lumen 3016 and a relatively narrower distal needle lumen 3018, both of which will be described in greater detail below.

In comparison to other proximal drive blocks described above, the proximal drive block 3020 of jack assembly 3000 defines two vertically longitudinal lumens. The first lumen is a drive screw lumen 3024. In this exemplary embodiment, the drive screw 740 is longitudinally fixedly connected to the proximal drive block 3020 but is rotationally freely connected thereto. To effect this connection, a distal drive screw coupler part 3052 is fixedly secured to the proximal end of the drive screw 740 within a central bore that is part of the drive screw lumen 3024 of the proximal drive block 3020. The distal drive screw coupler part 3052 is shaped to be able to spin along its vertical longitudinal axis (coaxial with the vertical longitudinal axis of the drive screw 740) freely within the central bore of the drive screw lumen 3024. A distal portion of the drive screw lumen 3024 is necked down to have a diameter just large enough to allow a portion of the drive screw 740 (e.g., non-threaded) to spin therewithin substantially without friction. Through a circular port 3100 in a side of the proximal drive block 3020, the distal drive screw coupler part 3052 can be, for example, spot-welded to the proximal non-threaded end of the drive screw 740. With such a connection, the drive screw 740 is longitudinally fixedly grounded to the proximal drive block 3020 within the central bore of the drive screw lumen 3024. This means that rotation of the drive screw 740 causes the distal drive block 3010 to move towards the proximal drive block 3020 and, thereby, cause an expansion of the stent lattice 110 connected to the jack assembly 3000, for example, at bosses 3600 shown in FIG. 36. Fasteners 3610 in the form of washers, rivet heads, or welds, for example, can hold the stent lattice 110 to the bosses 3600. Further explanation of the drive screw coupler 3052, 3054 is made below with regard to the disconnector drive block 3030.

The second lumen within the proximal drive block 3020 of jack assembly 3000 is a retainer screw lumen 3022. A distal portion of the retainer screw lumen 3022 is shaped to fixedly hold a proximal end of the support rod 3080 therein; in other words, the support rod 3080 is fastened at the distal portion of the retainer screw lumen 3022 and moves only with movement of the proximal drive block 3020. Fastening can occur by any measures, for example, by corresponding threads, welding, press fitting, or with adhesives. A proximal portion of the retainer screw lumen 3022 has interior threads corresponding to exterior threads of the retainer screw 760. Accordingly, disconnection of the disconnector drive block 3030 from the proximal drive block 3020 is carried out by rotation of the retainer screw 760 fixedly connected to disconnector wire 770. Connection between the retainer screw 760 and the disconnector wire 770 can be accomplished by any measures, including for example, a hollow coupler sheath fixedly connected to both the distal end of the disconnector coupler wire 770 and the proximal end of the retainer screw 760 as shown in FIG. 30. As described above, the retainer screw 760 keeps the proximal drive block 3020 and the disconnector drive block 3030 longitudinally grounded to one another until after implantation of the stent lattice 110 and separation of the delivery system occurs.

This exemplary embodiment also has an alternative to the device and method for uncoupling the drive screw 740 from the remainder of the jack assembly 3000, in particular, the two-part drive screw coupler 3052, 3054. The distal drive screw coupler part 3052 as, at its proximal end, a mechanical coupler that is, in this exemplary embodiment, a semicircular boss extending in the proximal direction away from the drive screw 740. The proximal drive screw coupler part 3054, has a corresponding semicircular boss extending in the distal direction towards the drive screw 740. These can be seen, in particular, in the enlarged view of FIG. 37. Therefore, when the two semicircular bosses are allowed to interconnect, any rotation of the proximal drive screw coupler part 3054 will cause a corresponding rotation of the distal drive screw coupler part 3052. The disconnector drive block 3030 has a screw coupler bore 3031 shaped to retain the distal drive screw coupler part 3052 therein. As in the proximal drive block 3020, the screw coupler bore 3031 is shaped to surround the proximal drive screw coupler part 3054 and allow the proximal drive screw coupler part 3054 to rotate freely therewithin substantially without friction. A proximal portion of the screw coupler bore 3031 is necked down to a smaller diameter to prevent removal of the proximal drive screw coupler part 3054 after it is fixedly connected to the drive wire 750 either directly or through, for example, a hollow coupler as shown in FIGS. 30 to 37.

Implantation of the stent lattice 110 with the jack assembly 3000 is described with regard to FIGS. 30 through 35. First, rotation of the drive screw 740 causes the distal drive block 3010 to move towards the proximal drive block 3020, thereby expanding the stent lattice 110 to the desired implantation diameter. This movement is shown in the transition between FIG. 30 and FIG. 31. Now that the stent lattice 110 is properly within the implantation site, deployment of the needles 3070 can occur. Deployment starts by advancing the needle sub-assembly 3090 as shown in the transition between FIGS. 31 and 32. Continued distal movement of the needle subassembly 3090 causes the needle 3070 to extend out from the distal upper surface 3011 and, due to the preset curvature of the memory-shaped needle 3070, the tip of the needle 3070 curves outward and into the tissue of the implantation site. This curvature is not illustrated in FIGS. 32 and 33 because the curvature projects out of the plane of these figures.

In comparison to previous proximal drive blocks above, the disconnector drive block 3030 does not have a lumen associated with the needle 3070. Only distal drive block 3010 has a lumen therein to accommodate the needle 3070. More specifically, the distal drive block 3010 includes a distal needle lumen 3018 and a proximal needle lumen 3016. The distal needle lumen 3018 is shaped to accommodate the needle 3070 only. In contrast to other needle lumens, however, the proximal needle lumen 3016 is non-circular in cross-section and, in the exemplary embodiment, is ovular in cross-section. This shape occurs because the memory-shaped needle 3070 is supported on its side along its proximal extent by a needle support 3092, which is fastened side-to-side, for example, by welding. The needle support 3092 has a relatively higher columnar strength than the needle 3070 and, therefore, when fixedly connected to the side of the needle 3070, the needle support 3092 significantly increases the connection strength to the needle 3070 at its side than if the needle 3070 was controlled only from the very proximal end thereof. A high-strength, exterior threaded needle base 3094 is fixedly attached to the proximal end of the needle support 3092. This configuration also keeps the needle clocked properly so that its bend direction is away from the center of the lattice and most directly attaches to the vessel wall.

Figure 36:
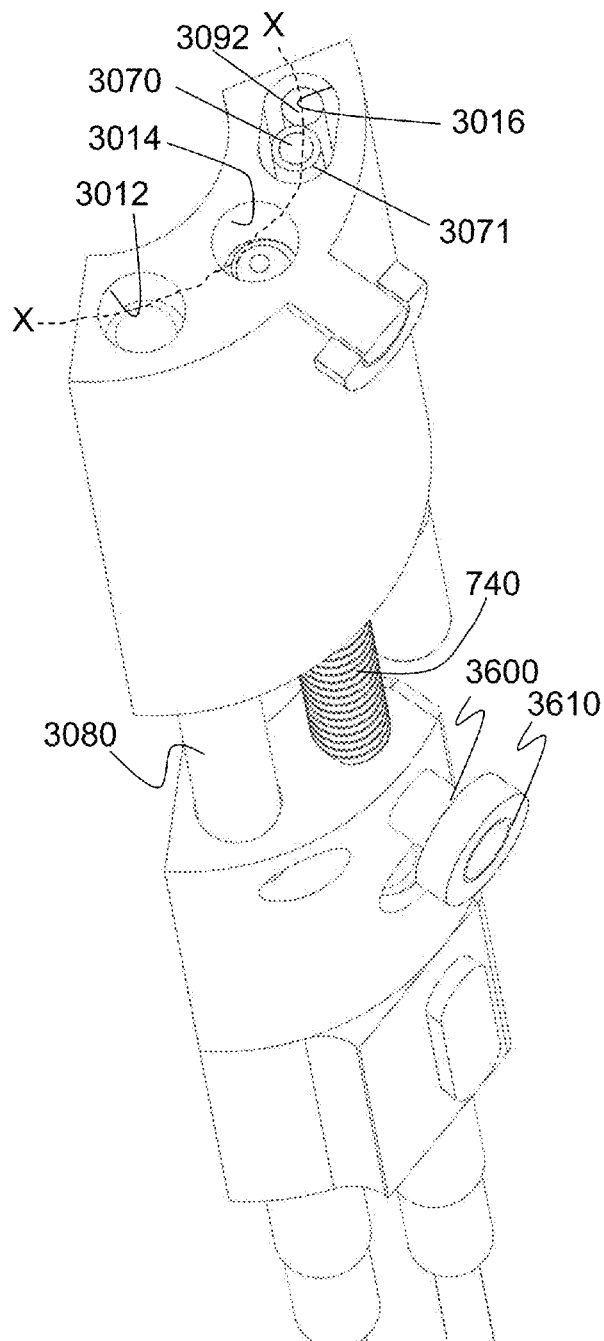
FIG. 36 is a fragmentary, partially cross-sectional, perspective view from above the jack assembly of FIG. 30 showing the interior of the distal drive block.

Control of the needle 3070 is, as above, carried out by a needle disconnect wire 3098 (depicted with dashed lines). Attached to the distal end of the disconnect wire 3098 is a needle disconnect nut 3096 defining a distal bore with interior threads corresponding to the exterior threads of the needle base 3094. In this configuration, therefore, rotation of the needle disconnect wire 3098 causes the needle disconnect nut 3096 to either secure to the needle base 3094 or remove from the needle base 3094 so that disconnection of the delivery system from the stent lattice 110 can occur. The top side of the distal drive block 3010 is cross-sectioned in FIG. 36 at the boss 3600 to show the shapes of the various lumens therein. As described above, the support rod lumen 3012 is a smooth, circular-cross-sectional bore to allow the support rod 3080 to slide longitudinally vertically therein. Similarly, the distal-portion of the drive screw lumen 3014 is also a smooth, circular-cross-sectional bore to allow the drive screw 740 to move longitudinally vertically therein as it is rotated and the threads engage the proximal threaded portion of the drive screw lumen 3014. The proximal needle lumen 3016, in contrast, is non circular (e.g., ovular) to accommodate the cylindrical-shaped needle 3070 and the side-by-side-connected, cylindrical-shaped, needle support 3092. As shown in the view of FIG. 36, at least the contacting portion of the needle 3070 to the needle support 3092 is shrouded with a connector sleeve 3071, which has material properties that allow it to be fixedly connected to the needle 3070 and, at the same time, to the needle support 3092.

Extension of the needle 3070 out from the distal upper surface 3011 by the distal movement of the disconnect wire 3098 is illustrated by the transition from FIG. 31 to FIG. 32. Only a small portion of the needle 3070 extends from the distal upper surface 3011 because the views of FIGS. 30 to 33 are vertical cross-sections along a curved intermediate plane shown, diagrammatically, with dashed line X-X in FIG. 36. As the needle 3070 extends in front of this sectional plane, it is cut off in these figures. FIGS. 34 and 35, however clearly show the extended needle 3070 curving out and away from the outer side surface 3415, however, merely for clarity purposes, the needle 3070 is rotated on its longitudinal axis slightly to the right so that it can be seen in FIG. 34 and seen better in FIG. 35. It is note that another exemplary embodiment of the needle 3070 includes a hooked or bent needle tip 3072. Correspondingly, the distal drive block 3010 includes a needle tip groove 3013 to catch the bent needle tip 3072 and utilize it in a way to keep tension on the needle 3070 and the needle disconnect wire 3098. The bend in the needle tip 3072 also allows the needle 3070 to penetrate earlier and deeper than without such a bend. Another advantage for having this bend is that it requires more load to straighten out the tip bend than the overall memory shape of the needle and, thereby, it keeps the needle located distally in the jack assembly 3000. If space allowed in the distal drive block, a plurality of needles (e.g., a forked tongue) could be used.

Figure 37:
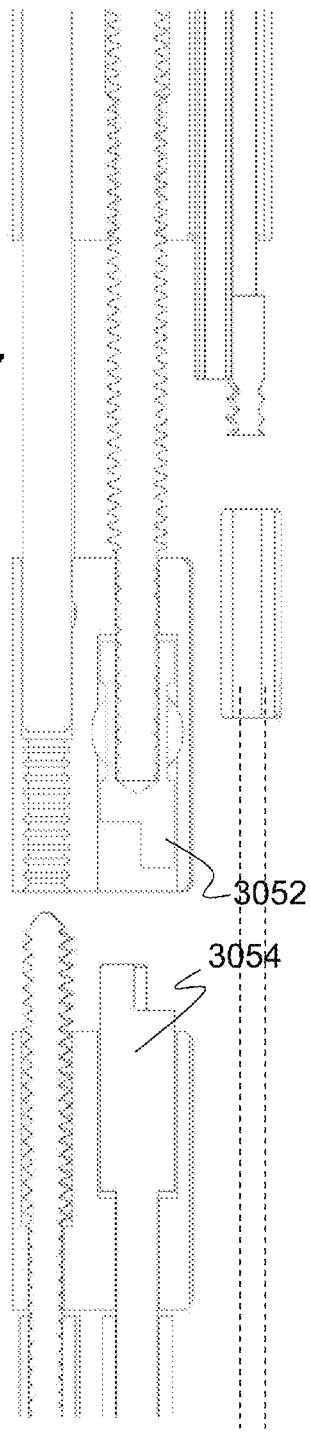
FIG. 37 is a fragmentary, enlarged, cross-sectional view of the jack assembly of FIG. 33.
Figure 38:
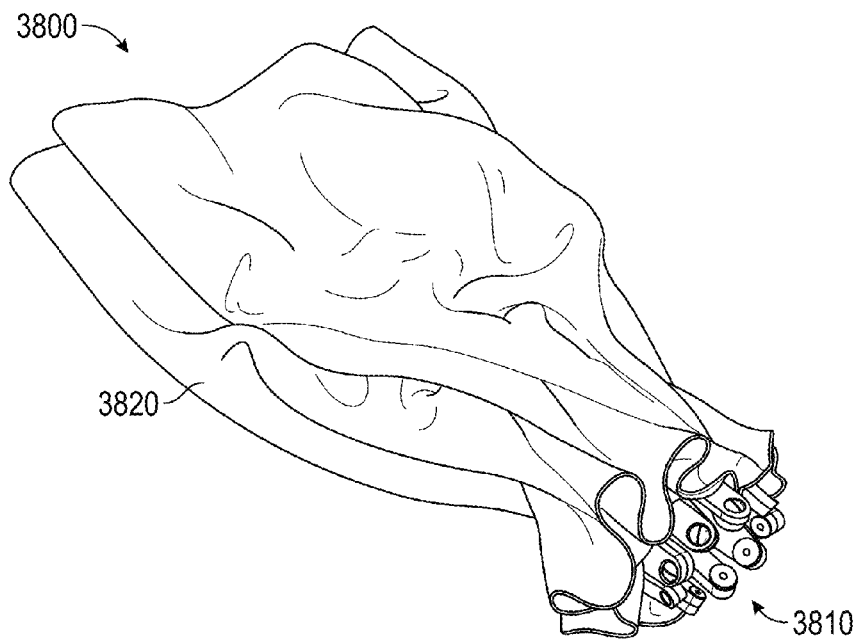
FIG. 38 is a photograph of a perspective view from above the upstream end of another exemplary embodiment of an actively controllable stent graft according to the invention in a substantially contracted state.

Removal of the delivery system is described with regard to FIGS. 32, 33, and 37 after the stent lattice 110 is implanted and the needle 3070 of each jack assembly 3000 is extended. The retainer screw 760 keeps the proximal drive block 3020 and the disconnector drive block 3030 longitudinally grounded to one another up until implantation of the stent lattice 110 and extension of the needles 3070 (if needles 3070 are included). Separation of the delivery system begins by rotation of the disconnector wire 770 to unscrew the retainer screw 760 from the retainer screw lumen 3022, which occurs as shown in the transition from FIG. 32 to FIG. 33. Because the two parts of the drive screw coupler 3052, 3054 are not longitudinally fastened to one another, the drive screw coupler 3052, 3054 does not hinder disconnection of the disconnector drive block 3030 in any way. Before, at the same time, or after removal of the retainer screw 760 from the retainer screw lumen 3022, the needle disconnect wire 3098 is rotated to, thereby, correspondingly rotate the needle disconnect nut 3096. After a number of rotations, a needle disconnect nut 3096 is entirely unscrewed from the threads of the needle base 3094, which is shown in FIG. 33, for example. The delivery system, including the disconnector drive block 3030, its control wires (drive wire 750 and disconnect wire 770), and the needle disconnect wire 3098 and disconnect nut 3096, can now be removed from the implantation site.

Figure 39:
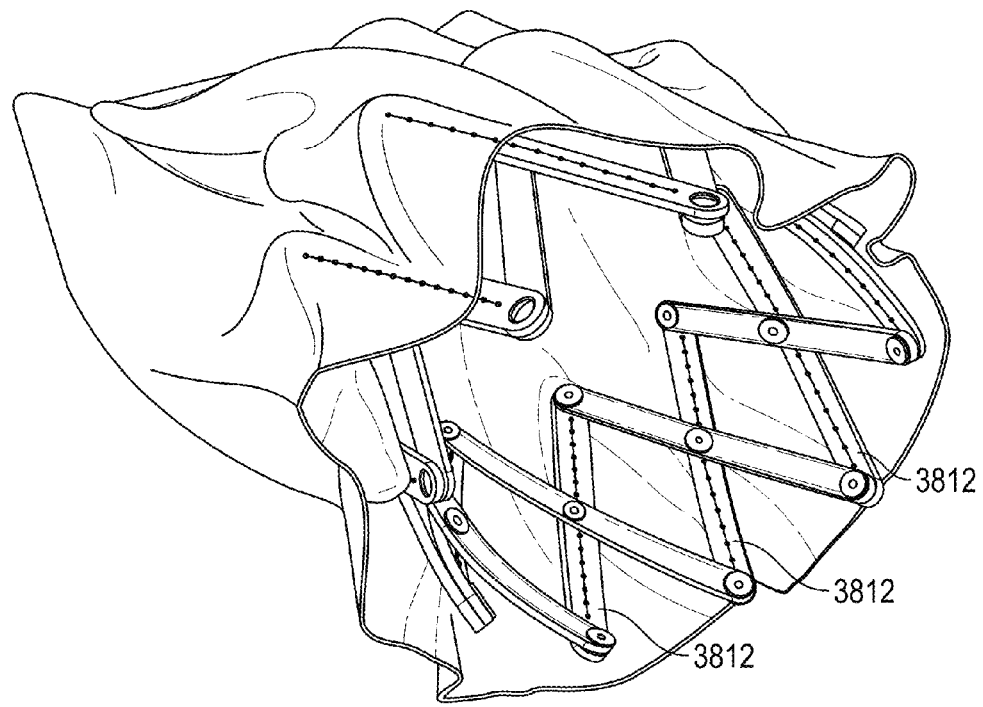
FIG. 39 is a photograph of a perspective view of the stent graft of FIG. 38 in a partially expanded state.
Figure 40:
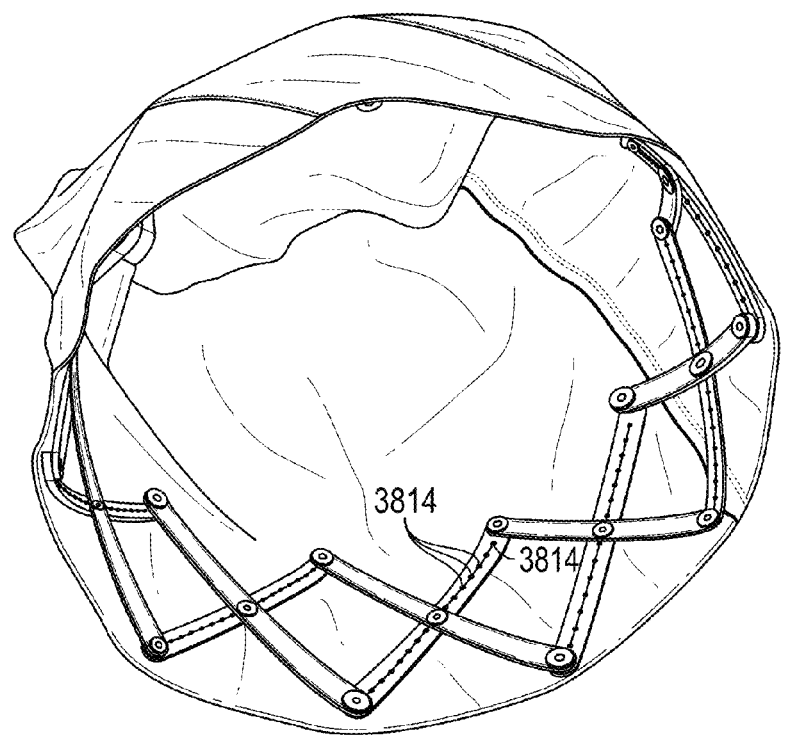
FIG. 40 is a photograph of a perspective view of the stent graft of FIG. 38 in an expanded state.
Figure 41:
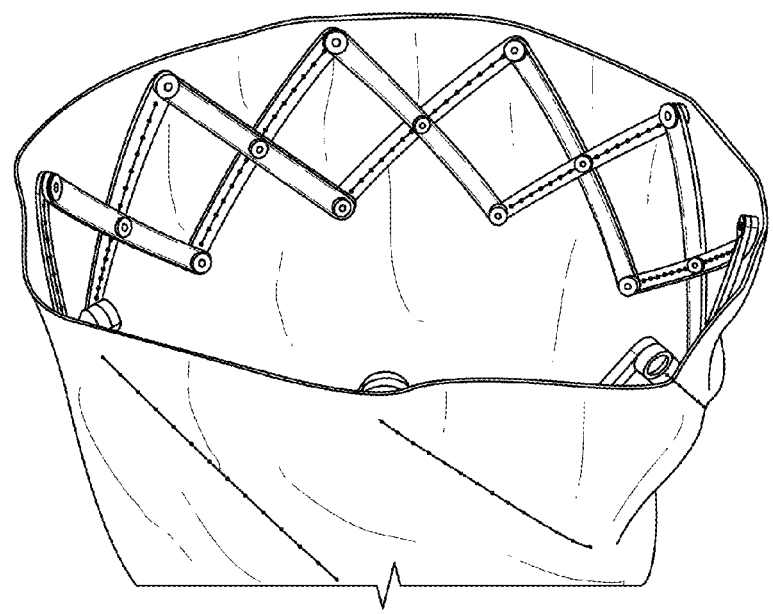
FIG. 41 is a photograph of a side perspective view of the stent graft of FIG. 38 in an expanded state.
Figure 42:
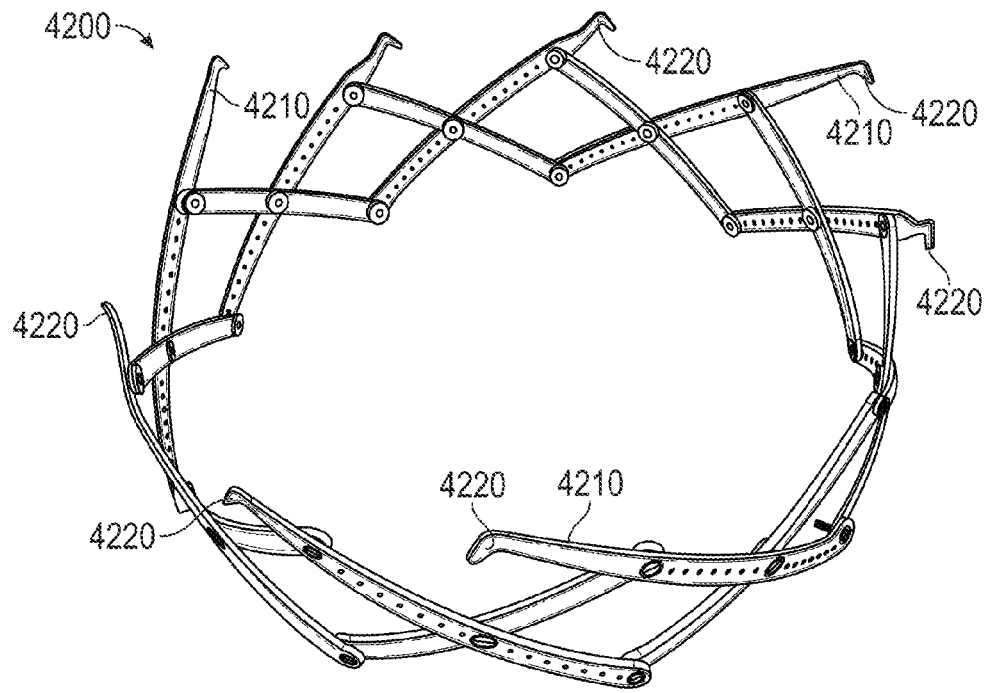
FIG. 42 is a photograph of a perspective view of another exemplary embodiment of an actively controllable stent for a stent graft according to the invention in a substantially expanded state with integral upstream anchors.
Figure 43:
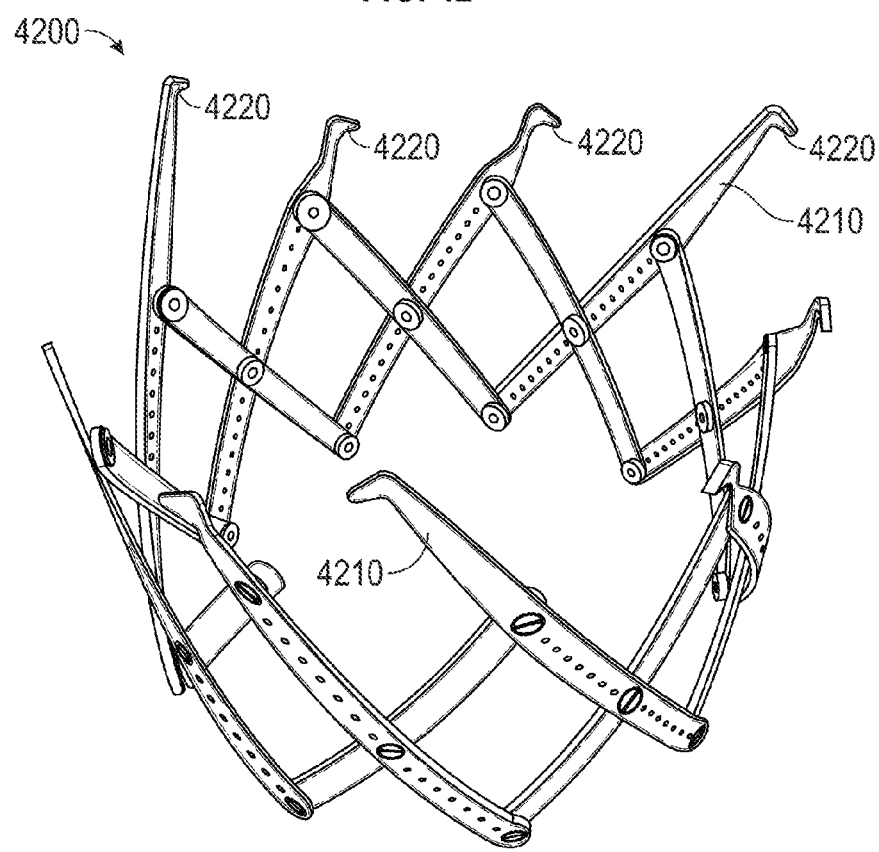
FIG. 43 is a photograph of a perspective view of the stent of FIG. 42 in a partially expanded state.
Figure 44:
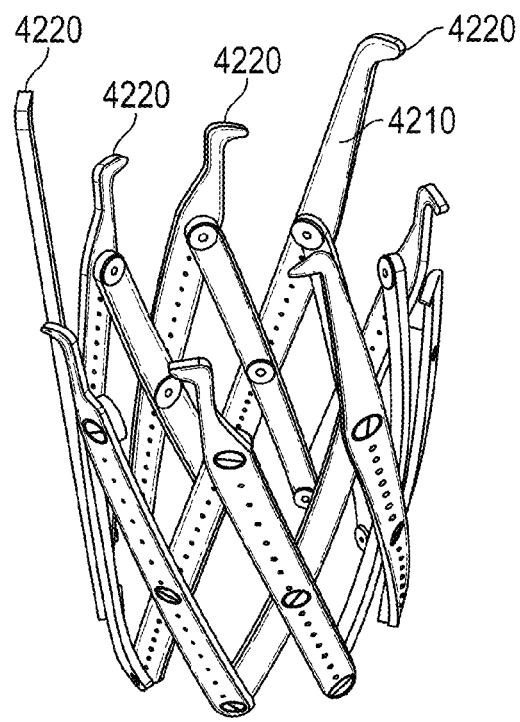
FIG. 44 is a photograph of a perspective view of the stent of FIG. 42 in another partially expanded state.
Figure 45:
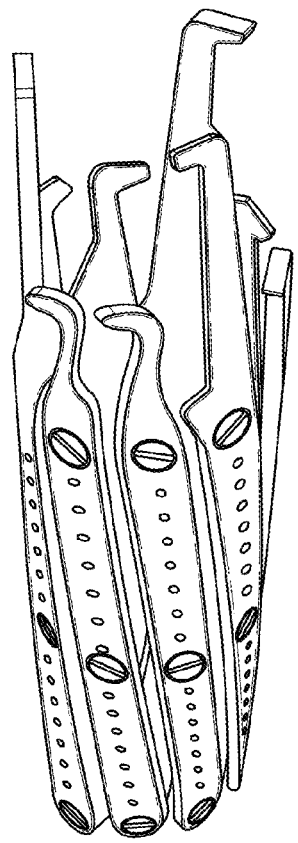
FIG. 45 is a photograph of a perspective view of the stent of FIG. 42 in a substantially contracted state.
Figure 46:
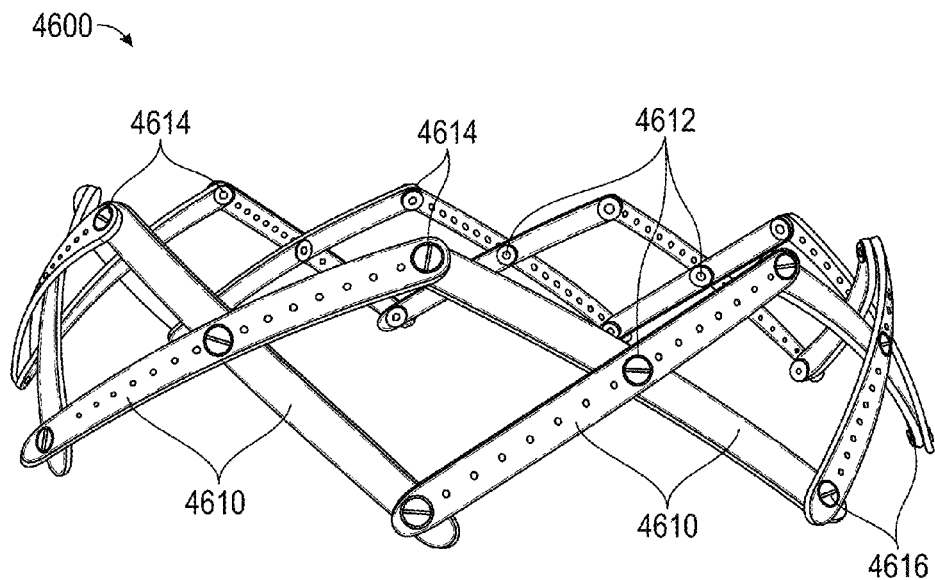
FIG. 46 is a photograph of a side perspective view of another exemplary embodiment of an actively controllable stent for a stent graft according to the invention in a substantially expanded state with a tapered outer exterior.
Figure 47:
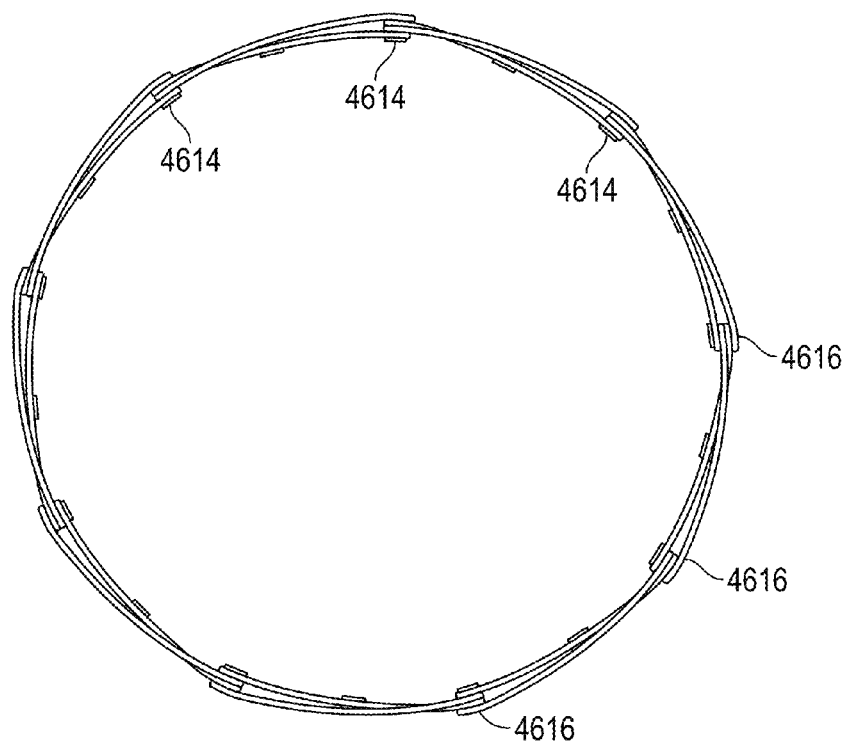
FIG. 47 is a photograph of a top perspective view of the stent of FIG. 46.

Other exemplary embodiments of the stent lattice according to the invention is shown with regard to FIGS. 38 to 50. In a first exemplary embodiment, the stent lattice is a proximal stent 3810 of a stent graft 3800. The proximal stent 3810 is connected to and covered on its exterior circumferential surface with a graft 3820. With the proximal stent 3810 in a partially expanded state in FIG. 39 and other expanded states in FIGS. 40 and 41, it can be seen that the outer struts 3812 have at least one throughbore 3814, in particular, a line of throughbores from one end to the other, extending through the outer strut 3812 in a radial direction. These throughbores allow the graft 3820 to be sewn to the outer struts 3812.

As described above, it can be beneficial for stents to have barbs, hooks, or other measures that catch and do not release tissue when they contact the tissue at or near an implantation site. FIGS. 42 to 45 illustrate one exemplary embodiment of the invention. When constructing the stent lattice 4200, attachment of the three pivot points makes each outer strut 4230 curve about its center pivot point, as can be seen in the lower right corner of FIG. 44, for example. Past the outer two pivot points of each outer strut 4230, however, there is no curve imparted. The invention takes advantage of this and provides extensions 4210 and barbs 4220 on one or more ends of the outer struts 4230 because the lack of curvature at the ends of the outer strut 4230 means that the outer portion will extend outward from the circumferential outer surface of the stent lattice 4200. In the expanded configuration of the stent lattice 4200 shown in FIG. 42, it can be seen that the extensions 4210 and barbs 4220 each project radially outward from the outer circumferential surface of the stent lattice 4200 and the points of the barbs 4220 also point radially outward, even if at a shallow angle.

Figure 48:
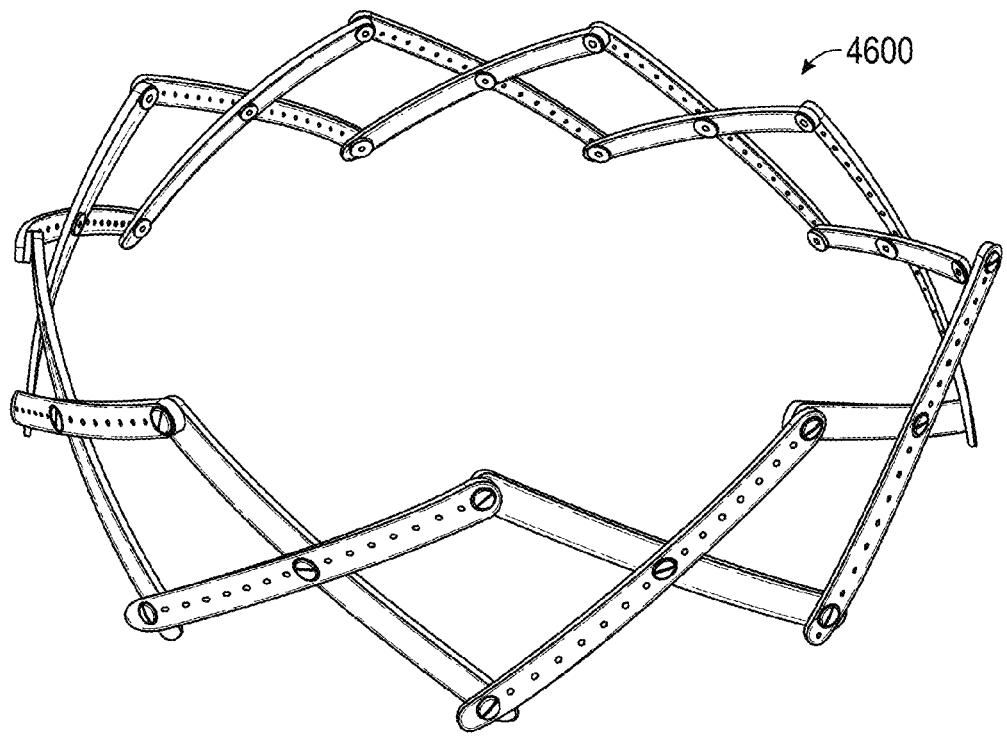
FIG. 48 is a photograph of a perspective view of the stent of FIG. 46 from above a side.
Figure 49:
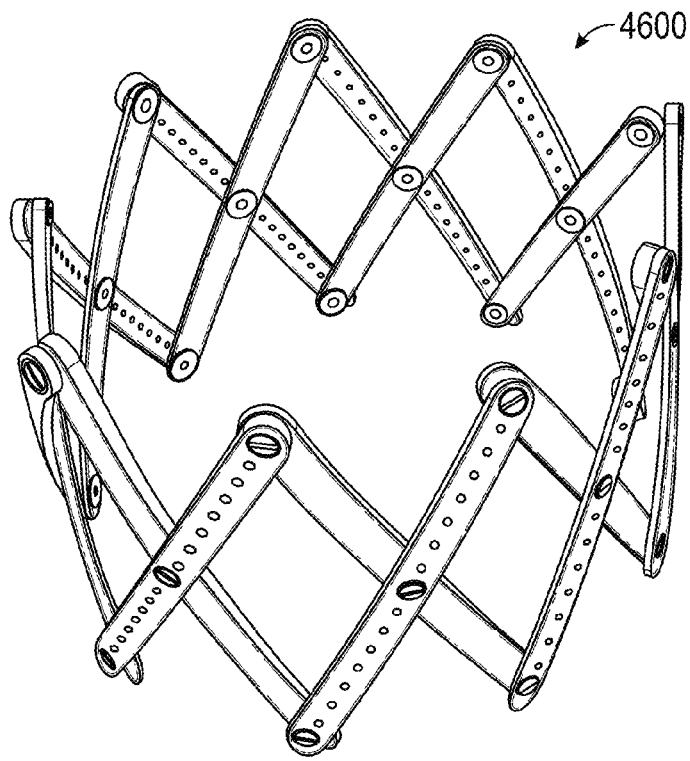
FIG. 49 is a photograph of a perspective view of the stent of FIG. 46 from above a side with the stent in a partially expanded state.
Figure 50:
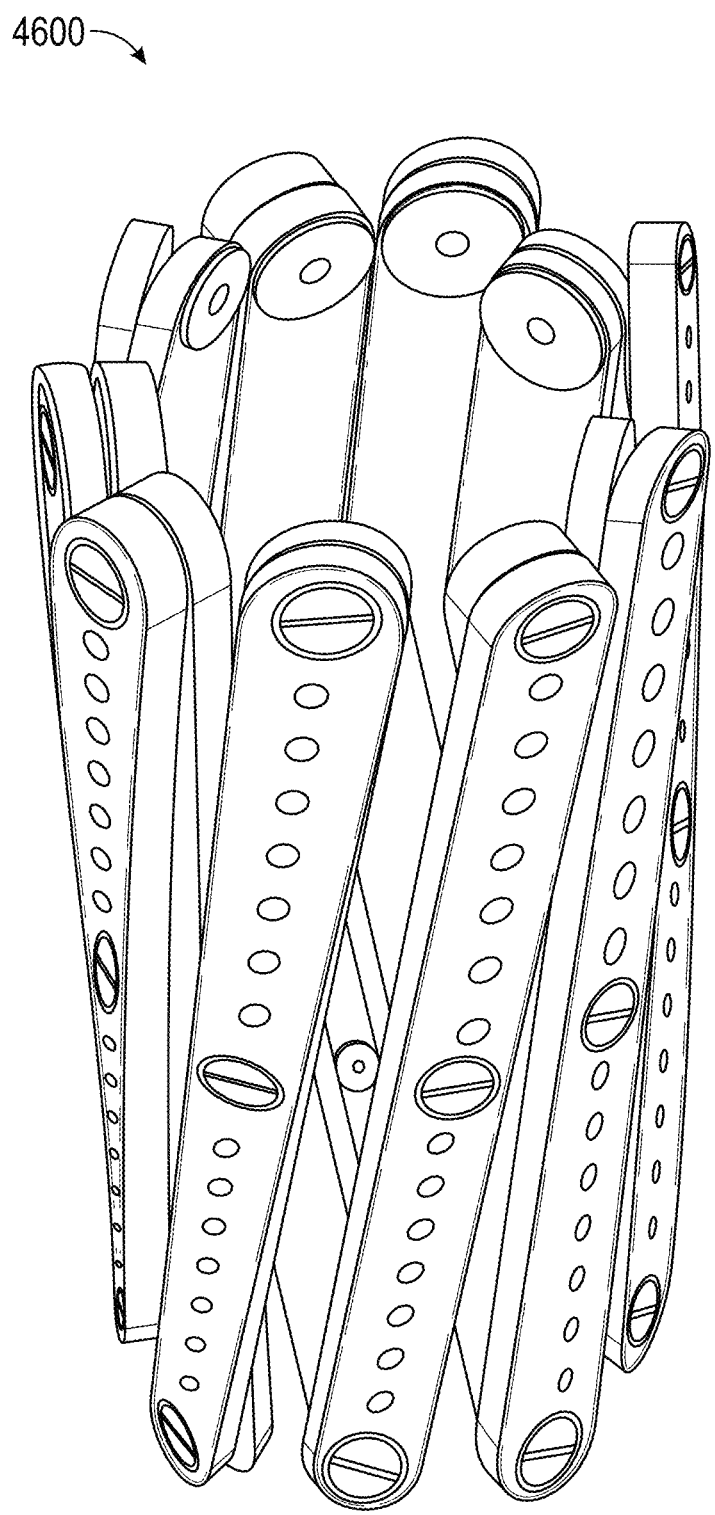
FIG. 50 is a photograph of a perspective view of the stent of FIG. 46 from above a side with the stent in a substantially contracted state.

It is noted that each of the exemplary embodiments of the stent lattices illustrated above has the intermediate pivot point at the center point of each strut. Having the intermediate pivot point in the center is only exemplary and can be moved away from the center of each strut. For example, as shown in FIGS. 46 to 50, the stent lattice 4600 can have the intermediate center pivot 4612 of the struts 4610 be closer to one end 4614 than the other end 4616. When the center pivot 4612 is off-center, the side closer to the one end 4614 tilts inwards so that the outer circumferential surface of the stent lattice 4600 takes the shape of a cone. FIGS. 48, 49, and 50 illustrate the conical stent lattice 4600 expanded, partially expanded, and almost completely retracted, respectively.

Figure 51:
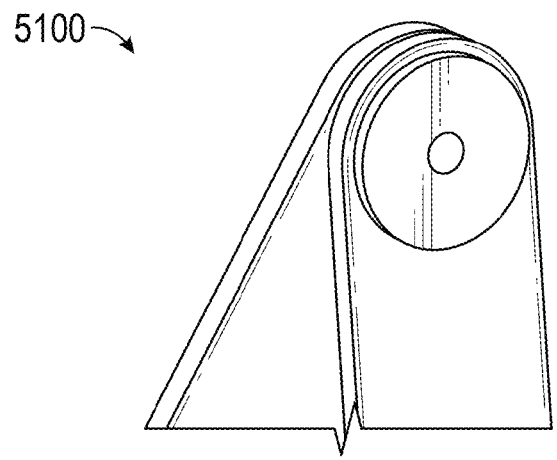
FIG. 51 is a photograph of an exemplary embodiment of a low-profile joint assembly for actively controllable stents/stent grafts according to the invention.
Figure 52:
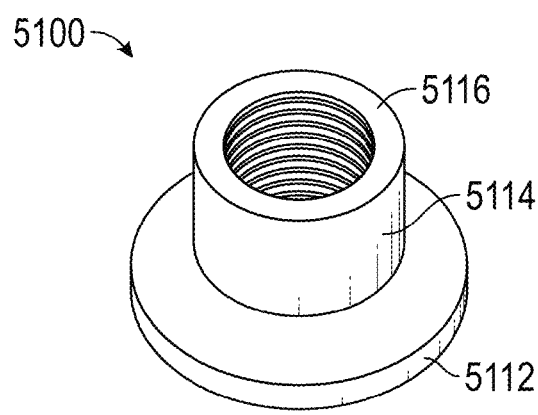
FIG. 52 is a photograph of struts of the joint assembly of FIG. 51 separated from one another.
Figure 53:
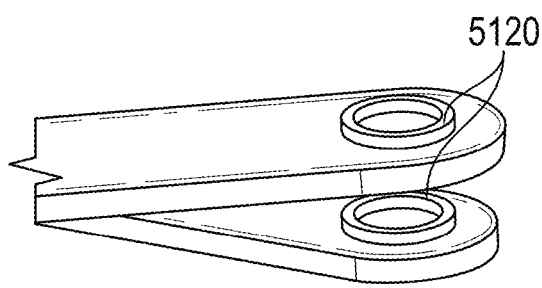
FIG. 53 is a photograph of a rivet of the joint assembly of FIG. 51.
Figure 54:
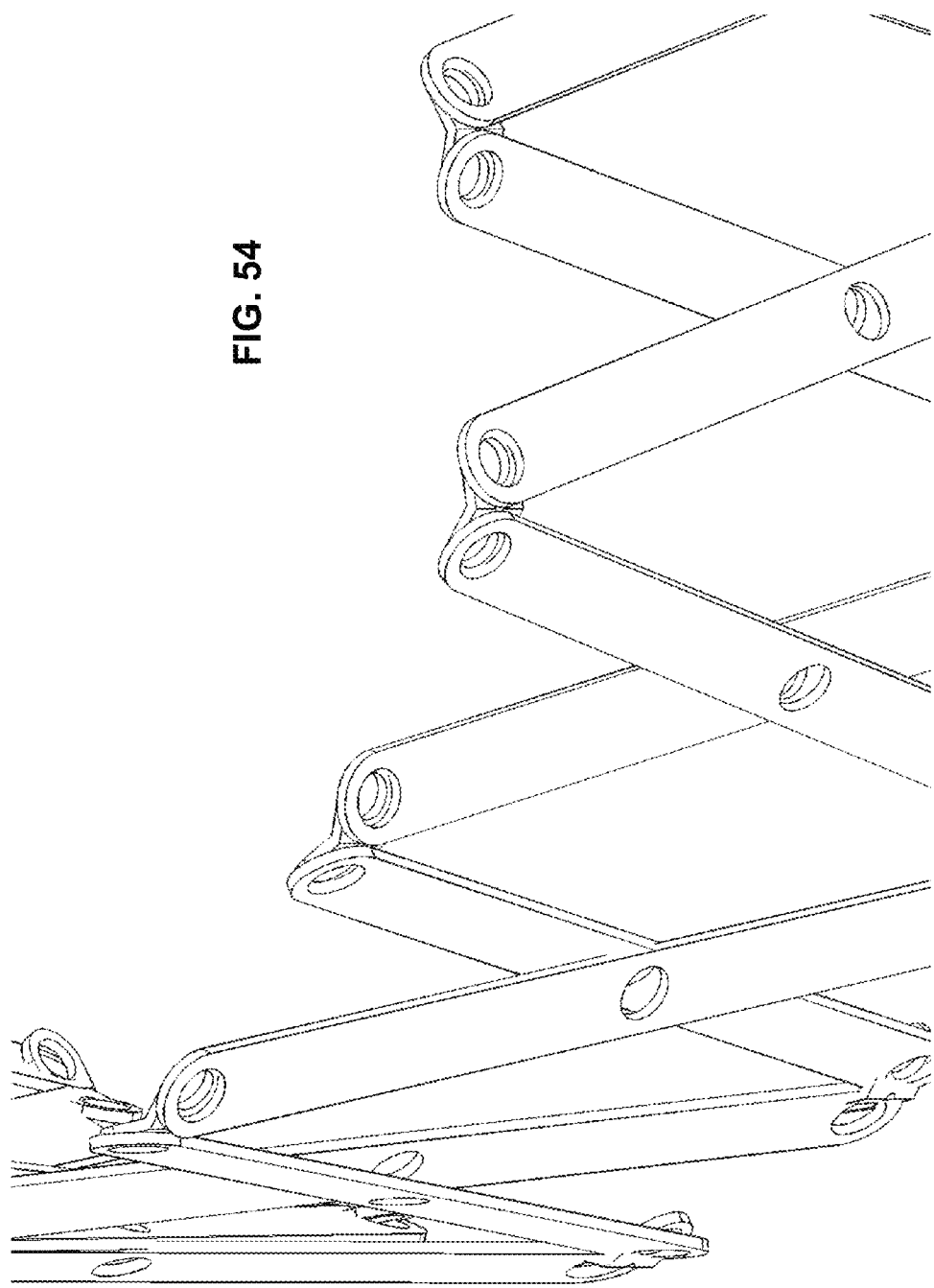
FIG. 54 is a fragmentary, side perspective view of another exemplary embodiment of an actively controllable stent system for a stent graft according to the invention in a substantially expanded state with a tapered outer exterior.
Figure 55:
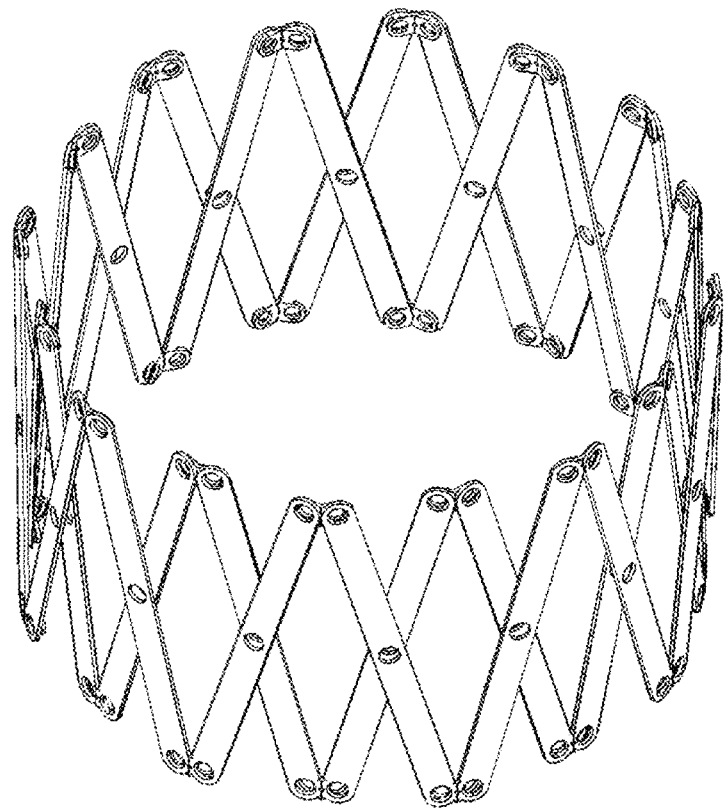
FIG. 55 is a side perspective view of the stent system of FIG. 54.
Figure 56:
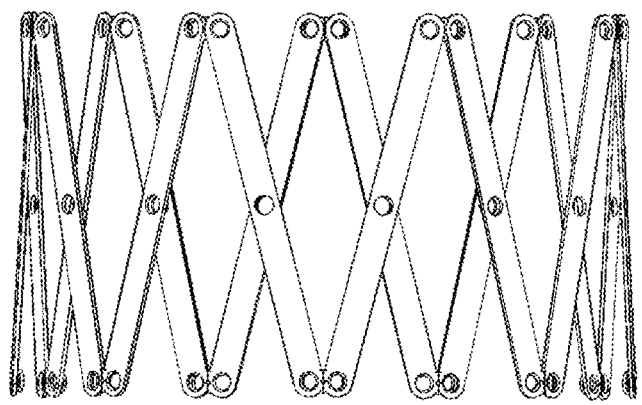
FIG. 56 is a side elevational view of the stent system of FIG. 54.

The exemplary stent lattice embodiments in FIGS. 38 to 50 show the pivot points connected by screws. Any number of possible pivoting connections can be used at one or more or all of the pivot points. One exemplary embodiment of a strut-connection assembly 5100 can be seen in FIGS. 51 to 53. Because the stent lattice of the invention is intended to be small and fit in very small anatomic sites (e.g., heart valve, aorta, and other blood vessels), it is desirable to have the lattice struts be as thin as possible (i.e., have a low profile). The profile of the screws shown in FIGS. 38 to 50 can be reduced even further by the inventive strut-connection system 5100 as shown in FIGS. 51 to 53. FIG. 51 illustrates one such low-profile connection, which is formed using a rivet 5110 and forming the rivet bores in the each of the strut ends with one of a protrusion 5120 and an opposing indention (not illustrated in FIG. 53). The rivet 5110 formed with a low-profile rivet head 5112 and intermediate cylindrical boss 5114, and a slightly outwardly expanded distal end 5116. By placing two of the ends of the struts next to one another as shown in FIG. 53, with one of the protrusions 5120 placed inside the indention of the opposing strut, the two strut ends form a pivot that is able to slide about the central pivot axis. The rivet 5110 is merely used to lock to strut ends against one another by having the expanded distal end 5116 enter through one of the non-illustrated indention sides of the strut and exit through the protrusion-side of the opposing strut. It is the features on the struts that form the pivot and not the features of the rivet 5110.

Figure 57:
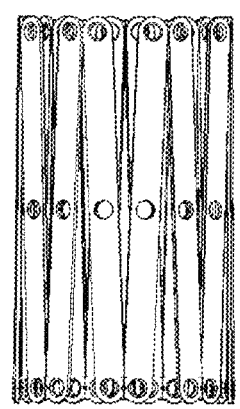
FIG. 57 is a side elevational view of the stent system of FIG. 54 in a substantially contracted state.
Figure 58:
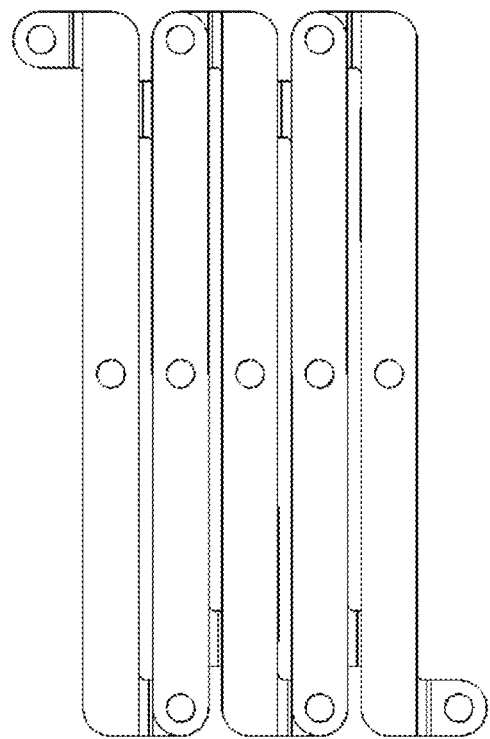
FIG. 58 is a side elevational view of another exemplary embodiment of a portion of an actively controllable stent system for a stent graft according to the invention in a substantially contracted state.
Figure 59:
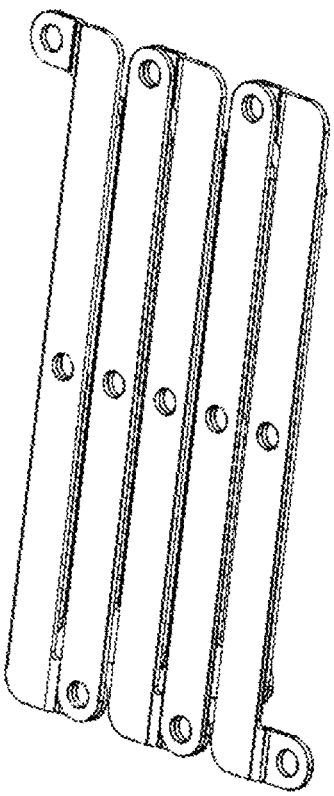
FIG. 59 is a perspective view of the stent system portion of FIG. 58.
Figure 60:
FIG. 60 is a top plan view of the stent system portion of FIG. 58.

FIGS. 54 to 63 illustrate various alternative configurations of the struts in stent lattices according to exemplary embodiments of the invention. Each of the different lattice configurations provides different characteristics. One issue that occurs with lattices having alternating struts is that expansion and contraction of the adjacent struts can adversely rub against the graft securing measures (e.g., stitchings). With that consideration, the invention provides two separate cylindrical sub-lattices in the embodiment of FIGS. 54 to 57. Each of the crossing points of the interior and exterior sub-lattices is connected via fasteners (e.g., rivets, screws, and the like). The outer ends of the struts, however, are not directly connected and, instead, are connected by intermediate hinge plates having two throughbores through which a fastener connects respectively to each of the adjacent strut ends. The intermediate hinge plates translate longitudinally towards each other upon expansion of the stent lattice and never have any portion of stent lattice pass in front or behind them. These hinge plates, therefore, could serve as connection points to the graft or could connect to a band or a rod, the band serving to join the two hinge plates together and, thereby, further spread the expansion forces on the graft. In an exemplary embodiment where the graft material has a transition zone where expansible material transitions to non-expansible material (and back again if desired), such bands or rods could extend further past the longitudinal end of the lattice and provide an attachment or securing point for a non-expansible portion of the graft material. In this configuration, as shown in FIG. 57, for example, if graft material is attached to the outer sub-lattice, then, there is no interruption and the graft is not damaged with the struts acting as scissors. FIGS. 58 to 63 illustrate another exemplary embodiment of the strut lattices according to the invention in which the inner sub-lattice is shorter in the longitudinally vertical direction than the outer sub-lattice.

The exemplary actively controllable stent lattices of the invention can be used in devices and methods in which prior art self-expanding stents have been used. In addition to the example of a proximal stent shown in the exemplary stent graft of FIGS. 38 to 41, the technology described herein and shown in the instant stent delivery systems and methods for delivering such devices can be use in any stent graft or implant, such as those used in abdominal or thoracic aneurysm repair. Additionally, the exemplary stent lattices of the invention can be used in replacement heart valves, for example.

Referring now to the figures of the drawings in detail and first, particularly to FIGS. 64 to 70, there is shown a first exemplary embodiment of an actively controllable aortic valve assembly and methods and systems for controlling and implanting such devices. Even though the exemplary embodiment is shown for an aortic valve, the invention is not limited thereto. The invention is equally applicable to pulmonary, mitral and tricuspid valves.

The inventive technology used, for example, with regard to aortic valve repair includes a replacement aortic valve assembly 6400 according to the invention. One exemplary aortic valve assembly 6400 is depicted in FIGS. 64 and 65. FIG. 64 illustrates an adjustable lattice assembly 6410 similar to that shown in FIG. 103. In particular, the lattice assembly 6410 includes a number of struts 6412 crossing one another in pairs and pivotally connected to one another in an alternating manner at crossing points 6420 and end points 6422 of the struts 6412. Like the embodiment in FIG. 103, the lattice assembly 6410 is controlled, in this exemplary embodiment, by a set of three jack assemblies 6430 each having a proximal drive block 6432, a distal drive block 6434, and a drive screw 740 connecting the proximal and distal drive blocks 6432, 6434 together. In this exemplary embodiment, the drive screw 740 performs as above, it is is longitudinally fixed but rotationally freely connected to the distal and proximal drive blocks 6432, 6434 such that, when rotated in one direction, the distal and proximal drive blocks 6432, 6434 move away from one another and, when rotated in the other direction, the distal and proximal drive blocks 6432, 6434 move towards one another. In such a configuration, the former movement radially contracts the lattice assembly 6410 and the latter movement expands the lattice assembly 6410. The lattice assembly 6410 shown in FIGS. 64 and 65 is in its expanded state, ready for implantation such that it accommodates to the natural geometry of the implantation site. Connected at least to the three jack assemblies 6430 at an interior side of one or both of the distal and proximal drive blocks 6432, 6434 is an exemplary embodiment of a three-leaf valve assembly 6440 (e.g., an aortic valve assembly). The valve assembly 6440 can be made of any desired material and, in an exemplary configuration, is made of bovine pericardial tissue or latex.

An exemplary embodiment of a delivery system and method shown in FIGS. 66 to 70 and disclosed herein can be used to percutaneously deploy the inventive aortic valve assembly 6440 in what is currently referred to as Transcatheter Aortic-Valve Implantation, known in the art under the acronym TAVI. As set forth above, this system and method can equally be used to deploy replacement pulmonary, mitral and tricuspid valves as well. The configuration of the delivery system and the valve assembly 6440 as an aortic valve assembly provide significant advantages over the prior art. As is known, current TAVI procedures have a risk of leak between an implanted device and the aortic valve annulus, referred to as perivalvular leak. Other disadvantages of prior art TAVI procedures include both migration (partial movement) and embolism (complete release). The reason for such movement is because the prior art replacement aortic valves are required before use and entry into the patient, to be crushed manually by the surgeon onto an interior balloon that will be used to expand that valve when ready for implantation. Because the native annulus of the implantation site is not circular, and due to the fact that the balloon forces the implanted pre-crushed valve to take a final shape of the circular balloon, prior art implants do not conform to the native annulus. Not only are such prior art systems hard to use, they provide no possibility of repositioning the implanted valve once the balloon has expanded.

Figure 70:
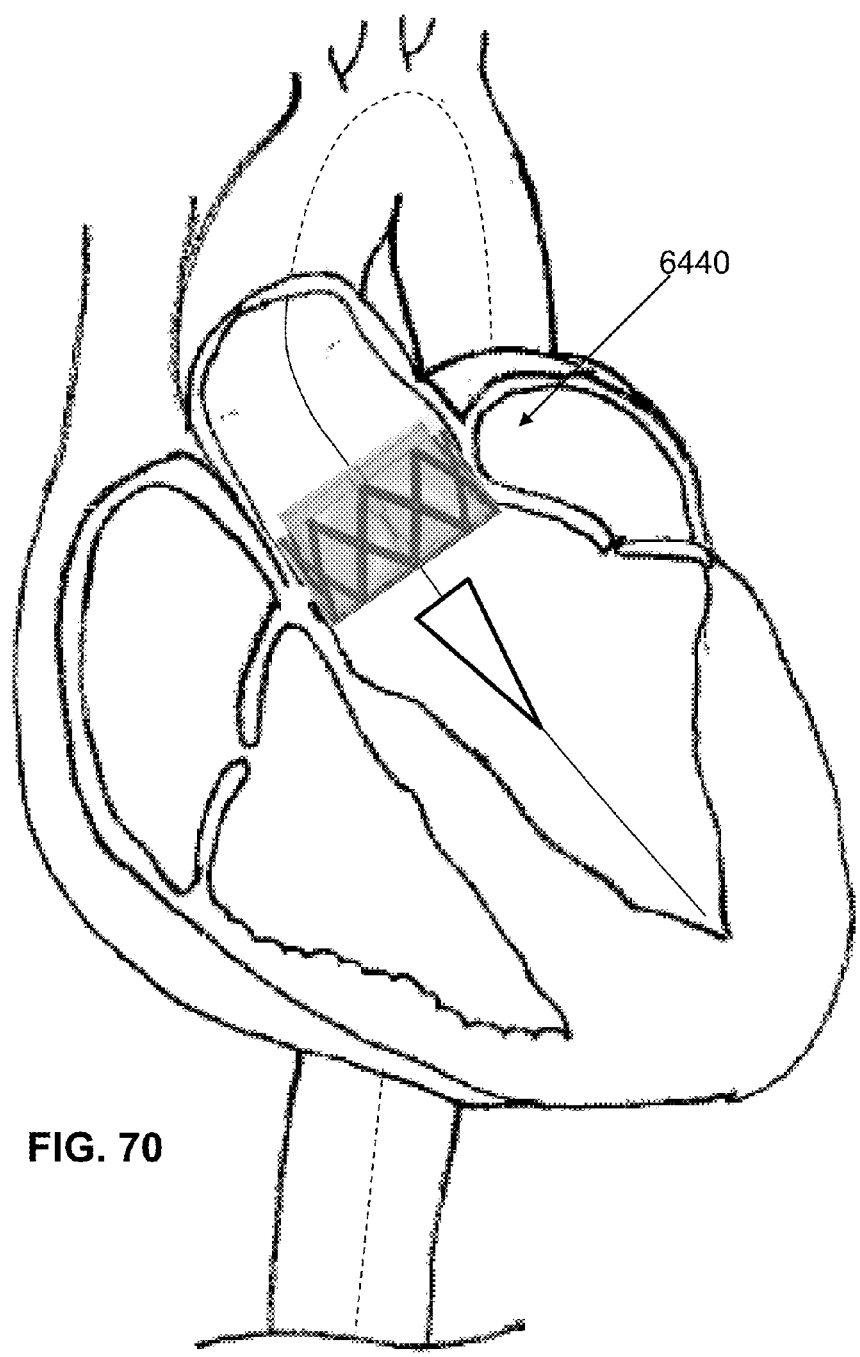
FIG. 70 is a fragmentary, enlarged, perspective view of the delivery system and the aortic valve assembly of FIG. 69 implanted at an aortic valve implantation site.
Figure 71:
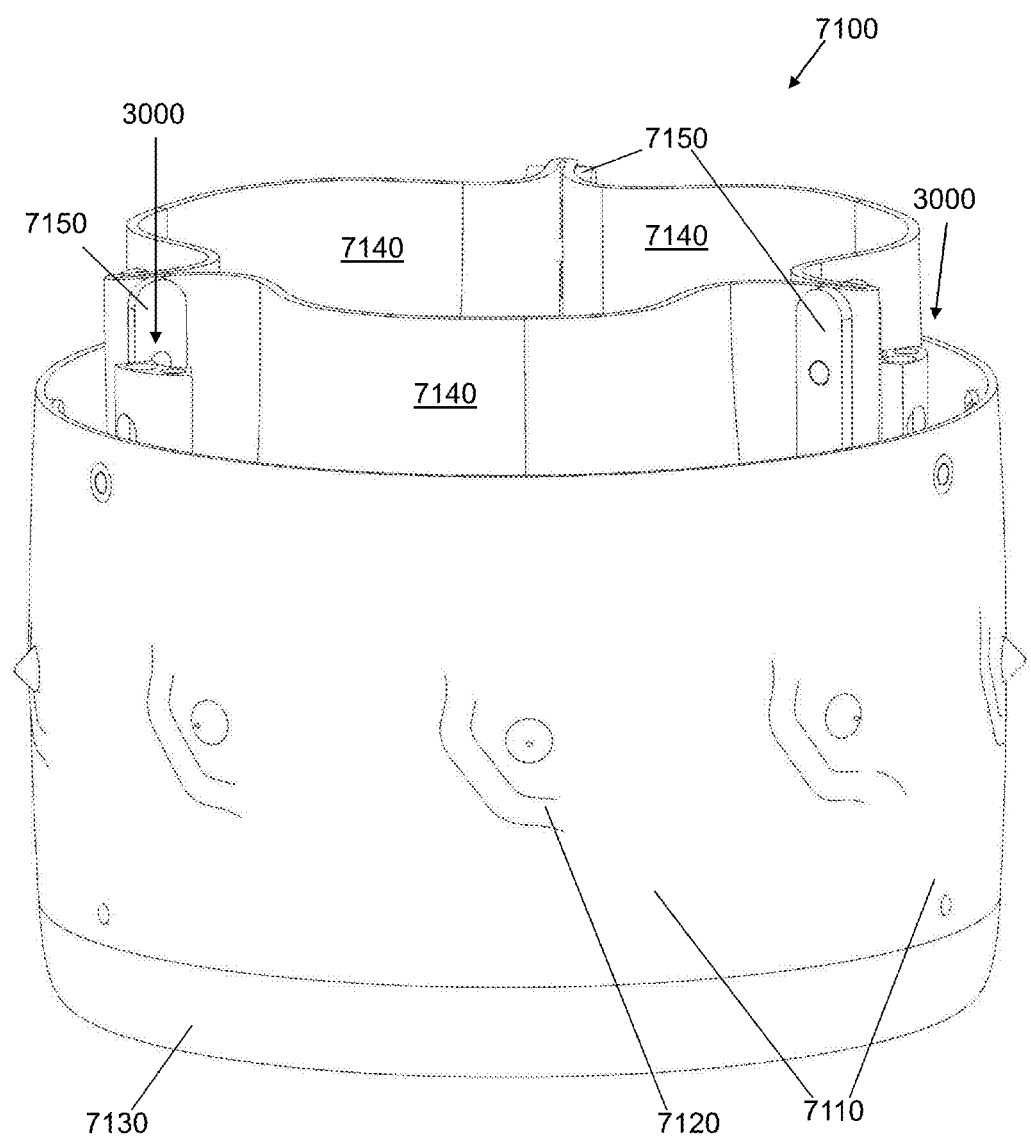
FIG. 71 is a perspective view of a side of another exemplary embodiment of a replacement aortic valve assembly according to the invention in an expanded state with the graft material partially transparent.
Figure 72:
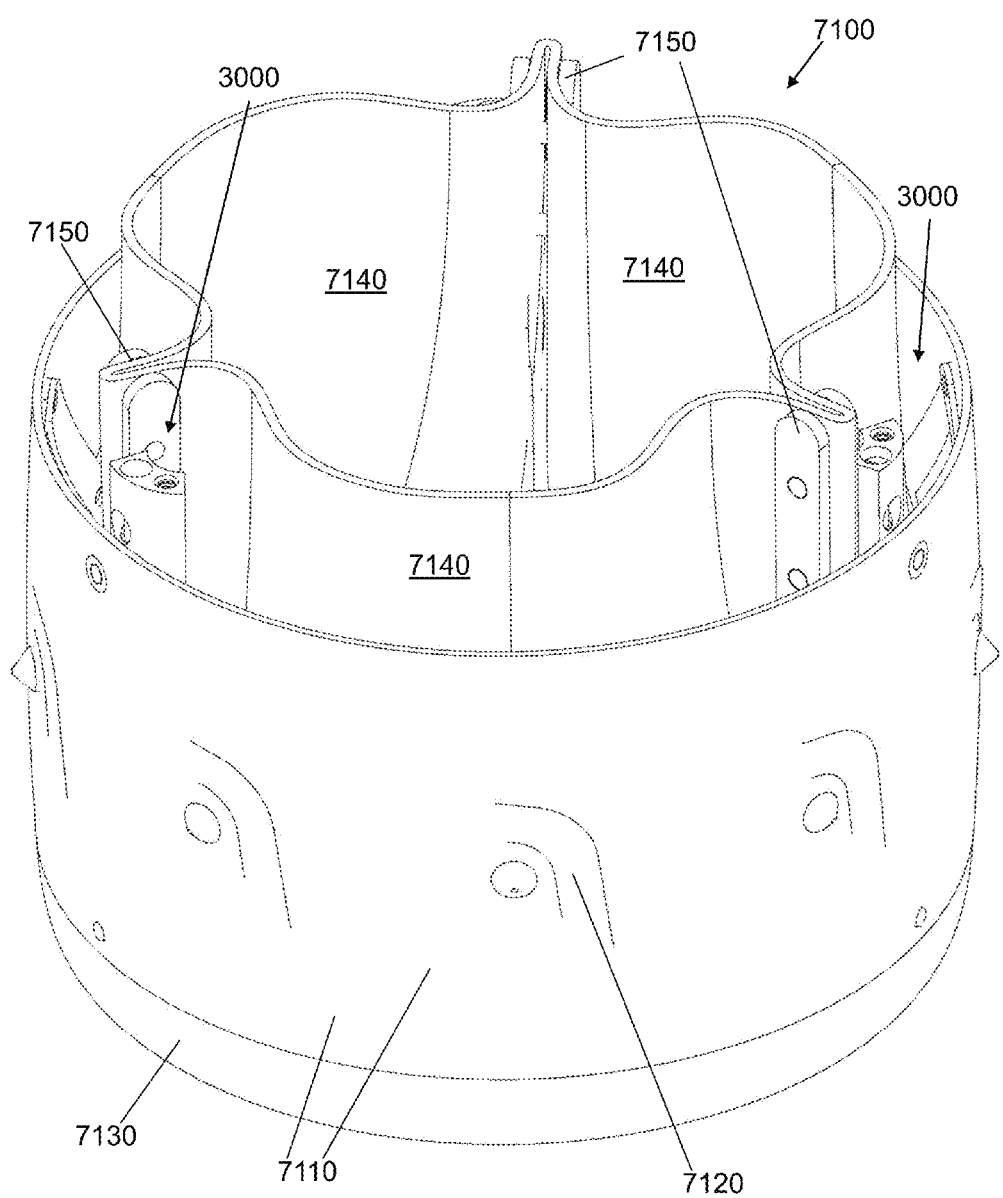
FIG. 72 is a perspective view of the replacement aortic valve assembly of FIG. 71 from above a downstream side thereof.

The progression of FIGS. 66 to 70 illustrates an exemplary implantation of the inventive aortic valve assembly 6440. Various features of the delivery system are not illustrated in these figures for reasons of clarity. Specifically, these figures show only the guidewire 6610 and the nose cone 6620 of the delivery system. FIG. 66 shows the guidewire 6610 already positioned and the aortic valve assembly 6440 in a collapsed state resting in the delivery system just distal of the nose cone 6620. In this illustration, the aortic valve assembly 6440 and nose cone 6620 are disposed in the right iliac artery. FIG. 67 depicts the aortic valve assembly 6440 and nose cone 6620 in an advanced position on the guidewire 6610 within the abdominal aorta adjacent the renal arteries. FIG. 68 shows the aortic valve assembly 6440 just adjacent the aortic valve implantation site. Finally, FIGS. 69 and 70 show the aortic valve assembly 6440 implanted in the heart before the nose cone 6620 and/or the guidewire 6610 are retracted.

The inventive delivery system and aortic valve assembly 6440 eliminate each of the disadvantageous features of the prior art. First, there is no need for the surgeon to manually crush the implanted prosthesis. Before the aortic valve assembly 6440 is inserted into the patient, the delivery system simply reduces the circumference of the lattice 6410 automatically and evenly to whatever diameter desired by the surgeon. The stent and valve assemblies described herein can be reduced to a loading diameter of between 4 mm and 8 mm, and, in particular, 6 mm, to fit inside a 16-20 French sheath, in particular, an 18 French or smaller delivery sheath. When the aortic valve assembly 6440 reaches the implantation site, the surgeon causes the delivery system to evenly and automatically expand the aortic valve assembly 6440. As this expansion is slow and even into the implant position, it is gentle on calcification at the implant site. Likewise, the even expansion allows the lattice structure to assume the native, non-circular perimeter of the implant site not only due to the way the delivery system expands the lattice assembly 6410, but also because the hinged connections of each of the struts 6412 allows the lattice assembly 6410 to bend and flex naturally after implantation dependent upon the corresponding tissue wall adjacent to each pivoting strut 6412 (assumption of the natural shape of the implantation wall also occurs with the alternative non-hinged embodiments disclosed herein). Due to these facts, a better seating of the implant occurs, which leads axiomatically to a better perivalvular seal. The inventive delivery system sizes the prosthesis precisely, instead of the gross adjustment and installation present in the prior art. Another significant disadvantage of the prior art is that a balloon is used within the central opening of the valve to expand the valve, thus completely occluding the aorta and causing tremendous backpressure on the heart, which can be hazardous to the patient. The valves described herein, in contrast, remain open during deployment to, thereby, allow continuous blood flow during initial deployment and subsequent repositioning during the procedure and also start the process of acting as a valve even when the implant is not fully seated at the implantation site.

Significantly, prior art TAVI systems require a laborious sizing process that requires the replacement valve to be sized directly to the particular patient's annulus, which sizing is not absolutely correct. With the delivery system and aortic valve assemblies described herein, however, the need to size the valve assembly beforehand no longer exists.

The aortic valve assembly 6440 is configured to have a valve leaf overlap 6542 (see FIG. 65) that is more than sufficient when the aortic valve assembly 6440 is at its greatest diameter and, when the aortic valve assembly 6440 is smaller than the greatest diameter, the valve leaf overlap 6542 merely increases accordingly. An exemplary range for this overlap can be between 1 mm and 3 mm.

A further significant advantage not provided by prior art TAVI systems is that the inventive delivery system and valve assembly can be expanded, contracted, and re-positioned as many times operatively as desired, but also the inventive delivery system and valve assembly can be re-docked postoperatively and re-positioned as desired. Likewise, the learning curve for using the inventive delivery system and valve assembly is drastically reduced for the surgeon because an automatic control handle (described in further detail below) performs each operation of extending, retracting, adjusting, tilting, expanding, and/or contracting at a mere touch of a button (see, e.g., FIGS. 105 to 107).

Another exemplary use of the inventive lattice assembly and delivery system is for a latticework-actuated basket filter, that can be either added to the disclosed devices, systems, and methods or stand-alone. Such an embolic umbrella can perform better than, for example, the EMBOL-X® Glide Protection System produced by Edward Life-sciences. Such a filter would be attached to the docking jacks so that it expands in place automatically as the device is expanded and would be removed with the delivery system without any additional efforts on the part of the surgeon.

Figure 75:
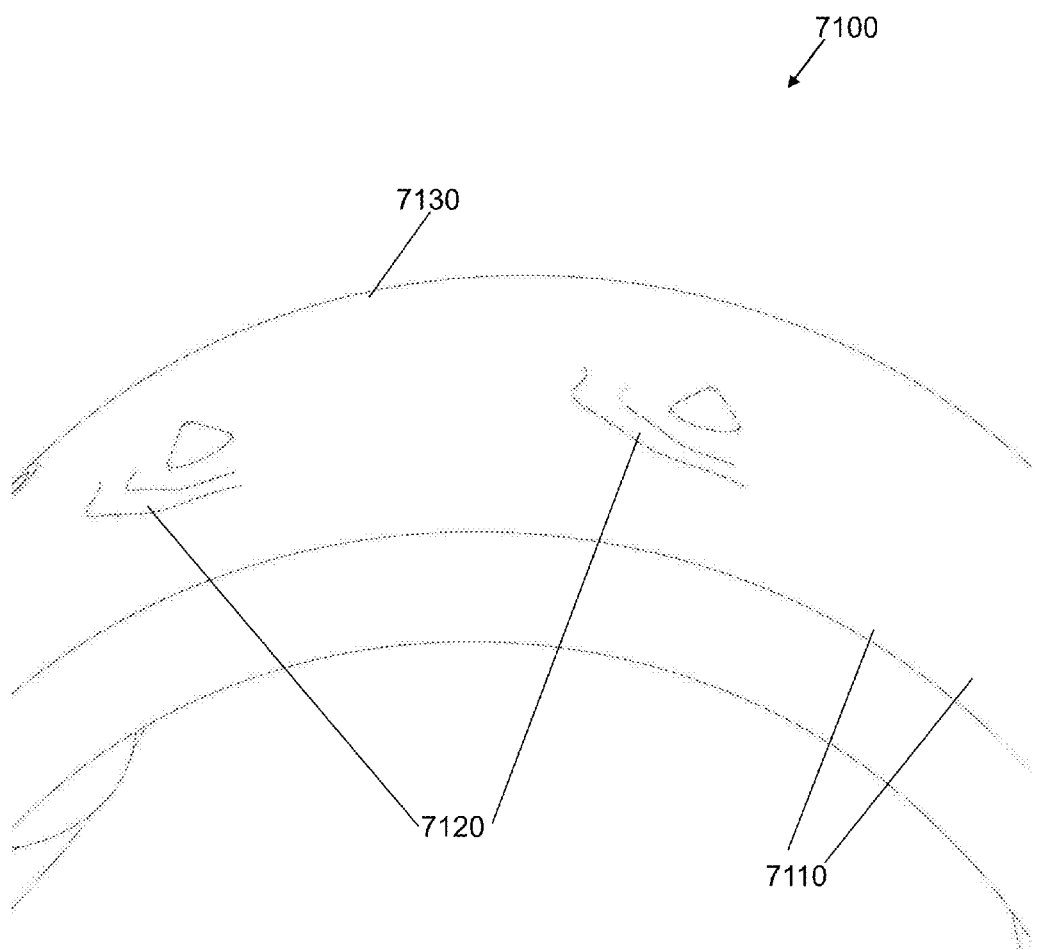
FIG. 75 is a perspective view of an enlarged portion of the replacement aortic valve assembly of FIG. 74.
Figure 76:
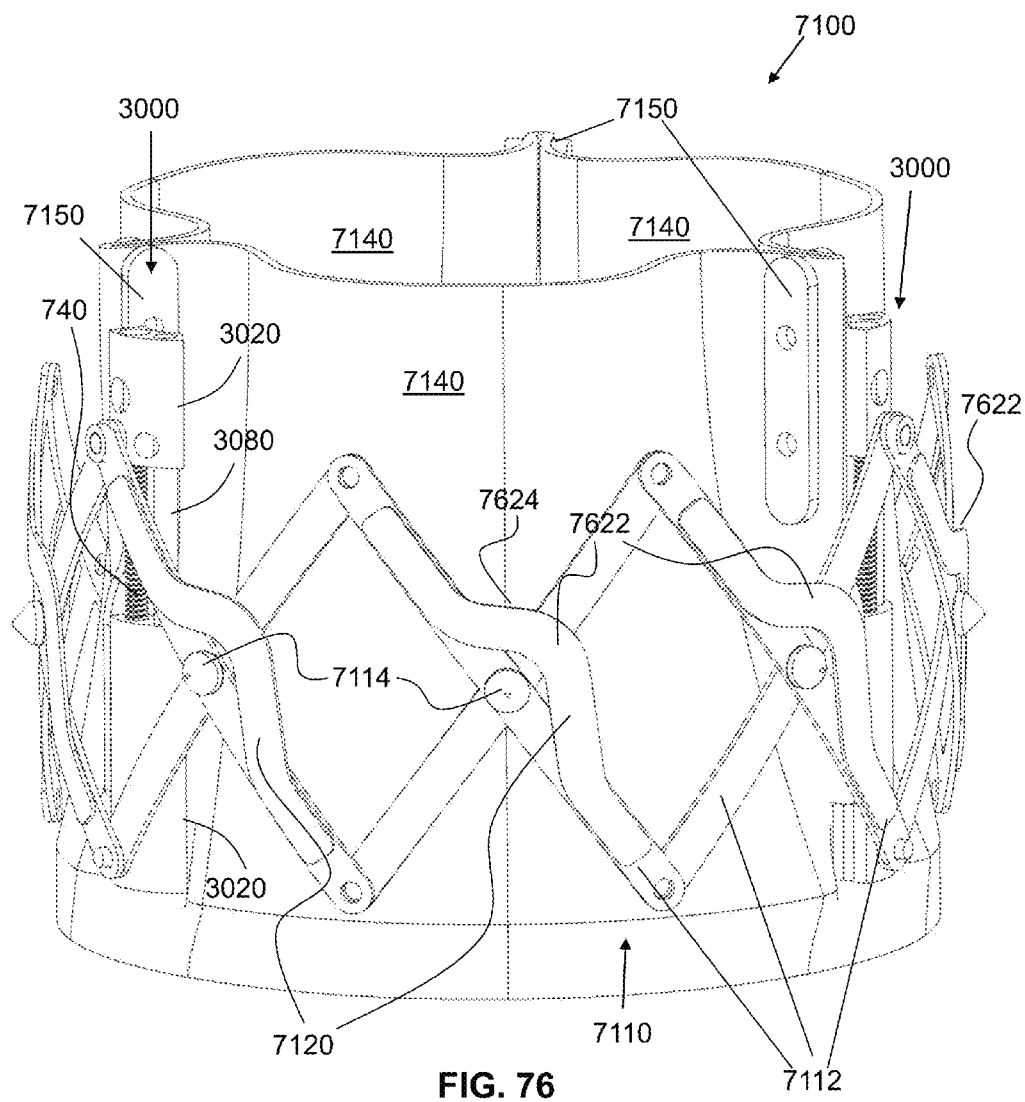
FIG. 76 is a perspective view of the replacement aortic valve assembly of FIG. 71 from a side thereof with the graft material removed.
Figure 77:
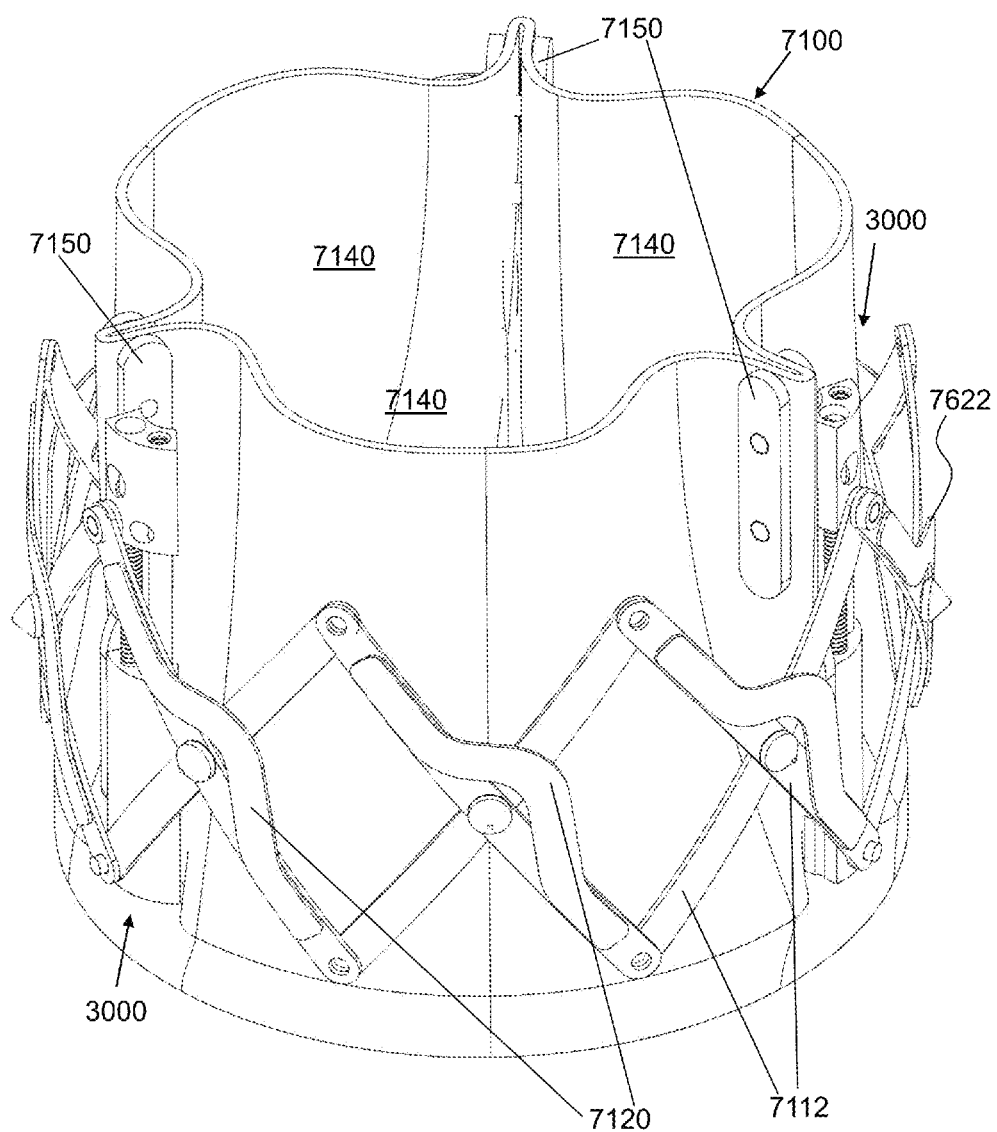
FIG. 77 is a perspective view of the replacement aortic valve assembly of FIG. 76 from above a downstream side thereof.

Another exemplary embodiment of a replacement heart valve assembly 7100 according to the invention is shown in FIGS. 71 to 83. Even though the exemplary embodiment is shown for an aortic valve, the invention is not limited thereto. This embodiment is equally applicable to pulmonary, mitral and tricuspid valves with appropriate changes to the valve leaflets, for example. The replacement heart valve assembly 7100 shown in various views in FIGS. 71 to 75 is comprised of a stent lattice 7110, graft enclosures 7120, jack assemblies 3000, graft material 7130, valve leaflets 7140, and commisure plates 7150. Operation and construction of the replacement heart valve assembly 7100 is explained with reference to FIGS. 76 to 83 with various views therein having the graft material 7130 and/or the valve leaflets 7140 removed. In FIGS. 75 and 76, the replacement heart valve assembly 7100 is in an expanded state (when used herein, "expanded state" does not mean that the state shown is the greatest expanded state of the prosthesis; it means that the prosthesis is expanded sufficiently enough to be sized for an implantation in some anatomic site) such that it accommodates to the natural geometry of the implantation site. With the graft material removed (see, e.g., FIG. 76), the structure around the three valve leaflets 7140 is easily viewed. The proximal and distal drive blocks 3020, 3010 have internal configurations and the support rod 3080, the drive screw 740, and the distal drive screw coupler part 3052 disposed therein.

The stent lattice 7110 is similar to previous embodiments described herein except for the center pivot points of each strut 7112 of the stent lattice 7110 and the graft enclosures 7120. In the exemplary embodiment shown, the center pivot points are not merely pivoting connections of two struts 7112 of the stent lattice 7110. In addition, the outer-most circumferential surface of the pivoting connection comprises a tissue anchor 7114, for example, in the form of a pointed cone in this exemplary embodiment. Other external tissue anchoring shapes are equally possible, including spikes, hooks, posts, and columns, to name a few. The exterior point of the tissue anchor 7114 supplements the outward external force imposed by the actively expanded stent lattice 7110 by providing structures that insert into the adjacent tissue, thereby further inhibiting migration and embolism.

The graft enclosures 7120 also supplement the outward external force imposed by the actively expanded stent lattice 7110 as explained below. A first characteristic of the graft enclosures 7120, however, is to secure the graft material 7130 to the replacement heart valve assembly 7100. The graft material 7130 needs to be very secure with respect to the stent lattice 7110. If the graft material 7130 was attached, for example, directly to the outer struts 7112 of the stent lattice 7110, the scissoring action that the adjacent struts 7112 perform as the stent lattice 7110 is expanded and contracted could adversely affect the security of the graft material 7130 thereto—this is especially true if the graft material 730 was sewn to the outer struts 7112 and the thread passed therethrough to the inside surface of the outer strut 7112, against which the outer surface of the inner strut 7112 scissors in use. Accordingly, the graft enclosures 7120 are provided at a plurality of the outer struts 7112 of the stent lattice 7110 as shown in FIGS. 71 to 87. Each graft enclosure 7120 is fixedly attached at one end of its ends to a corresponding end of an outer strut 7112. Then, the opposing, free end of the graft enclosure 7120 is woven through the inner side of the graft material 7130 and then back from the outer side of the graft material 7130 to the inner side thereof as shown in FIGS. 71 to 75, for example. The opposing, free end of the graft enclosure 7120 is fixedly attached to the other end of the outer strut 7112. This weaving reliably secures the outer circumferential side of the graft material 7130 to the stent lattice 7110.

As mentioned above, graft enclosures 7120 simultaneously supplement the outward external force imposed by the actively expanded stent lattice 7110 with edges and protrusions that secure the replacement heart valve assembly 7100 at the implantation site. More specifically, the graft enclosures 7120 are not linear as are the exemplary embodiment of the outer struts 7112 of the stent lattice 7110. Instead, they are formed with a central offset 7622, which can take any form and, in these exemplary embodiments, are wave-shaped. This central offset 7622 first allows the graft enclosure 7120 to not interfere with the tissue anchor 7114. The central offset 7622 also raises the central portion of the graft enclosure 7120 away from the stent lattice 7110, as can be seen, for example, to the right of FIGS. 76 and 77 and, in particular, in the views of FIGS. 82 and 83. The radially outward protrusion of the central offset 7622 inserts and/or digs into adjacent implantation site tissue to, thereby, inhibit any migration or embolism of the replacement heart valve assembly 7100. By shaping the central offset 7622 appropriately, a shelf 7624 is formed and provides a linear edge that traverses a line perpendicular to the flow of blood within the replacement heart valve assembly 7100. In the exemplary embodiment of the central offset 7622 shown in FIGS. 76, 77, and 79 to 81, the shelf 7624 is facing downstream and, therefore, substantially inhibits migration of the replacement heart valve assembly 7100 in the downstream direction when exposed to systolic pressure. Alternatively, the central offset 7622 can be shaped with the shelf 7624 is facing upstream and, therefore, substantially inhibits migration of the replacement heart valve assembly 7100 in the upstream direction when exposed to diastolic pressure. The graft material needs to be able to say intimately attached to the lattice throughout a desired range of terminal implantable diameters. To accomplish this, the graft material is made from a structure of material that moves in a fashion like that of the lattice. That is to say, as its diameter increases, its length decreases. This kind of movement can be accomplished with a braid of yarns or through the fabrication of graft material where its smallest scale fibers are oriented similarly to a braid, allowing them to go through a scissoring action similar to the lattice. One exemplary embodiment of the material is a high end-count braid made with polyester yarns (e.g., 288 ends using 40-120 denier yarn). This braid can, then, be coated with polyurethane, silicone, or similar materials to create stability and reduce permeability by joining all the yarns together. Likewise, a spun-fiber tube can be made with similar polymers forming strands from approximately 2-10 microns in diameter. These inventive graft fabrication methods provide for a material that will be about 0.005" to 0.0015" (0.127 mm to 0.381 mm) thick and have all the physical properties necessary. A thin material is desirable to reduce the compacted diameter for easier introduction into the patient. This material is also important in a stent graft prosthesis where the lattice is required to seal over a large range of possible terminal diameters. The adjustable material is able to make the transition from the final terminal diameter of the upstream cuff to the main body of the graft.

Figure 73:
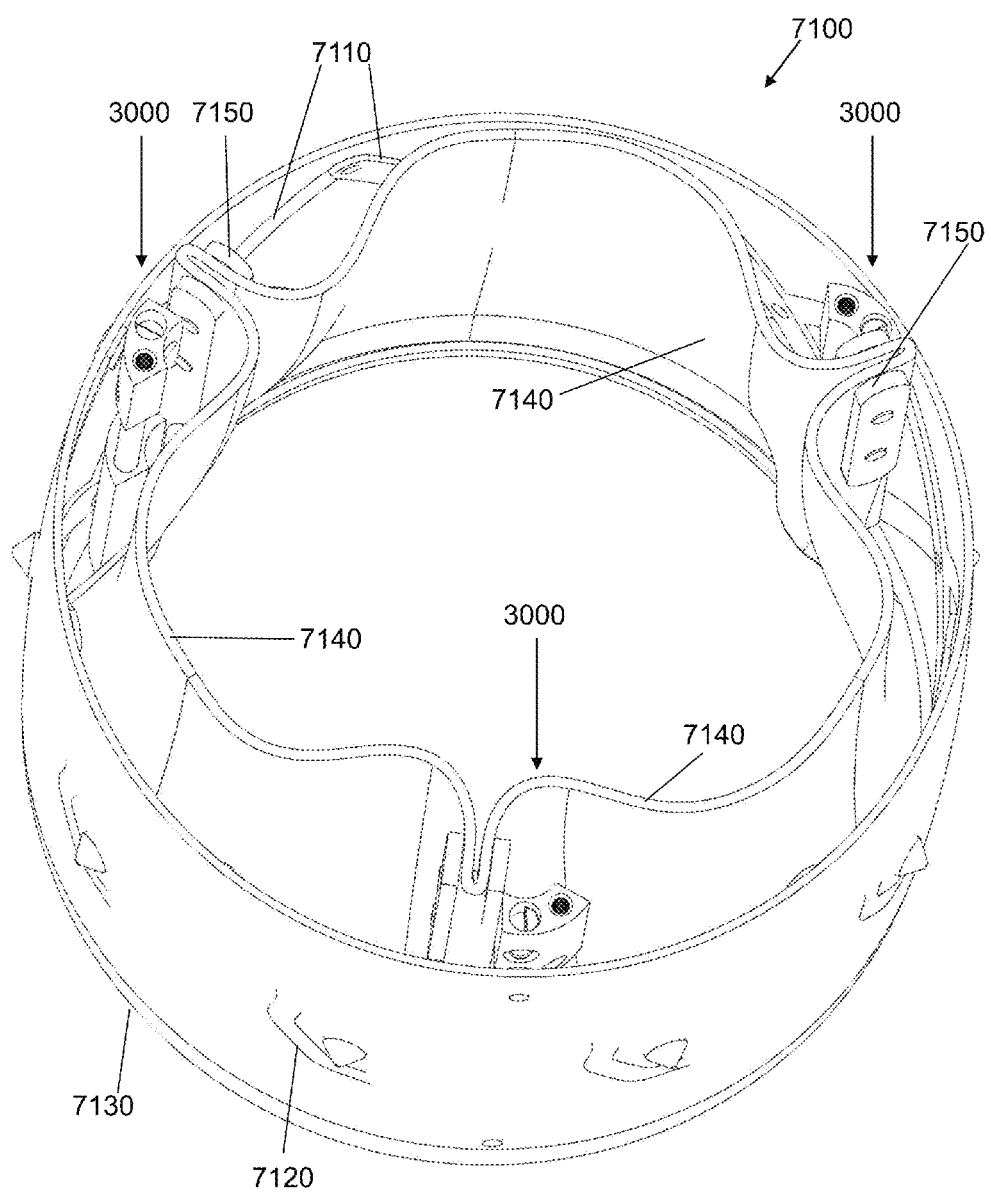
FIG. 73 is a perspective view of the replacement aortic valve assembly of FIG. 71 from above a downstream end thereof.
Figure 74:
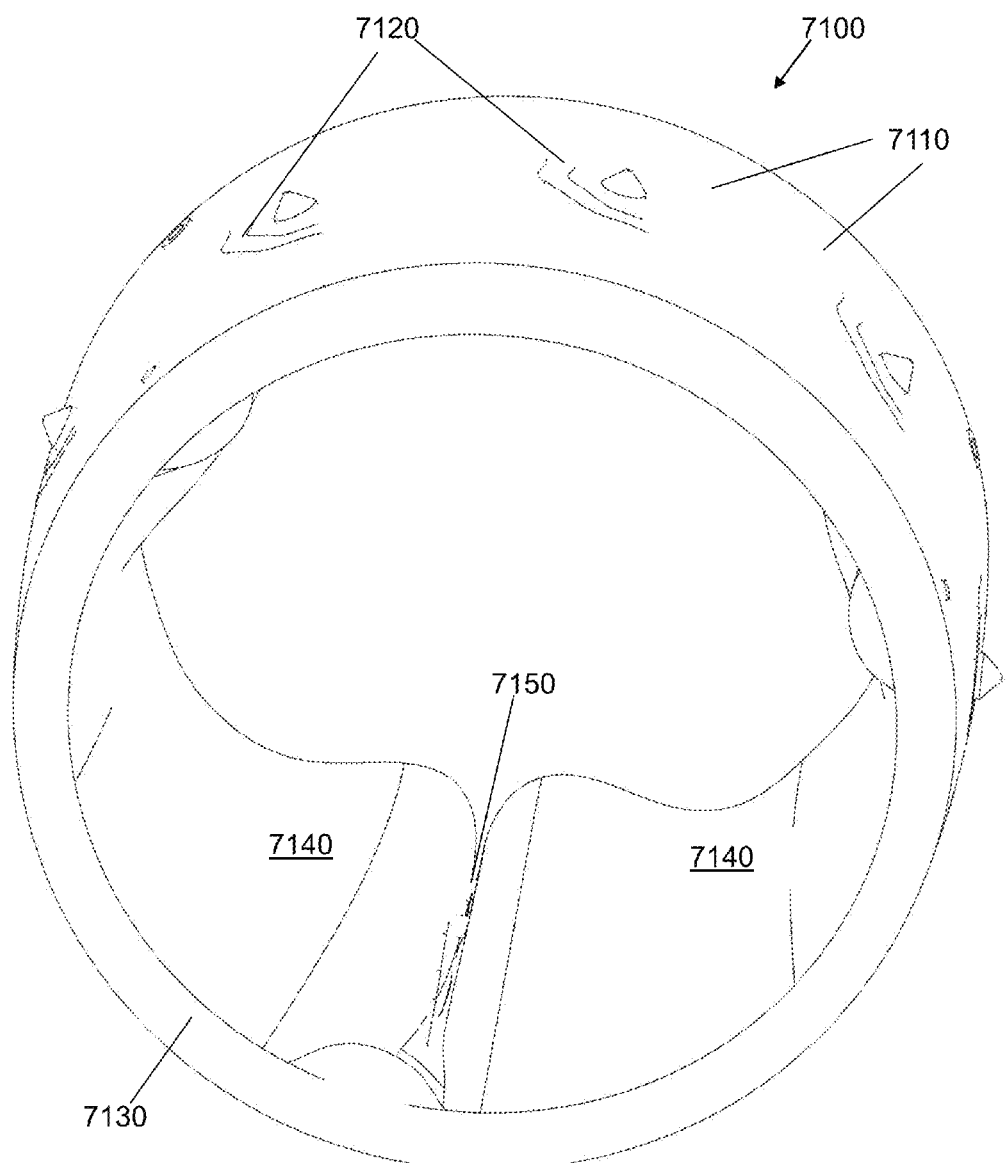
FIG. 74 is a perspective view of the replacement aortic valve assembly of FIG. 71 from below an upstream end thereof.
Figure 82:
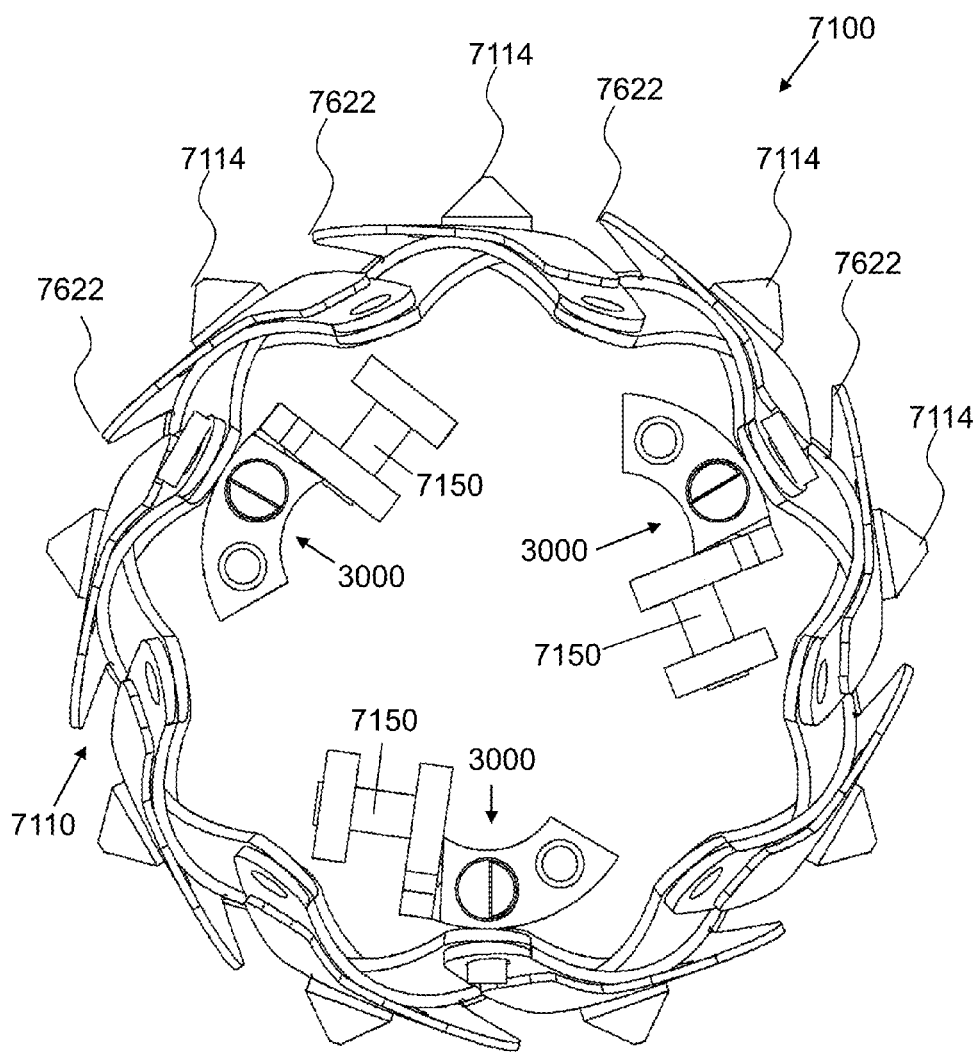
FIG. 82 is a downstream plan view of the replacement aortic valve assembly of FIG. 79 in an intermediate expanded state.
Figure 83:
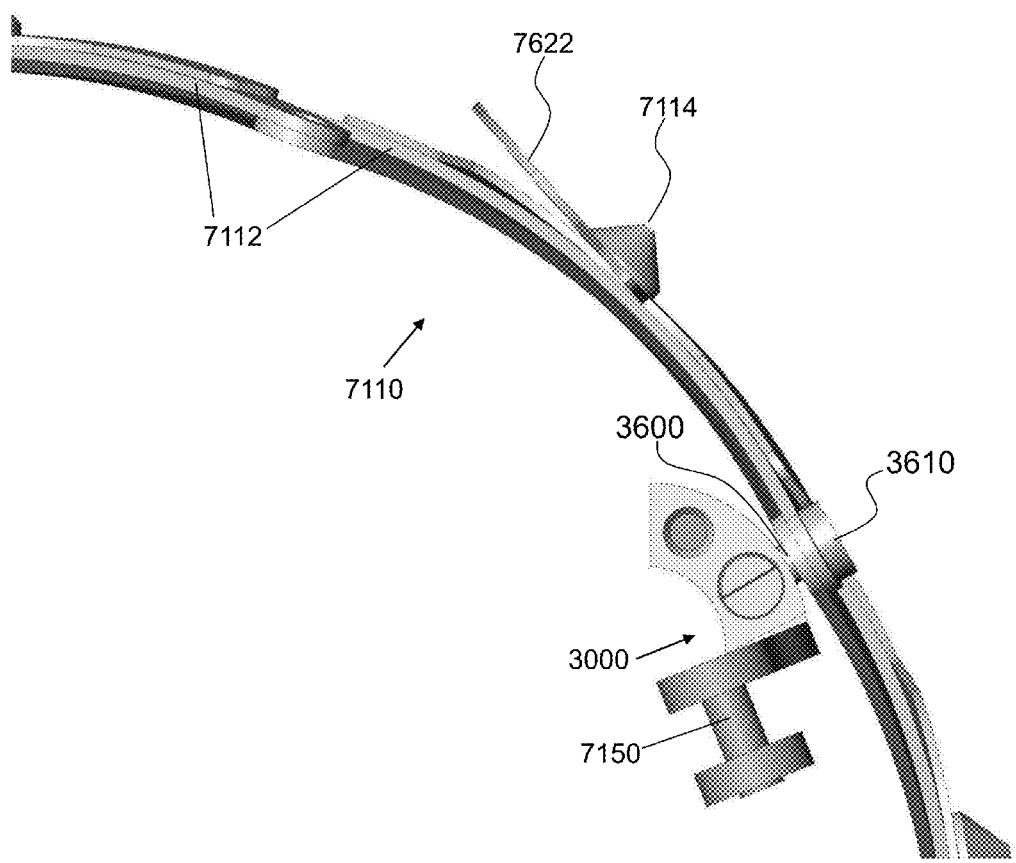
FIG. 83 is an enlarged downstream plan view of a portion of the replacement aortic valve assembly of FIG. 79 in an expanded state.

As best shown in FIG. 73, the valve leaflets 7140 are connected by commisure plates 7150 to the jack assemblies 3000. Fixed connection of the commisure plates 7150 to the jack assemblies 3000 is best shown in FIGS. 82 and 83. Each valve leaflet 7140 is connected between two adjacent commisure plates 7150. Each commisure plate 7150 is comprises of two vertically disposed flat plates having rounded edges connected, for example, by pins projecting orthogonally to the flat plates. Pinching of the flat plates against the two adjacent valve leaflets 7140 securely retains the valve leaflets 7140 therein while, at the same time, does not form sharp edges that would tend to tear the captured valve leaflets 7140 therein during prolonged use. This configuration, however, is merely exemplary. This could be replaced with a simpler rod design around which the leaflets are wrapped and stitched into place.

Figure 78:
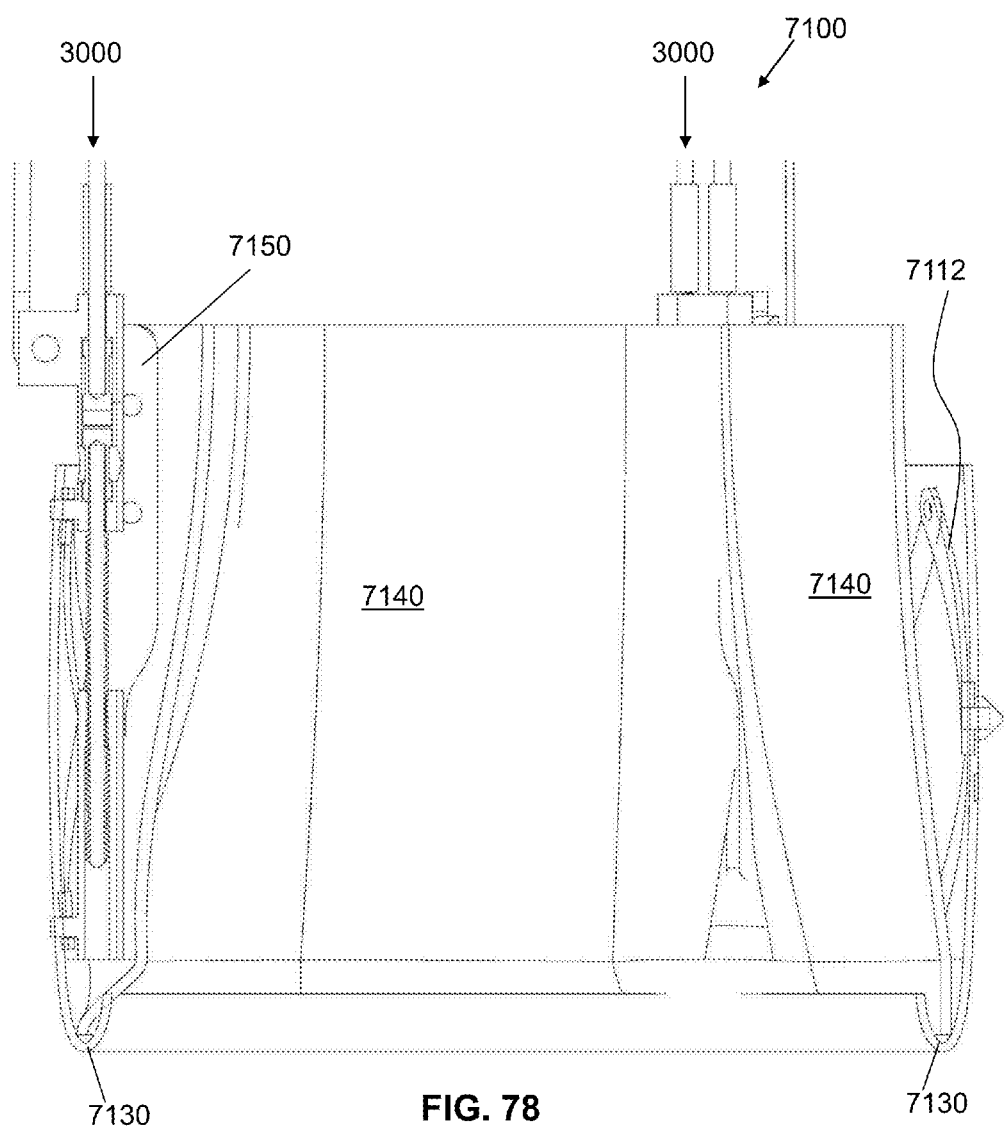
FIG. 78 is a side elevation, vertical cross-sectional view of the replacement aortic valve assembly of FIG. 76.

Even though each valve leaflet 7140 can be a structure separate from the other valve leaflets 7140, FIGS. 71 to 78 illustrate the three leaflets 7140 as one piece of leaf-forming material pinched, respectively, between each of the three sets of commisure plates 7150 (the material can, alternatively, pinch around the commisure plate or plates). The upstream end of the valve leaflets 7140 must be secured for the replacement heart valve assembly 7100 to function. Therefore, in an exemplary embodiment, the upstream end of the graft material 7130 is wrapped around and fixedly connected to the replacement heart valve assembly 7100 at the upstream side of the valve leaflets 7140, as shown in FIG. 78. In such a configuration, the upstream edge of the valve leaflets 7140 is secured to the graft material 7130 entirely around the circumference of the stent lattice 7110. Stitches can pass through the two layers of graft and the upstream edge of the leaflet material to form a hemmed edge.

Figure 79:
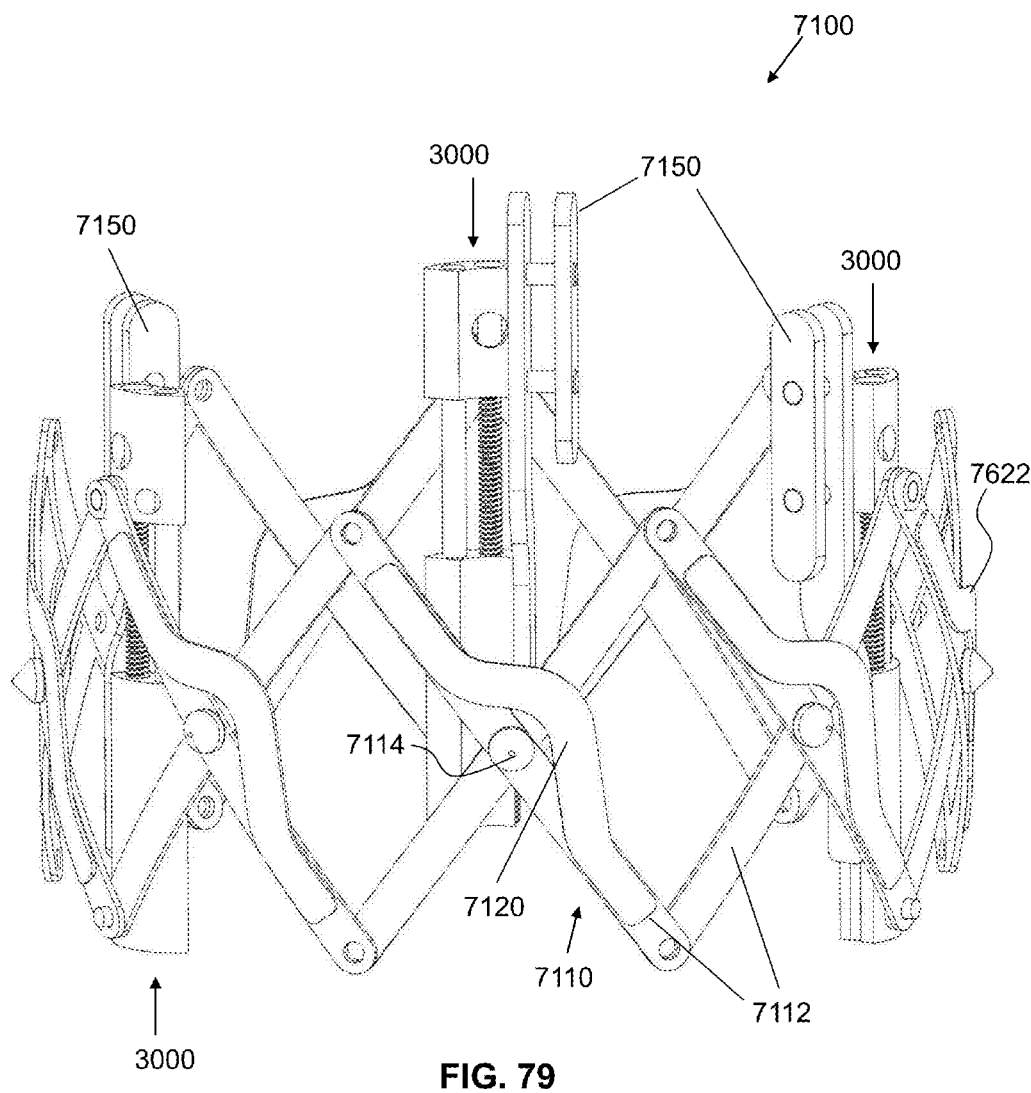
FIG. 79 is a perspective view of the replacement aortic valve assembly of FIG. 76 from a side thereof with the valve material removed, with the stent lattice in an expanded state.
Figure 80:
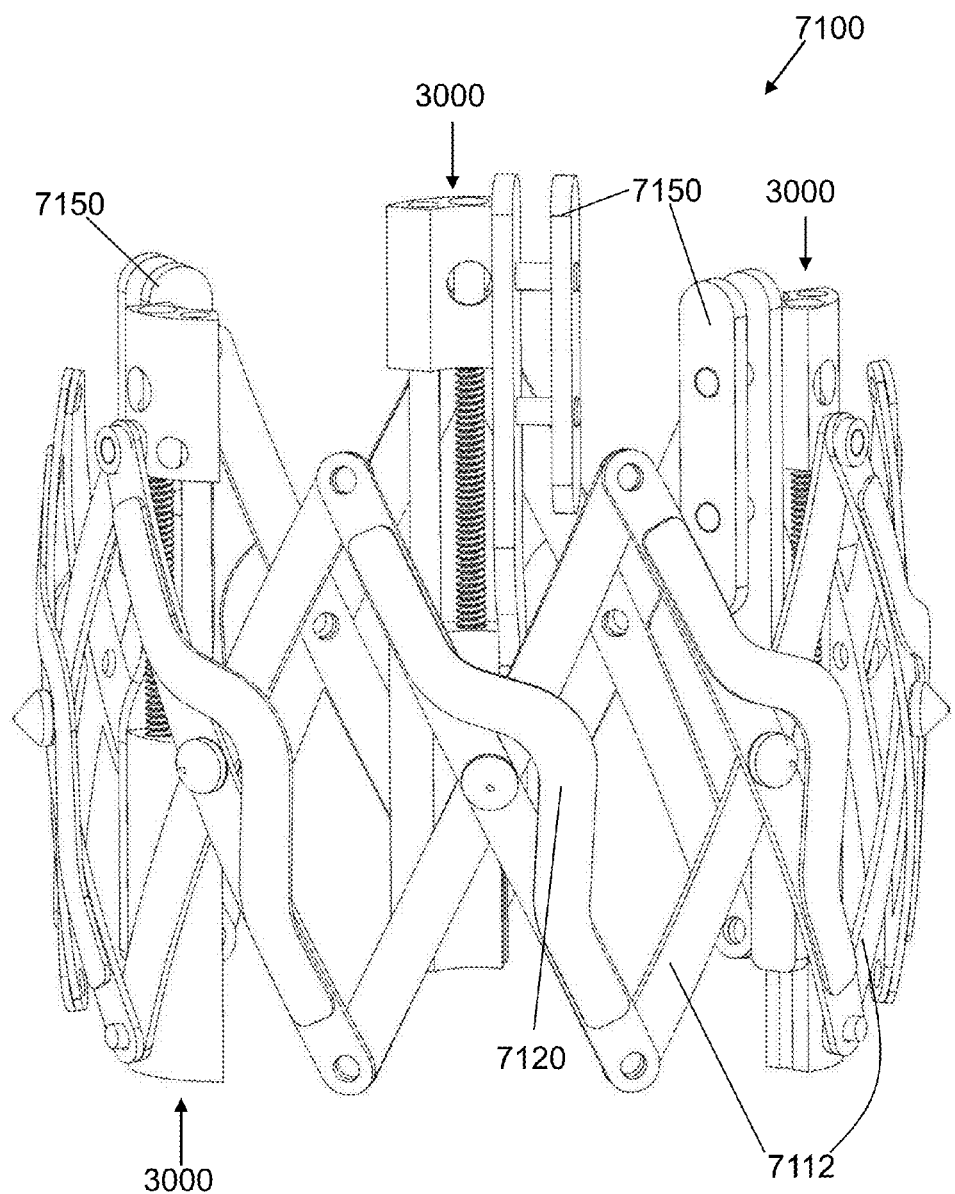
FIG. 80 is a perspective view of the replacement aortic valve assembly of FIG. 79 with the stent lattice in an intermediate expanded state.
Figure 81:
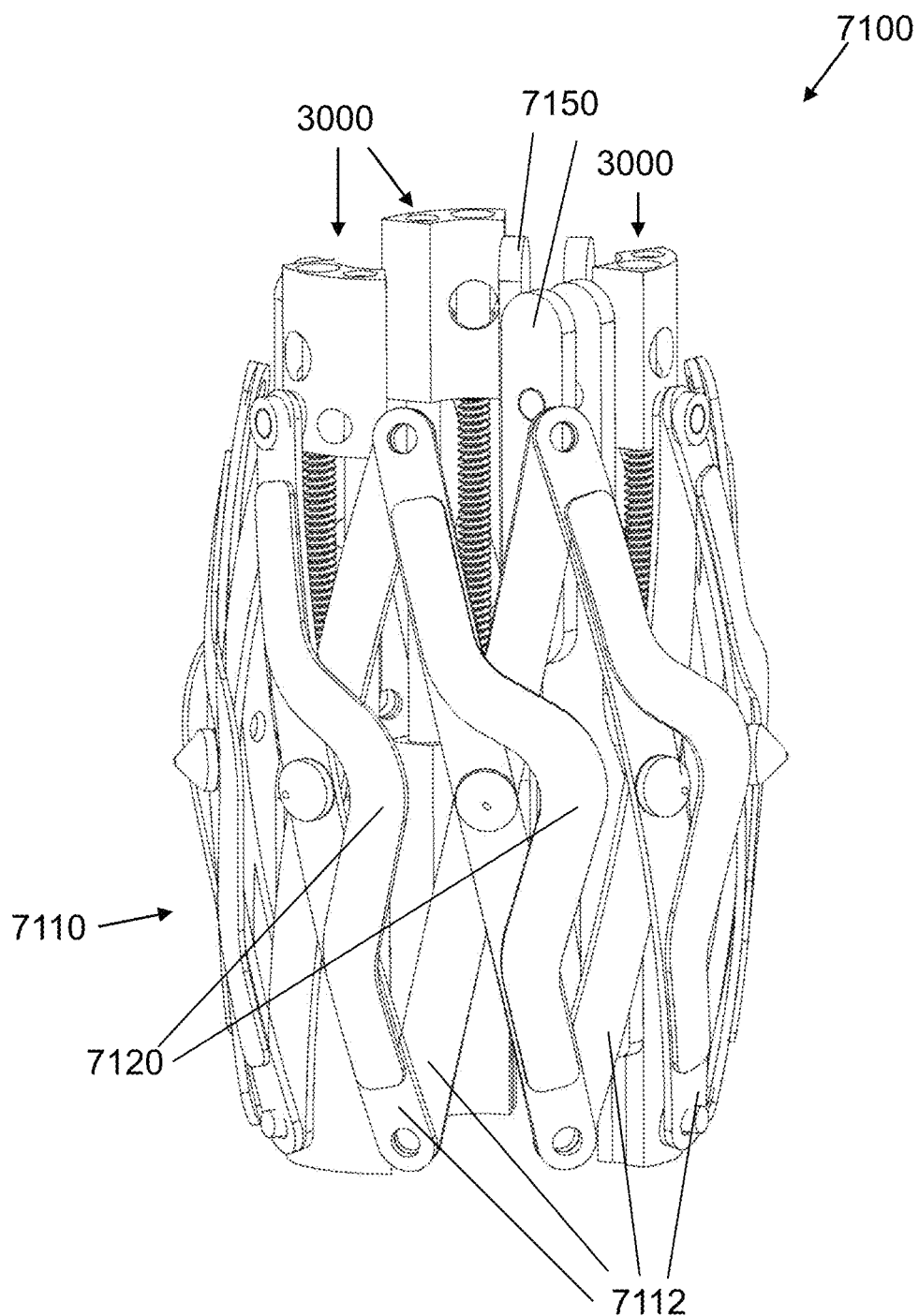
FIG. 81 is a perspective view of the replacement aortic valve assembly of FIG. 79 with the stent lattice in an almost contracted state.

FIGS. 79 to 81 show the stent lattice 7110 in various expanded and contracted states with both the graft material 7130 and the valve leaflets 7140 removed. FIG. 79 illustrates the stent lattice 7110 and jack assemblies 3000 in an expanded state where the tissue anchor 7114 and the central offset 7622 protrude radially out from the outer circumferential surface of the stent lattice 7110 such that the stent lattice 7110 accommodates to the natural geometry of the implantation site. FIG. 80 illustrates the stent lattice 7110 and the jack assemblies 3000 in an intermediate expanded state and FIG. 81 illustrates the stent lattice 7110 and the jack assemblies 3000 in a substantially contracted state.

Figure 84:
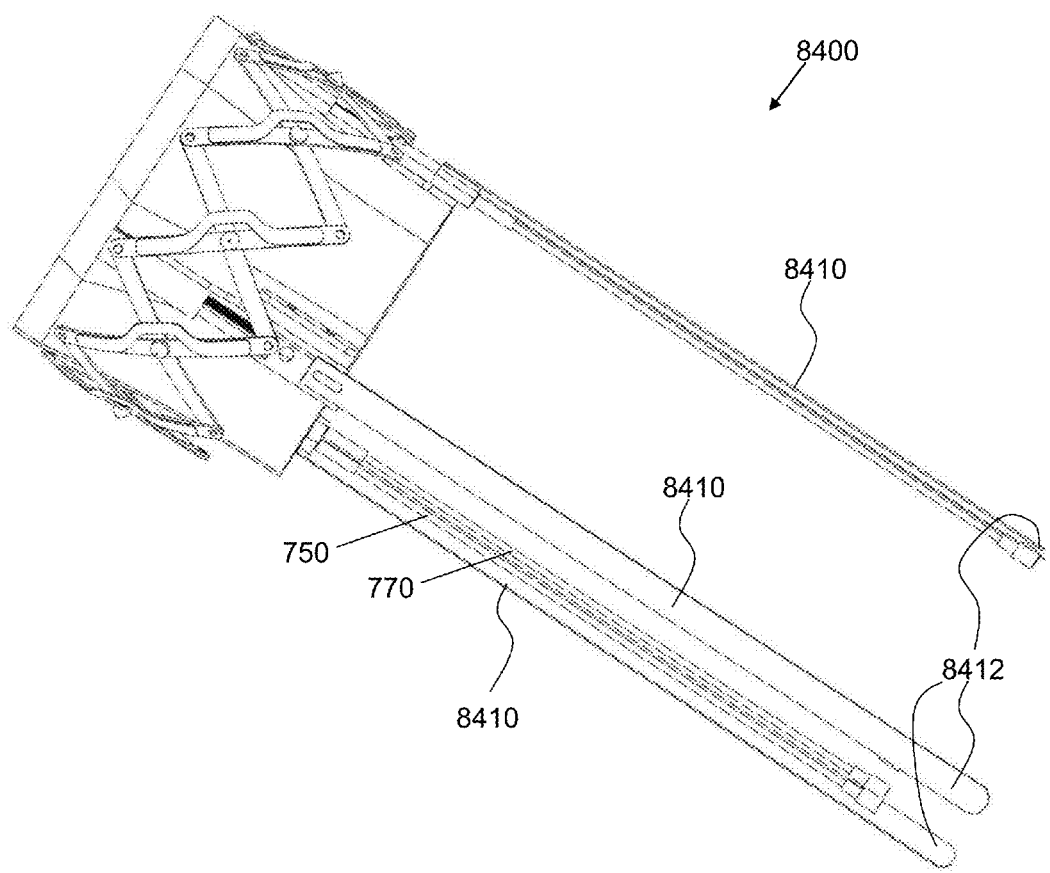
FIG. 84 is a side elevational view of the replacement aortic valve assembly of FIG. 79 in an expanded state, with graft material removed, and with distal portions of an exemplary embodiment of a valve delivery system.
Figure 85:
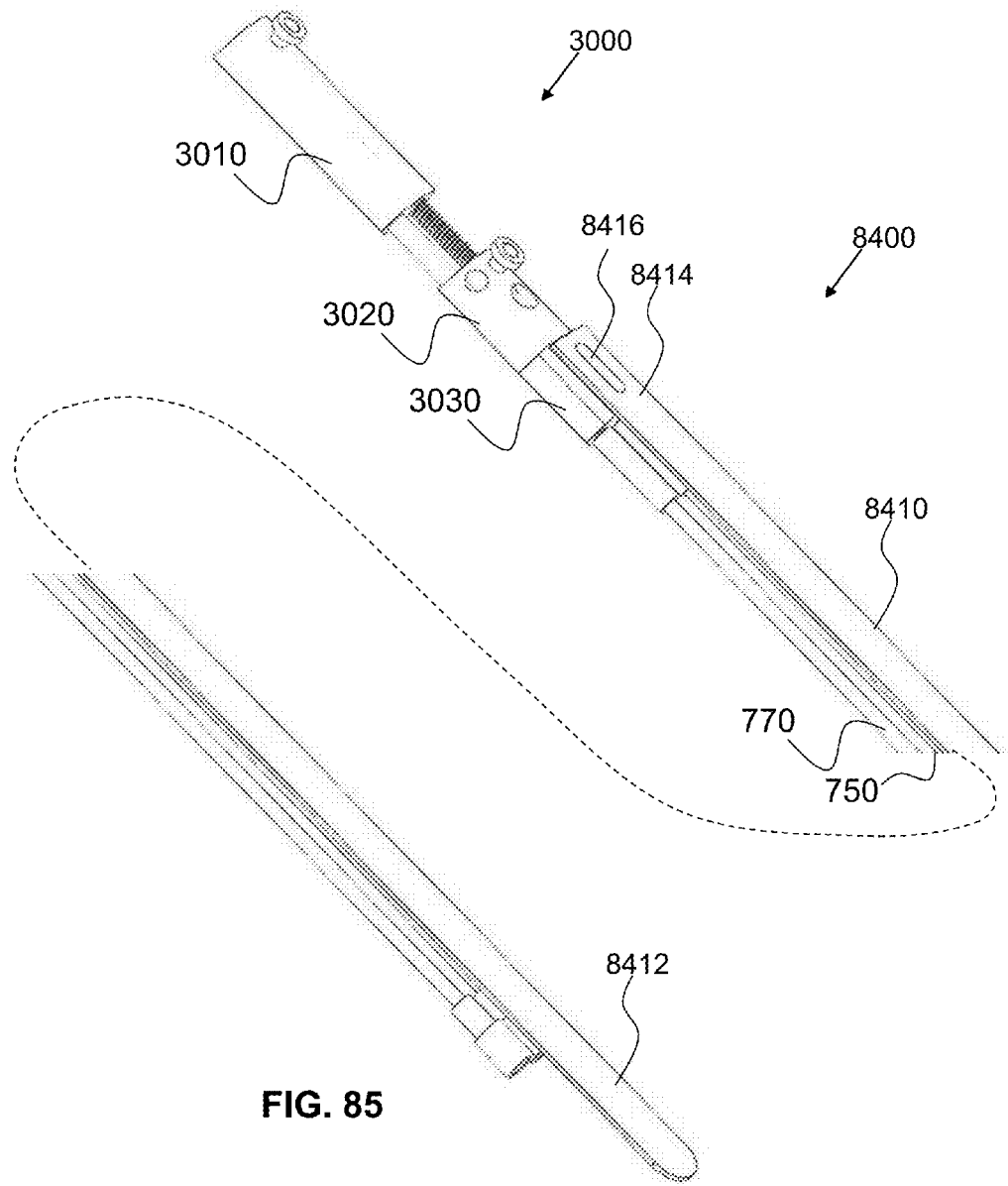
FIG. 85 is a perspective view of an exemplary embodiment of a jack assembly of the replacement aortic valve assembly of FIG. 84 from a side thereof with the valve delivery system sectioned.

FIGS. 84 and 85 show an exemplary embodiment of a support system 8400 of the delivery system and method according to the invention for both supporting the jack assemblies 3000 and protecting the various control wires 750, 770, 2182, 3098 of the jack assemblies 3000. In these figures, the support bands 8410 are shown as linear. This orientation is merely due to the limitations of the computer drafting software used to create the figures. These support bands 8410 would only be linear as shown when unconnected to the remainder of the delivery system for the replacement heart valve assembly 7100. When connected to the distal end of the delivery system, as diagrammatically shown, for example, in FIGS. 1, 3, 4, and 9 with a wire-guide block 116, all control wires 750, 770, 2182, 3098 will be directed inwardly and held thereby. Similarly, the proximal ends 8412 of the support bands 8410 will be secured to the wire-guide block 116 and, therefore, will bend radially inward. In the exemplary embodiment of the support bands 8410 shown in FIGS. 84 and 85, the distal ends 8414 thereof are fixedly secured to the disconnector drive block 3030 by an exemplary hinge assembly 8416. In this exemplary embodiment, therefore, the support bands 8410 are of a material and thickness that allows the delivery system to function. For example, while traveling towards the implantation site, the replacement heart valve assembly 7100 will traverse through a curved architecture. Accordingly, the support bands 8410 will have to bend correspondingly to the curved architecture while, at the same time, providing enough support for the control wires 750, 770, 2182, 3098 to function in any orientation or curvature of the delivery system.

Figure 86:
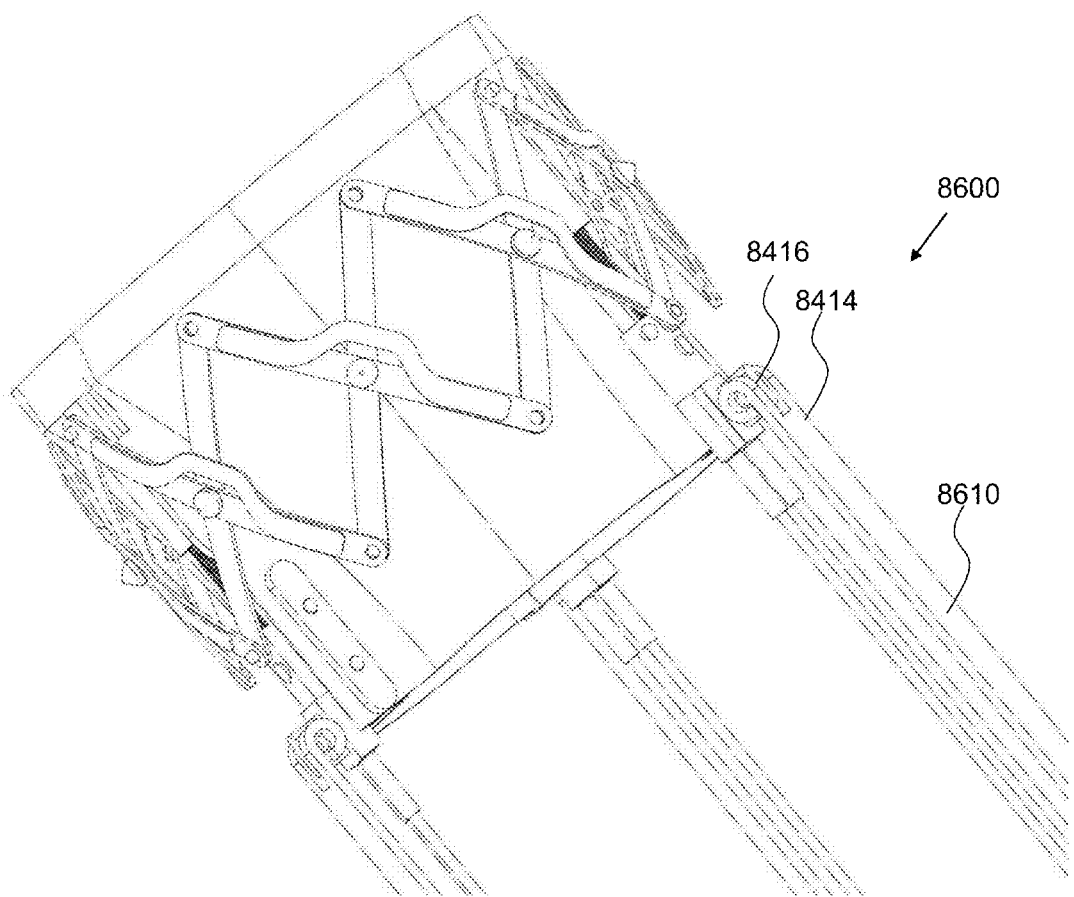
FIG. 86 is a perspective view of the replacement aortic valve assembly of FIG. 79 in an expanded state, with graft material removed, and with distal portions of another exemplary embodiment of a valve delivery system.
Figure 87:
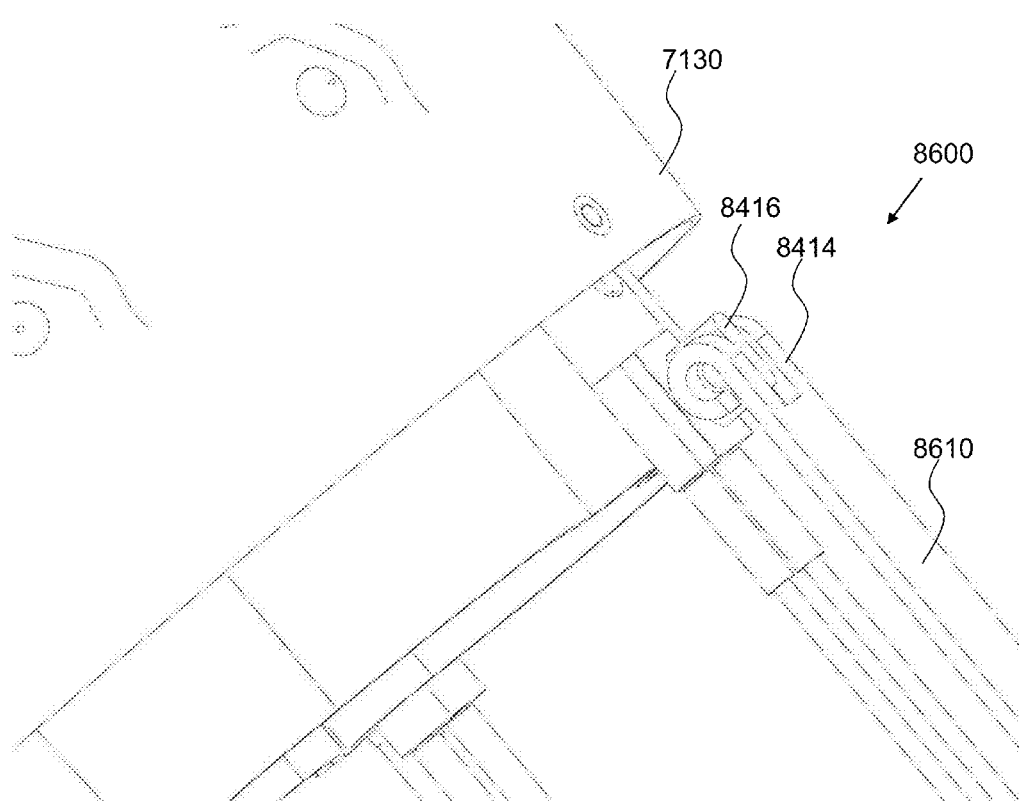
FIG. 87 is a fragmentary, enlarged perspective view of the replacement aortic valve assembly of FIG. 86 with graft material shown.
Figure 88:
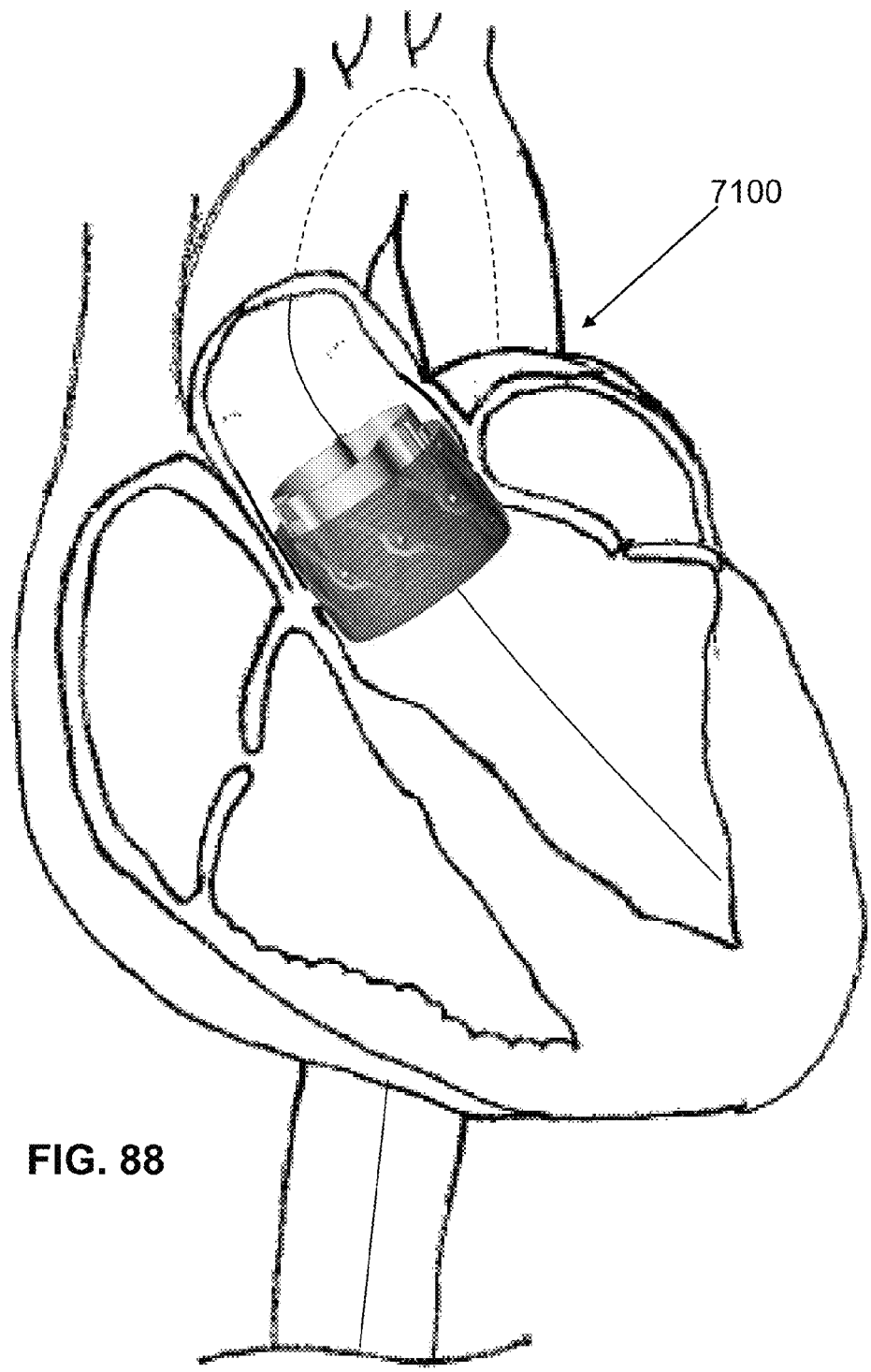
FIG. 88 is a fragmentary, enlarged, perspective view of the delivery system and the aortic valve assembly of FIG. 71 implanted at an aortic valve implantation site.
Figure 89:
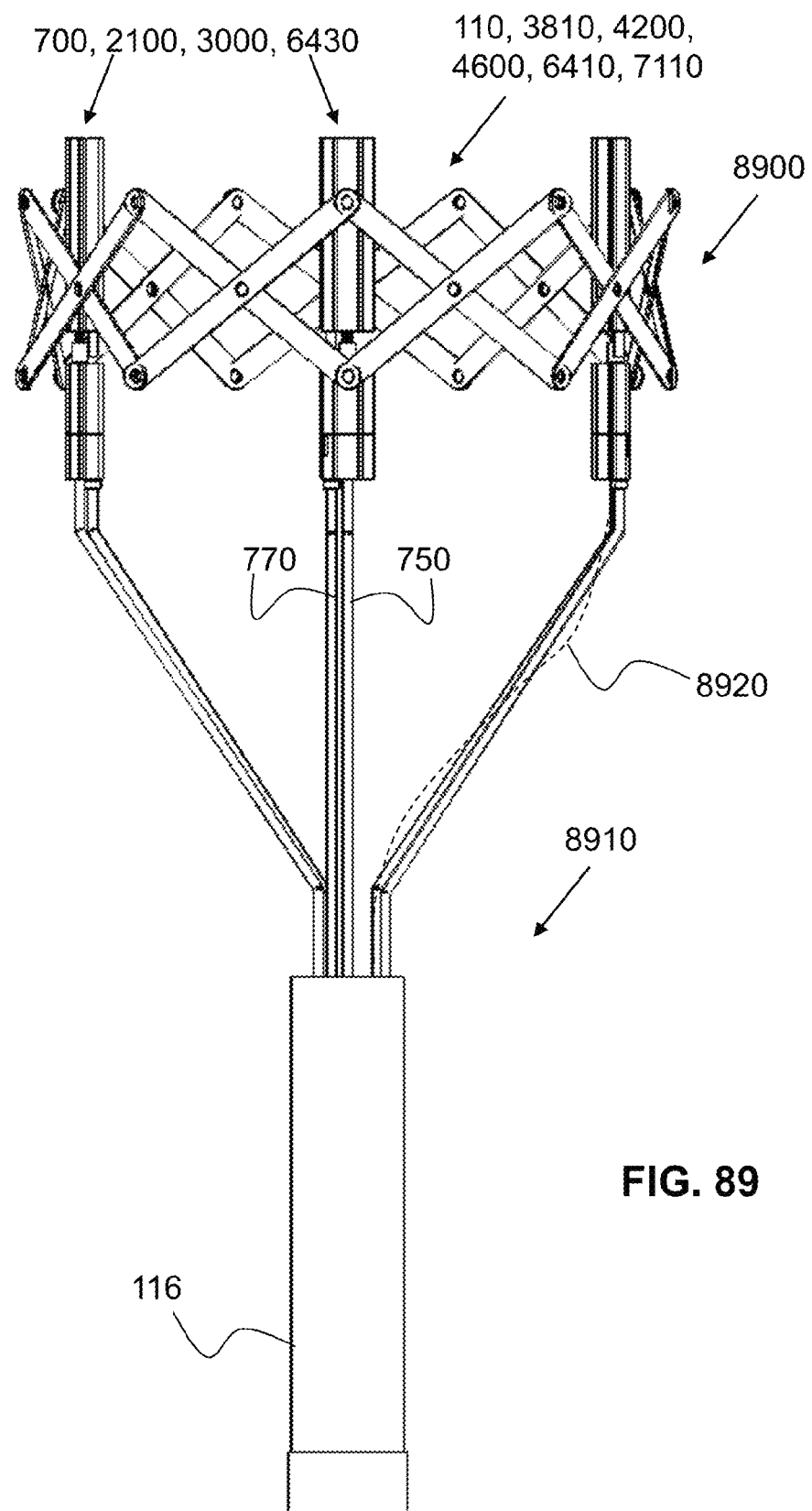
FIG. 89 is a fragmentary, side elevational view of another exemplary embodiment of an actively controllable and tiltable stent graft system according to the invention in a partially expanded state and a non-tilted state.

An alternative exemplary connection assembly of the support bands 8610 according to the invention is shown in FIGS. 86 and 87. The distal end 8614 of each support band 8610 is connected to the disconnector drive block 3030 by a hinge assembly 8416. The hinge assembly 8416, for example, can be formed by a cylindrical fork at the distal end 8614 of the support band 8610, an axle (not illustrated, and a radially extending boss of the disconnector drive block 3030 defining an axle bore for the axle to connect the cylindrical fork to the boss. In such a configuration, the support bands 8610 can have different material or physical properties than the support bands 8410 because bending movements are adjusted for with the hinge assembly 8416 instead of with the bending of the support bands 8410 themselves. The proximal end of the support bands 8610 are not shown in either FIG. 86 or 87. Nonetheless, the proximal ends can be the same as the distal end of the support bands 8610 or can be like the distal end 8614 of the support bands 8410. By pre-biasing the support bands to the outside, they can help reduce or eliminate the force required to deflect the control wires. An embodiment of the replacement heart valve assembly 7100 as an aortic valve is shown implanted within the diseased valve leaflets of a patient's heart in FIG. 88. As can be seen in this figure, the natural valve takes up some room at the midline of the replacement heart valve assembly 7100. Therefore, the stent lattice of the replacement heart valve assembly 7100 can be made to have a waistline, i.e., a narrower midline, to an hourglass shape instead of the barrel shape. In such a configuration, the replacement heart valve assembly 7100 is naturally positioned and held in place.

A further exemplary embodiment of the inventive actively controllable stent lattice and the delivery system and method for delivering the stent lattice are shown in FIGS. 89 to 93. In this embodiment, the prosthesis 8900 includes a stent lattice 110, 3810, 4200, 4600, 6410, 7110 and three jack assemblies 700, 2100, 3000, 6430. These figures also illustrate a distal portion of an exemplary embodiment of a delivery system 8910 for the inventive prosthesis 8900. Shown with each jack assembly 700, 2100, 3000, 6430 are the drive and disconnect wires 750, 700, which are illustrated as extending proximally from the respective jack assembly 700, 2100, 3000, 6430 into a wire guide block 116. Due to the limitations of the program generating the drawing figures, these wires 750, 770 have angular bends when traversing from the respective jack assembly 700, 2100, 3000, 6430 towards the wire guide block 116. These wires, however, do not have such angled bends in the invention. Instead, these wires 750, 770 form a gradual and flattened S-shape that is illustrated diagrammatically in FIG. 89 with a dashed line 8920. Operation of the prosthesis 8900 is as described above in all respects except for one additional feature regarding the wires 750, 770. In other words, rotation of the drive wire 750 in respective directions will contract and expand the stent lattice 110, 3810, 4200, 4600, 6410, 7110. Then, when the stent lattice 110, 3810, 4200, 4600, 6410, 7110 is implanted correctly in the desired anatomy, the disconnect wire 770 will be rotated to uncouple the proximal disconnector drive block and, thereby, allow removal of the delivery system 8910. This embodiment provides the delivery system 8910 with a prosthesis-tilting function. More specifically, in the non-illustrated handle portion of the delivery system 8910, each pair of drive and disconnect wires 750, 770 are able to be longitudinally fixed to one another and, when all of the pairs are fixed respectively, each pair can be moved distally and/or proximally.

Figure 90:
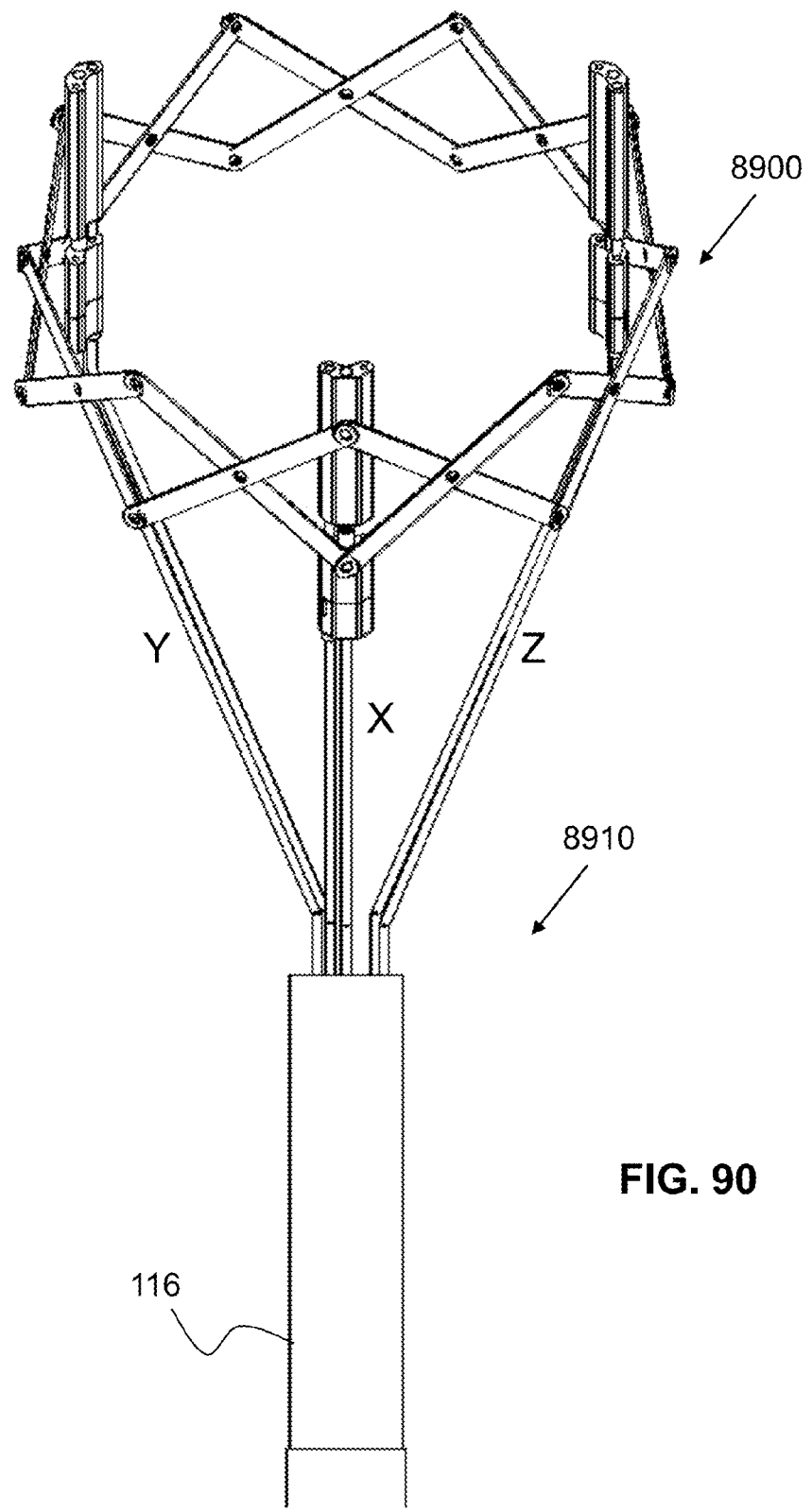
FIG. 90 is a fragmentary, side elevational view of the system of FIG. 89 in a partially tilted state from a front thereof.
Figure 91:
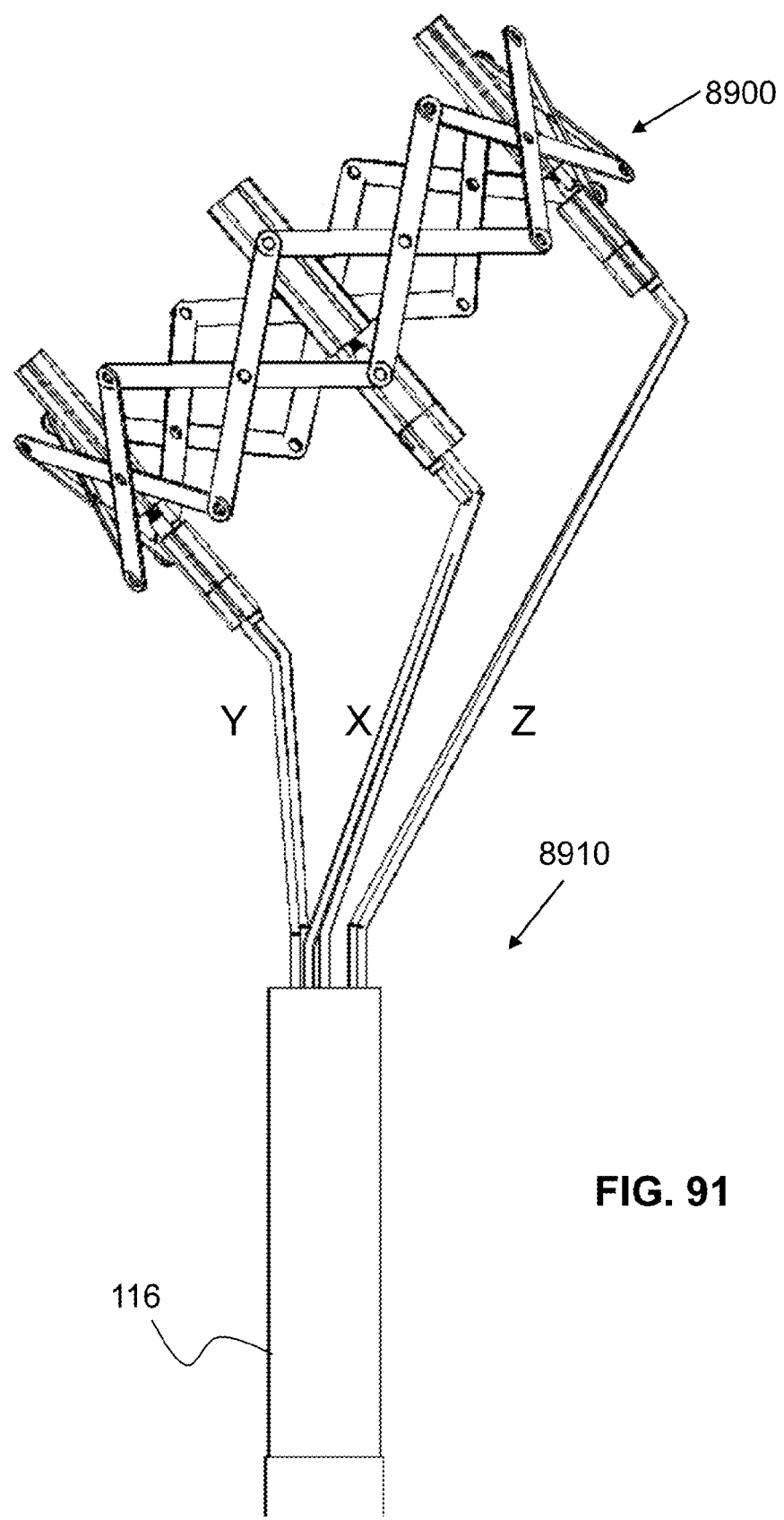
FIG. 91 is a fragmentary, side elevational view of the system of FIG. 90 in another partially tilted state.
Figure 92:
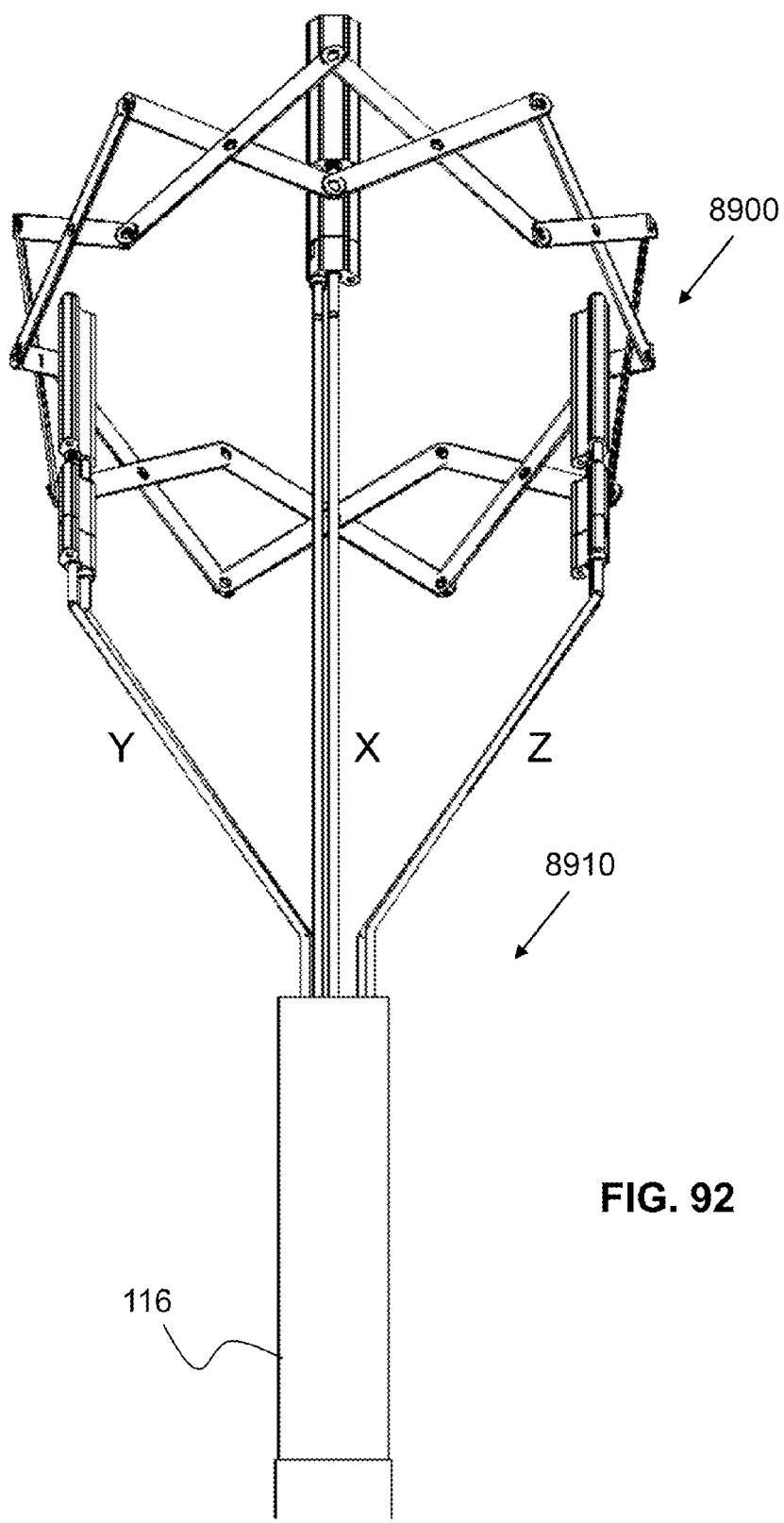
FIG. 92 is a fragmentary, side elevational view of the system of FIG. 90 in yet another partially tilted state.
Figure 93:
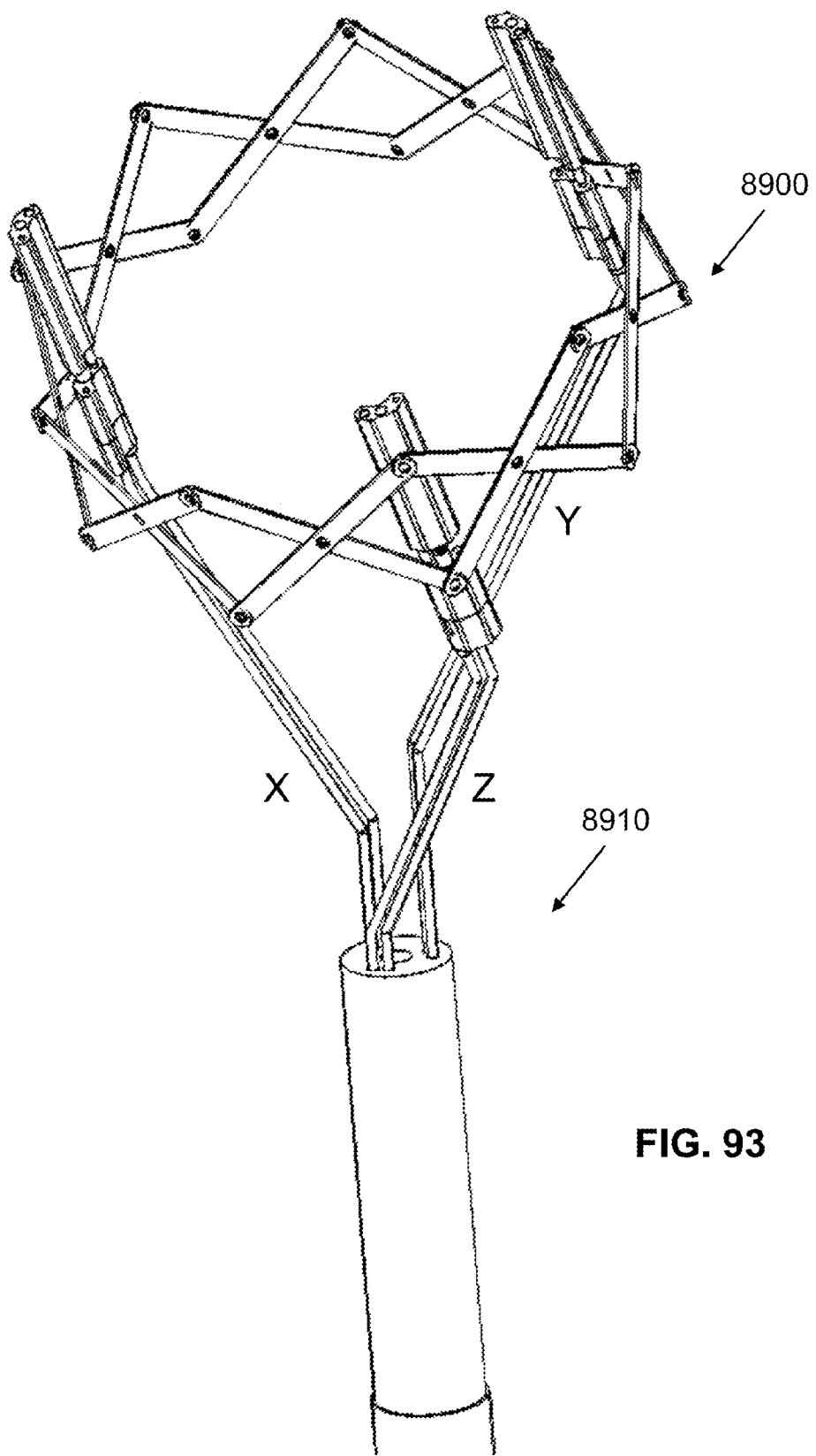
FIG. 93 is a fragmentary, perspective view of the system of FIG. 90 in yet another partially tilted state.

In such a configuration, therefore, if the wires 750, 770 labeled with the letter X are moved proximally together and the other two pairs of wires Y and Z are moved distally, then the entire prosthesis 8900 will tilt into the configuration shown in FIG. 90. Alternatively, if the wires X are kept in position, the wires Y are moved proximally and the wires Z are moved distally, then the entire prosthesis 8900 will tilt into the configuration shown in FIG. 91. Likewise, if the wires X are moved distally and the wires Y and Z are moved proximally, then the entire prosthesis 8900 will tilt into the configuration shown in FIG. 92. Finally, if the wires X are extended distally, the wires Y are extended further distally, and the wires Z are moved proximally, then the entire prosthesis 8900 will tilt into the configuration shown in FIG. 93.

Figure 94:
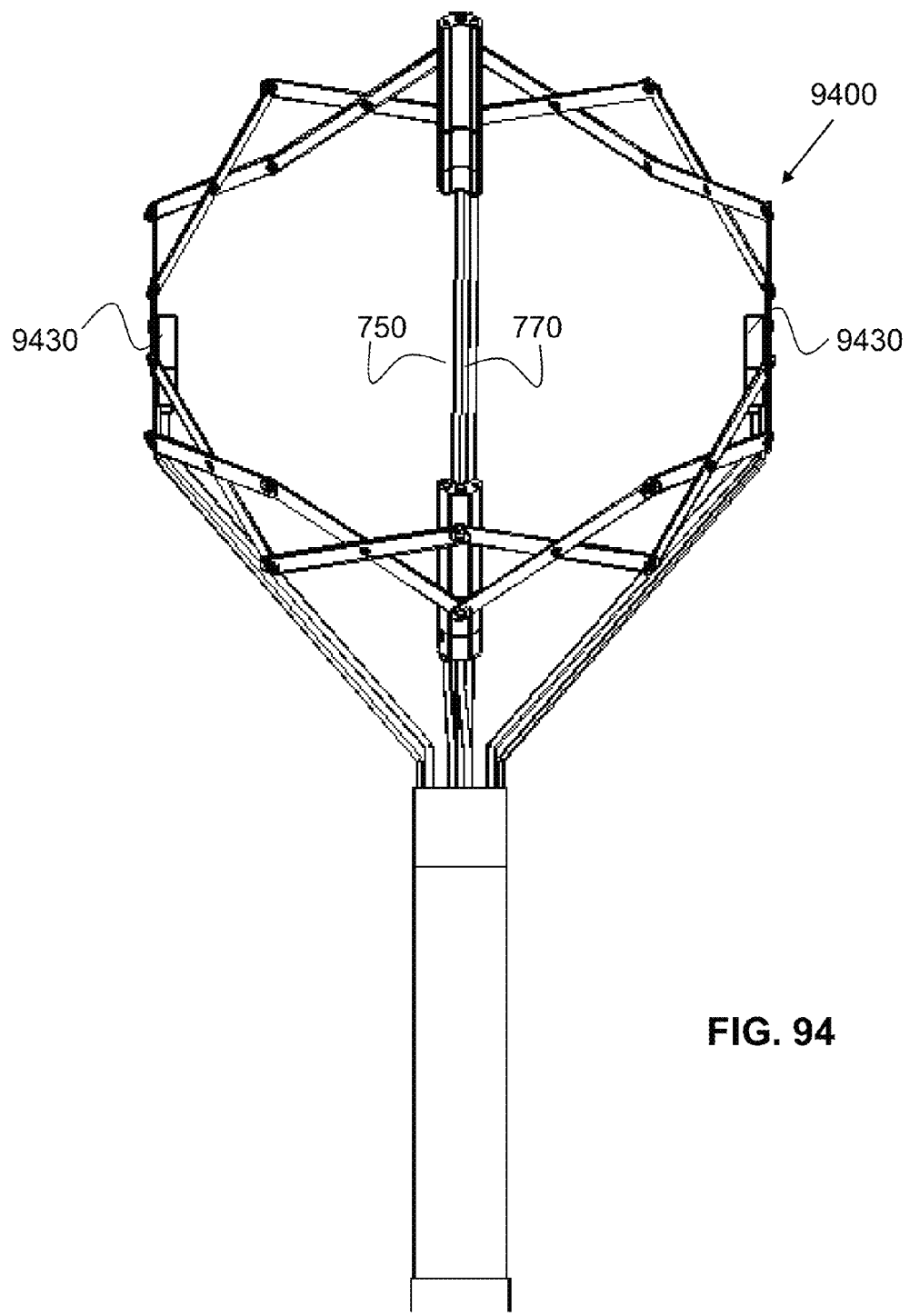
FIG. 94 is a fragmentary, partially cross-sectional, side elevational view of another exemplary embodiment of an actively controllable and tiltable stent graft system according to the invention in an expanded state and a partially front-side tilted state
Figure 95:
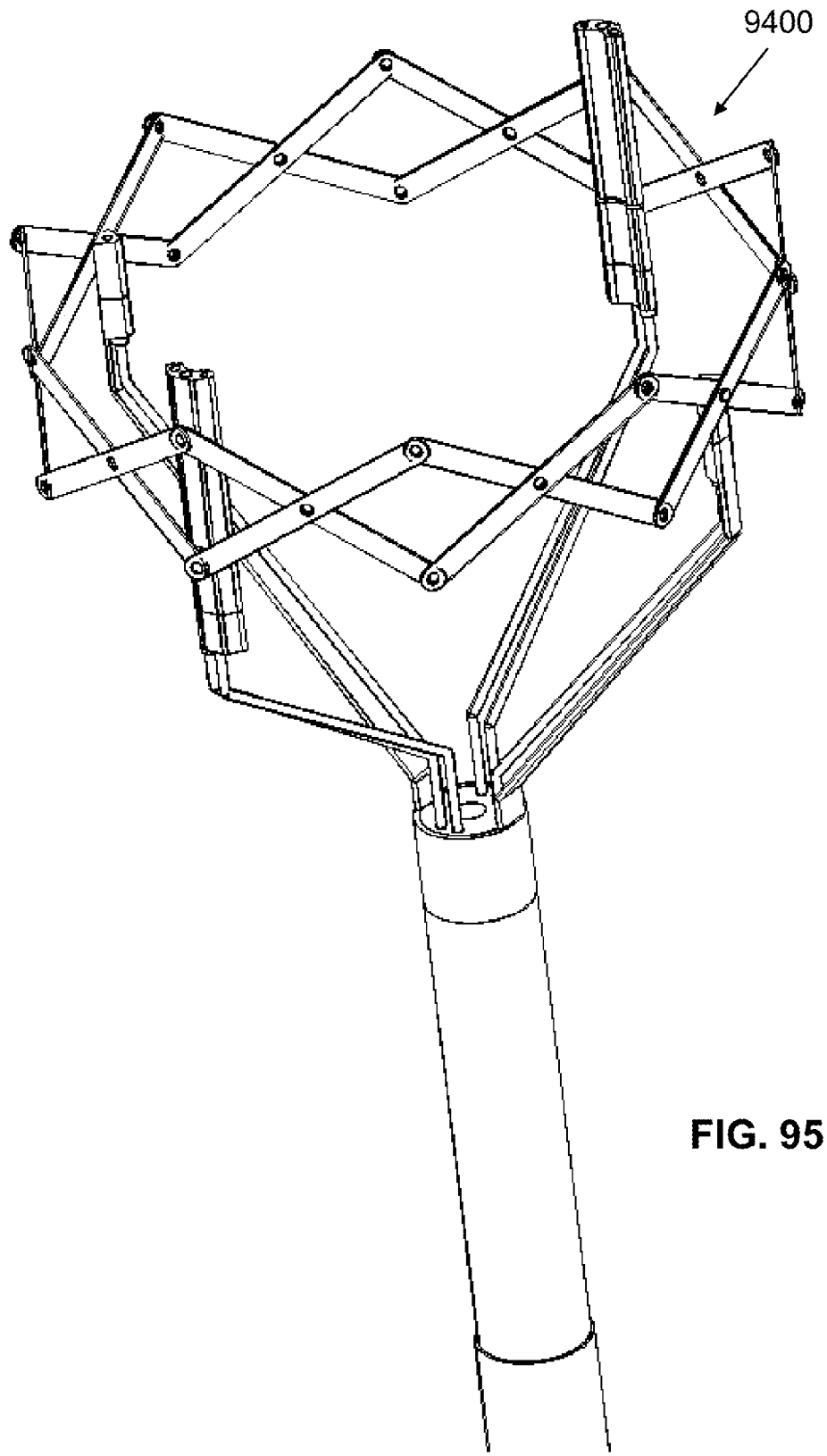
FIG. 95 is a fragmentary, perspective view of the system of FIG. 94 in a non-tilted state.
Figure 96:
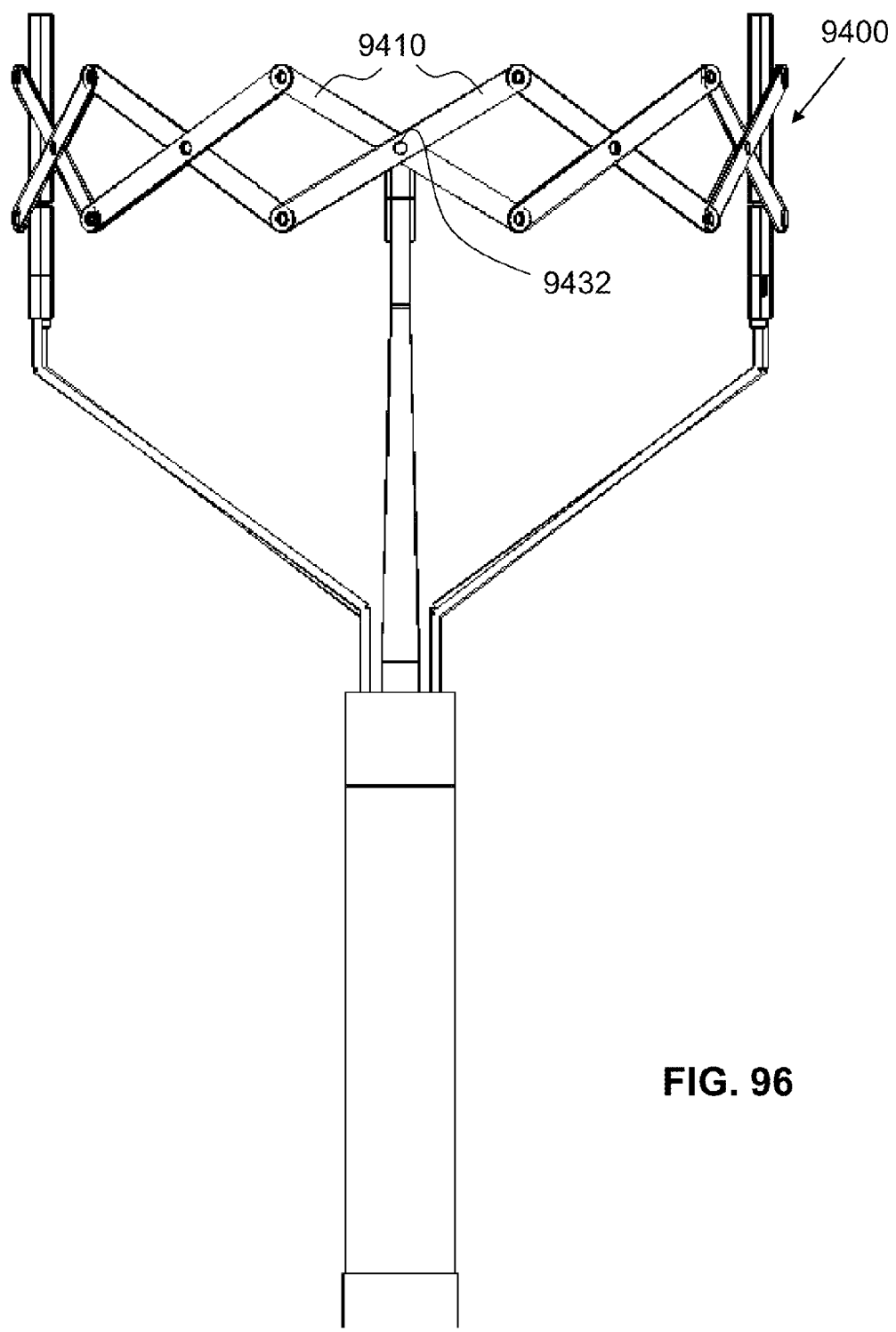
FIG. 96 is a fragmentary, side elevational view of the system of FIG. 94 in a non-tilted state.
Figure 97:
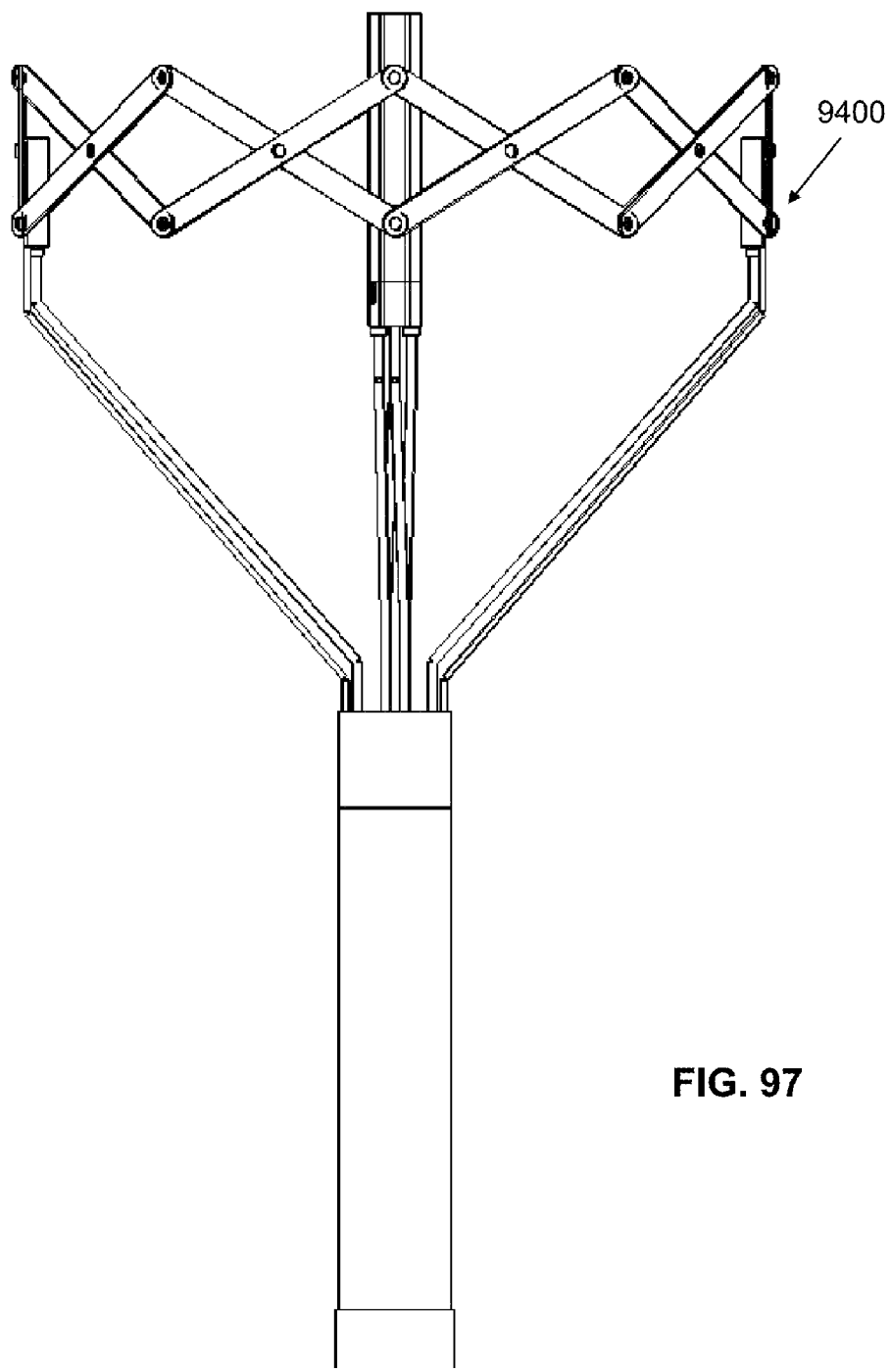
FIG. 97 is a fragmentary, side elevational view of the system of FIG. 96 rotated approximately 90 degrees with respect to the view of FIG. 96.
Figure 98:
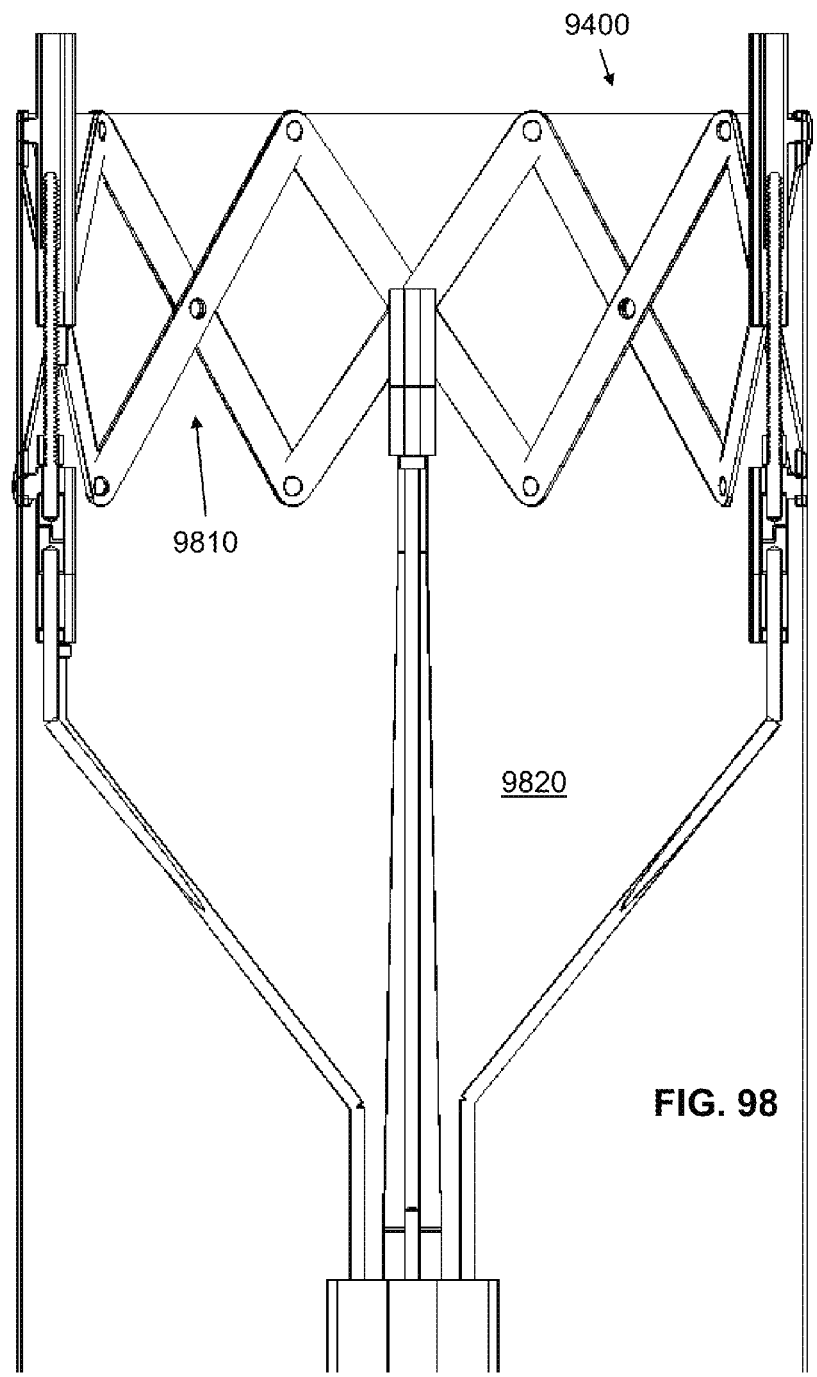
FIG. 98 is a fragmentary, longitudinally cross-sectional, side elevational view of the system of FIG. 94 showing the rear half of the system and a tubular graft material in a non-tilted state and partially expanded state.
Figure 99:
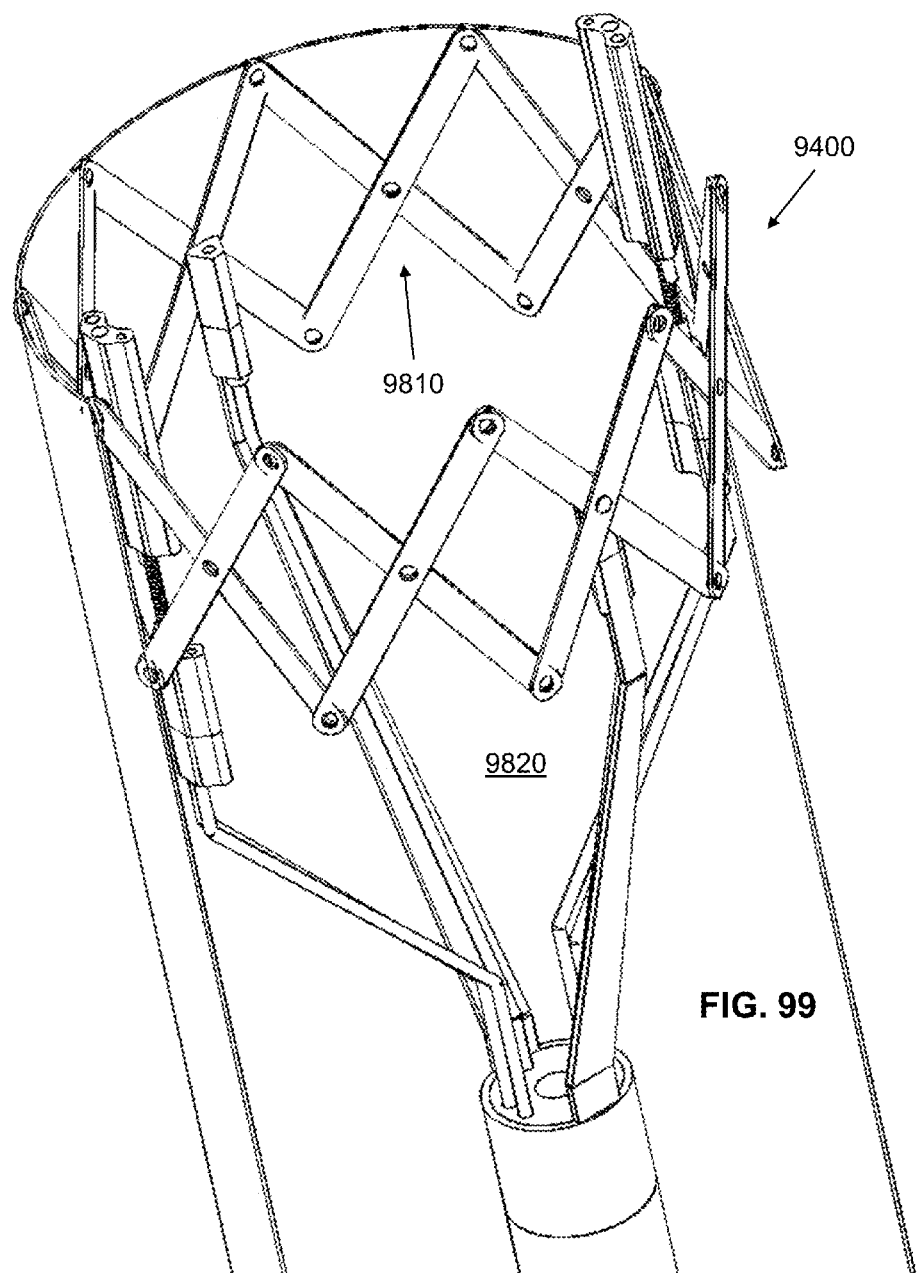
FIG. 99 is fragmentary, partially cross-sectional, perspective view of the system of FIG. 94 showing the rear half of the tubular graft material and in a non-tilted state and a partially expanded state.

Still a further exemplary embodiment of the inventive actively controllable stent lattice and the delivery system and method for delivering the stent lattice are shown in FIGS. 94 to 102. In this embodiment, the prosthesis 9400 is a stent graft having a proximal, actively controlled stent lattice 110, 3810, 4200, 4600, 6410, 7110 and only two opposing jack assemblies 700, 2100, 3000, 6430. Instead of two additional jack assemblies 700, 2100, 3000, 6430, this embodiment contains two opposing pivoting disconnector drive blocks 9430. These disconnector drive blocks 9430, as shown for example in the view of FIG. 96 rotated circumferentially ninety degrees, have bosses 9432 extending radially outward and forming the central pivot joint for the two crossing struts 9410. The two disconnector drive blocks 9430 act as pivots to allow the prosthesis 9400 to tilt in the manner of a swashplate when the two opposing sets of control wires 750, 770 are moved in opposing distal and proximal directions. FIG. 94 shows the near set of control wires 750, 770 moved proximally and the far set moved distally. In FIG. 95, the swashplate of the prosthesis 9400 is untilted, as is the prosthesis 9400 in FIGS. 96 and 97, the latter of which is merely rotated ninety degrees as compared to the former. FIGS. 98 and 99 depict the prosthesis 9400 as part of a stent graft having the stent lattice 9810 inside a proximal end of a tubular shaped graft 9820.

Figure 100:
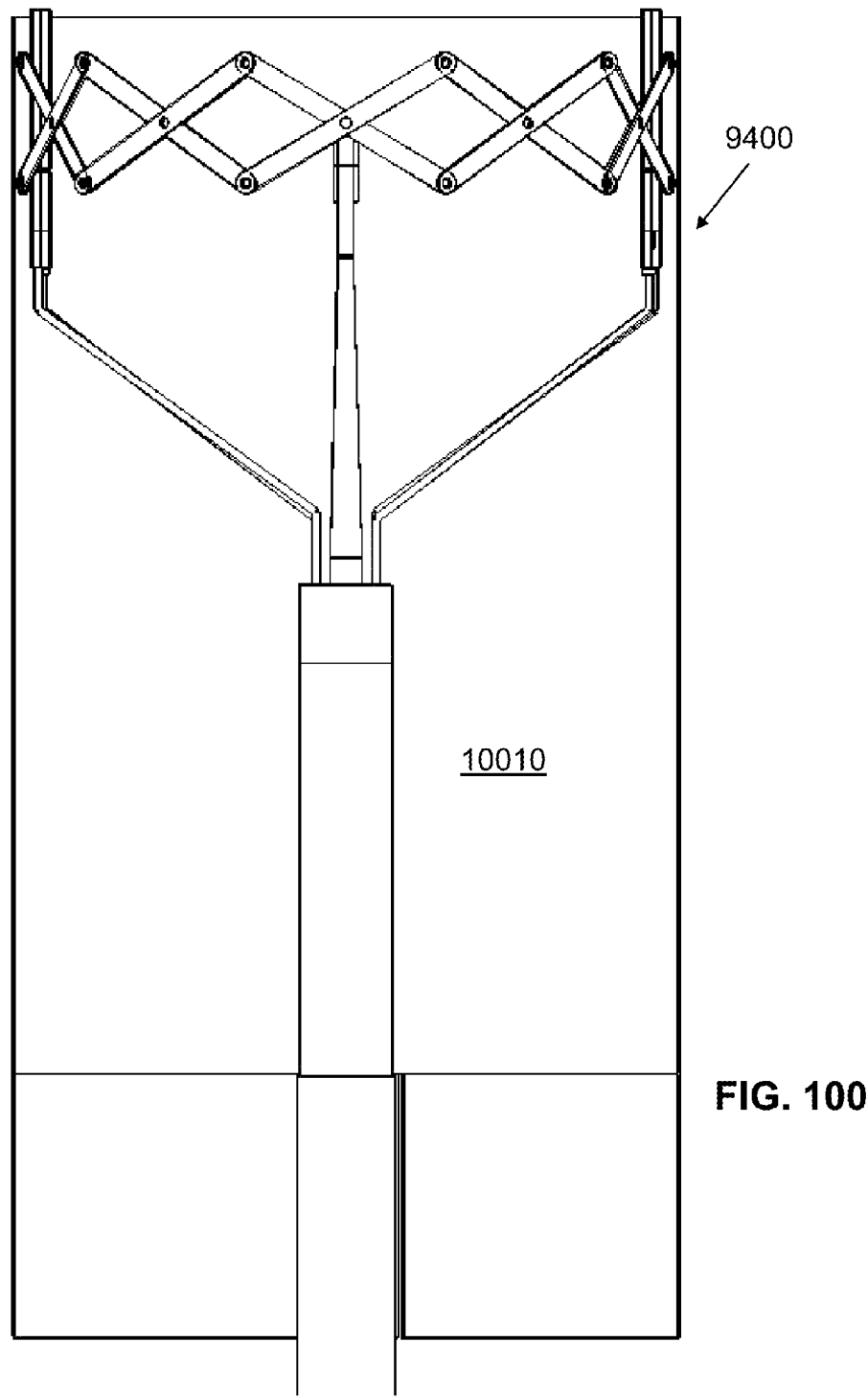
FIG. 100 is a fragmentary, partially cross-sectional, side elevational view of the system of FIG. 94 showing the rear half of graft material for a bifurcated vessel and in a non-tilted state.
Figure 101:
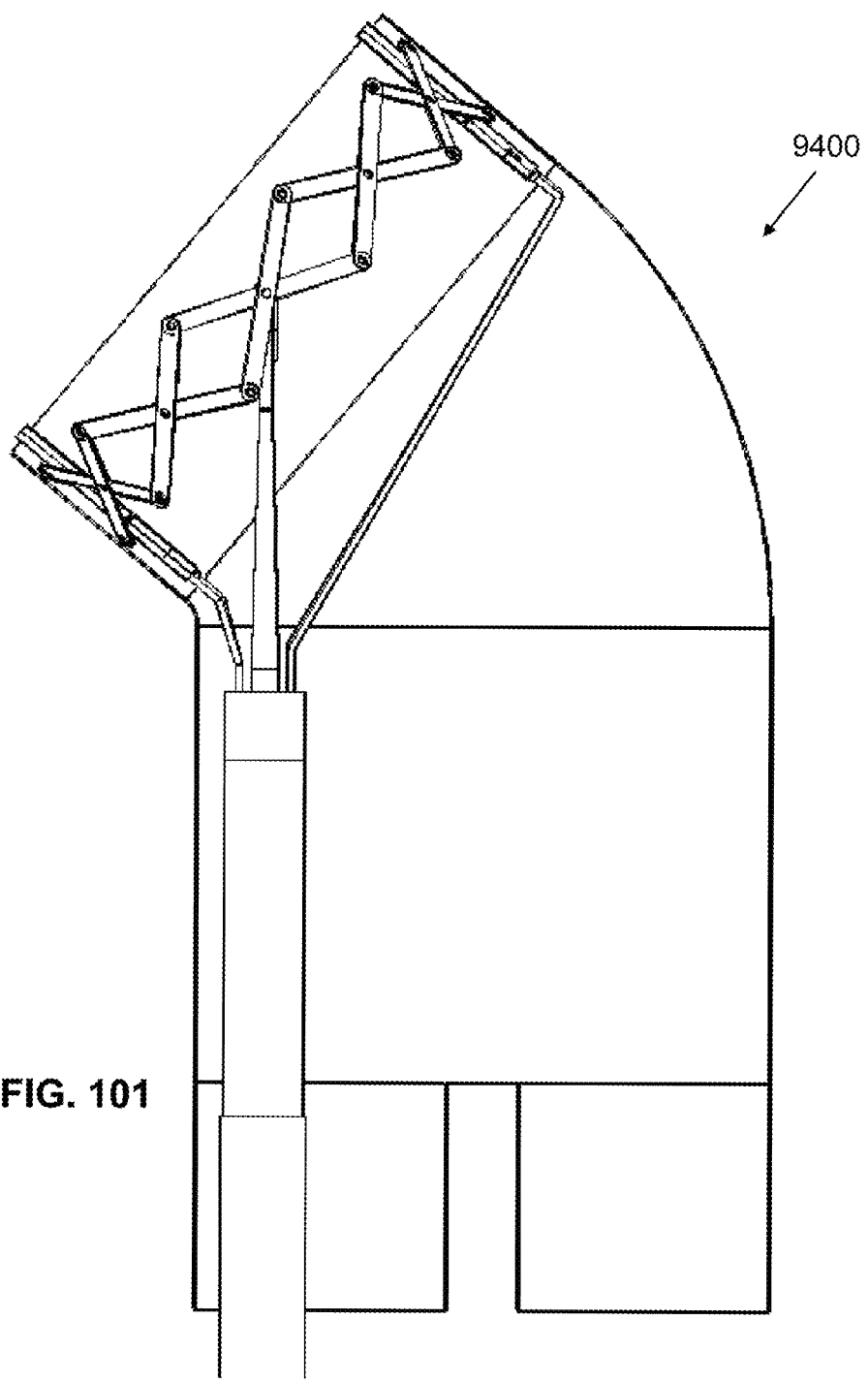
FIG. 101 is a fragmentary, partially cross-sectional, side elevational view of the system of FIG. 100 in an expanded state and a partially tilted state.
Figure 102:
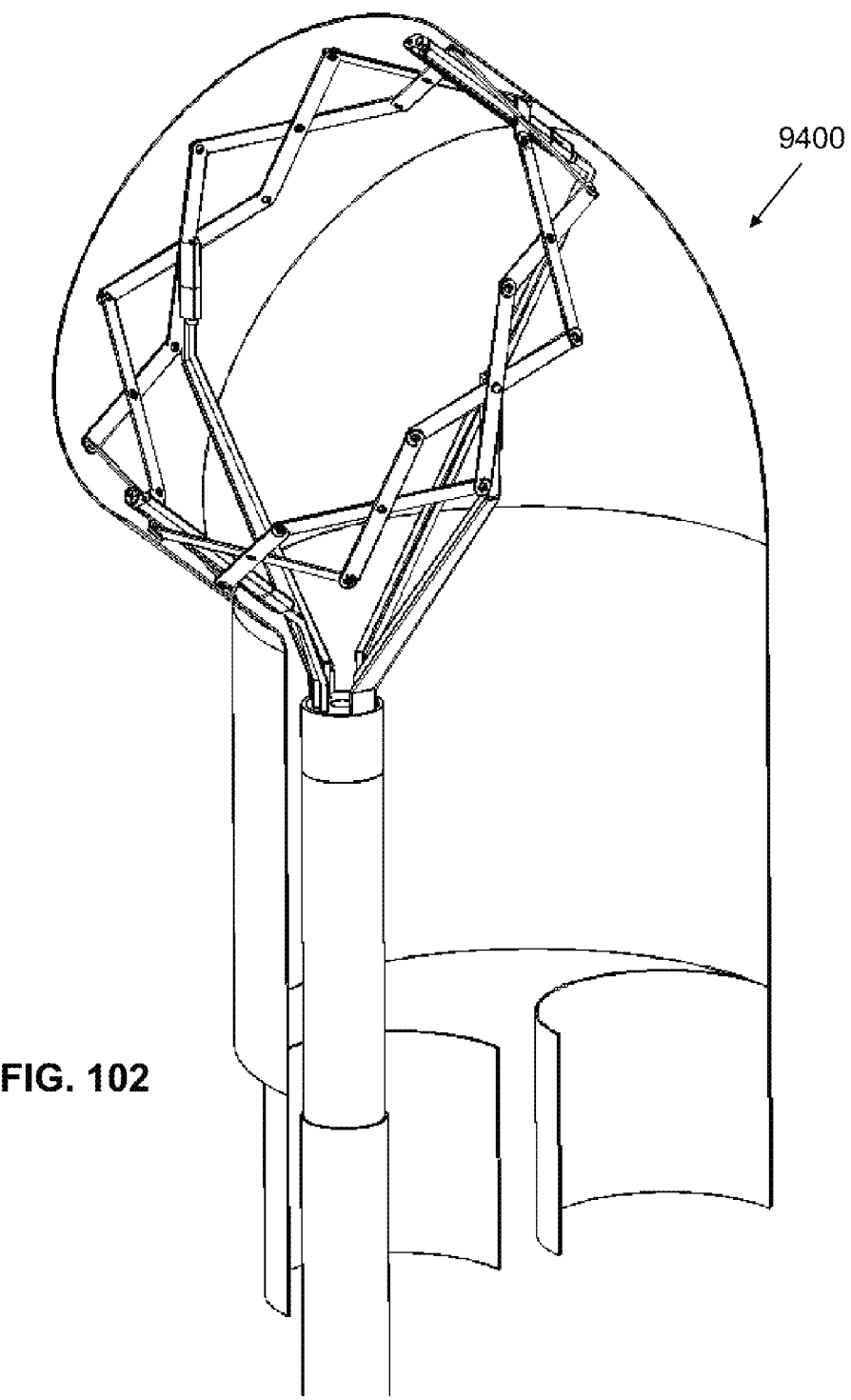
FIG. 102 is a fragmentary, partially cross-sectional, side elevational view of the system of FIG. 101 rotated approximately 45 degrees with respect to the view of FIG. 101.

The prosthesis 9400 in FIGS. 100 to 102 is also a stent graft but, in this exemplary embodiment, the graft 10010 is bifurcated, for example, to be implanted in an abdominal aorta. FIGS. 101 and 102 show how the proximal end of the prosthesis 9400 can be tilted with the swashplate assembly of the invention, for example, in order to traverse a tortuous vessel in which the prosthesis 9400 is to be implanted, such as a proximal neck of abdominal aortic aneurysm.

Figure 103:
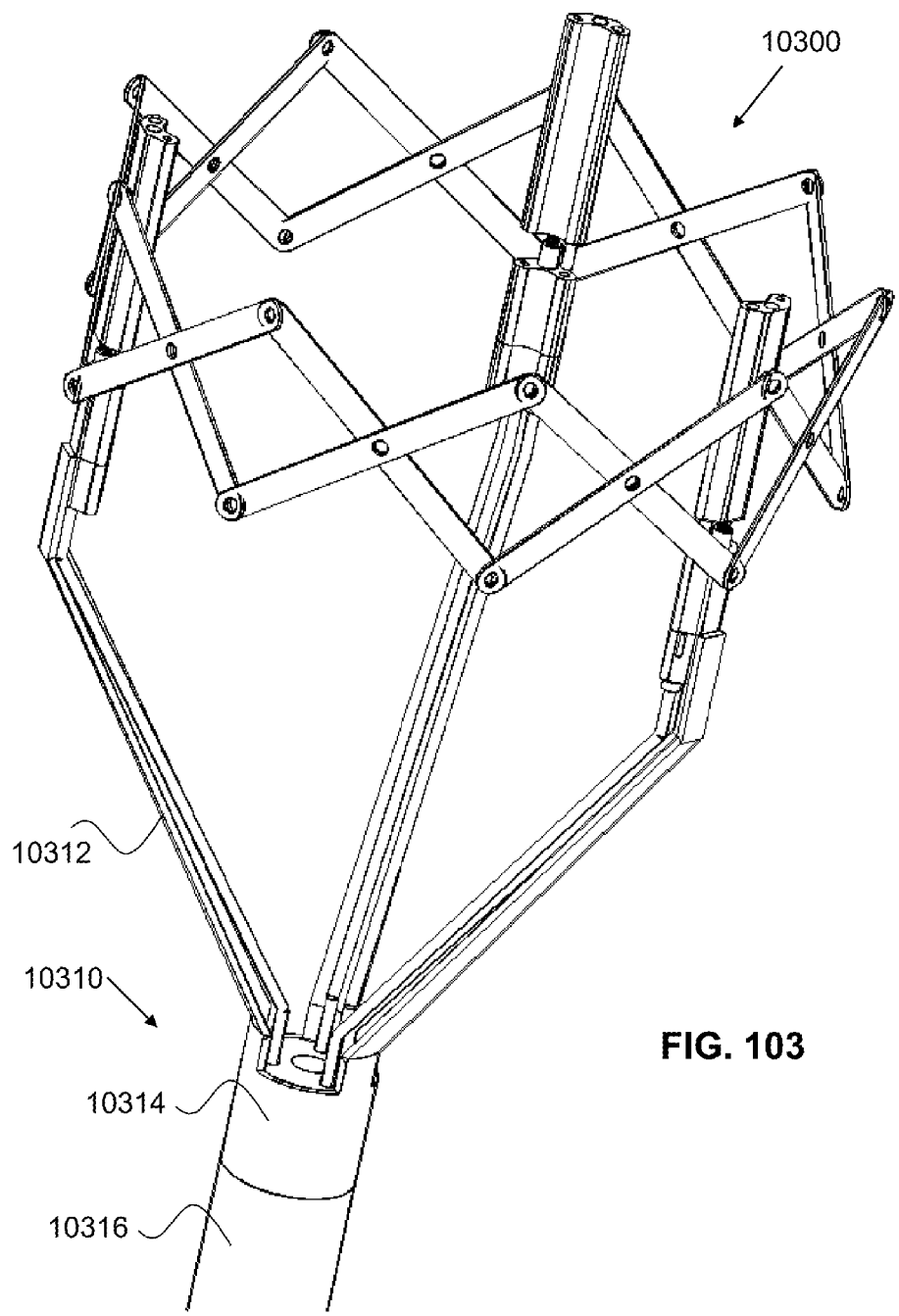
FIG. 103 is a fragmentary, side perspective view of another exemplary embodiment of an actively controllable stent graft system according to the invention in an expanded state.
Figure 104:
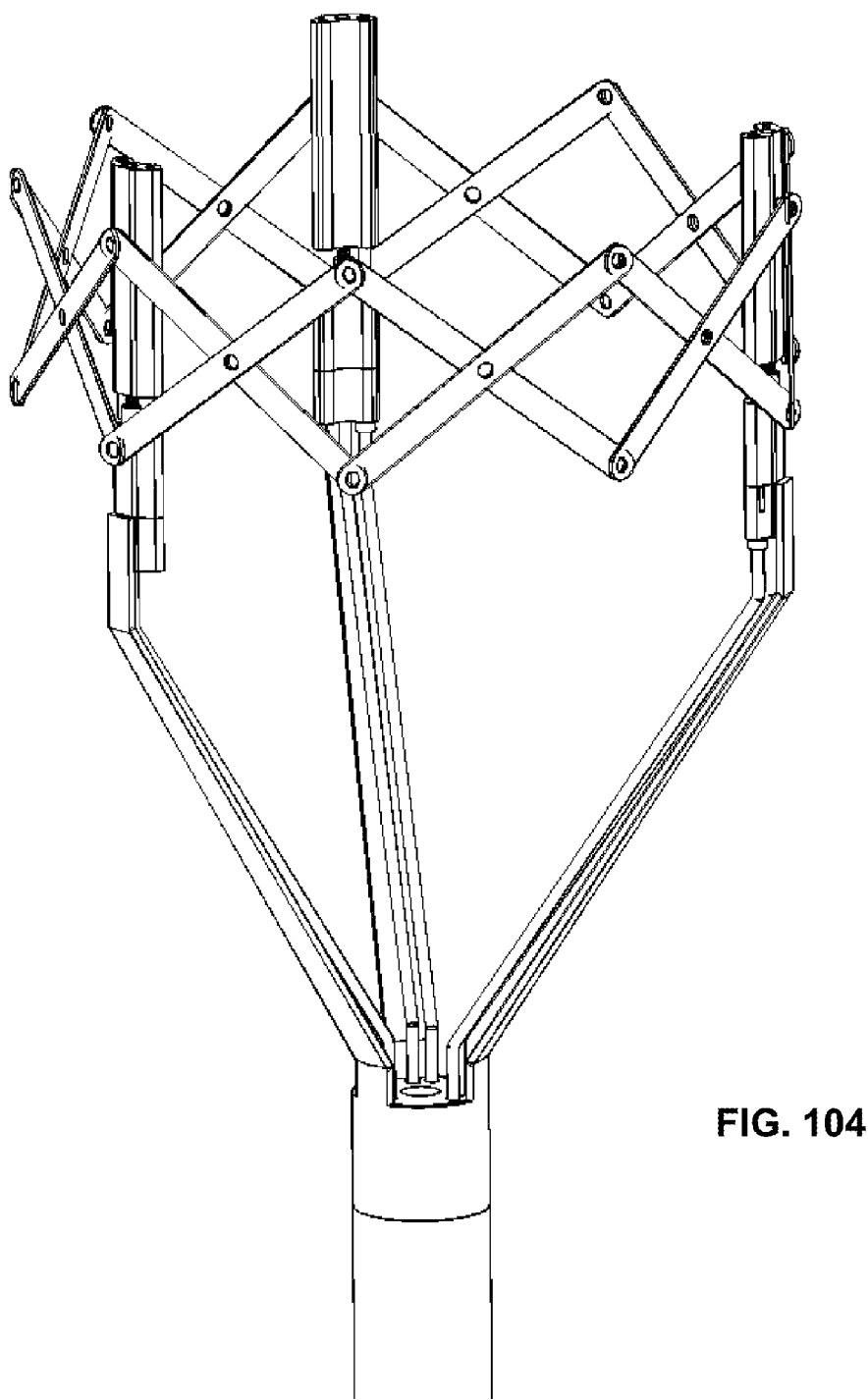
FIG. 104 is a fragmentary, side elevational view of the system of FIG. 103.

The exemplary embodiment of the prosthesis 10300 shown in FIGS. 103 and 104 does not include the swashplate assembly. Instead, the delivery system includes a distal support structure 10310 that ties all of the support bands 10312 to a cylindrical support base 10314 connected at the distal end of the delivery catheter 10316.

An exemplary embodiment of the entire delivery system 10500 for the prosthesis 10300 is depicted in FIGS. 105 to 107. In FIG. 105, the delivery system is entirely self-contained and self-powered and includes the actively controllable stent lattice with an integral control system 10510. The prosthesis 10300 is in an expanded state and the graft material is in cross-section to show a rear half. An alternative to the integral control system 10510 is a wireless control device 10600 that wirelessly communicates 10610 control commands to the system. Another alternative to the integral control system 10510 shown in FIG. 107 separates the control device 10700 with a cord 10710 for communicating control commands to the system. In this exemplary embodiment, the controls comprise four rocker switches 10712, 10714, 10716, 10718 arranged in a square, each of the switches having a forward position, a neutral central position, and a rearward position.

Figure 108:
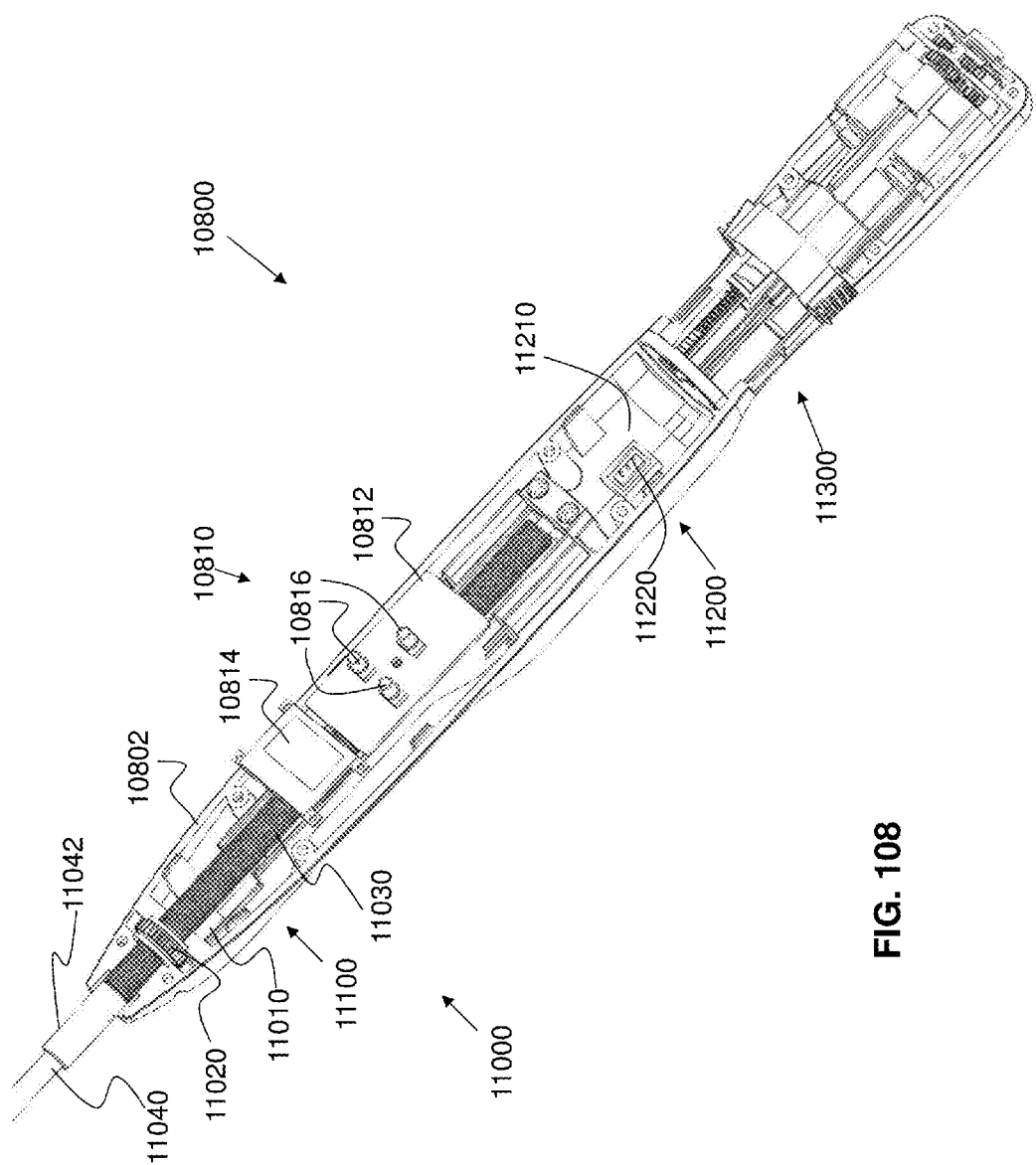
FIG. 108 is a fragmentary, perspective view of a control handle of an exemplary embodiment of a self-contained, self-powered, actively controllable prosthesis delivery device according to the invention from above a left side thereof with the upper handle half and power pack removed.
Figure 109:
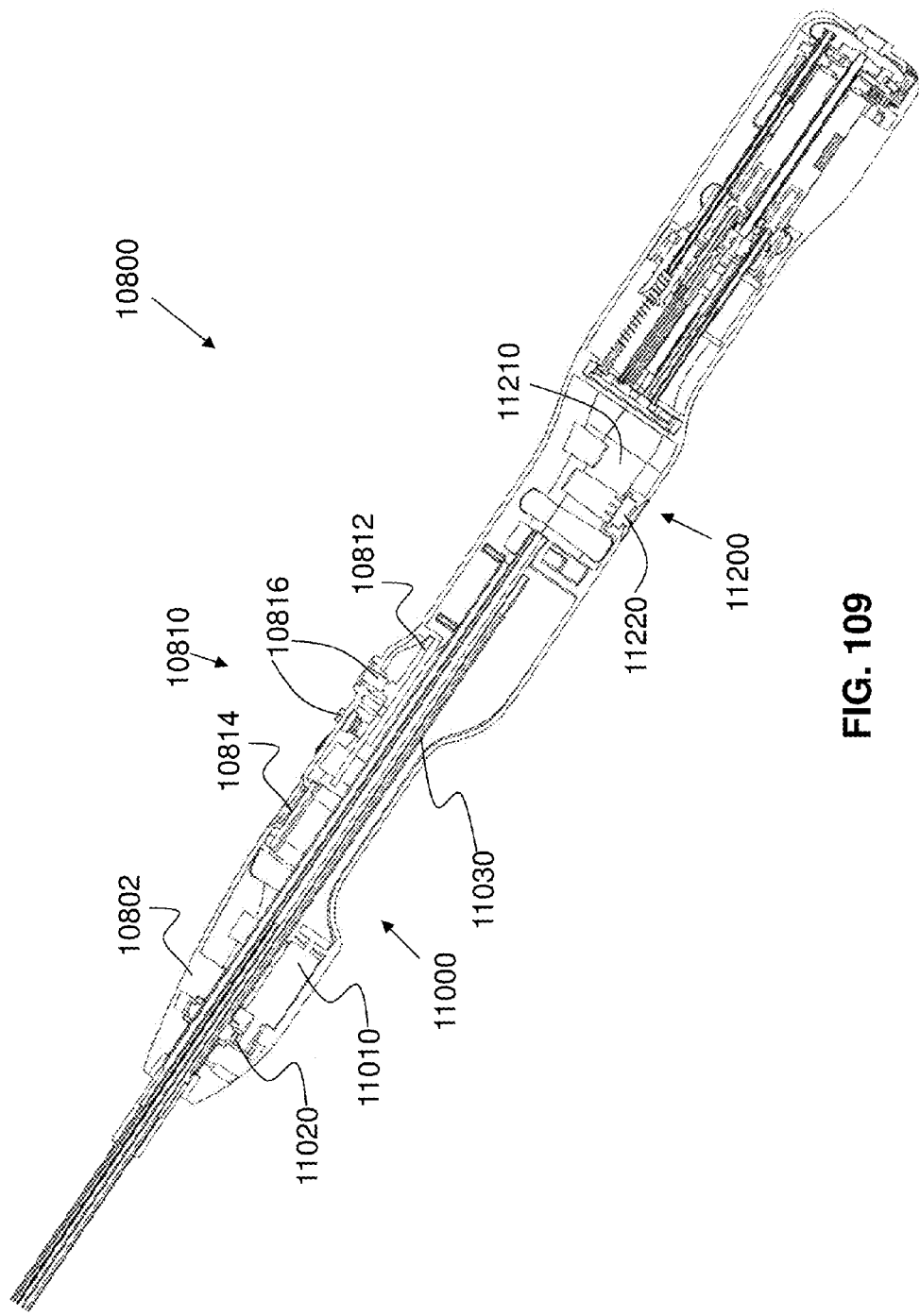
FIG. 109 is a fragmentary, vertically cross-sectional view of the handle of FIG. 108 with the power pack removed.
Figure 110:
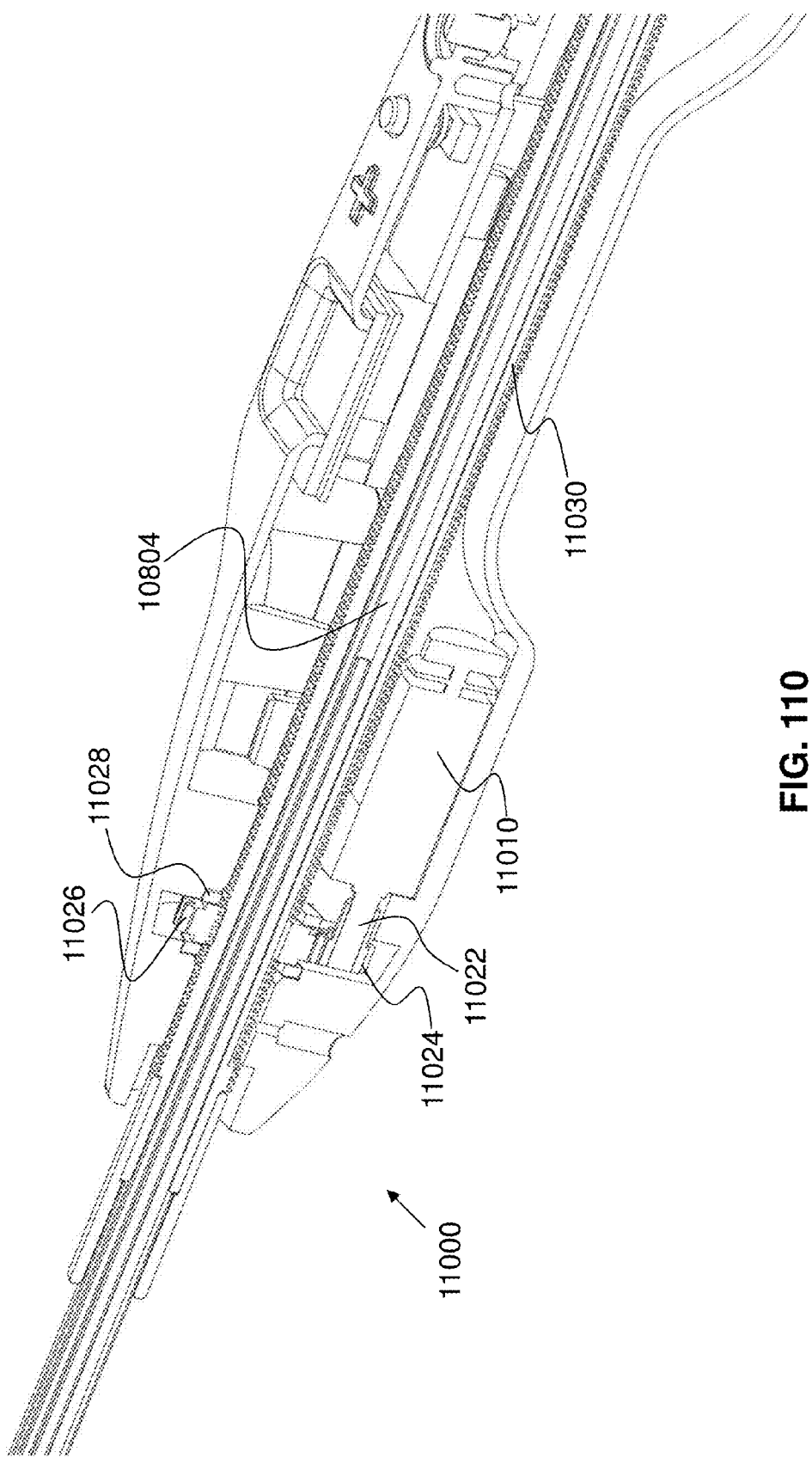
FIG. 110 is a fragmentary, enlarged, vertically cross-sectional and perspective view of a sheath-movement portion of the handle of FIG. 108 from above a left side thereof.

Yet another exemplary embodiment of a control handle 10800 for operating a prosthesis having the actively controllable stent lattice according to the invention is depicted in FIGS. 108 to 118. The views of FIGS. 108 and 109 show various sub-assemblies contained within the control handle 10800. A user-interface sub-assembly 10810 includes a circuit board 10812 having circuitry programmed to carry out operation of the systems and methods according to the invention. Electronics of the user-interface sub-assembly 10810 comprise a display 10814 and various user input devices 10816, such as buttons, switches, levers, toggles, and the like. A sheath-movement sub-assembly 11000 includes a sheath-movement motor 11010, a sheath movement transmission 11020, a sheath movement driveshaft 11030, and a translatable delivery sheath 11040. A strain relief 11042 is provided to support the delivery sheath 11040 at the handle shell 10802. A power sub-assembly 11200 is sized to fit within the handle 10800 in a power cell compartment 11210 containing therein power contacts 11220 that are electrically connected to at least the circuit board 10812 for supplying power to all electronics on the control handle 10800 including all of the motors. A needle-movement sub-assembly 11300 controls deployment of the needles and keeps tension on the needles continuously even when the delivery sheath 11040 is bent through tortuous anatomy and different bends are being imposed on each of the needles. The needles are three in number in this exemplary embodiment. Finally, a jack engine 11600 controls all movements with regard to the jack assemblies.

The user-interface sub-assembly 10810 allows the surgeon to obtain real-time data on all aspects of the delivery system 10800. For example, the display 10814 is programmed to show the user, among other information, deployment status of the stent lattices, the current diameter of the stent lattices, any swashplate articulation angle of the stent lattice to better approximate an actual curved landing site, all data from various sensors in the system, and to give audio feedback associated with any of the information. One informational feedback to user can be an indicator on the display 10814 that the delivery sheath 11040 is retracted sufficiently far to completely unsheath the prosthesis. Other information can be a force feedback indicator showing how much force is being imparted on the lattice from the vessel wall, e.g., through a torque meter, a graphical change in resistance to the stepper motor, a mechanical slip clutch, direct load/pressure sensors on lattice. With such information, the prosthesis can have Optimal Lattice Expansion (OLE), achieve its best seal, migration and embolization is decreased, the amount of outward force can be limited (i.e., a force ceiling) to stop expansion before tissue damage occurs. A visual indicator can even show in a 1:1 ratio the actual diameter position of the stent lattice. Other possible sensors for taking measurements inside and/or outside the prosthesis (e.g., above and below touchdown points of lattice) can be added into the inventive powered handle. These devices include, for example, intravascular ultrasound, a video camera, a flow wire to detect flow showing blood passing around prosthesis/double lumen catheter and showing pressure gradients, a Doppler device, an intrinsic pressure sensor/transducer, and an impedance of touchdown zone.

Having all of the user interface actuators 10816 within reach of a single finger of the user provides unique and significant advantages by allowing the surgeon to have one-hand operation of the entire system throughout the entire implantation procedure. In all mechanical prior art systems when torque is applied, the second hand is needed. Pushing of single button or toggling a multi-part switch eliminates any need for the user's second hand. Using different kinds of buttons/switches allows the user to be provided with advanced controls, such as the ability to have coarse and fine adjustments for any sub-procedure. For example, expansion of the lattice can be, initially, coarse by automatically directly expanded out to a given, pre-defined diameter. Then, further expansion can be with fine control, such as a millimeter at a time. The varying of diameter can be both in the open and close directions. If the prosthesis needs to be angled, before, during, and/or after varying the expansion diameter, the user can individually manipulate each jack screw or control wires to gimbal the upstream end of implant so that it complies with vessel orientation; both during diameter/articulation changes, the physician can inject contrast to confirm leak-tightness. Even though the exemplary embodiment of the needle deployment shown is manual, this deployment can be made automatic so that, once the prosthesis is implanted, and only after the user indicates implantation is final, an automatic deployment of the engaging anchors can be made. With regard to undocking the delivery system, this release can be with a single touch, for example, of a push button. Also, with an integrated contrast injection assembly, a single touch can cause injection of contrast media at the implantation site.

Figure 111:
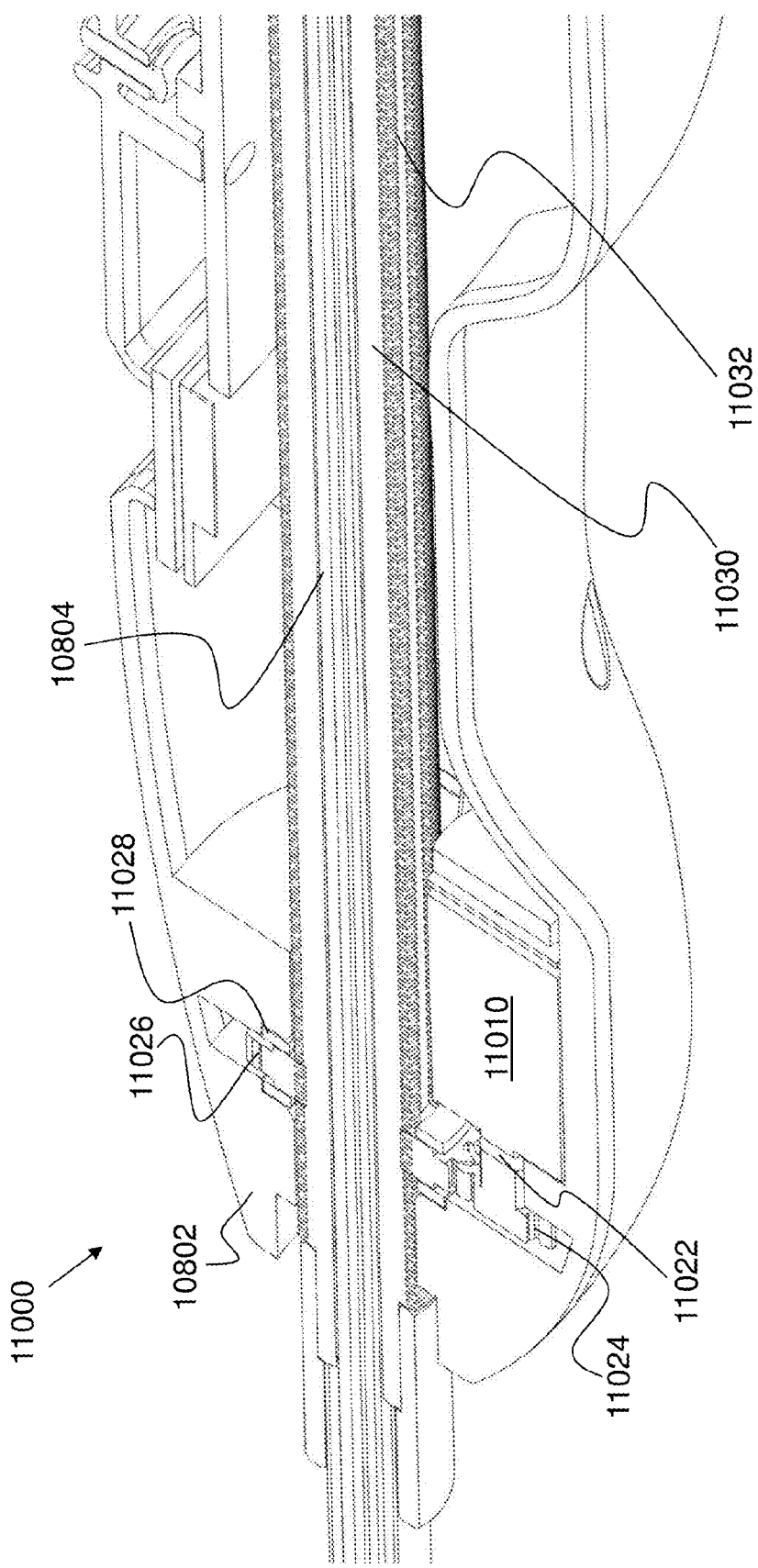
FIG. 111 is a fragmentary, further enlarged, vertically cross-sectional view of the sheath-movement portion of FIG. 110 from below a left side thereof.
Figure 112:
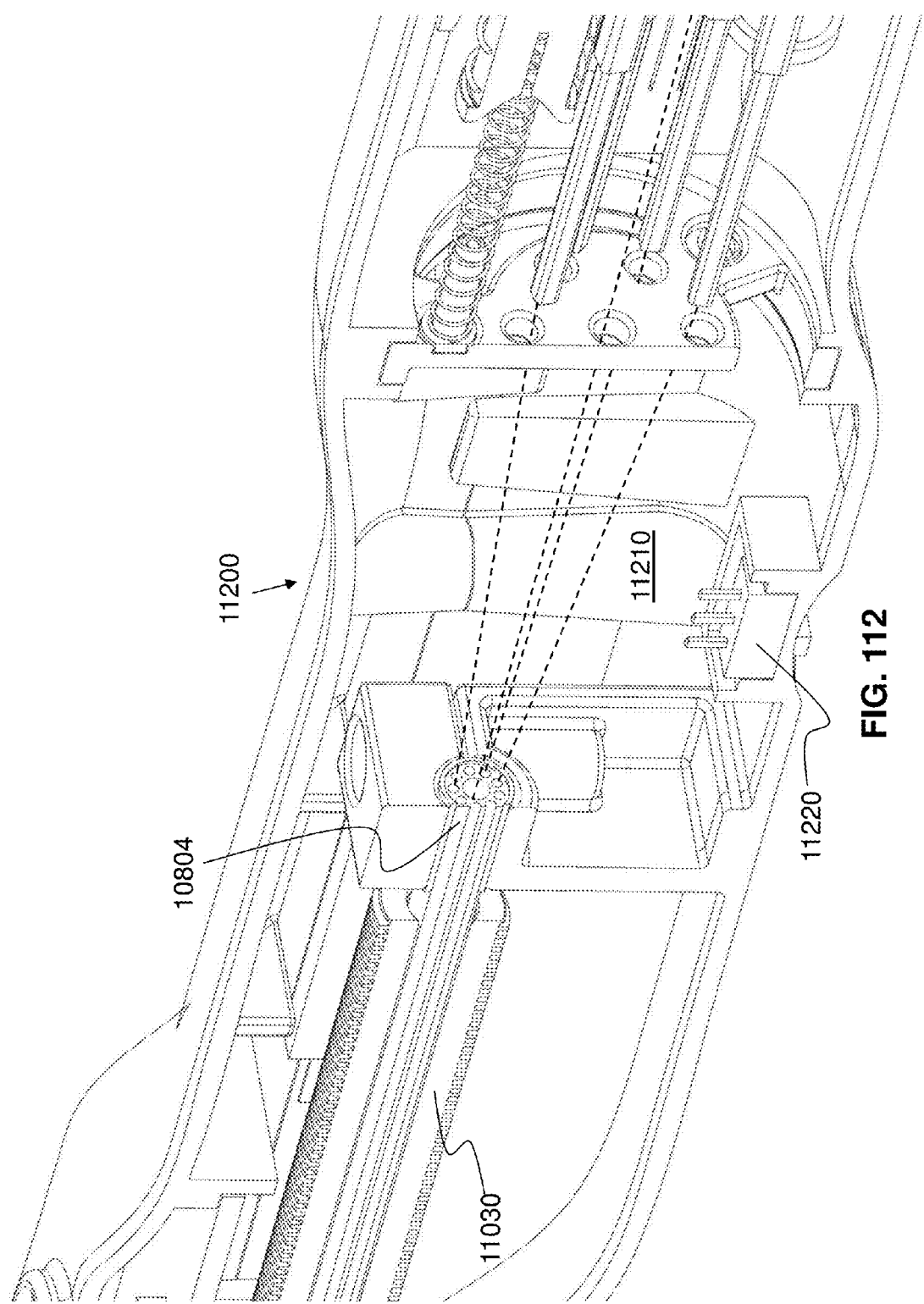
FIG. 112 is a fragmentary, enlarged, vertically cross-sectional view of a power portion of the handle of FIG. 108 viewed from a proximal side thereof.

The sheath-movement sub-assembly 11000 also can be controlled by a single button or switch on the circuit board 10812. If the user interface is a two-position toggle, distal depression can correspond with sheath extension and proximal depression can correspond with sheath retraction. Such a switch is operable to actuate the sheath movement motor 11010 in the two rotation directions. Rotation of the motor axle 11022, therefore, causes the transmission 11024, 11026 to correspondingly rotate, thereby forcing the threaded sheath movement driveshaft 11030 to either extend distally or retract proximally. The exemplary embodiment of the transmission includes a first gear 11024 directly connected to the motor axle 11022. The first gear 11024 is meshed with the outside teeth of a larger, hollow, driveshaft gear. The interior bore of the driveshaft gear 11026 has threads corresponding to the exterior threads of the sheath movement driveshaft 11030. As such, when the driveshaft gear 11026 rotates, the sheath movement driveshaft 11030 translates. The driveshaft gear 11026 is surrounded by a bushing 11028 to allow rotation within the housing shell 10802. In order to prevent rotation of the sheath movement driveshaft 11030, as shown in FIG. 111, the sheath movement driveshaft 11030 has a longitudinal keyway 11032 that has a cross-sectional shape corresponding to a key that is grounded to the handle shell 10802. The sheath movement driveshaft 11030 also is hollow to accommodate a multi-lumen rod 10804 (shown best in FIG. 112) housing, within each respective lumen, any of the control wires 750, 770, 2182, 3098 and the guidewire 6610, these lumens corresponding to those within the wire guide block 116 at the distal end of the delivery sheath 10040.

The size and shape of the power sub-assembly 11200 is limited in shape only by the power cell compartment 11210 and the various wires and rods that traverse from the needle-movement sub-assembly 11300 and the jack engine 11600 therethrough until they enter the lumens of the multi-lumen rod 10804. Some of these wires and rods are illustrated with dashed lines in FIG. 112. Power distribution to the circuit board 10812 and/or the motors is carious out through power contacts 11220. Such power distribution lines are not illustrated for reasons of clarity. This method or similar such as a rack and pinion or drag wheels can be used to drive the sheath extension and retraction.

Figure 113:
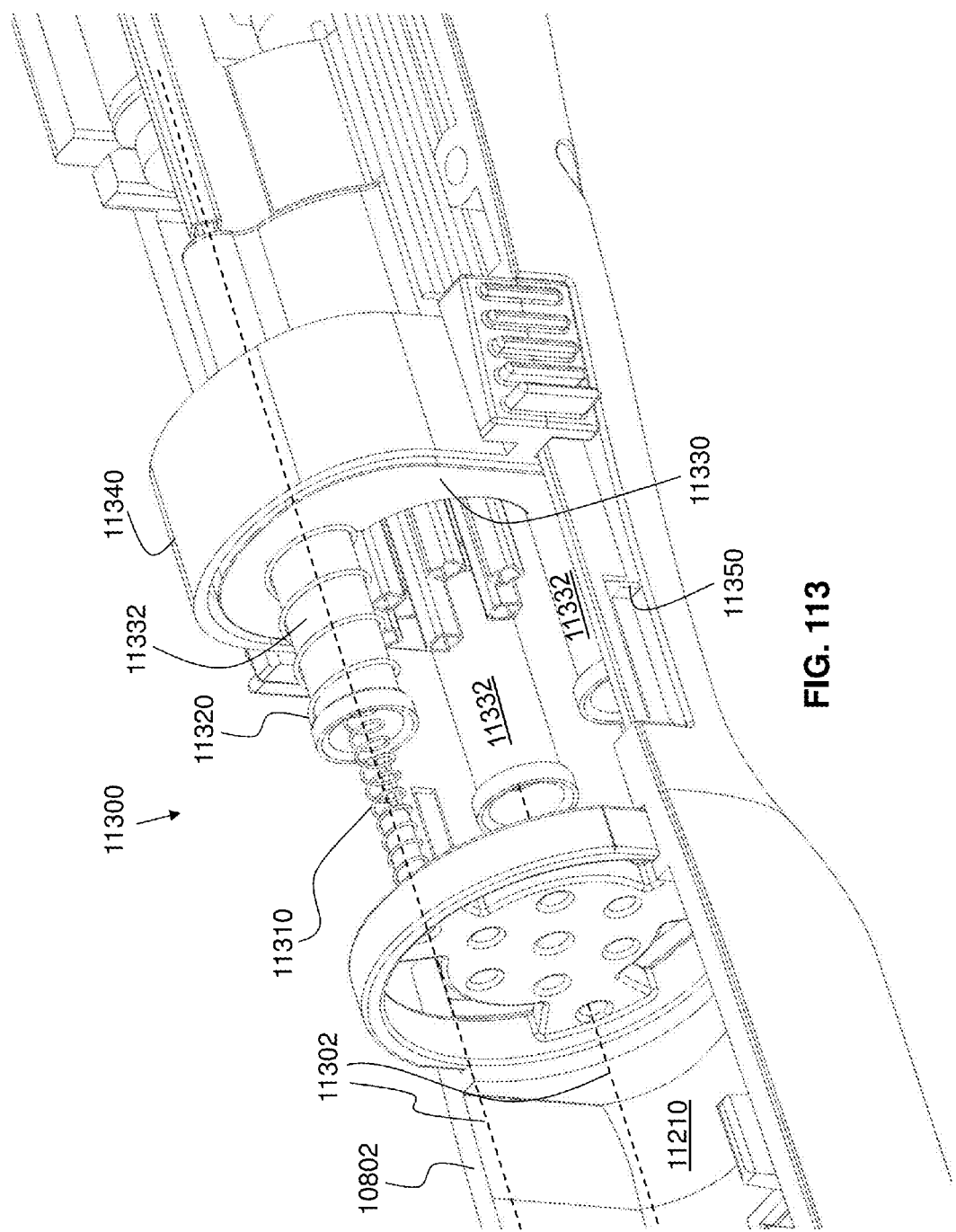
FIG. 113 is a fragmentary, perspective view of a needle control portion of the handle of FIG. 108 from above a distal side with the upper handle half and power pack removed and with the needle control in a lattice-contracted and needle-stowed position.
Figure 114:
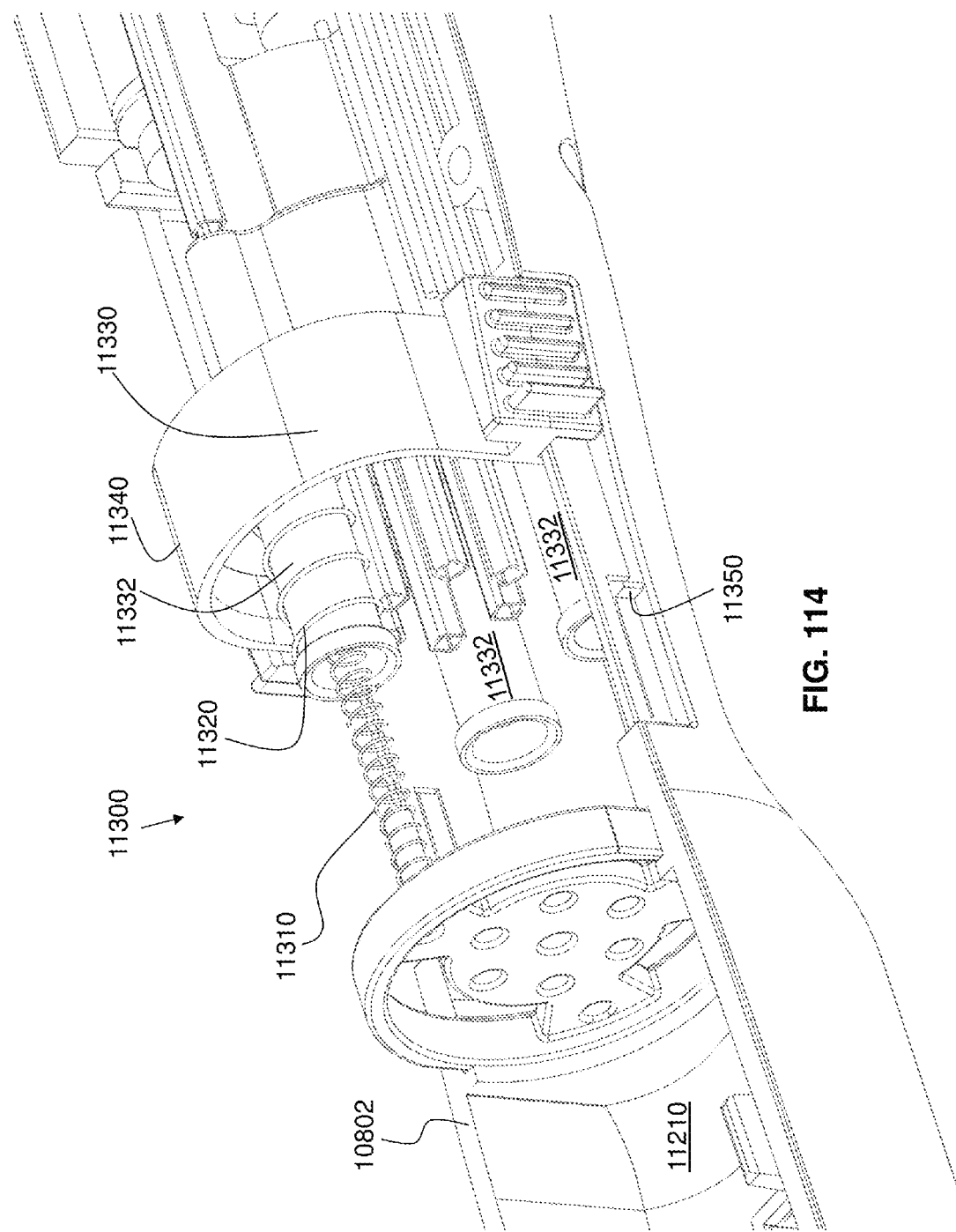
FIG. 114 is a fragmentary, perspective view of the needle control portion of the handle of FIG. 113 with the needle control in a lattice-expanded and needle-stowed position.
Figure 115:
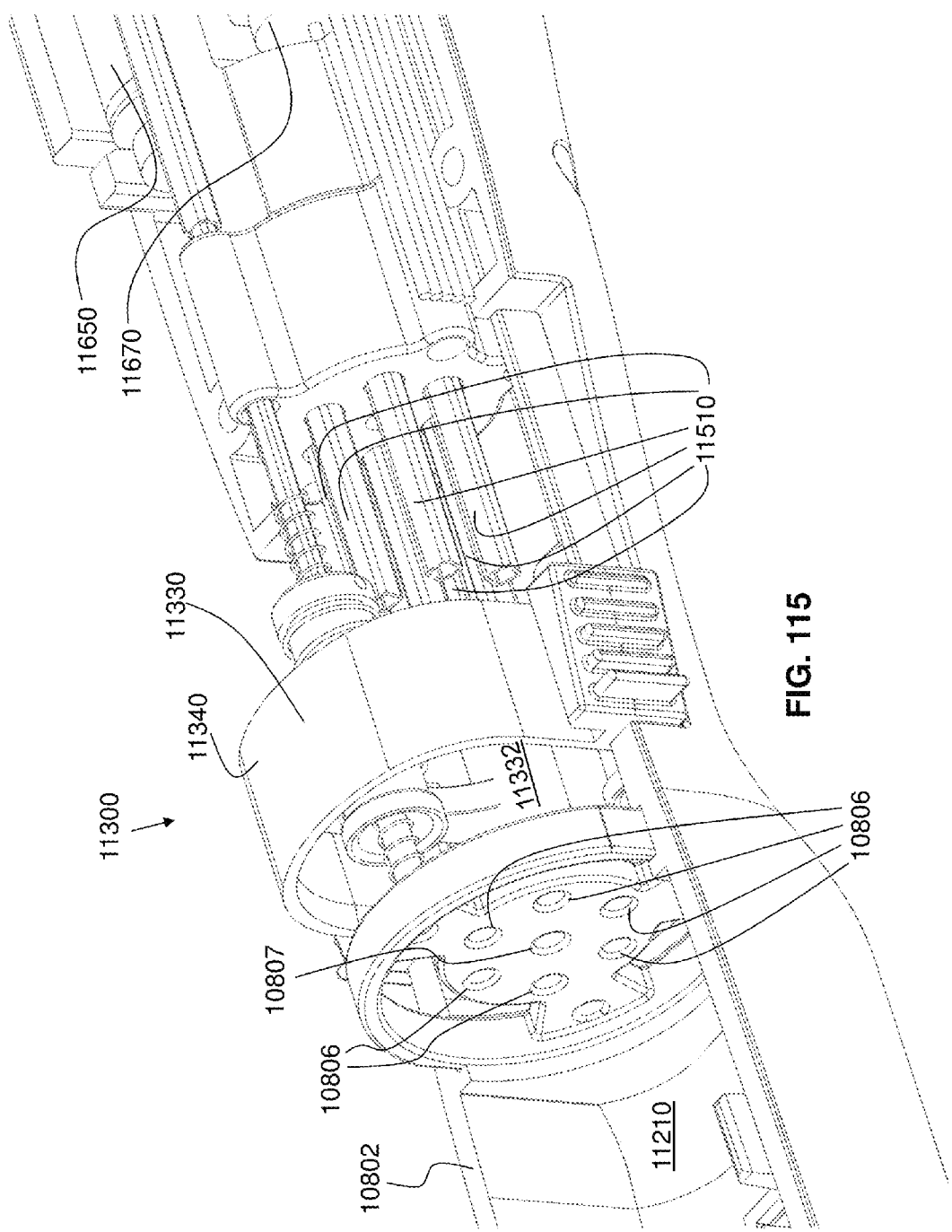
FIG. 115 is a fragmentary, perspective view of the needle control portion of the handle of FIG. 114 with the needle control in a needle-extended position.
Figure 116:
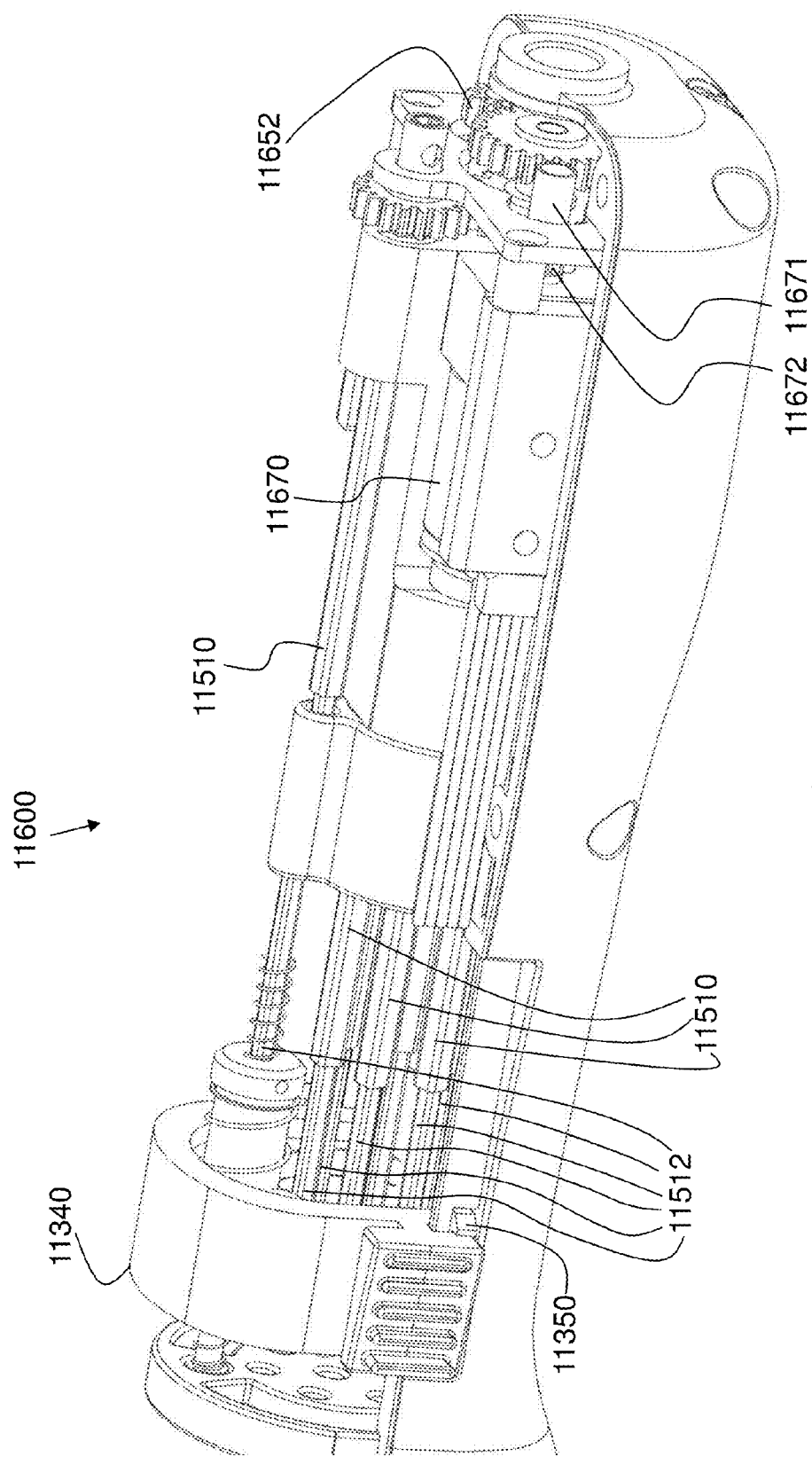
FIG. 116 is a fragmentary, perspective view of an engine portion of the handle of FIG. 108 from above a left side thereof with the upper handle half removed.

The needle-movement sub-assembly 11300 is described with reference to FIGS. 113 to 115, and best with regard to FIG. 113. Each of the needle rods 11302 that connect to the needles in the prosthesis to the needle-movement sub-assembly 11300 is associated with a tension spring 11310, an overstroke spring 11320, and a control tube 11332. The three control tubes 11332 are longitudinally held with respect to a control slider 11330 by the overstroke spring 11320. As long as the force on the needles is not greater than the force of the overstroke spring 11320, movement of the needle rod 11302 will follow the control slider 11330. A needle deployment yoke 11340 slides with respect to the shell 10802 of the control handle 10800. When the needle deployment yoke 11340 contacts the control slider 11330 as it moves distally, the needle deployment yoke 11340 carries the control slider 11330 and the needle rods 11302 distally to, thereby, deploy the needles. The transition from FIGS. 113 to 114 shows how the tension spring 11310 keeps tension on the needles by biasing the control slider 11330 proximally. Deployment of the needles is shown by the transition from FIGS. 114 to 115. As mentioned above, the needles 3070 each a have bent needle tip 3072. In a configuration where the needles 3070 are connected directly all the way back to the needle-movement sub-assembly 11300, there is a high likelihood that bending of the delivery catheter 11040 will impart various different forces on the needle rods 11302. These forces will tend to pull or push the needle rods 11302 and, thereby possibly extend the needles 3070 when not desired. Accordingly, each tension spring 11310 is longitudinally connected to the needle rod 11302 to compensate for these movements and keep the bent needle tip 3072 within the needle tip groove of the 3013 distal drive block 3010.

Because deployment of the needles is intended (ideally) to be a one-time occurrence, a yoke capture 11350 is provided at the end of the yoke stroke. Capture of the yoke 11340 can be seen in FIG. 116. Of course, this capture can be released by the user if such release is desired. Finally, if too much force is imparted on the needles when being deployed, the force of the overstroke spring 11320 is overcome and the control tube 11332 is allowed to move with respect to the control slider 11330. The compression of the overstroke spring 11320 cannot be shown in FIG. 115 because of the limitation of the software that created FIG. 115.

The jack engine 11600 is configured to control all rotation of parts within the various jack assemblies 700, 2100, 3000, 6430. The exemplary embodiment of the control handle 10800 shown in FIGS. 108 to 118 utilizes three jack assemblies similar to jack assemblies 3000 and 6430. In other words, the needles are separate from the proximal drive blocks of both assemblies and only two rotational control wires 750, 770 are needed. Therefore, for the three jack assemblies, six total control wires are required—three for the drive wires 750 and three for the disconnect wires 770. These control wires 750, 770 are guided respectively through six throughbores 10806 (surrounding the central guidewire throughbore 10807 in FIG. 115) and proximally end and are longitudinally fixed to a distal part 11512 of each of six telescoping wire control columns 11510, shown in FIGS. 115 and 116. All control wires, even the needle rods 11302, terminate at and are fixed longitudinally to a distal part 11512 of a respective telescoping wire control column 11510. Each part of these telescoping wire control columns 11510, 11512 are rigid so that rotation of the proximal part thereof causes a corresponding rotation of the distal part 11512 and, thereby, rotation of the corresponding control wire 750 or 770. The reason why all control wires, even the needle rods 11302, terminate at and are fixed longitudinally to a distal part 11512 of a respective telescoping wire control column 11510 is because tortuous curving of the wires/rods from their proximal ends to the distal ends longitudinally fixed at the stent assembly to be implanted will cause the wires to move longitudinally. If there is no play, the wires/rods will impart a longitudinal force on any parts to which they are grounded, for example, to the threaded connection at the stent assembly at the distal end. This longitudinal force is undesirable and is to be avoided to prevent, for example, the drive screws from breaking loose of their threads. To avoid this potential problem, the proximal end of each wire/rod is longitudinally fixed to the distal part 11512 of a respective telescoping wire control column 11510. The distal part 11512 is keyed to the wire control column 11510, for example, by having an outer square rod shape slidably movable inside a corresponding interior square rod-shaped lumen of the proximal part of the wire control column 11510. In this configuration, therefore, any longitudinal force on any wire/rod will be taken up by the respective distal part 11512 moving longitudinally proximal or distal depending on the force being exerted on the respective wire/rod.

Torque limiting is required to prevent breaking the lattice or stripping the threads of the drive screw. This can be accomplished in software by current limiting or through a clutch mechanism disposed between the drive motors and the sun gears. An integral contrast injection system can be incorporated into the handle of the delivery system through another lumen. With a powered handle, therefore, a powered injection as part of handle is made possible.

Figure 117:
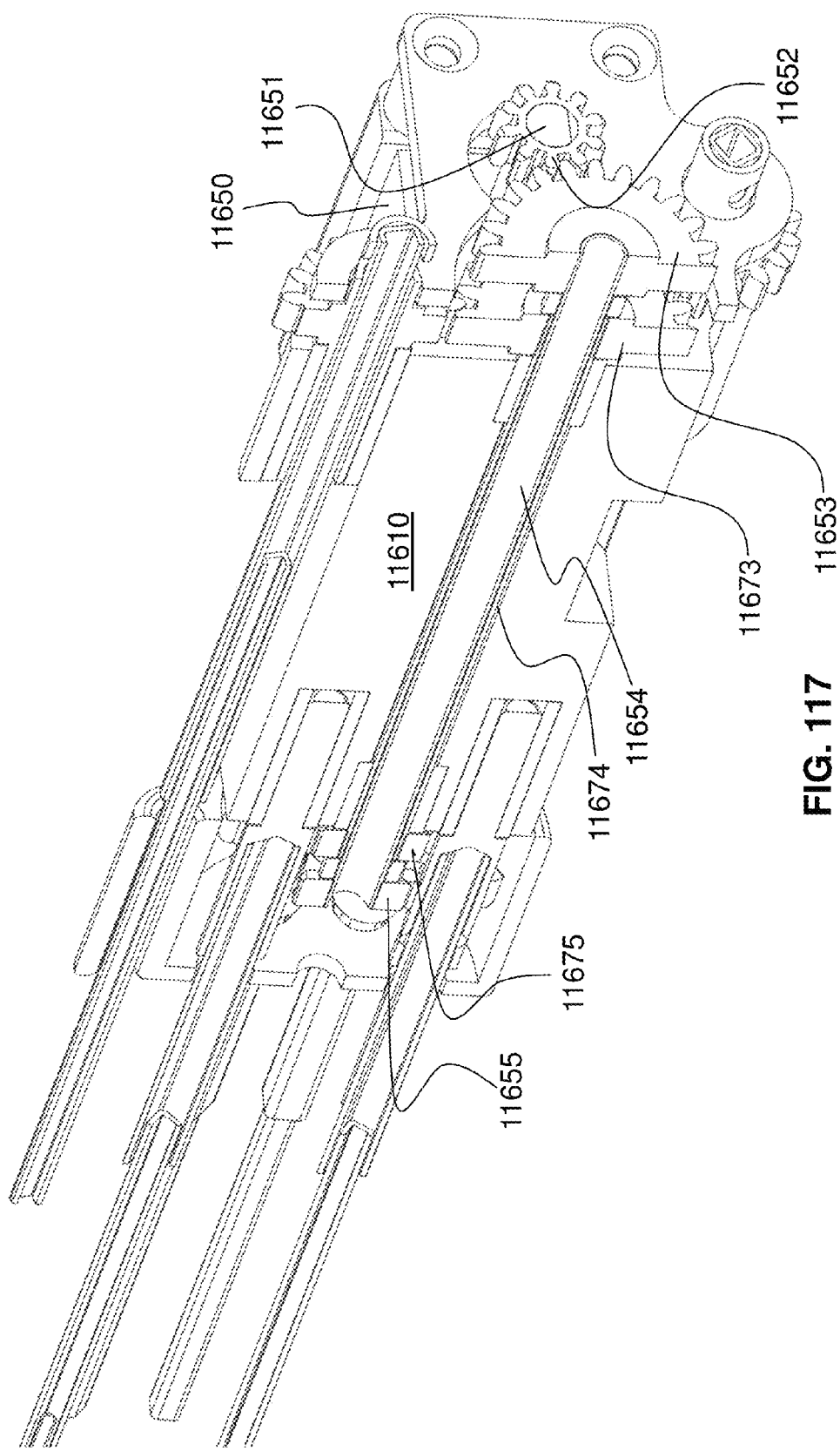
FIG. 117 is a fragmentary, enlarged, vertically cross-sectional view of the engine portion of FIG. 116 viewed from a proximal side thereof.
Figure 118:
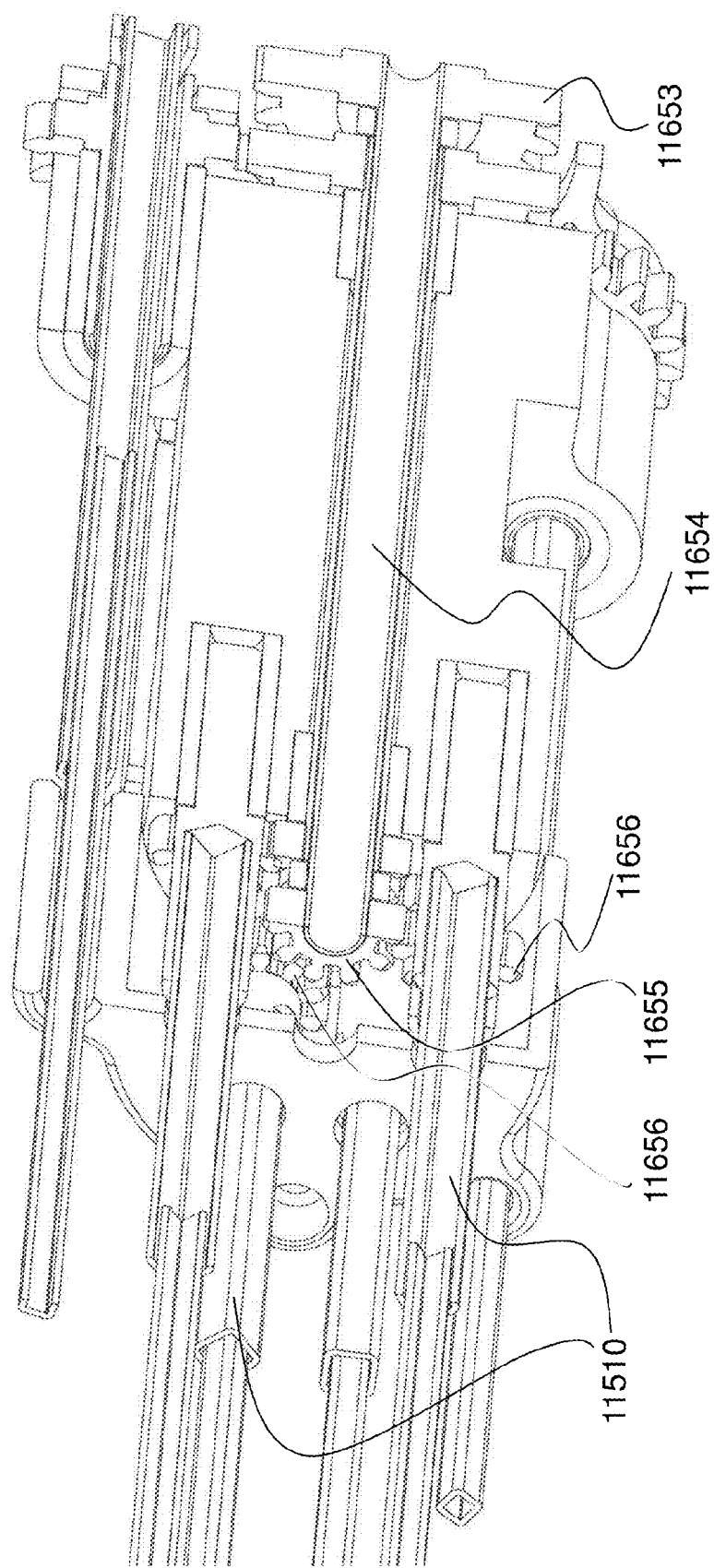
FIG. 118 is a fragmentary, enlarged, vertically cross-sectional view of the engine portion of the handle portion of FIG. 117 viewed from a distal side thereof.

Because all of the drive wires 750 need to rotate simultaneously, and due to the fact that all of the disconnect wires also need to rotate simultaneously, the jack engine 11600 includes a separate control motor 11650, 11670 (see FIG. 115) and separate transmission for each set of wires 750, 770. The view of FIG. 117 illustrates the transmission for the drive-screw control motor 11650. At the output shaft 11651 of the drive-screw control motor 11650 is a first drive gear 11652 interconnected with a larger second drive gear 11653. The second drive gear 11653 is part of a coaxial planetary gear assembly and has a central bore therein for passing therethrough the guidewire 6610. A hollow rod 11654 is fixedly connected in the central bore and extends through a transmission housing 11610 to a distal side thereof, at which is a third drive gear 11655, as shown in FIG. 118. The third drive gear 11655 is interconnected with three final drive gears 11656, each of the final drive gears 11656 being fixedly connected to a respective proximal part of one of the three telescoping wire control columns 11510 associated with each drive wire 750. Accordingly, when the drive-screw control motor 11650 rotates, the three final drive gears 11656 rotate the control columns 11510 that rotate the drive screws of the jack assemblies 3000, 6430.

The disconnect control motor 11670 operates in a similar manner. More specifically and with regard to FIG. 116, the output shaft 11671 of the disconnect control motor 11670 is a first disconnect gear 11672 interconnected with a larger second disconnect gear 11673. The second disconnect gear 11673 is part of a coaxial planetary gear assembly and has a central bore therein for passing therethrough the guidewire 6610. A hollow rod 11674 is fixedly connected in the central bore about the hollow rod 11654 and extends through the transmission housing 11610 to the distal side thereof, at which is a third disconnect gear 11675 (also disposed about the hollow rod 11654), as shown in FIG. 118. The third disconnect gear 11675 is interconnected with three final disconnect gears (not illustrated), each of the final disconnect gears being fixedly connected to a respective proximal part of one of the three telescoping wire control columns 11510 associated with each disconnect wire 770. Accordingly, when the disconnect control motor 11670 rotates, the three final disconnect gears rotate the control columns 11710 that rotate the retainer screws of the jack assemblies 3000, 6430. The activation of the disconnect drive also unscrews the needle connections when included. One exemplary embodiment for having the needles disconnect before the entire implant is set free from the docking jacks provides a lower number of threads on the needle disconnects.

Not illustrated herein is the presence of a manual release for all actuations of the delivery system. Such manual releases allow for either override of any or all of the electronic actuations or aborting the implantation procedure at any time during the surgery. Manual release sub-assemblies are present for retraction of the delivery sheath, expansion and contraction of all stent lattices, undocking of all disconnect drive blocks, and retraction of the distal nose cone into the delivery sheath.

Based upon the above, therefore, the delivery system control handle 10800 is entirely self-contained and self-powered and is able to actively control any prosthesis having the stent lattice and jack assemblies of the invention.

Figure 119:
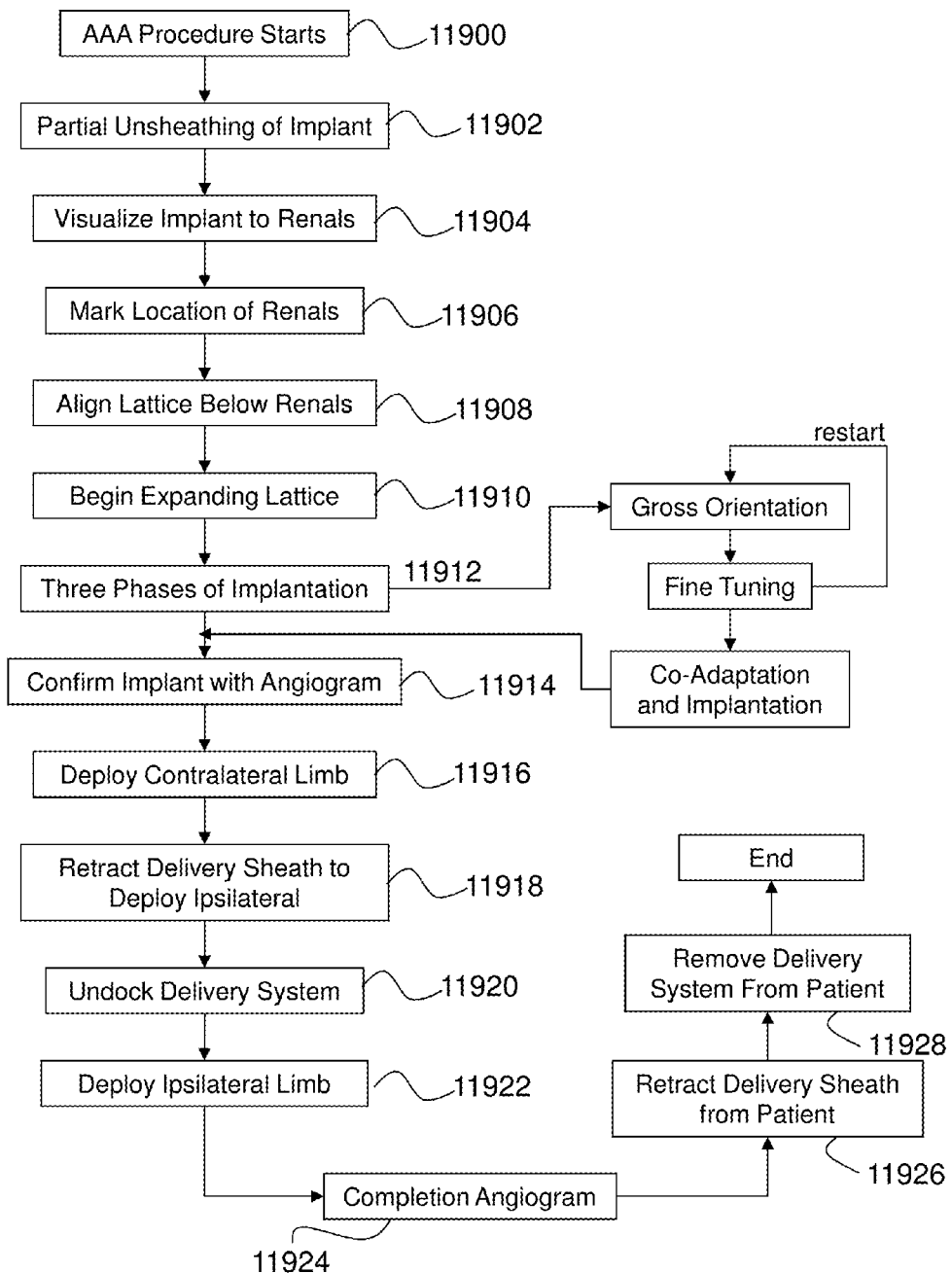
FIG. 119 is a flow diagram of an exemplary embodiment of a procedure for implanting an abdominal aorta prosthesis according to the invention.

An exemplary embodiment of a process for delivering an abdominal aortic stent graft of the invention as shown in FIG. 107 with the stent lattice as a proximal stent is described with regard to the flow chart of FIG. 119. The procedure is started in step 11900 where the lattice has been translated through the femoral artery to the implantation site just downstream of the renal arteries. Actuation of the upper left button rearward in Step 11902 causes the delivery sheath 10720 to unsheathe from the AAA implant 10730 sufficient to expose the actuatable end (e.g., stent lattice) of the implant 10730. In Step 11904, visualization, such as through fluoroscopy, provides the user with feedback to show where the distal end 10732 of the prosthesis 10730 is situated. In this position, the stent lattice is in a contracted state (the expanded state is shown in the view of FIG. 107). Radiopaque markers on the prosthesis 10730 are visible to show the proximal most points of the prosthesis 10730. In Step 11906, another surgery staff, typically, has marked the location of the renal arteries on the screen (on which the surgeon sees the markers) with a pen or marker. In Step 11908, the surgeon translates the lattice of the prosthesis 10730 with the radiopaque markers to a location targeted below the renal arteries. The physician begins to expand the lattice in Step 11910 by pressing the upper right button forward (i.e., forward=open and rearward=close). Depending upon the desire of the surgeon or as set in the programming of the control device 10700, the lattice can open incrementally (which is desirable due to blood flow issues) or can be expanded fluidly outward. Implantation occurs in Step 11912 and has three phases. In the first phase of implantation, the physician performs a gross orientation of the proximal end of the prosthesis 10730 until touchdown in the abdominal aorta. In the second phase, the physician fine-tunes the implantation using intermittent expansion prior to coaptition in all three dimensions and, in the third phase, the proximal end of the implant 10730 is either satisfactorily coadapted or, if the physician is not satisfied with the coaptition, then the physician reduces the diameter of the stent lattice and starts, again, with phase two. It is noted that the control device 10700 can be programmed to, at the first touch of the upper right button, to go to a particular diameter opening. For example, if the implantation site is 20 mm, then the control device 10700 can be programmed to expand directly to 15 mm and, for each touch of the upper right button thereafter, expansion will only occur by 1 mm increments no matter how long the upper right button is pushed forward. During Step 11912, the physician is able to view all of the various feedback devices on the control handle, such as the real time diameter of the prosthesis, the angulation thereof, a comparison to a predetermined aortic diameter of the touchdown point, an intra-vascular ultrasound assessing proximity to wall, and when wall touch occurs. With the digital display 10711 of the invention, the physician can even see an actual representation of the expanding lattice demonstrating all of the characteristics above. During the various implantation phases, the physician can pause at any time to change implant position. Angulation of the stent lattice can be done actively or while paused. As the outer graft material approaches the wall, adjustment of the entire delivery device continues until complete coaptation of the prosthesis 10730, where it is insured that the location with respect to the renal arteries is good, along with proper angulation. As the stent graft touches the aortic wall, the physician can analyze all of the feedback devices to make implantation changes. At any time if the physician questions the implantation, then restart occurs to readjust the stent lattice along with a return to phase two. Further, as coaptation occurs, any other fixation devices can be utilized, for example, passive tines/barbs, a outwardly moving flex-band that presses retention device (e.g., through graft) and into aortic wall, the tissue anchor 7114, and the graft enclosures 7120. For such devices, there is no secondary action required to disengage/retract tines that are engaged. In Step 11914, the physician performs an angiogram to determine positioning of the implantation (the angiogram can be either separate or integral with the delivery system 10700), and if the positioning is not as desired, the physician can retract the stent lattice and use the sheath 10720 to re-collapse the stent lattice using the graft material to ease delivery sheath 1020 back over the lattice. However, if the physician determines that there is good positioning, the physician retracts the delivery sheath 10720 by pressing the upper left button rearward until at least contralateral gate is exposed. It is noted that stabilization of the ipsilateral graft material with the delivery system 10700 allows for better cannulization of the contralateral gate for a secondary prosthesis.

In Step 11916, the contralateral limb is deployed as is known in the art. However, if desired, the contralateral limb can also include the actively expanded stent lattice according to the invention. It is also desirable to perform a balloon expansion at the graft-to-graft junction if the contralateral limb utilizes a self-expanding distal stent. If the actively controllable stent lattice is used, then Steps 11900 to 11914 are repeated but for the contralateral limb. In Step 11918, the delivery sheath 10720 is retracted by pressing the upper left button rearward until ipsilateral limb is deployed. The prosthesis 10730 is, now, ready to be finally deployed.

In Step 11920, the physician actuates the lower left button rearward to unscrew the retainer screws and, thereby undock the disconnect drive blocks from the prosthesis 10730. One significant advantage of the delivery system 10700 is that there is no surge either distal or proximal when undocking occurs and finally releases the prosthesis because the entire undocking movement is merely an unscrewing of a rod from a threaded hole. The upper left button is pressed forward to extend the delivery sheath 10720 so that it connects with the distal end of nose cone 10740 while making sure that the open distal end of the delivery sheath 10720 does not catch any part of the ipsilateral distal stent or the actively controlled proximal stent. It is at this point where the manual override would be employed if the surgeon wanted to feel the redocking of the delivery sheath 10720 to the nose cone 10740. If desired, using the lower right button pressing rearward, the physician can retract the nose cone 10740 into the distal end of the delivery sheath 10720 with the lower right button. In Step 11922, if the ipsilateral distal stent is self-expanding, the physician performs a final balloon expansion. However, if the ipsilateral distal stent utilizes the actively controllable stent lattice of the invention, Steps 11900 to 11914 are repeated but for the ipsilateral limb. A completion angiogram is performed in Step 11924 to make sure the prosthesis did not shift and that all leak possibilities have been ruled out. In an exemplary embodiment where the control system 10700 includes an integral dye system, the physician would extend the system proximal to the proximal active lattice. Finally, in Step 11926, the lower right button is pressed rearward to retract the delivery system as much as possible into the handle and, in Step 11928, the delivery system 10700 is removed from the patient.

FIG. 120 shows an exemplary embodiment of a self-expanding/forcibly-expanding lattice of an implantable stent assembly 12000 having nine lattice segments 12010 in a self-expanded native position as will be described below. In one exemplary embodiment, each of the nine lattice segments is formed with one-half of either a threaded or smooth bore 12012 for respective coordination with either a threaded or smooth portion of a jack screw 12020. In another exemplary embodiment, the nine lattice segments are formed from one integral piece of a shape memory metal (e.g., Nitinol) and with a jack screw 12020 disposed between adjacent pairs of repeating portions of the lattice and through the wall of the stent lattice. In the views shown in FIGS. 120 and 121, each jack screw 12020 is placed in a non-engaged state to allow crimp of the stent lattice for loading into a stent delivery system. In this regard, FIG. 121 illustrates the stent assembly 12000 in a contracted/crimped state for loading into the stent delivery system. In this non-engaged state, as the stent assembly 12000 is crimped for delivery, the proximal jack strut 12014 surrounding the non-threaded portion of each jack screw 12020 can slide thereabout with play between the two positions shown in FIGS. 120 and 121 without hindrance or bottoming out the distal drive screw coupler part 12052 while the lattice expands longitudinally when contracted by the delivery sheath of the delivery system. When the stent assembly 12000 is allowed to self-expand back to the position shown in FIG. 120, the jack screw 12020 moves into the bore of the distal jack strut 12014 until the distal drive screw coupler part 12052 hits the proximal end of the proximal jack strut 12014. Accordingly, with rotation of the jack screw 12020 in the stent-expansion direction, after the distal drive screw coupler part 12052 hits the proximal end of the proximal jack strut 12012, further lattice-expanding movement of the drive screw 12020 starts moving the proximal jack strut 12014 towards the distal jack strut 12013 to expand the stent assembly 12000.

Longitudinally, the stent assembly 12000 is provided with pairs of jack struts 12013, 12014 connected by a respective jack screw 12020 and intermediate non-moving struts 12030. In the exemplary embodiment of the stent assembly 12000 shown, there are nine pairs of jack struts 12013, 12014 and nine non-moving struts 12030. This number is merely exemplary and there can be, for example, only six of each or any other number desired. Connecting the pairs of jack struts 12013, 12014 and the non-moving struts 12030 are laterally extending arms 12040. As the stent assembly 12000 is either contracted or expanded, the arms 12040 each pivot at their two endpoints, one at a respective non-moving strut 12030 and the other at a respective one of a pair of jack struts 12013, 12014. As can be seen from the configuration shown in FIG. 121, when the stent assembly 12000 is contracted (e.g., for installation into the delivery sheath), the arms 12040 move towards a longitudinal orientation. Conversely, when the stent assembly 12000 is expanded (e.g., for implantation), the arms 12040 move towards a longitudinal orientation.

FIG. 122 shows the lattice after being allowed to return to its native position, for example, at a deployment site. Each jack screw 12020 is in an engaged state for controlled further outward expansion of the lattice. As the lattice is sized for implantation, the delivery system forcibly expands the lattice, as shown in the progression of FIGS. 123, 124, and 125. In the view of FIG. 125, the lattice is about to enter a maximum expansion state, which occurs when the proximal surface of the distal jack strut 12013 contacts the distal surface of the proximal jack strut 12014. It is noted that this exemplary embodiment does not show features of a valve sub-assembly. Valve sub-assemblies, such as shown in FIGS. 135 to 136 are envisioned to be used with this stent assembly 12000 but is not shown for reasons of clarity.

FIG. 126 is an alternative exemplary embodiment of a portion of a self-expanding/forcibly-expanding lattice of an implantable stent assembly 12600. In the portion of the configuration shown, a separate jack screw assembly 12610 connects the two adjacent lattice segments (here the non-moving strut 12616 is shown in a vertical cross-section passing through the mid-line thereof). Separate jack tube halves 12612, 12613 are connected respectively to upper and lower jack-contact struts 12614 of the two adjacent lattice segments. In the exemplary embodiment shown, the external threads of the jack screw 12620 are engaged with the interior threads of the distal jack tube half 12612. A lattice-disconnect tube 12630 of the stent delivery system is engaged to cover a pair of drive screw coupler parts therein. FIG. 127 shows the lattice-disconnect tube 12630 disengaged from the pair of drive screw coupler parts 12752, 12754. This connected state of the pair of drive screw coupler parts 12752, 12754 is idealized because, due to the natural lateral/radial forces existing in the disconnect joint, once the lattice-disconnect tube 12630 retracts proximally past the coupling of the drive screw coupler parts 12752, 12754, the two drive screw coupler parts 12752, 12754 will naturally separate, as shown in the view of FIG. 128. In this disconnected view, the proximal member of the pair of drive screw coupler parts 12752, 12754, which is part of the delivery system, is partially retracted into the central bore of the lattice-disconnect tube 12630.

FIG. 129 illustrates another exemplary embodiment of a self-expanding/forcibly-expanding lattice of an implantable stent assembly. This assembly also has nine separate lattice segments, but more or less in number is equally possible, for example, six segments. In this embodiment, a proximal disconnect block 12930 and disconnect subassemblies 12931, 12932 of a stent delivery system is an alternative to the lattice-disconnect tubes 12630 of the embodiment of FIGS. 126 to 128. Here, a proximal disconnect block 12930 is in an engaged state covering the pair of drive screw coupler parts 13052, 13054 therein. After the disconnect block 12930 is retracted in a proximal direction, all of the lattice-disconnect arms 12932 are removed from covering the pair of drive screw coupler parts 13052, 13054, thereby allowing disconnect of the lattice 12900 from the delivery system, as shown in FIG. 130. The proximal disconnect block 12930 allows all of the pairs of drive screw coupler parts 13052, 13054 to be coupled together for simultaneous release.

FIGS. 131 and 132 show an alternative to the exemplary embodiment of the self-expanding/forcibly-expanding lattice of FIGS. 126 to 130. Here, the intermediate jack tubes halves 13112, 13113 for receiving one jack screw 13120 therein are connected to the adjacent lattice segments with the adjacent lattice segments 13114 not directly on opposing sides of the jack tubes 13112, 13113. The angle that the two adjacent lattice segments make is less than 180 degrees and greater than 90 degrees. In particular, the angle is between 130 degrees and 150 degrees and, more specifically, is about 140 degrees, as shown in FIG. 132.

FIG. 133 is another exemplary embodiment of a self-expanding/forcibly-expanding lattice of an implantable stent assembly 13300. In this embodiment, there are nine lattice segments but more or less is equally possible, for example, six segments. Here, the distal and proximal jack struts 13313, 13314 of the lattice are locally thicker to accommodate and connect to non-illustrated jack screw assemblies.

FIG. 134 is another exemplary embodiment of a self-expanding/forcibly-expanding lattice of an implantable stent assembly 13400. In this embodiment, there are nine lattice segments but more or less is equally possible, for example, six segments. Instead of having the non-illustrated jack screws pass entirely through the material of the lattice as shown in previous embodiments, here, the jack struts of the lattice are elongated and the elongated portions are bent-over to form tabs 13413, 13414 for connecting to non-illustrated jack screw assemblies. The tabs 13413, 13414 are shown here as bent inwards, but they can also be bent to face outwards. To operate the jacks, various ones of each of the set of longitudinal tabs are threaded or smooth.

FIGS. 135 to 137 show another exemplary embodiment of the self-expanding/forcibly-expanding lattice of an implantable valve assembly 13500. The jack assemblies are similar to the embodiment of FIGS. 120 to 125. Here, however, there are six lattice segments. The intermediate non-moving struts 13530 between the jacks 13520 form commisure connections and include through-bores 13532 for connecting the valve end points of the intermediate valve 13540 to the lattice. The valve here is shown with three leaflets 13542 and therefore three commisure connections exist at three of the non-moving struts 13530. The valve assembly is shown in FIGS. 135 and 136 in an expanded position that can be commensurate with an implantation position of the valve assembly. FIG. 137, in comparison, shows the lattice of the valve assembly 13500 in a natural, non-expanded state.

FIGS. 138 to 142 show another exemplary embodiment of the self-expanding/forcibly-expanding lattice of an stent assembly 13800. As in the above embodiments, this exemplary embodiment does not show features of a valve sub-assembly for reasons of clarity even though valve sub-assemblies, such as shown in FIGS. 135 to 136, are envisioned to be used with this stent assembly 13800. Here, the lattice of the stent assembly 13800 has six lattice segments. Instead of having the jack screws contact longitudinal bores in the wall of the lattice, pairs of jack tubes 13812, 13813 are connected (e.g., laser welded) to respective longitudinal pairs of jack connection struts 13822, 13823. The embodiment shows the jack tubes 13812, 13813 connected on the interior of the lattice but they can also be connected on the exterior, or the pairs can even be staggered on the interior and exterior in any way and in any number. The jack tubes 13812, 13813 are formed with interior threads or interior smooth bores.

After being forcibly contracted, the lattice of FIG. 138 can be further compressed within the delivery sheath of the delivery system, an orientation that is shown in FIG. 139. After delivery to the implantation site, the lattice is expanded for implementation. FIGS. 140 to 142 show various expansion stages of the lattice in various perspective views with FIG. 142 showing the lattice expanded near a maximum expansion extent.

The exemplary embodiments of the valve assemblies described herein seeks to have a valve that is sized and formed for a minimum deployment diameter. This valve is secured inside the stent lattice/frame that is capable of expanding to a much larger final diameter than the internal valve. The commisures of the valve are secured to the frame with a mechanical linkage that allows the frame to expand and keep the valve at a proper size to minimize regurgitation. A lower skirt of the valve is attached to the stent through a loose connection of the variable diameter braided graft or a similar device. This configuration allows the stent frame to continue to grow and fit into a variety of native annuli that are larger than the valve carried within the device.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A delivery apparatus, comprising:
a handle portion having an actuation mechanism, wherein the actuation mechanism includes a motor; and
at least one rotatable drive shaft having a proximal end portion and a distal end portion, wherein the proximal end portion is coupled to the motor, and the distal end portion is configured to be releasably coupled to a prosthetic heart valve,
wherein the actuation mechanism is configured to control and monitor expansion of the prosthetic heart valve and to control and monitor torque of the motor.

2. The delivery apparatus of claim 1, wherein the actuation mechanism further comprises a torque limiting member configured to limit an electrical current of the motor.

3. The delivery apparatus of claim 1, wherein the actuation mechanism further comprises a clutch mechanism configured to limit the torque transmitted to the drive shaft from the motor.

4. The delivery apparatus of claim 1, wherein the actuation mechanism further comprises a gear assembly coupled to the motor and the drive shaft and configured to transfer rotational movement of the motor to the drive shaft.

5. The delivery apparatus of claim 4, wherein the at least one drive shaft is a plurality of drive shafts, the motor includes an output shaft having a first gear, and the gear assembly includes a second gear, a connecting shaft, a third gear, and a plurality of fourth gears, and wherein the first gear is coupled to the second gear, the second gear is coupled to a first end of the connecting shaft, the third gear is coupled to a second end of the connecting shaft, the third gears are coupled to the fourth gears, and the fourth gears are coupled to respective ones of the drive shafts.

6. The delivery apparatus of claim 5, wherein the actuation mechanism further comprises a clutch mechanism disposed between the first gear and the second gear, the clutch mechanism configured to limit the torque transmitted to the drive shafts from the motor.

7. The delivery apparatus of claim 1, wherein the handle portion further comprises a user interface with a display configured to display a diameter of the prosthetic heart valve.

8. The delivery apparatus of claim 7, wherein the display is further configured to display a comparison of the diameter of the prosthetic heart valve to a diameter of a patient's native anatomy.

9. The delivery apparatus of claim 1, wherein the handle portion further comprises a user interface with a display configured to display when the prosthetic heart valve contacts a patient's native anatomy.

10. The delivery apparatus of claim 1, wherein the handle portion further comprises a user interface with a display configured to display the magnitude of force imparted on the prosthetic heart valve by a patient's native anatomy.

11. The delivery apparatus of claim 1, wherein the actuation mechanism is programmed to expand the prosthetic heart valve to a plurality of predetermined diameters upon actuating the actuation mechanism.

12. The delivery apparatus of claim 1, wherein one actuation of the actuation mechanism causes the prosthetic heart valve to expand to a first predetermined diameter that is at least 75% of a fully expanded diameter of the prosthetic heart valve, and another actuation of the actuation mechanism cause the prosthetic heart valve to expand from the first predetermined diameter to a second predetermined diameter that is 1 mm larger than the first predetermined diameter.

13. A delivery assembly, comprising:
a prosthetic heart valve having stent and a plurality of adjustable elements configured to radially expand and contract the stent; and
a delivery apparatus having a handle portion, first drive shaft, and a plurality of second drive shafts, wherein the handle portion has an actuation mechanism with a motor, the first drive shaft is coupled to the motor such that rotation of the motor causes rotation of the first drive shaft, first end portions of the second drive shafts are coupled to the first drive shaft such that rotation of the first shaft causes rotation of the second drive shafts, and second end portions of the second drive shafts are coupled to the adjustable elements of the prosthetic heart valve such that rotation of the second drive shafts causes movement of the adjustable elements to effect radial expansion or contraction of the prosthetic heart valve.

14. A delivery assembly, comprising:
a prosthetic heart valve having stent and a plurality of adjustable elements configured to radially expand and contract the stent; and
a delivery apparatus having a handle portion, first drive shaft, and a plurality of second drive shafts, wherein the handle portion has an actuation mechanism with a motor, the first drive shaft is coupled to the motor such that rotation of the motor causes rotation of the first drive shaft, first end portions of the second drive shafts are coupled to the first drive shaft such that rotation of the first shaft causes rotation of the second drive shafts, and second end portions of the second drive shafts are coupled to the adjustable elements of the prosthetic heart valve such that rotation of the second drive shafts causes movement of the adjustable elements to effect radial expansion or contraction of the prosthetic heart valve,
wherein actuating the actuation mechanism expands and contracts the prosthetic heart valve, and wherein the actuation mechanism is configured to control and monitor expansion of the prosthetic heart valve and to control and monitor torque applied to the prosthetic heart valve by the motor.

15. The delivery assembly of claim 14, wherein the handle portion further comprises at least one sensor and a user interface with a force feedback indicator, the at least one sensor configured to measure a force imparted on the prosthetic heart valve by a patient's native anatomy, and the force feedback indicator configured to display the force measured by the at least one sensor.

16. The delivery assembly of claim 15, wherein the at least one sensor is configured to measure the force by measuring resistance to the motor, and the force feedback indicator is configured to display a graphical change of the resistance to the motor.

17. The delivery assembly of claim 14, wherein the handle portion further comprises a torque meter configured to measure the torque of the motor, and the user interface is configured to display the torque measured by the torque meter.

18. The delivery assembly of claim 14, wherein the actuation mechanism comprises a mechanical slip clutch.

19. The delivery assembly of claim 14, wherein the handle portion further comprises a user interface configured to display a real-time diameter of the prosthetic heart valve.

20. The delivery assembly of claim 14, wherein the actuation mechanism further comprises a torque limiting member configured to limit the torque of the motor.

21. The delivery assembly of claim 14, wherein the actuation mechanism is configured such that actuating the actuation mechanism causes the prosthetic heart valve to expand to a predetermined diameter.

22. The delivery assembly of claim 14, wherein the stent comprises a plurality of lumens having internal threads formed therein, and wherein the adjustable elements comprise a plurality of drive screws having external threads formed thereon and configured to threadably engage the internal threads of the lumens.

23. The delivery assembly of claim 22, wherein the lumens are defined in struts of the stent.

24. The delivery assembly of claim 22, wherein the stent is at least partially self-expanding.

* * * * *